US012570958B2

(12) United States Patent
Emtage et al.

(10) Patent No.:  US 12,570,958 B2
(45) Date of Patent:  Mar. 10, 2026

(54) SINGLE- AND MULTI-CHAIN CHIMERIC ANTIGEN RECEPTORS

(71) Applicant: Cell Design Labs, Inc., Emeryville, CA (US)

(72) Inventors: Peter Emtage, Lafayette, CA (US); Sarah Wyman, Oakland, CA (US)

(73) Assignee: Cell Design Labs, Inc., Emeryville, CA (US)

( * ) Notice: Subject to any disclaimer, the term of this patent is extended or adjusted under 35 U.S.C. 154(b) by 389 days.

(21) Appl. No.: 16/226,158

(22) Filed: Dec. 19, 2018

(65) Prior Publication Data

US 2019/0194617 A1      Jun. 27, 2019

Related U.S. Application Data

(60) Provisional application No. 62/767,212, filed on Nov. 14, 2018, provisional application No. 62/609,895, filed on Dec. 22, 2017.

(51) Int. Cl.
| | |
|---|---|
| *C12N 5/0783* | (2010.01) |
| *A61K 40/11* | (2025.01) |
| *A61K 40/31* | (2025.01) |
| *A61K 40/42* | (2025.01) |
| *A61P 35/00* | (2006.01) |
| *C07K 14/47* | (2006.01) |
| *C07K 14/705* | (2006.01) |
| *C07K 14/725* | (2006.01) |
| *C07K 16/28* | (2006.01) |
| *C07K 16/46* | (2006.01) |
| *C12N 15/62* | (2006.01) |

(52) U.S. Cl.
CPC ............ *C12N 5/0636* (2013.01); *A61K 40/11* (2025.01); *A61K 40/31* (2025.01); *A61K 40/4211* (2025.01); *A61P 35/00* (2018.01); *C07K 14/4748* (2013.01); *C07K 14/7051* (2013.01); *C07K 14/70521* (2013.01); *C07K 16/28* (2013.01); *C07K 16/283* (2013.01); *C07K 16/2863* (2013.01); *C07K 16/46* (2013.01); *C12N 15/62* (2013.01); *A61K 2239/38* (2023.05); *A61K 2239/48* (2023.05); *C07K 2319/03* (2013.01); *C07K 2319/70* (2013.01)

(58) Field of Classification Search
CPC .................. C12N 5/0636; C12N 15/62; A61K 39/001112; A61K 35/17; A61K 39/0011; C07K 14/4748; C07K 14/7051; C07K 14/70521; C07K 16/28; C07K 16/283; C07K 16/2863; C07K 16/46
See application file for complete search history.

(56) References Cited

U.S. PATENT DOCUMENTS

| | | | | |
|---|---|---|---|---|
| 10,342,829 B2* | 7/2019 | Smith | ..................... | A61P 21/00 |
| 10,577,417 B2* | 3/2020 | Beatty | ..................... | A61P 37/04 |
| 2014/0134142 A1* | 5/2014 | Smith | ..................... | A61P 43/00 |
| | | | | 435/69.6 |
| 2015/0306141 A1* | 10/2015 | Jensen | .................... | A61P 15/00 |
| | | | | 435/325 |
| 2016/0096902 A1* | 4/2016 | Cooper | ........... | C07K 14/70503 |
| | | | | 435/254.2 |
| 2017/0081411 A1* | 3/2017 | Engels | ................. | A61K 38/177 |

FOREIGN PATENT DOCUMENTS

| | | |
|---|---|---|
| WO | 14127261 A1 | 8/2014 |
| WO | 2016123333 A1 | 8/2016 |

OTHER PUBLICATIONS

Oberschmidt et al. "Redirected Primary Human Chimeric Antigen Receptor Natural Killer Cells As an "Off-the-Shelf Immunotherapy" for Improvement in Cancer Treatment", Front Immunol. Jun. 9, 2017;8:654. (Year: 2017).*
Chicaybam et al. "Chimeric Antigen Receptors in Cancer Immuno-Gene Therapy: Current Status and Future Directions", International Reviews of Immunology, 30:5-6, 294-311 (Year: 2011).*
Wang et al. "Generation of Potent T-cell Immunotherapy for Cancer using DAP12-based, Multichain, Chimeric Immunoreceptors," Cancer Immunol. Res., 2015, vol. 3, pp. 815-826 (Year: 2015).*
Lynn et al. "Targeting of folate receptor ß on acute myeloid leukemia blasts with chimeric antigen receptor-expressing T cells", Blood. May 28, 2015;125(22):3466-76 (Year: 2015).*
Wang et al. "Generation of Potent T-cell Immunotherapy for Cancer using DAP12-based, Multichain, Chimeric Immunoreceptors", Cancer Immunol Res. Jul. 2015;3(7):815-26 (Year: 2015).*
Baeuerle et al., "BiTE: Teaching antibodies to engage T-cells for cancer therapy," Curr. Opin. Mol. Ther., 2009, 11(1):22-30.
Barrett et al. Annu Rev Med (2014) 65:333-47.
Cartellieri et al., J Biomed Biotechnol (2010) 956304.
Cheadle et al. Immunol Rev (2014) 257(1):91-106.
Cromie et al., "Nanobodies and their Use in GPCR Drug Discovery," Curr. Top. Med. Chem., 2016, 15:2543-2557.
Fedorov et al. Sci Transl Med (2013) 5(215):215ra172.
Glienke et al. Front Pharmacol (2015) 6:21.

(Continued)

*Primary Examiner* — Daniel E Kolker
*Assistant Examiner* — Peter Johansen
(74) *Attorney, Agent, or Firm* — Fish & Richardson P.C.

(57) ABSTRACT

Provided herein are single-chain and multi-chain chimeric antigen receptors, nucleic acids encoding the same, and mammalian cells expressing the same. Also provided are methods of treating a cancer in a subject using a mammalian cell expressing any of these single-chain and multi-chain chimeric antigen receptors.

33 Claims, 5 Drawing Sheets

Specification includes a Sequence Listing.

(56) References Cited

OTHER PUBLICATIONS

Kakarla & Gottschalk 52 Cancer J (2014) 20(2):151-5.

Lanier, DAP10- and DAP12-associated receptors in innate immunity, Immunol Rev., Jan227(1):150-60. doi: 10.1111/i.1600-065X. 2008.00720.x, 2009.

Pegram et al. Cancer J (2014) 20(2):127-33.

Pluckthun, Antibodies from *E. coli*. Rosenberg M. & Moore G.P. (Eds.), The Pharmacology of Monoclonal Antibodies, vol. 113, pp. 269-315, Spinger-Verlag, New York, 1994.

Riddell et al. Cancer J (2014) 20(2):141-4.

Sadelain et al. Cancer Discov (2013) 3(4):388-98.

Van Bockstaele et al., "The development of nanobodies for therapeutic applications," Curr. Opin. Investig. Drugs, 2009, 10(11):1212-1224.

Guedan, Sonia, et al. "Engineering and design of chimeric antigen receptors." Molecular Therapy-Methods & Clinical Development 12 (2019): 145-156.

Dotti, Gianpietro, et al. "Design and development of therapies using chimeric antigen receptor-expressing T cells." Immunological reviews 257.1 (2014): 107-126.

Duong, Connie P. M. et al., "Engineering T Cell Function Using Chimeric Antigen Receptors Identified Using a DNA Library Approach", PLoS ONE, vol. 8, No. 5, May 7, 2013 (May 7, 2013), p. e63037, XP055664591.

Zhao, Ruocong et al., "DNAX-activating protein 10 co-stimulation enhances the anti-tumor efficacy of chimeric antigen receptor T cells", Oncolmmunology, vol. 8, No. 1, Nov. 2, 2018 (Nov. 2, 2018), pp. 1-12, XP093024066.

* cited by examiner

SEQUENCE LISTING

```
<160> NUMBER OF SEQ ID NOS: 86

<210> SEQ ID NO 1
<211> LENGTH: 44
<212> TYPE: PRT
<213> ORGANISM: Homo sapiens

<400> SEQUENCE: 1

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys
        35                  40

<210> SEQ ID NO 2
<211> LENGTH: 132
<212> TYPE: DNA
<213> ORGANISM: Homo sapiens

<400> SEQUENCE: 2
accacgacgc cagcgccgcg accaccaaca ccggcgccca ccatcgcgtc gcagcccctg      60
tccctgcgcc cagaggcgtg ccggccagcg gcggggggcg cagtgcacac gaggggctg     120 gacttcgcct gt                                                        132

<210> SEQ ID NO 3
<211> LENGTH: 30
<212> TYPE: PRT
<213> ORGANISM: Homo sapiens

<400> SEQUENCE: 3

Gln Thr Thr Pro Gly Glu Arg Ser Ser Leu Pro Ala Phe Tyr Pro Gly
1               5                   10                  15
```

-continued

```
Thr Ser Gly Ser Cys Ser Gly Cys Gly Ser Leu Ser Leu Pro
            20              25              30

<210> SEQ ID NO 4
<211> LENGTH: 90
<212> TYPE: DNA
<213> ORGANISM: Homo sapiens

<400> SEQUENCE: 4
cagacaacac caggcgagag atctagcctg cccgccttct accctggcac cagcggctct          60
tgttctggct gtggcagcct gtctctgccc                                          90

<210> SEQ ID NO 5
<211> LENGTH: 220
<212> TYPE: PRT
<213> ORGANISM: Homo sapiens

<400> SEQUENCE: 5

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
                100                 105                 110

Lys Ile Glu Val Met Tyr Pro Pro Tyr Leu Asp Asn Glu Lys Ser
            115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
                180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 6
<211> LENGTH: 25
<212> TYPE: PRT
<213> ORGANISM: Homo sapiens

<400> SEQUENCE: 6

Asp Ile Tyr Ile Trp Ala Pro Leu Ala Gly Thr Cys Gly Val Leu Leu
1               5                   10                  15

Leu Ser Leu Val Ile Thr Leu Tyr Cys
            20                  25
```

-continued

```
<210> SEQ ID NO 7
<211> LENGTH: 164
<212> TYPE: PRT
<213> ORGANISM: Homo sapiens

<400> SEQUENCE: 7

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Tyr
        50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
        130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 8
<211> LENGTH: 23
<212> TYPE: PRT
<213> ORGANISM: Homo sapiens

<400> SEQUENCE: 8

Leu Gly Leu Leu Val Ala Gly Val Leu Val Leu Leu Val Ser Leu Gly
1               5                   10                  15

Val Ala Ile His Leu Cys Cys
            20

<210> SEQ ID NO 9
<211> LENGTH: 26
<212> TYPE: PRT
<213> ORGANISM: Homo sapiens

<400> SEQUENCE: 9

Val Ala Ala Ile Leu Gly Leu Gly Leu Val Leu Gly Leu Leu Gly Pro
1               5                   10                  15

Leu Ala Ile Leu Leu Ala Leu Tyr Leu Leu
            20                  25

<210> SEQ ID NO 10
<211> LENGTH: 25
<212> TYPE: PRT
<213> ORGANISM: Homo sapiens

<400> SEQUENCE: 10

Ala Leu Ile Val Leu Gly Gly Val Ala Gly Leu Leu Leu Phe Ile Gly
1               5                   10                  15
```

-continued

```
Leu Gly Ile Phe Phe Cys Val Arg Cys
            20                  25

<210> SEQ ID NO 11
<211> LENGTH: 23
<212> TYPE: PRT
<213> ORGANISM: Homo sapiens

<400> SEQUENCE: 11

Leu Cys Tyr Leu Leu Asp Gly Ile Leu Phe Ile Tyr Gly Val Ile Leu
1               5                   10                  15

Thr Ala Leu Phe Leu Arg Val
            20

<210> SEQ ID NO 12
<211> LENGTH: 26
<212> TYPE: PRT
<213> ORGANISM: Homo sapiens

<400> SEQUENCE: 12

Trp Val Leu Val Val Val Gly Gly Val Leu Ala Cys Tyr Ser Leu Leu
1               5                   10                  15

Val Thr Val Ala Phe Ile Ile Phe Trp Val
            20                  25

<210> SEQ ID NO 13
<211> LENGTH: 24
<212> TYPE: PRT
<213> ORGANISM: Homo sapiens

<400> SEQUENCE: 13

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 14
<211> LENGTH: 24
<212> TYPE: PRT
<213> ORGANISM: Homo sapiens

<400> SEQUENCE: 14

Ala Leu Pro Ala Ala Leu Ala Val Ile Ser Phe Leu Leu Gly Leu Gly
1               5                   10                  15

Leu Gly Val Ala Cys Val Leu Ala
            20

<210> SEQ ID NO 15
<211> LENGTH: 72
<212> TYPE: DNA
<213> ORGANISM: Homo sapiens

<400> SEQUENCE: 15
atctatattt gggcacccct ggctggaacc tgcggagtgc tgctgctgtc tctcgtgatt      60
acactgtatt gc                                                          72

<210> SEQ ID NO 16
<211> LENGTH: 75
<212> TYPE: DNA
<213> ORGANISM: Homo sapiens

<400> SEQUENCE: 16
```

-continued

```
gatatctaca tctgggcgcc cttggccggg acttgtgggg tccttctcct gtcactggtt      60
atcacccttt actgc                                                        75

<210> SEQ ID NO 17
<211> LENGTH: 321
<212> TYPE: DNA
<213> ORGANISM: Artificial Sequence
<220> FEATURE:
<223> OTHER INFORMATION: Synthetic Sequence FMC63 VL

<400> SEQUENCE: 17
gacatccaga tgacccagac caccagcagc ctgagcgcca gcctgggcga tagagtgacc      60
atcagctgca gagccagcca ggacatcagc aagtacctga actggtatca gcagaaaccc     120
gacggcaccg tgaagctgct gatctaccac accagcagac tgcacagcgg cgtgcccagc     180
agattttctg gcagcggctc cggcaccgac tacagcctga ccatctccaa cctggaacag     240
gaagatatcg ctacctactt ctgtcagcaa ggcaacaccc tgccctacac cttcggcgga     300
ggcaccaagc tggaaatcac a                                                321

<210> SEQ ID NO 18
<211> LENGTH: 107
<212> TYPE: PRT
<213> ORGANISM: Artificial Sequence
<220> FEATURE:
<223> OTHER INFORMATION: Synthetic Sequence FMC63 VL

<400> SEQUENCE: 18

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 19
<211> LENGTH: 45
<212> TYPE: DNA
<213> ORGANISM: Artificial Sequence
<220> FEATURE:
<223> OTHER INFORMATION: Synthetic Sequence (G4S)3 linker

<400> SEQUENCE: 19
ggcggcggag gatctggcgg aggcggaagt ggcggagggg gatct                       45

<210> SEQ ID NO 20
<211> LENGTH: 360
<212> TYPE: DNA
<213> ORGANISM: Artificial Sequence
<220> FEATURE:
<223> OTHER INFORMATION: Synthetic Sequence FMC63 VH

<400> SEQUENCE: 20
```

-continued

```
gaagtgaaac tgcaggaaag cggccctggc ctggtggccc catctcagtc tctgagcgtg      60
acctgtaccg tgtccggcgt gtccctgcct gactatggcg tgtcctggat cagacagccc     120
cccagaaagg gcctggaatg gctgggagtg atctggggca gcgagacaac ctactacaac     180
agcgccctga gtcccggct gaccatcatc aaggacaact ccaagagcca ggtgttcctg      240
aagatgaaca gcctgcagac cgacgacacc gccatctact actgcgccaa gcactactac     300
tacggcggca gctacgccat ggactactgg ggccagggca aagcgtgac cgtgtctagc      360
```

<210> SEQ ID NO 21
<211> LENGTH: 120
<212> TYPE: PRT
<213> ORGANISM: Artificial Sequence
<220> FEATURE:
<223> OTHER INFORMATION: Synthetic Sequence FMC63 VH

<400> SEQUENCE: 21

```
Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120
```

<210> SEQ ID NO 22
<211> LENGTH: 10
<212> TYPE: PRT
<213> ORGANISM: Artificial Sequence
<220> FEATURE:
<223> OTHER INFORMATION: Linker peptide sequence

<400> SEQUENCE: 22

```
Gly Ser Gly Ser Gly Ser Gly Ser Gly Ser
1               5                   10
```

<210> SEQ ID NO 23
<211> LENGTH: 8
<212> TYPE: PRT
<213> ORGANISM: Artificial Sequence
<220> FEATURE:
<223> OTHER INFORMATION: Linker peptide sequence

<400> SEQUENCE: 23

```
Gly Ser Gly Ser Gly Ser Gly Ser
1               5
```

<210> SEQ ID NO 24
<211> LENGTH: 8
<212> TYPE: PRT
<213> ORGANISM: Artificial Sequence
<220> FEATURE:

-continued

<223> OTHER INFORMATION: Linker peptide sequence

<400> SEQUENCE: 24

Arg Ser Gly Ser Gly Ser Gly Ser
1               5

<210> SEQ ID NO 25
<211> LENGTH: 30
<212> TYPE: DNA
<213> ORGANISM: Artificial Sequence
<220> FEATURE:
<223> OTHER INFORMATION: Linker peptide sequence

<400> SEQUENCE: 25
ggatccggca gcggatctgg cagtggaagc                                            30

<210> SEQ ID NO 26
<211> LENGTH: 24
<212> TYPE: DNA
<213> ORGANISM: Artificial Sequence
<220> FEATURE:
<223> OTHER INFORMATION: Linker peptide sequence

<400> SEQUENCE: 26
ggatctggct ctggaagcgg cagc                                                  24

<210> SEQ ID NO 27
<211> LENGTH: 24
<212> TYPE: DNA
<213> ORGANISM: Artificial Sequence
<220> FEATURE:
<223> OTHER INFORMATION: Linker peptide sequence

<400> SEQUENCE: 27
agatccggat ctggaagtgg ctcc                                                  24

<210> SEQ ID NO 28
<211> LENGTH: 24
<212> TYPE: DNA
<213> ORGANISM: Artificial Sequence
<220> FEATURE:
<223> OTHER INFORMATION: Linker peptide sequence

<400> SEQUENCE: 28
ggaagtggat ctgggagcgg ctct                                                  24

<210> SEQ ID NO 29
<211> LENGTH: 24
<212> TYPE: DNA
<213> ORGANISM: Artificial Sequence
<220> FEATURE:
<223> OTHER INFORMATION: Linker peptide sequence

<400> SEQUENCE: 29
ggatcaggca gtggctctgg cagc                                                  24

<210> SEQ ID NO 30
<211> LENGTH: 18
<212> TYPE: DNA
<213> ORGANISM: Artificial Sequence
<220> FEATURE:
<223> OTHER INFORMATION: Linker peptide sequence

<400> SEQUENCE: 30
ggatctggaa gtggctcc                                                         18

```
<210> SEQ ID NO 31
<211> LENGTH: 15
<212> TYPE: PRT
<213> ORGANISM: Artificial Sequence
<220> FEATURE:
<223> OTHER INFORMATION: Linker peptide sequence

<400> SEQUENCE: 31

Gly Gly Gly Gly Ser Gly Gly Gly Gly Ser Gly Gly Gly Gly Ser
1               5                   10                  15

<210> SEQ ID NO 32
<211> LENGTH: 509
<212> TYPE: PRT
<213> ORGANISM: Homo sapiens

<400> SEQUENCE: 32

Met Gly Cys Gly Cys Ser Ser His Pro Glu Asp Asp Trp Met Glu Asn
1               5                   10                  15

Ile Asp Val Cys Glu Asn Cys His Tyr Pro Ile Val Pro Leu Asp Gly
            20                  25                  30

Lys Gly Thr Leu Leu Ile Arg Asn Gly Ser Glu Val Arg Asp Pro Leu
        35                  40                  45

Val Thr Tyr Glu Gly Ser Asn Pro Pro Ala Ser Pro Leu Gln Asp Asn
    50                  55                  60

Leu Val Ile Ala Leu His Ser Tyr Glu Pro Ser His Asp Gly Asp Leu
65                  70                  75                  80

Gly Phe Glu Lys Gly Glu Gln Leu Arg Ile Leu Glu Gln Ser Gly Glu
                85                  90                  95

Trp Trp Lys Ala Gln Ser Leu Thr Thr Gly Gln Glu Gly Phe Ile Pro
                100                 105                 110

Phe Asn Phe Val Ala Lys Ala Asn Ser Leu Glu Pro Glu Pro Trp Phe
            115                 120                 125

Phe Lys Asn Leu Ser Arg Lys Asp Ala Glu Arg Gln Leu Leu Ala Pro
        130                 135                 140

Gly Asn Thr His Gly Ser Phe Leu Ile Arg Glu Ser Glu Ser Thr Ala
145                 150                 155                 160

Gly Ser Phe Ser Leu Ser Val Arg Asp Phe Asp Gln Asn Gln Gly Glu
                165                 170                 175

Val Val Lys His Tyr Lys Ile Arg Asn Leu Asp Asn Gly Gly Phe Tyr
            180                 185                 190

Ile Ser Pro Arg Ile Thr Phe Pro Gly Leu His Glu Leu Val Arg His
        195                 200                 205

Tyr Thr Asn Ala Ser Asp Gly Leu Cys Thr Arg Leu Ser Arg Pro Cys
    210                 215                 220

Gln Thr Gln Lys Pro Gln Lys Pro Trp Trp Glu Asp Glu Trp Glu Val
225                 230                 235                 240

Pro Arg Glu Thr Leu Lys Leu Val Glu Arg Leu Gly Ala Gly Gln Phe
                245                 250                 255

Gly Glu Val Trp Met Gly Tyr Tyr Asn Gly His Thr Lys Val Ala Val
                260                 265                 270

Lys Ser Leu Lys Gln Gly Ser Met Ser Pro Asp Ala Phe Leu Ala Glu
            275                 280                 285

Ala Asn Leu Met Lys Gln Leu Gln His Gln Arg Leu Val Arg Leu Tyr
    290                 295                 300

Ala Val Val Thr Gln Glu Pro Ile Tyr Ile Ile Thr Glu Tyr Met Glu
```

```
305                     310                     315                     320

Asn Gly Ser Leu Val Asp Phe Leu Lys Thr Pro Ser Gly Ile Lys Leu
                325                     330                     335

Thr Ile Asn Lys Leu Leu Asp Met Ala Ala Gln Ile Ala Glu Gly Met
                340                     345                     350

Ala Phe Ile Glu Glu Arg Asn Tyr Ile His Arg Asp Leu Arg Ala Ala
                355                     360                     365

Asn Ile Leu Val Ser Asp Thr Leu Ser Cys Lys Ile Ala Asp Phe Gly
                370                     375                     380

Leu Ala Arg Leu Ile Glu Asp Asn Glu Tyr Thr Ala Arg Glu Gly Ala
385                     390                     395                     400

Lys Phe Pro Ile Lys Trp Thr Ala Pro Glu Ala Ile Asn Tyr Gly Thr
                405                     410                     415

Phe Thr Ile Lys Ser Asp Val Trp Ser Phe Gly Ile Leu Leu Thr Glu
                420                     425                     430

Ile Val Thr His Gly Arg Ile Pro Tyr Pro Gly Met Thr Asn Pro Glu
                435                     440                     445

Val Ile Gln Asn Leu Glu Arg Gly Tyr Arg Met Val Arg Pro Asp Asn
                450                     455                     460

Cys Pro Glu Glu Leu Tyr Gln Leu Met Arg Leu Cys Trp Lys Glu Arg
465                     470                     475                     480

Pro Glu Asp Arg Pro Thr Phe Asp Tyr Leu Arg Ser Val Leu Glu Asp
                485                     490                     495

Phe Phe Thr Ala Thr Glu Gly Gln Tyr Gln Pro Gln Pro
                500                     505
```

```
<210> SEQ ID NO 33
<211> LENGTH: 509
<212> TYPE: PRT
<213> ORGANISM: Homo sapiens

<400> SEQUENCE: 33

Met Gly Cys Val Cys Ser Ser Asn Pro Glu Asp Asp Trp Met Glu Asn
1               5                   10                  15

Ile Asp Val Cys Glu Asn Cys His Tyr Pro Ile Val Pro Leu Asp Ser
                20                  25                  30

Lys Ile Ser Leu Pro Ile Arg Asn Gly Ser Glu Val Arg Asp Pro Leu
        35                  40                  45

Val Thr Tyr Glu Gly Ser Leu Pro Pro Ala Ser Pro Leu Gln Asp Asn
        50                  55                  60

Leu Val Ile Ala Leu His Ser Tyr Glu Pro Ser His Asp Gly Asp Leu
65                  70                  75                  80

Gly Phe Glu Lys Gly Glu Gln Leu Arg Ile Leu Glu Gln Ser Gly Glu
                85                  90                  95

Trp Trp Lys Ala Gln Ser Leu Thr Thr Gly Gln Glu Gly Phe Ile Pro
                100                 105                 110

Phe Asn Phe Val Ala Lys Ala Asn Ser Leu Glu Pro Glu Pro Trp Phe
                115                 120                 125

Phe Lys Asn Leu Ser Arg Lys Asp Ala Glu Arg Gln Leu Leu Ala Pro
        130                 135                 140

Gly Asn Thr His Gly Ser Phe Leu Ile Arg Glu Ser Glu Ser Thr Ala
145                 150                 155                 160

Gly Ser Phe Ser Leu Ser Val Arg Asp Phe Asp Gln Asn Gln Gly Glu
                165                 170                 175
```

-continued

```
Val Val Lys His Tyr Lys Ile Arg Asn Leu Asp Asn Gly Gly Phe Tyr
            180                 185                 190

Ile Ser Pro Arg Ile Thr Phe Pro Gly Leu His Asp Leu Val Arg His
            195                 200                 205

Tyr Thr Asn Ala Ser Asp Gly Leu Cys Thr Lys Leu Ser Arg Pro Cys
            210                 215                 220

Gln Thr Gln Lys Pro Gln Lys Pro Trp Trp Glu Asp Glu Trp Glu Val
225                 230                 235                 240

Pro Arg Glu Thr Leu Lys Leu Val Glu Arg Leu Gly Ala Gly Gln Phe
            245                 250                 255

Gly Glu Val Trp Met Gly Tyr Tyr Asn Gly His Thr Lys Val Ala Val
            260                 265                 270

Lys Ser Leu Lys Gln Gly Ser Met Ser Pro Asp Ala Phe Leu Ala Glu
            275                 280                 285

Ala Asn Leu Met Lys Gln Leu Gln His Pro Arg Leu Val Arg Leu Tyr
            290                 295                 300

Ala Val Val Thr Gln Glu Pro Ile Tyr Ile Ile Thr Glu Tyr Met Glu
305                 310                 315                 320

Asn Gly Ser Leu Val Asp Phe Leu Lys Thr Pro Ser Gly Ile Lys Leu
            325                 330                 335

Asn Val Asn Lys Leu Leu Asp Met Ala Ala Gln Ile Ala Glu Gly Met
            340                 345                 350

Ala Phe Ile Glu Glu Gln Asn Tyr Ile His Arg Asp Leu Arg Ala Ala
            355                 360                 365

Asn Ile Leu Val Ser Asp Thr Leu Ser Cys Lys Ile Ala Asp Phe Gly
            370                 375                 380

Leu Ala Arg Leu Ile Glu Asp Asn Glu Tyr Thr Ala Arg Glu Gly Ala
385                 390                 395                 400

Lys Phe Pro Ile Lys Trp Thr Ala Pro Glu Ala Ile Asn Tyr Gly Thr
            405                 410                 415

Phe Thr Ile Lys Ser Asp Val Trp Ser Phe Gly Ile Leu Leu Thr Glu
            420                 425                 430

Ile Val Thr His Gly Arg Ile Pro Tyr Pro Gly Met Thr Asn Pro Glu
            435                 440                 445

Val Ile Gln Asn Leu Glu Arg Gly Tyr Arg Met Val Arg Pro Asp Asn
            450                 455                 460

Cys Pro Glu Glu Leu Tyr His Leu Met Met Leu Cys Trp Lys Glu Arg
465                 470                 475                 480

Pro Glu Asp Arg Pro Thr Phe Asp Tyr Leu Arg Ser Val Leu Asp Asp
            485                 490                 495

Phe Phe Thr Ala Thr Glu Gly Gln Tyr Gln Pro Gln Pro
            500                 505
```

```
<210> SEQ ID NO 34
<211> LENGTH: 335
<212> TYPE: PRT
<213> ORGANISM: Homo sapiens

<400> SEQUENCE: 34
```

```
Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
            35                  40                  45
```

-continued

```
Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
            115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
            195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
            275                 280                 285

Glu Ala Tyr Asp Thr Leu Ile Lys Asp Leu Lys Lys Ala Asn Leu Cys
    290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335
```

```
<210> SEQ ID NO 35
<211> LENGTH: 327
<212> TYPE: PRT
<213> ORGANISM: Homo sapiens

<400> SEQUENCE: 35
```

```
Met Leu Trp Ile Trp Ala Val Leu Pro Leu Val Leu Ala Gly Ser Gln
1               5                   10                  15

Leu Arg Val His Thr Gln Gly Thr Asn Ser Ile Ser Glu Ser Leu Lys
            20                  25                  30

Leu Arg Arg Arg Val Arg Glu Thr Asp Lys Asn Cys Ser Glu Gly Leu
        35                  40                  45

Tyr Gln Gly Gly Pro Phe Cys Cys Gln Pro Cys Gln Pro Gly Lys Lys
    50                  55                  60

Lys Val Glu Asp Cys Lys Met Asn Gly Gly Thr Pro Thr Cys Ala Pro
65                  70                  75                  80

Cys Thr Glu Gly Lys Glu Tyr Met Asp Lys Asn His Tyr Ala Asp Lys
```

```
                85              90              95

Cys Arg Arg Cys Thr Leu Cys Asp Glu Glu His Gly Leu Glu Val Glu
            100             105             110

Thr Asn Cys Thr Leu Thr Gln Asn Thr Lys Cys Lys Cys Lys Pro Asp
            115             120             125

Phe Tyr Cys Asp Ser Pro Gly Cys Glu His Cys Val Arg Cys Ala Ser
        130             135             140

Cys Glu His Gly Thr Leu Glu Pro Cys Thr Ala Thr Ser Asn Thr Asn
145             150             155             160

Cys Arg Lys Gln Ser Pro Arg Asn Arg Leu Trp Leu Leu Thr Ile Leu
                165             170             175

Val Leu Leu Ile Pro Leu Val Phe Ile Tyr Arg Lys Tyr Arg Lys Arg
            180             185             190

Lys Cys Trp Lys Arg Arg Gln Asp Asp Pro Glu Ser Arg Thr Ser Ser
            195             200             205

Arg Glu Thr Ile Pro Met Asn Ala Ser Asn Leu Ser Leu Ser Lys Tyr
        210             215             220

Ile Pro Arg Ile Ala Glu Asp Met Thr Ile Gln Glu Ala Lys Lys Phe
225             230             235             240

Ala Arg Glu Asn Asn Ile Lys Glu Gly Lys Ile Asp Glu Ile Met His
                245             250             255

Asp Ser Ile Gln Asp Thr Ala Glu Gln Lys Val Gln Leu Leu Leu Cys
            260             265             270

Trp Tyr Gln Ser His Gly Lys Ser Asp Ala Tyr Gln Asp Leu Ile Lys
            275             280             285

Gly Leu Lys Lys Ala Glu Cys Arg Arg Thr Leu Asp Lys Phe Gln Asp
        290             295             300

Met Val Gln Lys Asp Leu Gly Lys Ser Thr Pro Asp Thr Gly Asn Glu
305             310             315             320

Asn Glu Gly Gln Cys Leu Glu
                325
```

```
<210> SEQ ID NO 36
<211> LENGTH: 455
<212> TYPE: PRT
<213> ORGANISM: Homo sapiens

<400> SEQUENCE: 36

Met Gly Leu Ser Thr Val Pro Asp Leu Leu Leu Pro Leu Val Leu Leu
1               5               10              15

Glu Leu Leu Val Gly Ile Tyr Pro Ser Gly Val Ile Gly Leu Val Pro
            20              25              30

His Leu Gly Asp Arg Glu Lys Arg Asp Ser Val Cys Pro Gln Gly Lys
        35              40              45

Tyr Ile His Pro Gln Asn Asn Ser Ile Cys Cys Thr Lys Cys His Lys
        50              55              60

Gly Thr Tyr Leu Tyr Asn Asp Cys Pro Gly Pro Gly Gln Asp Thr Asp
65              70              75              80

Cys Arg Glu Cys Glu Ser Gly Ser Phe Thr Ala Ser Glu Asn His Leu
            85              90              95

Arg His Cys Leu Ser Cys Ser Lys Cys Arg Lys Glu Met Gly Gln Val
            100             105             110

Glu Ile Ser Ser Cys Thr Val Asp Arg Asp Thr Val Cys Gly Cys Arg
            115             120             125
```

```
Lys Asn Gln Tyr Arg His Tyr Trp Ser Glu Asn Leu Phe Gln Cys Phe
    130             135                 140

Asn Cys Ser Leu Cys Leu Asn Gly Thr Val His Leu Ser Cys Gln Glu
145             150                 155                 160

Lys Gln Asn Thr Val Cys Thr Cys His Ala Gly Phe Phe Leu Arg Glu
            165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
            195                 200                 205

Gly Thr Thr Val Leu Leu Pro Leu Val Ile Phe Phe Gly Leu Cys Leu
    210             215                 220

Leu Ser Leu Leu Phe Ile Gly Leu Met Tyr Arg Tyr Gln Arg Trp Lys
225             230                 235                 240

Ser Lys Leu Tyr Ser Ile Val Cys Gly Lys Ser Thr Pro Glu Lys Glu
            245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
            275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
            325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
            355                 360                 365

Leu Arg Trp Lys Glu Phe Val Arg Arg Leu Gly Leu Ser Asp His Glu
    370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
            405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
            435                 440                 445

Pro Ala Pro Ser Leu Leu Arg
    450                 455

<210> SEQ ID NO 37
<211> LENGTH: 454
<212> TYPE: PRT
<213> ORGANISM: Homo sapiens

<400> SEQUENCE: 37

Met Gly Leu Pro Thr Val Pro Gly Leu Leu Leu Ser Leu Val Leu Leu
1               5                   10                  15

Ala Leu Leu Met Gly Ile His Pro Ser Gly Val Thr Gly Leu Val Pro
            20                  25                  30

Ser Leu Gly Asp Arg Glu Lys Arg Asp Ser Leu Cys Pro Gln Gly Lys
            35                  40                  45
```

-continued

```
Tyr Val His Ser Lys Asn Asn Ser Ile Cys Cys Thr Lys Cys His Lys
    50                  55                  60

Gly Thr Tyr Leu Val Ser Asp Cys Pro Ser Pro Gly Arg Asp Thr Val
65                  70                  75                  80

Cys Arg Glu Cys Glu Lys Gly Thr Phe Thr Ala Ser Gln Asn Tyr Leu
                85                  90                  95

Arg Gln Cys Leu Ser Cys Lys Thr Cys Arg Lys Glu Met Ser Gln Val
            100                 105                 110

Glu Ile Ser Pro Cys Gln Ala Asp Lys Asp Thr Val Cys Gly Cys Lys
            115                 120                 125

Glu Asn Gln Phe Gln Arg Tyr Leu Ser Glu Thr His Phe Gln Cys Val
    130                 135                 140

Asp Cys Ser Pro Cys Phe Asn Gly Thr Val Thr Ile Pro Cys Lys Glu
145                 150                 155                 160

Thr Gln Asn Thr Val Cys Asn Cys His Ala Gly Phe Phe Leu Arg Glu
                165                 170                 175

Ser Glu Cys Val Pro Cys Ser His Cys Lys Lys Asn Glu Glu Cys Met
            180                 185                 190

Lys Leu Cys Leu Pro Pro Pro Leu Ala Asn Val Thr Asn Pro Gln Asp
            195                 200                 205

Ser Gly Thr Ala Val Leu Leu Pro Leu Val Ile Leu Leu Gly Leu Cys
    210                 215                 220

Leu Leu Ser Phe Ile Phe Ile Ser Leu Met Cys Arg Tyr Pro Arg Trp
225                 230                 235                 240

Arg Pro Glu Val Tyr Ser Ile Ile Cys Arg Asp Pro Val Pro Val Lys
                245                 250                 255

Glu Glu Lys Ala Gly Lys Pro Leu Thr Pro Ala Pro Ser Pro Ala Phe
            260                 265                 270

Ser Pro Thr Ser Gly Phe Asn Pro Thr Leu Gly Phe Ser Thr Pro Gly
            275                 280                 285

Phe Ser Ser Pro Val Ser Ser Thr Pro Ile Ser Pro Ile Phe Gly Pro
    290                 295                 300

Ser Asn Trp His Phe Met Pro Pro Val Ser Glu Val Val Pro Thr Gln
305                 310                 315                 320

Gly Ala Asp Pro Leu Leu Tyr Glu Ser Leu Cys Ser Val Pro Ala Pro
            325                 330                 335

Thr Ser Val Gln Lys Trp Glu Asp Ser Ala His Pro Gln Arg Pro Asp
            340                 345                 350

Asn Ala Asp Leu Ala Ile Leu Tyr Ala Val Val Asp Gly Val Pro Pro
    355                 360                 365

Ala Arg Trp Lys Glu Phe Met Arg Phe Met Gly Leu Ser Glu His Glu
    370                 375                 380

Ile Glu Arg Leu Glu Met Gln Asn Gly Arg Cys Leu Arg Glu Ala Gln
385                 390                 395                 400

Tyr Ser Met Leu Glu Ala Trp Arg Arg Arg Thr Pro Arg His Glu Asp
                405                 410                 415

Thr Leu Glu Val Val Gly Leu Val Leu Ser Lys Met Asn Leu Ala Gly
            420                 425                 430

Cys Leu Glu Asn Ile Leu Glu Ala Leu Arg Asn Pro Ala Pro Ser Ser
            435                 440                 445

Thr Thr Arg Leu Pro Arg
    450
```

```
<210> SEQ ID NO 38
<211> LENGTH: 461
<212> TYPE: PRT
<213> ORGANISM: Homo sapiens

<400> SEQUENCE: 38

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
            115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
            195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Phe Ala Leu Pro Val Gly Leu Ile Val Gly Val Thr Ala Leu Gly
            260                 265                 270

Leu Leu Ile Ile Gly Val Val Asn Cys Val Ile Met Thr Gln Val Lys
            275                 280                 285

Lys Lys Pro Leu Cys Leu Gln Arg Glu Ala Lys Val Pro His Leu Pro
    290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Ser Leu Glu Ser Ser Ala Ser
            325                 330                 335

Ala Leu Asp Arg Arg Ala Pro Thr Arg Asn Gln Pro Gln Ala Pro Gly
            340                 345                 350

Val Glu Ala Ser Gly Ala Gly Glu Ala Arg Ala Ser Thr Gly Ser Ser
            355                 360                 365

Asp Ser Ser Pro Gly Gly His Gly Thr Gln Val Asn Val Thr Cys Ile
    370                 375                 380
```

-continued

```
Val Asn Val Cys Ser Ser Ser Asp His Ser Ser Gln Cys Ser Ser Gln
385             390             395             400

Ala Ser Ser Thr Met Gly Asp Thr Asp Ser Ser Pro Ser Glu Ser Pro
                405             410             415

Lys Asp Glu Gln Val Pro Phe Ser Lys Glu Glu Cys Ala Phe Arg Ser
            420             425             430

Gln Leu Glu Thr Pro Glu Thr Leu Leu Gly Ser Thr Glu Glu Lys Pro
        435             440             445

Leu Pro Leu Gly Val Pro Asp Ala Gly Met Lys Pro Ser
    450             455             460

<210> SEQ ID NO 39
<211> LENGTH: 474
<212> TYPE: PRT
<213> ORGANISM: Mus musculus

<400> SEQUENCE: 39

Met Ala Pro Ala Ala Leu Trp Val Ala Leu Val Phe Glu Leu Gln Leu
1               5               10              15

Trp Ala Thr Gly His Thr Val Pro Ala Gln Val Val Leu Thr Pro Tyr
            20              25              30

Lys Pro Glu Pro Gly Tyr Glu Cys Gln Ile Ser Gln Glu Tyr Tyr Asp
        35              40              45

Arg Lys Ala Gln Met Cys Cys Ala Lys Cys Pro Pro Gly Gln Tyr Val
    50              55              60

Lys His Phe Cys Asn Lys Thr Ser Asp Thr Val Cys Ala Asp Cys Glu
65              70              75              80

Ala Ser Met Tyr Thr Gln Val Trp Asn Gln Phe Arg Thr Cys Leu Ser
            85              90              95

Cys Ser Ser Ser Cys Thr Thr Asp Gln Val Glu Ile Arg Ala Cys Thr
            100             105             110

Lys Gln Gln Asn Arg Val Cys Ala Cys Glu Ala Gly Arg Tyr Cys Ala
        115             120             125

Leu Lys Thr His Ser Gly Ser Cys Arg Gln Cys Met Arg Leu Ser Lys
    130             135             140

Cys Gly Pro Gly Phe Gly Val Ala Ser Ser Arg Ala Pro Asn Gly Asn
145             150             155             160

Val Leu Cys Lys Ala Cys Ala Pro Gly Thr Phe Ser Asp Thr Thr Ser
            165             170             175

Ser Thr Asp Val Cys Arg Pro His Arg Ile Cys Ser Ile Leu Ala Ile
            180             185             190

Pro Gly Asn Ala Ser Thr Asp Ala Val Cys Ala Pro Glu Ser Pro Thr
        195             200             205

Leu Ser Ala Ile Pro Arg Thr Leu Tyr Val Ser Gln Pro Glu Pro Thr
    210             215             220

Arg Ser Gln Pro Leu Asp Gln Glu Pro Gly Pro Ser Gln Thr Pro Ser
225             230             235             240

Ile Leu Thr Ser Leu Gly Ser Thr Pro Ile Ile Glu Gln Ser Thr Lys
            245             250             255

Gly Gly Ile Ser Leu Pro Ile Gly Leu Ile Val Gly Val Thr Ser Leu
            260             265             270

Gly Leu Leu Met Leu Gly Leu Val Asn Cys Ile Ile Leu Val Gln Arg
    275             280             285

Lys Lys Lys Pro Ser Cys Leu Gln Arg Asp Ala Lys Val Pro His Val
```

-continued

```
       290               295               300

Pro Asp Glu Lys Ser Gln Asp Ala Val Gly Leu Glu Gln Gln His Leu
305               310               315               320

Leu Thr Thr Ala Pro Ser Ser Ser Ser Ser Ser Leu Glu Ser Ser Ala
              325               330               335

Ser Ala Gly Asp Arg Arg Ala Pro Pro Gly Gly His Pro Gln Ala Arg
              340               345               350

Val Met Ala Glu Ala Gln Gly Phe Gln Glu Ala Arg Ala Ser Ser Arg
              355               360               365

Ile Ser Asp Ser Ser His Gly Ser His Gly Thr His Val Asn Val Thr
              370               375               380

Cys Ile Val Asn Val Cys Ser Ser Ser Asp His Ser Ser Gln Cys Ser
385               390               395               400

Ser Gln Ala Ser Ala Thr Val Gly Asp Pro Asp Ala Lys Pro Ser Ala
              405               410               415

Ser Pro Lys Asp Glu Gln Val Pro Phe Ser Gln Glu Glu Cys Pro Ser
              420               425               430

Gln Ser Pro Cys Glu Thr Thr Glu Thr Leu Gln Ser His Glu Lys Pro
              435               440               445

Leu Pro Leu Gly Val Pro Asp Met Gly Met Lys Pro Ser Gln Ala Gly
       450               455               460

Trp Phe Asp Gln Ile Ala Val Lys Val Ala
465               470
```

```
<210> SEQ ID NO 40
<211> LENGTH: 240
<212> TYPE: PRT
<213> ORGANISM: Homo sapiens

<400> SEQUENCE: 40

Met Glu Glu Ser Val Val Arg Pro Ser Val Phe Val Val Asp Gly Gln
1               5               10               15

Thr Asp Ile Pro Phe Thr Arg Leu Gly Arg Ser His Arg Arg Gln Ser
              20               25               30

Cys Ser Val Ala Arg Val Gly Leu Gly Leu Leu Leu Leu Leu Met Gly
              35               40               45

Ala Gly Leu Ala Val Gln Gly Trp Phe Leu Leu Gln Leu His Trp Arg
       50               55               60

Leu Gly Glu Met Val Thr Arg Leu Pro Asp Gly Pro Ala Gly Ser Trp
65               70               75               80

Glu Gln Leu Ile Gln Glu Arg Arg Ser His Glu Val Asn Pro Ala Ala
              85               90               95

His Leu Thr Gly Ala Asn Ser Ser Leu Thr Gly Ser Gly Gly Pro Leu
              100               105               110

Leu Trp Glu Thr Gln Leu Gly Leu Ala Phe Leu Arg Gly Leu Ser Tyr
              115               120               125

His Asp Gly Ala Leu Val Val Thr Lys Ala Gly Tyr Tyr Tyr Ile Tyr
              130               135               140

Ser Lys Val Gln Leu Gly Gly Val Gly Cys Pro Leu Gly Leu Ala Ser
145               150               155               160

Thr Ile Thr His Gly Leu Tyr Lys Arg Thr Pro Arg Tyr Pro Glu Glu
              165               170               175

Leu Glu Leu Leu Val Ser Gln Gln Ser Pro Cys Gly Arg Ala Thr Ser
              180               185               190
```

Ser Ser Arg Val Trp Trp Asp Ser Ser Phe Leu Gly Gly Val Val His
    195                 200                 205

Leu Glu Ala Gly Glu Lys Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240

<210> SEQ ID NO 41
<211> LENGTH: 239
<212> TYPE: PRT
<213> ORGANISM: Mus musculus

<400> SEQUENCE: 41

Met Glu Ser Val Val Gln Pro Ser Val Phe Val Val Asp Gly Gln Thr
1               5                   10                  15

Asp Ile Pro Phe Arg Arg Leu Glu Gln Asn His Arg Arg Arg Arg Cys
            20                  25                  30

Gly Thr Val Gln Val Ser Leu Ala Leu Val Leu Leu Leu Gly Ala Gly
            35                  40                  45

Leu Ala Thr Gln Gly Trp Phe Leu Leu Arg Leu His Gln Arg Leu Gly
    50                  55                  60

Asp Ile Val Ala His Leu Pro Asp Gly Gly Lys Gly Ser Trp Glu Lys
65                  70                  75                  80

Leu Ile Gln Asp Gln Arg Ser His Gln Ala Asn Pro Ala Ala His Leu
                85                  90                  95

Thr Gly Ala Asn Ala Ser Leu Ile Gly Ile Gly Gly Pro Leu Leu Trp
                100                 105                 110

Glu Thr Arg Leu Gly Leu Ala Phe Leu Arg Gly Leu Thr Tyr His Asp
            115                 120                 125

Gly Ala Leu Val Thr Met Glu Pro Gly Tyr Tyr Tyr Val Tyr Ser Lys
    130                 135                 140

Val Gln Leu Ser Gly Val Gly Cys Pro Gln Gly Leu Ala Asn Gly Leu
145                 150                 155                 160

Pro Ile Thr His Gly Leu Tyr Lys Arg Thr Ser Arg Tyr Pro Lys Glu
                165                 170                 175

Leu Glu Leu Leu Val Ser Arg Arg Ser Pro Cys Gly Arg Ala Asn Ser
            180                 185                 190

Ser Arg Val Trp Trp Asp Ser Ser Phe Leu Gly Gly Val Val His Leu
    195                 200                 205

Glu Ala Gly Glu Glu Val Val Val Arg Val Pro Gly Asn Arg Leu Val
    210                 215                 220

Arg Pro Arg Asp Gly Thr Arg Ser Tyr Phe Gly Ala Phe Met Val
225                 230                 235

<210> SEQ ID NO 42
<211> LENGTH: 199
<212> TYPE: PRT
<213> ORGANISM: Homo sapiens

<400> SEQUENCE: 42

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
            35                  40                  45

-continued

```
Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
                100                 105                 110

Ile Phe Asp Pro Pro Pro Phe Lys Val Thr Leu Thr Gly Gly Tyr Leu
                115                 120                 125

His Ile Tyr Glu Ser Gln Leu Cys Cys Gln Leu Lys Phe Trp Leu Pro
        130                 135                 140

Ile Gly Cys Ala Ala Phe Val Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
                180                 185                 190

Arg Leu Thr Asp Val Thr Leu
        195
```

```
<210> SEQ ID NO 43
<211> LENGTH: 200
<212> TYPE: PRT
<213> ORGANISM: Mus musculus

<400> SEQUENCE: 43
```

```
Met Lys Pro Tyr Phe Cys Arg Val Phe Val Phe Cys Phe Leu Ile Arg
1               5                   10                  15

Leu Leu Thr Gly Glu Ile Asn Gly Ser Ala Asp His Arg Met Phe Ser
                20                  25                  30

Phe His Asn Gly Gly Val Gln Ile Ser Cys Lys Tyr Pro Glu Thr Val
            35                  40                  45

Gln Gln Leu Lys Met Arg Leu Phe Arg Glu Arg Glu Val Leu Cys Glu
    50                  55                  60

Leu Thr Lys Thr Lys Gly Ser Gly Asn Ala Val Ser Ile Lys Asn Pro
65                  70                  75                  80

Met Leu Cys Leu Tyr His Leu Ser Asn Asn Ser Val Ser Phe Phe Leu
                85                  90                  95

Asn Asn Pro Asp Ser Ser Gln Gly Ser Tyr Tyr Phe Cys Ser Leu Ser
                100                 105                 110

Ile Phe Asp Pro Pro Pro Phe Gln Glu Arg Asn Leu Ser Gly Gly Tyr
                115                 120                 125

Leu His Ile Tyr Glu Ser Gln Leu Cys Cys Gln Leu Lys Leu Trp Leu
        130                 135                 140

Pro Val Gly Cys Ala Ala Phe Val Val Val Leu Leu Phe Gly Cys Ile
145                 150                 155                 160

Leu Ile Ile Trp Phe Ser Lys Lys Lys Tyr Gly Ser Ser Val His Asp
                165                 170                 175

Pro Asn Ser Glu Tyr Met Phe Met Ala Ala Val Asn Thr Asn Lys Lys
                180                 185                 190

Ser Arg Leu Ala Gly Val Thr Ser
        195                 200
```

```
<210> SEQ ID NO 44
```

```
<211> LENGTH: 255
<212> TYPE: PRT
<213> ORGANISM: Homo sapiens

<400> SEQUENCE: 44

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
        130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
        210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 45
<211> LENGTH: 42
<212> TYPE: PRT
<213> ORGANISM: Homo sapiens

<400> SEQUENCE: 45

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 46
<211> LENGTH: 126
<212> TYPE: DNA
<213> ORGANISM: Homo sapiens

<400> SEQUENCE: 46
```

```
aaaaggggcc ggaaaaagct gctgtatatt ttcaaacagc cttttatgag gcctgtgcag        60
acaacacagg aagaggacgg ctgtagctgt cggttccccg aagaggaaga ggggggctgc       120
gaactg                                                                  126
```

<210> SEQ ID NO 47
<211> LENGTH: 41
<212> TYPE: PRT
<213> ORGANISM: Homo sapiens

<400> SEQUENCE: 47

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu
        35                  40
```

<210> SEQ ID NO 48
<211> LENGTH: 123
<212> TYPE: DNA
<213> ORGANISM: Homo sapiens

<400> SEQUENCE: 48

```
aaacggggca aaagaaaact cctgtatata ttcaaacaac catttatgag accagtacaa        60
actactcaag aggaagatgg ctgtagctgc cgatttccag aagaagaaga aggaggatgt       120
gaa                                                                     123
```

<210> SEQ ID NO 49
<211> LENGTH: 256
<212> TYPE: PRT
<213> ORGANISM: Mus musculus

<400> SEQUENCE: 49

```
Met Gly Asn Asn Cys Tyr Asn Val Val Val Ile Val Leu Leu Leu Val
1               5                   10                  15

Gly Cys Glu Lys Val Gly Ala Val Gln Asn Ser Cys Asp Asn Cys Gln
            20                  25                  30

Pro Gly Thr Phe Cys Arg Lys Tyr Asn Pro Val Cys Lys Ser Cys Pro
        35                  40                  45

Pro Ser Thr Phe Ser Ser Ile Gly Gly Gln Pro Asn Cys Asn Ile Cys
    50                  55                  60

Arg Val Cys Ala Gly Tyr Phe Arg Phe Lys Lys Phe Cys Ser Ser Thr
65                  70                  75                  80

His Asn Ala Glu Cys Glu Cys Ile Glu Gly Phe His Cys Leu Gly Pro
                85                  90                  95

Gln Cys Thr Arg Cys Glu Lys Asp Cys Arg Pro Gly Gln Glu Leu Thr
            100                 105                 110

Lys Gln Gly Cys Lys Thr Cys Ser Leu Gly Thr Phe Asn Asp Gln Asn
        115                 120                 125

Gly Thr Gly Val Cys Arg Pro Trp Thr Asn Cys Ser Leu Asp Gly Arg
    130                 135                 140

Ser Val Leu Lys Thr Gly Thr Thr Glu Lys Asp Val Val Cys Gly Pro
145                 150                 155                 160

Pro Val Val Ser Phe Ser Pro Ser Thr Thr Ile Ser Val Thr Pro Glu
                165                 170                 175

Gly Gly Pro Gly Gly His Ser Leu Gln Val Leu Thr Leu Phe Leu Ala
```

```
            180             185             190

Leu Thr Ser Ala Leu Leu Leu Ala Leu Ile Phe Ile Thr Leu Leu Phe
        195             200             205

Ser Val Leu Lys Trp Ile Arg Lys Lys Phe Pro His Ile Phe Lys Gln
        210             215             220

Pro Phe Lys Lys Thr Thr Gly Ala Ala Gln Glu Glu Asp Ala Cys Ser
225             230             235             240

Cys Arg Cys Pro Gln Glu Glu Glu Gly Gly Gly Gly Gly Tyr Glu Leu
                245             250             255
```

<210> SEQ ID NO 50
<211> LENGTH: 260
<212> TYPE: PRT
<213> ORGANISM: Homo sapiens

<400> SEQUENCE: 50

```
Met Ala Arg Pro His Pro Trp Trp Leu Cys Val Leu Gly Thr Leu Val
1               5               10              15

Gly Leu Ser Ala Thr Pro Ala Pro Lys Ser Cys Pro Glu Arg His Tyr
                20              25              30

Trp Ala Gln Gly Lys Leu Cys Cys Gln Met Cys Glu Pro Gly Thr Phe
        35              40              45

Leu Val Lys Asp Cys Asp Gln His Arg Lys Ala Ala Gln Cys Asp Pro
        50              55              60

Cys Ile Pro Gly Val Ser Phe Ser Pro Asp His His Thr Arg Pro His
65              70              75              80

Cys Glu Ser Cys Arg His Cys Asn Ser Gly Leu Leu Val Arg Asn Cys
                85              90              95

Thr Ile Thr Ala Asn Ala Glu Cys Ala Cys Arg Asn Gly Trp Gln Cys
                100             105             110

Arg Asp Lys Glu Cys Thr Glu Cys Asp Pro Leu Pro Asn Pro Ser Leu
        115             120             125

Thr Ala Arg Ser Ser Gln Ala Leu Ser Pro His Pro Gln Pro Thr His
        130             135             140

Leu Pro Tyr Val Ser Glu Met Leu Glu Ala Arg Thr Ala Gly His Met
145             150             155             160

Gln Thr Leu Ala Asp Phe Arg Gln Leu Pro Ala Arg Thr Leu Ser Thr
                165             170             175

His Trp Pro Pro Gln Arg Ser Leu Cys Ser Ser Asp Phe Ile Arg Ile
                180             185             190

Leu Val Ile Phe Ser Gly Met Phe Leu Val Phe Thr Leu Ala Gly Ala
        195             200             205

Leu Phe Leu His Gln Arg Arg Lys Tyr Arg Ser Asn Lys Gly Glu Ser
        210             215             220

Pro Val Glu Pro Ala Glu Pro Cys His Tyr Ser Cys Pro Arg Glu Glu
225             230             235             240

Glu Gly Ser Thr Ile Pro Ile Gln Glu Asp Tyr Arg Lys Pro Glu Pro
                245             250             255

Ala Cys Ser Pro
                260
```

<210> SEQ ID NO 51
<211> LENGTH: 48
<212> TYPE: PRT
<213> ORGANISM: Homo sapiens -continued

<400> SEQUENCE: 51

```
Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45
```

<210> SEQ ID NO 52
<211> LENGTH: 250
<212> TYPE: PRT
<213> ORGANISM: Mus musculus

<400> SEQUENCE: 52

```
Met Ala Trp Pro Pro Pro Tyr Trp Leu Cys Met Leu Gly Thr Leu Val
1               5                   10                  15

Gly Leu Ser Ala Thr Leu Ala Pro Asn Ser Cys Pro Asp Lys His Tyr
            20                  25                  30

Trp Thr Gly Gly Gly Leu Cys Cys Arg Met Cys Glu Pro Gly Thr Phe
        35                  40                  45

Phe Val Lys Asp Cys Glu Gln Asp Arg Thr Ala Ala Gln Cys Asp Pro
    50                  55                  60

Cys Ile Pro Gly Thr Ser Phe Ser Pro Asp Tyr His Thr Arg Pro His
65                  70                  75                  80

Cys Glu Ser Cys Arg His Cys Asn Ser Gly Phe Leu Ile Arg Asn Cys
                85                  90                  95

Thr Val Thr Ala Asn Ala Glu Cys Ser Cys Ser Lys Asn Trp Gln Cys
                100                 105                 110

Arg Asp Gln Glu Cys Thr Glu Cys Asp Pro Pro Leu Asn Pro Ala Leu
            115                 120                 125

Thr Arg Gln Pro Ser Glu Thr Pro Ser Pro Gln Pro Pro Pro Thr His
    130                 135                 140

Leu Pro His Gly Thr Glu Lys Pro Ser Trp Pro Leu His Arg Gln Leu
145                 150                 155                 160

Pro Asn Ser Thr Val Tyr Ser Gln Arg Ser Ser His Arg Pro Leu Cys
                165                 170                 175

Ser Ser Asp Cys Ile Arg Ile Phe Val Thr Phe Ser Ser Met Phe Leu
                180                 185                 190

Ile Phe Val Leu Gly Ala Ile Leu Phe Phe His Gln Arg Arg Asn His
                195                 200                 205

Gly Pro Asn Glu Asp Arg Gln Ala Val Pro Glu Glu Pro Cys Pro Tyr
            210                 215                 220

Ser Cys Pro Arg Glu Glu Glu Gly Ser Ala Ile Pro Ile Gln Glu Asp
225                 230                 235                 240

Tyr Arg Lys Pro Glu Pro Ala Phe Tyr Pro
                245                 250
```

<210> SEQ ID NO 53
<211> LENGTH: 277
<212> TYPE: PRT
<213> ORGANISM: Homo sapiens

<400> SEQUENCE: 53

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
```

-continued

```
                20              25              30

Gly Asp Thr Tyr Pro Ser Asn Asp Arg Cys Cys His Glu Cys Arg Pro
        35              40              45

Gly Asn Gly Met Val Ser Arg Cys Ser Arg Ser Gln Asn Thr Val Cys
    50              55              60

Arg Pro Cys Gly Pro Gly Phe Tyr Asn Asp Val Val Ser Ser Lys Pro
65              70              75              80

Cys Lys Pro Cys Thr Trp Cys Asn Leu Arg Ser Gly Ser Glu Arg Lys
                85              90              95

Gln Leu Cys Thr Ala Thr Gln Asp Thr Val Cys Arg Cys Arg Ala Gly
            100             105             110

Thr Gln Pro Leu Asp Ser Tyr Lys Pro Gly Val Asp Cys Ala Pro Cys
        115             120             125

Pro Pro Gly His Phe Ser Pro Gly Asp Asn Gln Ala Cys Lys Pro Trp
        130             135             140

Thr Asn Cys Thr Leu Ala Gly Lys His Thr Leu Gln Pro Ala Ser Asn
145             150             155             160

Ser Ser Asp Ala Ile Cys Glu Asp Arg Asp Pro Pro Ala Thr Gln Pro
            165             170             175

Gln Glu Thr Gln Gly Pro Pro Ala Arg Pro Ile Thr Val Gln Pro Thr
            180             185             190

Glu Ala Trp Pro Arg Thr Ser Gln Gly Pro Ser Thr Arg Pro Val Glu
            195             200             205

Val Pro Gly Gly Arg Ala Val Ala Ala Ile Leu Gly Leu Gly Leu Val
    210             215             220

Leu Gly Leu Leu Gly Pro Leu Ala Ile Leu Leu Ala Leu Tyr Leu Leu
225             230             235             240

Arg Arg Asp Gln Arg Leu Pro Pro Asp Ala His Lys Pro Pro Gly Gly
            245             250             255

Gly Ser Phe Arg Thr Pro Ile Gln Glu Glu Gln Ala Asp Ala His Ser
            260             265             270

Thr Leu Ala Lys Ile
        275
```

```
<210> SEQ ID NO 54
<211> LENGTH: 42
<212> TYPE: PRT
<213> ORGANISM: Homo sapiens

<400> SEQUENCE: 54

Ala Leu Tyr Leu Leu Arg Arg Asp Gln Arg Leu Pro Pro Asp Ala His
1               5               10              15

Lys Pro Pro Gly Gly Gly Ser Phe Arg Thr Pro Ile Gln Glu Glu Gln
            20              25              30

Ala Asp Ala His Ser Thr Leu Ala Lys Ile
        35              40
```

```
<210> SEQ ID NO 55
<211> LENGTH: 272
<212> TYPE: PRT
<213> ORGANISM: Mus musculus

<400> SEQUENCE: 55

Met Tyr Val Trp Val Gln Gln Pro Thr Ala Leu Leu Leu Leu Ala Leu
1               5               10              15

Thr Leu Gly Val Thr Ala Arg Arg Leu Asn Cys Val Lys His Thr Tyr
```

```
                   20                25                30
Pro Ser Gly His Lys Cys Cys Arg Glu Cys Gln Pro Gly His Gly Met
        35                40                45

Val Ser Arg Cys Asp His Thr Arg Asp Thr Leu Cys His Pro Cys Glu
    50                55                60

Thr Gly Phe Tyr Asn Glu Ala Val Asn Tyr Asp Thr Cys Lys Gln Cys
65                70                75                80

Thr Gln Cys Asn His Arg Ser Gly Ser Glu Leu Lys Gln Asn Cys Thr
            85                90                95

Pro Thr Gln Asp Thr Val Cys Arg Cys Arg Pro Gly Thr Gln Pro Arg
            100               105               110

Gln Asp Ser Gly Tyr Lys Leu Gly Val Asp Cys Val Pro Cys Pro Pro
        115               120               125

Gly His Phe Ser Pro Gly Asn Asn Gln Ala Cys Lys Pro Trp Thr Asn
        130               135               140

Cys Thr Leu Ser Gly Lys Gln Thr Arg His Pro Ala Ser Asp Ser Leu
145               150               155               160

Asp Ala Val Cys Glu Asp Arg Ser Leu Leu Ala Thr Leu Leu Trp Glu
            165               170               175

Thr Gln Arg Pro Thr Phe Arg Pro Thr Thr Val Gln Ser Thr Thr Val
            180               185               190

Trp Pro Arg Thr Ser Glu Leu Pro Ser Pro Pro Thr Leu Val Thr Pro
            195               200               205

Glu Gly Pro Ala Phe Ala Val Leu Leu Gly Leu Gly Leu Gly Leu Leu
        210               215               220

Ala Pro Leu Thr Val Leu Leu Ala Leu Tyr Leu Leu Arg Lys Ala Trp
225               230               235               240

Arg Leu Pro Asn Thr Pro Lys Pro Cys Trp Gly Asn Ser Phe Arg Thr
            245               250               255

Pro Ile Gln Glu Glu His Thr Asp Ala His Phe Thr Leu Ala Lys Ile
            260               265               270

<210> SEQ ID NO 56
<211> LENGTH: 351
<212> TYPE: PRT
<213> ORGANISM: Homo sapiens

<400> SEQUENCE: 56

Met Ser Phe Pro Cys Lys Phe Val Ala Ser Phe Leu Leu Ile Phe Asn
1               5                 10                15

Val Ser Ser Lys Gly Ala Val Ser Lys Glu Ile Thr Asn Ala Leu Glu
            20                25                30

Thr Trp Gly Ala Leu Gly Gln Asp Ile Asn Leu Asp Ile Pro Ser Phe
        35                40                45

Gln Met Ser Asp Asp Ile Asp Asp Ile Lys Trp Glu Lys Thr Ser Asp
        50                55                60

Lys Lys Lys Ile Ala Gln Phe Arg Lys Glu Lys Glu Thr Phe Lys Glu
65                70                75                80

Lys Asp Thr Tyr Lys Leu Phe Lys Asn Gly Thr Leu Lys Ile Lys His
            85                90                95

Leu Lys Thr Asp Asp Gln Asp Ile Tyr Lys Val Ser Ile Tyr Asp Thr
            100               105               110

Lys Gly Lys Asn Val Leu Glu Lys Ile Phe Asp Leu Lys Ile Gln Glu
        115               120               125
```

-continued

```
Arg Val Ser Lys Pro Lys Ile Ser Trp Thr Cys Ile Asn Thr Thr Leu
    130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
                165                 170                 175

Thr Thr Ser Leu Ser Ala Lys Phe Lys Cys Thr Ala Gly Asn Lys Val
                180                 185                 190

Ser Lys Glu Ser Ser Val Glu Pro Val Ser Cys Pro Glu Lys Gly Leu
                195                 200                 205

Asp Ile Tyr Leu Ile Ile Gly Ile Cys Gly Gly Gly Ser Leu Leu Met
    210                 215                 220

Val Phe Val Ala Leu Leu Val Phe Tyr Ile Thr Lys Arg Lys Lys Gln
225                 230                 235                 240

Arg Ser Arg Arg Asn Asp Glu Glu Leu Glu Thr Arg Ala His Arg Val
                245                 250                 255

Ala Thr Glu Glu Arg Gly Arg Lys Pro His Gln Ile Pro Ala Ser Thr
                260                 265                 270

Pro Gln Asn Pro Ala Thr Ser Gln His Pro Pro Pro Pro Gly His
                275                 280                 285

Arg Ser Gln Ala Pro Ser His Arg Pro Pro Pro Gly His Arg Val
    290                 295                 300

Gln His Gln Pro Gln Lys Arg Pro Pro Ala Pro Ser Gly Thr Gln Val
305                 310                 315                 320

His Gln Gln Lys Gly Pro Pro Leu Pro Arg Pro Arg Val Gln Pro Lys
                325                 330                 335

Pro Pro His Gly Ala Ala Glu Asn Ser Leu Ser Pro Ser Ser Asn
                340                 345                 350
```

```
<210> SEQ ID NO 57
<211> LENGTH: 344
<212> TYPE: PRT
<213> ORGANISM: Mus musculus

<400> SEQUENCE: 57

Met Lys Cys Lys Phe Leu Gly Ser Phe Phe Leu Leu Phe Ser Leu Ser
1               5                   10                  15

Gly Lys Gly Ala Asp Cys Arg Asp Asn Glu Thr Ile Trp Gly Val Leu
                20                  25                  30

Gly His Gly Ile Thr Leu Asn Ile Pro Asn Phe Gln Met Thr Asp Asp
        35                  40                  45

Ile Asp Glu Val Arg Trp Val Arg Arg Gly Thr Leu Val Ala Glu Phe
    50                  55                  60

Lys Arg Lys Lys Pro Pro Phe Leu Ile Ser Glu Thr Tyr Glu Val Leu
65                  70                  75                  80

Ala Asn Gly Ser Leu Lys Ile Lys Lys Pro Met Met Arg Asn Asp Ser
                85                  90                  95

Gly Thr Tyr Asn Val Met Val Tyr Gly Thr Asn Gly Met Thr Arg Leu
                100                 105                 110

Glu Lys Asp Leu Asp Val Arg Ile Leu Glu Arg Val Ser Lys Pro Met
        115                 120                 125

Ile His Trp Glu Cys Pro Asn Thr Thr Leu Thr Cys Ala Val Leu Gln
    130                 135                 140

Gly Thr Asp Phe Glu Leu Lys Leu Tyr Gln Gly Glu Thr Leu Leu Asn
145                 150                 155                 160
```

```
Ser Leu Pro Gln Lys Asn Met Ser Tyr Gln Trp Thr Asn Leu Asn Ala
            165                 170                 175

Pro Phe Lys Cys Glu Ala Ile Asn Pro Val Ser Lys Glu Ser Lys Met
            180                 185                 190

Glu Val Val Asn Cys Pro Glu Lys Gly Leu Ser Phe Tyr Val Thr Val
            195                 200                 205

Gly Val Gly Ala Gly Gly Leu Leu Leu Val Leu Leu Val Ala Leu Phe
        210                 215                 220

Ile Phe Cys Ile Cys Lys Arg Arg Lys Arg Asn Arg Arg Arg Lys Asp
225                 230                 235                 240

Glu Glu Leu Glu Ile Lys Ala Ser Arg Thr Ser Thr Val Glu Arg Gly
            245                 250                 255

Pro Lys Pro His Ser Thr Pro Ala Ala Ala Ala Gln Asn Ser Val Ala
            260                 265                 270

Leu Gln Ala Pro Pro Pro Gly His His Leu Gln Thr Pro Gly His
            275                 280                 285

Arg Pro Leu Pro Pro Gly His Arg Thr Arg Glu His Gln Gln Lys Lys
        290                 295                 300

Arg Pro Pro Pro Ser Gly Thr Gln Ile His Gln Gln Lys Gly Pro Pro
305                 310                 315                 320

Leu Pro Arg Pro Arg Val Gln Pro Lys Pro Pro Cys Gly Ser Gly Asp
            325                 330                 335

Gly Val Ser Leu Pro Pro Pro Asn
            340

<210> SEQ ID NO 58
<211> LENGTH: 495
<212> TYPE: PRT
<213> ORGANISM: Homo sapiens

<400> SEQUENCE: 58

Met Pro Met Gly Ser Leu Gln Pro Leu Ala Thr Leu Tyr Leu Leu Gly
1               5                   10                  15

Met Leu Val Ala Ser Cys Leu Gly Arg Leu Ser Trp Tyr Asp Pro Asp
            20                  25                  30

Phe Gln Ala Arg Leu Thr Arg Ser Asn Ser Lys Cys Gln Gly Gln Leu
            35                  40                  45

Glu Val Tyr Leu Lys Asp Gly Trp His Met Val Cys Ser Gln Ser Trp
        50                  55                  60

Gly Arg Ser Ser Lys Gln Trp Glu Asp Pro Ser Gln Ala Ser Lys Val
65                  70                  75                  80

Cys Gln Arg Leu Asn Cys Gly Val Pro Leu Ser Leu Gly Pro Phe Leu
            85                  90                  95

Val Thr Tyr Thr Pro Gln Ser Ser Ile Ile Cys Tyr Gly Gln Leu Gly
            100                 105                 110

Ser Phe Ser Asn Cys Ser His Ser Arg Asn Asp Met Cys His Ser Leu
            115                 120                 125

Gly Leu Thr Cys Leu Glu Pro Gln Lys Thr Thr Pro Pro Thr Thr Arg
        130                 135                 140

Pro Pro Pro Thr Thr Thr Pro Glu Pro Thr Ala Pro Pro Arg Leu Gln
145                 150                 155                 160

Leu Val Ala Gln Ser Gly Gly Gln His Cys Ala Gly Val Val Glu Phe
            165                 170                 175

Tyr Ser Gly Ser Leu Gly Gly Thr Ile Ser Tyr Glu Ala Gln Asp Lys
```

```
                180                185                190

Thr Gln Asp Leu Glu Asn Phe Leu Cys Asn Asn Leu Gln Cys Gly Ser
        195                200                205

Phe Leu Lys His Leu Pro Glu Thr Glu Ala Gly Arg Ala Gln Asp Pro
        210                215                220

Gly Glu Pro Arg Glu His Gln Pro Leu Pro Ile Gln Trp Lys Ile Gln
225                230                235                240

Asn Ser Ser Cys Thr Ser Leu Glu His Cys Phe Arg Lys Ile Lys Pro
                245                250                255

Gln Lys Ser Gly Arg Val Leu Ala Leu Leu Cys Ser Gly Phe Gln Pro
                260                265                270

Lys Val Gln Ser Arg Leu Val Gly Gly Ser Ser Ile Cys Glu Gly Thr
        275                280                285

Val Glu Val Arg Gln Gly Ala Gln Trp Ala Ala Leu Cys Asp Ser Ser
        290                295                300

Ser Ala Arg Ser Ser Leu Arg Trp Glu Glu Val Cys Arg Glu Gln Gln
305                310                315                320

Cys Gly Ser Val Asn Ser Tyr Arg Val Leu Asp Ala Gly Asp Pro Thr
                325                330                335

Ser Arg Gly Leu Phe Cys Pro His Gln Lys Leu Ser Gln Cys His Glu
                340                345                350

Leu Trp Glu Arg Asn Ser Tyr Cys Lys Lys Val Phe Val Thr Cys Gln
                355                360                365

Asp Pro Asn Pro Ala Gly Leu Ala Ala Gly Thr Val Ala Ser Ile Ile
        370                375                380

Leu Ala Leu Val Leu Leu Val Val Leu Leu Val Val Cys Gly Pro Leu
385                390                395                400

Ala Tyr Lys Lys Leu Val Lys Lys Phe Arg Gln Lys Lys Gln Arg Gln
                405                410                415

Trp Ile Gly Pro Thr Gly Met Asn Gln Asn Met Ser Phe His Arg Asn
                420                425                430

His Thr Ala Thr Val Arg Ser His Ala Glu Asn Pro Thr Ala Ser His
        435                440                445

Val Asp Asn Glu Tyr Ser Gln Pro Pro Arg Asn Ser His Leu Ser Ala
        450                455                460

Tyr Pro Ala Leu Glu Gly Ala Leu His Arg Ser Ser Met Gln Pro Asp
465                470                475                480

Asn Ser Ser Asp Ser Asp Tyr Asp Leu His Gly Ala Gln Arg Leu
                485                490                495
```

<210> SEQ ID NO 59
<211> LENGTH: 494
<212> TYPE: PRT
<213> ORGANISM: Mus musculus

<400> SEQUENCE: 59

```
Met Asp Ser His Glu Val Leu Leu Ala Ala Thr Tyr Leu Leu Gly Thr
1                5                10                15

Leu Ala Ala Phe Cys Leu Gly Gln Ser Gly Arg Gly Gly Leu Asp Ile
                20                25                30

Gln Val Met Leu Ser Gly Ser Asn Ser Lys Cys Gln Gly Gln Val Glu
        35                40                45

Ile Gln Met Glu Asn Lys Trp Lys Thr Val Cys Ser Ser Ser Trp Arg
        50                55                60
```

-continued

```
Leu Ser Gln Asp His Ser Lys Asn Ala Gln Gln Ala Ser Ala Val Cys
65              70                  75                  80

Lys Gln Leu Arg Cys Gly Asp Pro Leu Ala Leu Gly Pro Phe Pro Ser
                85                  90                  95

Leu Asn Arg Pro Gln Asn Gln Val Phe Cys Gln Gly Ser Pro Trp Ser
            100                 105             110

Ile Ser Asn Cys Asn Asn Thr Ser Ser Gln Asp Gln Cys Leu Pro Leu
        115                 120             125

Ser Leu Ile Cys Leu Glu Pro Gln Arg Thr Thr Pro Pro Thr Thr
    130                 135             140

Thr Pro Pro Thr Thr Val Pro Glu Pro Thr Ala Pro Pro Arg Leu Gln
145             150                 155                 160

Leu Val Pro Gly His Glu Gly Leu Arg Cys Thr Gly Val Val Glu Phe
            165                 170             175

Tyr Asn Gly Ser Trp Gly Gly Thr Ile Leu Tyr Lys Ala Lys Asp Arg
            180                 185             190

Pro Leu Gly Leu Gly Asn Leu Ile Cys Lys Ser Leu Gln Cys Gly Ser
        195                 200             205

Phe Leu Thr His Leu Ser Gly Thr Glu Ala Ala Gly Thr Pro Ala Pro
    210                 215             220

Ala Glu Leu Arg Asp Pro Arg Pro Leu Pro Ile Arg Trp Glu Ala Pro
225             230             235                 240

Asn Gly Ser Cys Val Ser Leu Gln Gln Cys Phe Gln Lys Thr Thr Ala
            245             250                 255

Gln Glu Gly Gly Gln Ala Leu Thr Val Ile Cys Ser Asp Phe Gln Pro
        260                 265             270

Lys Val Gln Ser Arg Leu Val Gly Gly Ser Ser Val Cys Glu Gly Ile
        275             280             285

Ala Glu Val Arg Gln Arg Ser Gln Trp Glu Ala Leu Cys Asp Ser Ser
    290             295             300

Ala Ala Arg Gly Arg Gly Arg Trp Glu Glu Leu Cys Arg Glu Gln Gln
305             310             315                 320

Cys Gly Asp Leu Ile Ser Phe His Thr Val Asp Ala Asp Lys Thr Ser
            325             330             335

Pro Gly Phe Leu Cys Ala Gln Glu Lys Leu Ser Gln Cys Tyr His Leu
            340             345             350

Gln Lys Lys Lys His Cys Asn Lys Arg Val Phe Val Thr Cys Gln Asp
        355             360             365

Pro Asn Pro Ala Gly Leu Ala Pro Gly Thr Val Ala Ser Ile Ile Leu
    370             375             380

Thr Leu Val Leu Leu Val Val Leu Leu Ala Met Cys Gly Pro Leu Val
385             390             395                 400

Tyr Lys Lys Leu Val Lys Lys Phe Arg Gln Lys Lys Gln Arg Gln Trp
            405             410             415

Ile Gly Pro Thr Gly Val Asn Gln Asn Met Ser Phe His Arg Ser His
            420             425             430

Thr Ala Thr Val Arg Ser Gln Val Glu Asn Pro Thr Ala Ser His Val
        435             440             445

Asp Asn Glu Tyr Ser Gln Pro Pro Arg Asn Ser His Leu Ser Ala Tyr
    450             455             460

Pro Ala Leu Glu Gly Ala Leu His Arg Ser Ser Thr Gln Pro Asp Asn
465             470             475             480

Ser Ser Asp Ser Asp Tyr Asp Leu Gln Val Ala Gln Arg Leu
```

```
              485                 490

<210> SEQ ID NO 60
<211> LENGTH: 595
<212> TYPE: PRT
<213> ORGANISM: Homo sapiens

<400> SEQUENCE: 60

Met Arg Val Leu Leu Ala Ala Leu Gly Leu Leu Phe Leu Gly Ala Leu
1               5                   10                  15

Arg Ala Phe Pro Gln Asp Arg Pro Phe Glu Asp Thr Cys His Gly Asn
                20                  25                  30

Pro Ser His Tyr Tyr Asp Lys Ala Val Arg Arg Cys Cys Tyr Arg Cys
            35                  40                  45

Pro Met Gly Leu Phe Pro Thr Gln Gln Cys Pro Gln Arg Pro Thr Asp
        50                  55                  60

Cys Arg Lys Gln Cys Glu Pro Asp Tyr Tyr Leu Asp Glu Ala Asp Arg
65                  70                  75                  80

Cys Thr Ala Cys Val Thr Cys Ser Arg Asp Asp Leu Val Glu Lys Thr
                85                  90                  95

Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe Phe His
            115                 120                 125

Ser Val Cys Pro Ala Gly Met Ile Val Lys Phe Pro Gly Thr Ala Gln
        130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
                165                 170                 175

Ala Lys Pro Thr Pro Val Ser Pro Ala Thr Ser Ser Ala Ser Thr Met
                180                 185                 190

Pro Val Arg Gly Gly Thr Arg Leu Ala Gln Glu Ala Ala Ser Lys Leu
            195                 200                 205

Thr Arg Ala Pro Asp Ser Pro Ser Ser Val Gly Arg Pro Ser Ser Asp
        210                 215                 220

Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Glu Ala Gly Arg Cys
                245                 250                 255

Thr Ala Cys Val Ser Cys Ser Arg Asp Asp Leu Val Glu Lys Thr Pro
                260                 265                 270

Cys Ala Trp Asn Ser Ser Arg Thr Cys Glu Cys Arg Pro Gly Met Ile
            275                 280                 285

Cys Ala Thr Ser Ala Thr Asn Ser Cys Ala Arg Cys Val Pro Tyr Pro
        290                 295                 300

Ile Cys Ala Ala Glu Thr Val Thr Lys Pro Gln Asp Met Ala Glu Lys
305                 310                 315                 320

Asp Thr Thr Phe Glu Ala Pro Pro Leu Gly Thr Gln Pro Asp Cys Asn
                325                 330                 335

Pro Thr Pro Glu Asn Gly Glu Ala Pro Ala Ser Thr Ser Pro Thr Gln
            340                 345                 350

Ser Leu Leu Val Asp Ser Gln Ala Ser Lys Thr Leu Pro Ile Pro Thr
        355                 360                 365
```

-continued

```
Ser Ala Pro Val Ala Leu Ser Ser Thr Gly Lys Pro Val Leu Asp Ala
    370             375             380

Gly Pro Val Leu Phe Trp Val Ile Leu Val Leu Val Val Val Gly
385             390             395             400

Ser Ser Ala Phe Leu Leu Cys His Arg Arg Ala Cys Arg Lys Arg Ile
            405             410             415

Arg Gln Lys Leu His Leu Cys Tyr Pro Val Gln Thr Ser Gln Pro Lys
            420             425             430

Leu Glu Leu Val Asp Ser Arg Pro Arg Arg Ser Ser Thr Gln Leu Arg
            435             440             445

Ser Gly Ala Ser Val Thr Glu Pro Val Ala Glu Glu Arg Gly Leu Met
    450             455             460

Ser Gln Pro Leu Met Glu Thr Cys His Ser Val Gly Ala Ala Tyr Leu
465             470             475             480

Glu Ser Leu Pro Leu Gln Asp Ala Ser Pro Ala Gly Gly Pro Ser Ser
            485             490             495

Pro Arg Asp Leu Pro Glu Pro Arg Val Ser Thr Glu His Thr Asn Asn
            500             505             510

Lys Ile Glu Lys Ile Tyr Ile Met Lys Ala Asp Thr Val Ile Val Gly
            515             520             525

Thr Val Lys Ala Glu Leu Pro Glu Gly Arg Gly Leu Ala Gly Pro Ala
    530             535             540

Glu Pro Glu Leu Glu Glu Glu Leu Glu Ala Asp His Thr Pro His Tyr
545             550             555             560

Pro Glu Gln Glu Thr Glu Pro Pro Leu Gly Ser Cys Ser Asp Val Met
            565             570             575

Leu Ser Val Glu Glu Glu Gly Lys Glu Asp Pro Leu Pro Thr Ala Ala
            580             585             590

Ser Gly Lys
            595

<210> SEQ ID NO 61
<211> LENGTH: 498
<212> TYPE: PRT
<213> ORGANISM: Mus musculus

<400> SEQUENCE: 61

Met Ser Ala Leu Leu Thr Ala Ala Gly Leu Leu Phe Leu Gly Met Leu
1               5               10              15

Gln Ala Phe Pro Thr Asp Arg Pro Leu Lys Thr Thr Cys Ala Gly Asp
            20              25              30

Leu Ser His Tyr Pro Gly Glu Ala Ala Arg Asn Cys Cys Tyr Gln Cys
            35              40              45

Pro Ser Gly Leu Ser Pro Thr Gln Pro Cys Pro Arg Gly Pro Ala His
    50              55              60

Cys Arg Lys Gln Cys Ala Pro Asp Tyr Tyr Val Asn Glu Asp Gly Lys
65              70              75              80

Cys Thr Ala Cys Val Thr Cys Leu Pro Gly Leu Val Glu Lys Ala Pro
            85              90              95

Cys Ser Gly Asn Ser Pro Arg Ile Cys Glu Cys Gln Pro Gly Met His
            100             105             110

Cys Cys Thr Pro Ala Val Asn Ser Cys Ala Arg Cys Lys Leu His Cys
            115             120             125

Ser Gly Glu Glu Val Val Lys Ser Pro Gly Thr Ala Lys Lys Asp Thr
    130             135             140
```

-continued

```
Ile Cys Glu Leu Pro Ser Ser Gly Ser Gly Pro Asn Cys Ser Asn Pro
145                 150                 155                 160

Gly Asp Arg Lys Thr Leu Thr Ser His Ala Thr Pro Gln Ala Met Pro
                165                 170                 175

Thr Leu Glu Ser Pro Ala Asn Asp Ser Ala Arg Ser Leu Leu Pro Met
                180                 185                 190

Arg Val Thr Asn Leu Val Gln Glu Asp Ala Thr Glu Leu Val Lys Val
                195                 200                 205

Pro Glu Ser Ser Ser Ser Lys Ala Arg Glu Pro Ser Pro Asp Pro Gly
        210                 215                 220

Asn Ala Glu Lys Asn Met Thr Leu Glu Leu Pro Ser Pro Gly Thr Leu
225                 230                 235                 240

Pro Asp Ile Ser Thr Ser Glu Asn Ser Lys Glu Pro Ala Ser Thr Ala
                245                 250                 255

Ser Thr Leu Ser Leu Val Val Asp Ala Trp Thr Ser Ser Arg Met Gln
                260                 265                 270

Pro Thr Ser Pro Leu Ser Thr Gly Thr Pro Phe Leu Asp Pro Gly Pro
        275                 280                 285

Val Leu Phe Trp Val Ala Met Val Val Leu Leu Val Gly Ser Gly Ser
        290                 295                 300

Phe Leu Leu Cys Tyr Trp Lys Ala Cys Arg Arg Arg Phe Gln Gln Lys
305                 310                 315                 320

Phe His Leu Asp Tyr Leu Val Gln Thr Phe Gln Pro Lys Met Glu Gln
                325                 330                 335

Thr Asp Ser Cys Pro Thr Glu Lys Leu Thr Gln Pro Gln Arg Ser Gly
                340                 345                 350

Ser Val Thr Asp Pro Ser Thr Gly His Lys Leu Ser Pro Val Ser Pro
                355                 360                 365

Pro Pro Ala Val Glu Thr Cys Ala Ser Val Gly Ala Thr Tyr Leu Glu
        370                 375                 380

Asn Leu Pro Leu Leu Asp Asp Ser Pro Ala Gly Asn Pro Phe Ser Pro
385                 390                 395                 400

Arg Glu Pro Pro Glu Pro Arg Val Ser Thr Glu His Thr Asn Asn Arg
                405                 410                 415

Ile Glu Lys Ile Tyr Ile Met Lys Ala Asp Thr Val Ile Val Gly Ser
                420                 425                 430

Val Lys Thr Glu Val Pro Glu Gly Arg Ala Pro Ala Gly Ser Thr Glu
        435                 440                 445

Ser Glu Leu Glu Ala Glu Leu Glu Val Asp His Ala Pro His Tyr Pro
        450                 455                 460

Glu Gln Glu Thr Glu Pro Pro Leu Gly Ser Cys Thr Glu Val Met Phe
465                 470                 475                 480

Ser Val Glu Glu Gly Gly Lys Glu Asp His Gly Pro Thr Thr Val Ser
                485                 490                 495

Glu Lys
```

```
<210> SEQ ID NO 62
<211> LENGTH: 277
<212> TYPE: PRT
<213> ORGANISM: Homo sapiens

<400> SEQUENCE: 62

Met Val Arg Leu Pro Leu Gln Cys Val Leu Trp Gly Cys Leu Leu Thr
1               5                   10                  15
```

-continued

```
Ala Val His Pro Glu Pro Pro Thr Ala Cys Arg Glu Lys Gln Tyr Leu
            20              25              30

Ile Asn Ser Gln Cys Cys Ser Leu Cys Gln Pro Gly Gln Lys Leu Val
            35              40              45

Ser Asp Cys Thr Glu Phe Thr Glu Thr Glu Cys Leu Pro Cys Gly Glu
    50              55              60

Ser Glu Phe Leu Asp Thr Trp Asn Arg Glu Thr His Cys His Gln His
65              70              75              80

Lys Tyr Cys Asp Pro Asn Leu Gly Leu Arg Val Gln Gln Lys Gly Thr
                85              90              95

Ser Glu Thr Asp Thr Ile Cys Thr Cys Glu Glu Gly Trp His Cys Thr
            100             105             110

Ser Glu Ala Cys Glu Ser Cys Val Leu His Arg Ser Cys Ser Pro Gly
        115             120             125

Phe Gly Val Lys Gln Ile Ala Thr Gly Val Ser Asp Thr Ile Cys Glu
    130             135             140

Pro Cys Pro Val Gly Phe Phe Ser Asn Val Ser Ser Ala Phe Glu Lys
145             150             155             160

Cys His Pro Trp Thr Ser Cys Glu Thr Lys Asp Leu Val Val Gln Gln
                165             170             175

Ala Gly Thr Asn Lys Thr Asp Val Val Cys Gly Pro Gln Asp Arg Leu
            180             185             190

Arg Ala Leu Val Val Ile Pro Ile Ile Phe Gly Ile Leu Phe Ala Ile
        195             200             205

Leu Leu Val Leu Val Phe Ile Lys Lys Val Ala Lys Lys Pro Thr Asn
    210             215             220

Lys Ala Pro His Pro Lys Gln Glu Pro Gln Glu Ile Asn Phe Pro Asp
225             230             235             240

Asp Leu Pro Gly Ser Asn Thr Ala Ala Pro Val Gln Glu Thr Leu His
            245             250             255

Gly Cys Gln Pro Val Thr Gln Glu Asp Gly Lys Glu Ser Arg Ile Ser
            260             265             270

Val Gln Glu Arg Gln
        275
```

<210> SEQ ID NO 63
<211> LENGTH: 63
<212> TYPE: PRT
<213> ORGANISM: Homo sapiens

<400> SEQUENCE: 63

```
Lys Lys Val Ala Lys Lys Pro Thr Asn Lys Ala Pro His Pro Lys Gln
1               5               10              15

Glu Pro Gln Glu Ile Asn Phe Pro Asp Asp Leu Pro Gly Ser Asn Thr
            20              25              30

Ala Ala Pro Val Gln Glu Thr Leu His Gly Cys Gln Pro Val Thr Gln
        35              40              45

Ala Glu Asp Gly Lys Glu Ser Arg Ile Ser Val Gln Glu Arg Gln
    50              55              60
```

<210> SEQ ID NO 64
<211> LENGTH: 289
<212> TYPE: PRT
<213> ORGANISM: Mus musculus

<400> SEQUENCE: 64

```
Met Val Ser Leu Pro Arg Leu Cys Ala Leu Trp Gly Cys Leu Leu Thr
1               5                   10                  15

Ala Val His Leu Gly Gln Cys Val Thr Cys Ser Asp Lys Gln Tyr Leu
            20                  25                  30

His Asp Gly Gln Cys Cys Asp Leu Cys Gln Pro Gly Ser Arg Leu Thr
        35                  40                  45

Ser His Cys Thr Ala Leu Glu Lys Thr Gln Cys His Pro Cys Asp Ser
    50                  55                  60

Gly Glu Phe Ser Ala Gln Trp Asn Arg Glu Ile Arg Cys His Gln His
65                  70                  75                  80

Arg His Cys Glu Pro Asn Gln Gly Leu Arg Val Lys Lys Glu Gly Thr
                85                  90                  95

Ala Glu Ser Asp Thr Val Cys Thr Cys Lys Glu Gly Gln His Cys Thr
                100                 105                 110

Ser Lys Asp Cys Glu Ala Cys Ala Gln His Thr Pro Cys Ile Pro Gly
            115                 120                 125

Phe Gly Val Met Glu Met Ala Thr Glu Thr Thr Asp Thr Val Cys His
    130                 135                 140

Pro Cys Pro Val Gly Phe Phe Ser Asn Gln Ser Ser Leu Phe Glu Lys
145                 150                 155                 160

Cys Tyr Pro Trp Thr Ser Cys Glu Asp Lys Asn Leu Glu Val Leu Gln
            165                 170                 175

Lys Gly Thr Ser Gln Thr Asn Val Ile Cys Gly Leu Lys Ser Arg Met
            180                 185                 190

Arg Ala Leu Leu Val Ile Pro Val Val Met Gly Ile Leu Ile Thr Ile
        195                 200                 205

Phe Gly Val Phe Leu Tyr Ile Lys Lys Val Val Lys Lys Pro Lys Asp
    210                 215                 220

Asn Glu Ile Leu Pro Pro Ala Ala Arg Arg Gln Asp Pro Gln Glu Met
225                 230                 235                 240

Glu Asp Tyr Pro Gly His Asn Thr Ala Ala Pro Val Gln Glu Thr Leu
                245                 250                 255

His Gly Cys Gln Pro Val Thr Gln Glu Asp Gly Lys Glu Ser Arg Ile
            260                 265                 270

Ser Val Gln Glu Arg Gln Val Thr Asp Ser Ile Ala Leu Arg Pro Leu
        275                 280                 285

Val
```

```
<210> SEQ ID NO 65
<211> LENGTH: 41
<212> TYPE: PRT
<213> ORGANISM: Homo sapiens

<400> SEQUENCE: 65

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

```
<210> SEQ ID NO 66
<211> LENGTH: 218
<212> TYPE: PRT
<213> ORGANISM: Mus musculus
```

-continued

<400> SEQUENCE: 66

```
Met Thr Leu Arg Leu Leu Phe Leu Ala Leu Asn Phe Phe Ser Val Gln
1               5                   10                  15

Val Thr Glu Asn Lys Ile Leu Val Lys Gln Ser Pro Leu Leu Val Val
            20                  25                  30

Asp Ser Asn Glu Val Ser Leu Ser Cys Arg Tyr Ser Tyr Asn Leu Leu
        35                  40                  45

Ala Lys Glu Phe Arg Ala Ser Leu Tyr Lys Gly Val Asn Ser Asp Val
    50                  55                  60

Glu Val Cys Val Gly Asn Gly Asn Phe Thr Tyr Gln Pro Gln Phe Arg
65                  70                  75                  80

Ser Asn Ala Glu Phe Asn Cys Asp Gly Asp Phe Asp Asn Glu Thr Val
                85                  90                  95

Thr Phe Arg Leu Trp Asn Leu His Val Asn His Thr Asp Ile Tyr Phe
                100                 105                 110

Cys Lys Ile Glu Phe Met Tyr Pro Pro Pro Tyr Leu Asp Asn Glu Arg
            115                 120                 125

Ser Asn Gly Thr Ile Ile His Ile Lys Glu Lys His Leu Cys His Thr
    130                 135                 140

Gln Ser Ser Pro Lys Leu Phe Trp Ala Leu Val Val Val Ala Gly Val
145                 150                 155                 160

Leu Phe Cys Tyr Gly Leu Leu Val Thr Val Ala Leu Cys Val Ile Trp
                165                 170                 175

Thr Asn Ser Arg Arg Asn Arg Leu Leu Gln Ser Asp Tyr Met Asn Met
                180                 185                 190

Thr Pro Arg Arg Pro Gly Leu Thr Arg Lys Pro Tyr Gln Pro Tyr Ala
            195                 200                 205

Pro Ala Arg Asp Phe Ala Ala Tyr Arg Pro
    210                 215
```

<210> SEQ ID NO 67
<211> LENGTH: 1170
<212> TYPE: PRT
<213> ORGANISM: Homo sapiens

<400> SEQUENCE: 67

```
Met Lys Asp Ser Cys Ile Thr Val Met Ala Met Ala Leu Leu Ser Gly
1               5                   10                  15

Phe Phe Phe Phe Ala Pro Ala Ser Ser Tyr Asn Leu Asp Val Arg Gly
            20                  25                  30

Ala Arg Ser Phe Ser Pro Pro Arg Ala Gly Arg His Phe Gly Tyr Arg
        35                  40                  45

Val Leu Gln Val Gly Asn Gly Val Ile Val Gly Ala Pro Gly Glu Gly
    50                  55                  60

Asn Ser Thr Gly Ser Leu Tyr Gln Cys Gln Ser Gly Thr Gly His Cys
65                  70                  75                  80

Leu Pro Val Thr Leu Arg Gly Ser Asn Tyr Thr Ser Lys Tyr Leu Gly
                85                  90                  95

Met Thr Leu Ala Thr Asp Pro Thr Asp Gly Ser Ile Leu Ala Cys Asp
                100                 105                 110

Pro Gly Leu Ser Arg Thr Cys Asp Gln Asn Thr Tyr Leu Ser Gly Leu
            115                 120                 125

Cys Tyr Leu Phe Arg Gln Asn Leu Gln Gly Pro Met Leu Gln Gly Arg
    130                 135                 140
```

-continued

```
Pro Gly Phe Gln Glu Cys Ile Lys Gly Asn Val Asp Leu Val Phe Leu
145                 150                 155                 160

Phe Asp Gly Ser Met Ser Leu Gln Pro Asp Glu Phe Gln Lys Ile Leu
                165                 170                 175

Asp Phe Met Lys Asp Val Met Lys Lys Leu Ser Asn Thr Ser Tyr Gln
            180                 185                 190

Phe Ala Ala Val Gln Phe Ser Thr Ser Tyr Lys Thr Glu Phe Asp Phe
            195                 200                 205

Ser Asp Tyr Val Lys Arg Lys Asp Pro Asp Ala Leu Leu Lys His Val
        210                 215                 220

Lys His Met Leu Leu Leu Thr Asn Thr Phe Gly Ala Ile Asn Tyr Val
225                 230                 235                 240

Ala Thr Glu Val Phe Arg Glu Glu Leu Gly Ala Arg Pro Asp Ala Thr
                245                 250                 255

Lys Val Leu Ile Ile Ile Thr Asp Gly Glu Ala Thr Asp Ser Gly Asn
            260                 265                 270

Ile Asp Ala Ala Lys Asp Ile Ile Arg Tyr Ile Ile Gly Ile Gly Lys
            275                 280                 285

His Phe Gln Thr Lys Glu Ser Gln Glu Thr Leu His Lys Phe Ala Ser
        290                 295                 300

Lys Pro Ala Ser Glu Phe Val Lys Ile Leu Asp Thr Phe Glu Lys Leu
305                 310                 315                 320

Lys Asp Leu Phe Thr Glu Leu Gln Lys Lys Ile Tyr Val Ile Glu Gly
                325                 330                 335

Thr Ser Lys Gln Asp Leu Thr Ser Phe Asn Met Glu Leu Ser Ser Ser
            340                 345                 350

Gly Ile Ser Ala Asp Leu Ser Arg Gly His Ala Val Val Gly Ala Val
            355                 360                 365

Gly Ala Lys Asp Trp Ala Gly Gly Phe Leu Asp Leu Lys Ala Asp Leu
        370                 375                 380

Gln Asp Asp Thr Phe Ile Gly Asn Glu Pro Leu Thr Pro Glu Val Arg
385                 390                 395                 400

Ala Gly Tyr Leu Gly Tyr Thr Val Thr Trp Leu Pro Ser Arg Gln Lys
                405                 410                 415

Thr Ser Leu Leu Ala Ser Gly Ala Pro Arg Tyr Gln His Met Gly Arg
            420                 425                 430

Val Leu Leu Phe Gln Glu Pro Gln Gly Gly Gly His Trp Ser Gln Val
            435                 440                 445

Gln Thr Ile His Gly Thr Gln Ile Gly Ser Tyr Phe Gly Gly Glu Leu
        450                 455                 460

Cys Gly Val Asp Val Asp Gln Asp Gly Glu Thr Glu Leu Leu Leu Ile
465                 470                 475                 480

Gly Ala Pro Leu Phe Tyr Gly Glu Gln Arg Gly Gly Arg Val Phe Ile
                485                 490                 495

Tyr Gln Arg Arg Gln Leu Gly Phe Glu Glu Val Ser Glu Leu Gln Gly
            500                 505                 510

Asp Pro Gly Tyr Pro Leu Gly Arg Phe Gly Glu Ala Ile Thr Ala Leu
            515                 520                 525

Thr Asp Ile Asn Gly Asp Gly Leu Val Asp Val Ala Val Gly Ala Pro
        530                 535                 540

Leu Glu Glu Gln Gly Ala Val Tyr Ile Phe Asn Gly Arg His Gly Gly
545                 550                 555                 560
```

```
Leu Ser Pro Gln Pro Ser Gln Arg Ile Glu Gly Thr Gln Val Leu Ser
              565                 570                 575

Gly Ile Gln Trp Phe Gly Arg Ser Ile His Gly Val Lys Asp Leu Glu
              580                 585                 590

Gly Asp Gly Leu Ala Asp Val Ala Val Gly Ala Glu Ser Gln Met Ile
              595                 600                 605

Val Leu Ser Ser Arg Pro Val Val Asp Met Val Thr Leu Met Ser Phe
          610                 615                 620

Ser Pro Ala Glu Ile Pro Val His Glu Val Glu Cys Ser Tyr Ser Thr
625                 630                 635                 640

Ser Asn Lys Met Lys Glu Gly Val Asn Ile Thr Ile Cys Phe Gln Ile
              645                 650                 655

Lys Ser Leu Ile Pro Gln Phe Gln Gly Arg Leu Val Ala Asn Leu Thr
              660                 665                 670

Tyr Thr Leu Gln Leu Asp Gly His Arg Thr Arg Arg Arg Gly Leu Phe
              675                 680                 685

Pro Gly Gly Arg His Glu Leu Arg Arg Asn Ile Ala Val Thr Thr Ser
          690                 695                 700

Met Ser Cys Thr Asp Phe Ser Phe His Phe Pro Val Cys Val Gln Asp
705                 710                 715                 720

Leu Ile Ser Pro Ile Asn Val Ser Leu Asn Phe Ser Leu Trp Glu Glu
              725                 730                 735

Glu Gly Thr Pro Arg Asp Gln Arg Ala Gln Gly Lys Asp Ile Pro Pro
              740                 745                 750

Ile Leu Arg Pro Ser Leu His Ser Glu Thr Trp Glu Ile Pro Phe Glu
              755                 760                 765

Lys Asn Cys Gly Glu Asp Lys Lys Cys Glu Ala Asn Leu Arg Val Ser
          770                 775                 780

Phe Ser Pro Ala Arg Ser Arg Ala Leu Arg Leu Thr Ala Phe Ala Ser
785                 790                 795                 800

Leu Ser Val Glu Leu Ser Leu Ser Asn Leu Glu Glu Asp Ala Tyr Trp
              805                 810                 815

Val Gln Leu Asp Leu His Phe Pro Pro Gly Leu Ser Phe Arg Lys Val
              820                 825                 830

Glu Met Leu Lys Pro His Ser Gln Ile Pro Val Ser Cys Glu Glu Leu
              835                 840                 845

Pro Glu Glu Ser Arg Leu Leu Ser Arg Ala Leu Ser Cys Asn Val Ser
          850                 855                 860

Ser Pro Ile Phe Lys Ala Gly His Ser Val Ala Leu Gln Met Met Phe
865                 870                 875                 880

Asn Thr Leu Val Asn Ser Ser Trp Gly Asp Ser Val Glu Leu His Ala
              885                 890                 895

Asn Val Thr Cys Asn Asn Glu Asp Ser Asp Leu Leu Glu Asp Asn Ser
              900                 905                 910

Ala Thr Thr Ile Ile Pro Ile Leu Tyr Pro Ile Asn Ile Leu Ile Gln
              915                 920                 925

Asp Gln Glu Asp Ser Thr Leu Tyr Val Ser Phe Thr Pro Lys Gly Pro
          930                 935                 940

Lys Ile His Gln Val Lys His Met Tyr Gln Val Arg Ile Gln Pro Ser
945                 950                 955                 960

Ile His Asp His Asn Ile Pro Thr Leu Glu Ala Val Val Gly Val Pro
              965                 970                 975

Gln Pro Pro Ser Glu Gly Pro Ile Thr His Gln Trp Ser Val Gln Met
```

-continued

```
        980             985             990
Glu Pro Pro Val Pro Cys His Tyr  Glu Asp Leu Glu Arg  Leu Pro Asp
    995                 1000                1005

Ala Ala  Glu Pro Cys Leu Pro  Gly Ala Leu Phe Arg  Cys Pro Val
    1010                1015                1020

Val Phe  Arg Gln Glu Ile Leu  Val Gln Val Ile Gly  Thr Leu Glu
    1025                1030                1035

Leu Val  Gly Glu Ile Glu Ala  Ser Ser Met Phe Ser  Leu Cys Ser
    1040                1045                1050

Ser Leu  Ser Ile Ser Phe Asn  Ser Ser Lys His Phe  His Leu Tyr
    1055                1060                1065

Gly Ser  Asn Ala Ser Leu Ala  Gln Val Val Met Lys  Val Asp Val
    1070                1075                1080

Val Tyr  Glu Lys Gln Met Leu  Tyr Leu Tyr Val Leu  Ser Gly Ile
    1085                1090                1095

Gly Gly  Leu Leu Leu Leu Leu  Leu Ile Phe Ile Val  Leu Tyr Lys
    1100                1105                1110

Val Gly  Phe Phe Lys Arg Asn  Leu Lys Glu Lys Met  Glu Ala Gly
    1115                1120                1125

Arg Gly  Val Pro Asn Gly Ile  Pro Ala Glu Asp Ser  Glu Gln Leu
    1130                1135                1140

Ala Ser  Gly Gln Glu Ala Gly  Asp Pro Gly Cys Leu  Lys Pro Leu
    1145                1150                1155

His Glu  Lys Asp Ser Glu Ser  Gly Gly Gly Lys Asp
    1160                1165                1170
```

```
<210> SEQ ID NO 68
<211> LENGTH: 59
<212> TYPE: PRT
<213> ORGANISM: Homo sapiens

<400> SEQUENCE: 68

Tyr Lys Val Gly Phe Phe Lys Arg Asn Leu Lys Glu Lys Met Glu Ala
1               5                   10                  15

Gly Arg Gly Val Pro Asn Gly Ile Pro Ala Glu Asp Ser Glu Gln Leu
            20                  25                  30

Ala Ser Gly Gln Glu Ala Gly Asp Pro Gly Cys Leu Lys Pro Leu His
        35                  40                  45

Glu Lys Asp Ser Glu Ser Gly Gly Gly Lys Asp
    50                  55
```

```
<210> SEQ ID NO 69
<211> LENGTH: 1162
<212> TYPE: PRT
<213> ORGANISM: Mus musculus

<400> SEQUENCE: 69

Met Ser Phe Arg Ile Ala Gly Pro Arg Leu Leu Leu Leu Gly Leu Gln
1               5                   10                  15

Leu Phe Ala Lys Ala Trp Ser Tyr Asn Leu Asp Thr Arg Pro Thr Gln
            20                  25                  30

Ser Phe Leu Ala Gln Ala Gly Arg His Phe Gly Tyr Gln Val Leu Gln
        35                  40                  45

Ile Glu Asp Gly Val Val Val Gly Ala Pro Gly Glu Gly Asp Asn Thr
    50                  55                  60

Gly Gly Leu Tyr His Cys Arg Thr Ser Ser Glu Phe Cys Gln Pro Val
```

```
65                      70                      75                      80

Ser Leu His Gly Ser Asn His Thr Ser Lys Tyr Leu Gly Met Thr Leu
                85                      90                      95

Ala Thr Asp Ala Ala Lys Gly Ser Leu Leu Ala Cys Asp Pro Gly Leu
                100                     105                     110

Ser Arg Thr Cys Asp Gln Asn Thr Tyr Leu Ser Gly Leu Cys Tyr Leu
                115                     120                     125

Phe Pro Gln Ser Leu Glu Gly Pro Met Leu Gln Asn Arg Pro Ala Tyr
        130                     135                     140

Gln Glu Cys Met Lys Gly Lys Val Asp Leu Val Phe Leu Phe Asp Gly
145                     150                     155                     160

Ser Gln Ser Leu Asp Arg Lys Asp Phe Glu Lys Ile Leu Glu Phe Met
                165                     170                     175

Lys Asp Val Met Arg Lys Leu Ser Asn Thr Ser Tyr Gln Phe Ala Ala
                180                     185                     190

Val Gln Phe Ser Thr Asp Cys Arg Thr Glu Phe Thr Phe Leu Asp Tyr
                195                     200                     205

Val Lys Gln Asn Lys Asn Pro Asp Val Leu Leu Gly Ser Val Gln Pro
        210                     215                     220

Met Phe Leu Leu Thr Asn Thr Phe Arg Ala Ile Asn Tyr Val Val Ala
225                     230                     235                     240

His Val Phe Lys Glu Glu Ser Gly Ala Arg Pro Asp Ala Thr Lys Val
                245                     250                     255

Leu Val Ile Ile Thr Asp Gly Glu Ala Ser Asp Lys Gly Asn Ile Ser
                260                     265                     270

Ala Ala His Asp Ile Thr Arg Tyr Ile Ile Gly Ile Gly Lys His Phe
                275                     280                     285

Val Ser Val Gln Lys Gln Lys Thr Leu His Ile Phe Ala Ser Glu Pro
        290                     295                     300

Val Glu Glu Phe Val Lys Ile Leu Asp Thr Phe Glu Lys Leu Lys Asp
305                     310                     315                     320

Leu Phe Thr Asp Leu Gln Arg Arg Ile Tyr Ala Ile Glu Gly Thr Asn
                325                     330                     335

Arg Gln Asp Leu Thr Ser Phe Asn Met Glu Leu Ser Ser Ser Gly Ile
                340                     345                     350

Ser Ala Asp Leu Ser Lys Gly His Ala Val Val Gly Ala Val Gly Ala
        355                     360                     365

Lys Asp Trp Ala Gly Gly Phe Leu Asp Leu Arg Glu Asp Leu Gln Gly
        370                     375                     380

Ala Thr Phe Val Gly Gln Glu Pro Leu Thr Ser Asp Val Arg Gly Gly
385                     390                     395                     400

Tyr Leu Gly Tyr Thr Val Ala Trp Met Thr Ser Arg Ser Ser Arg Pro
                405                     410                     415

Leu Leu Ala Ala Gly Ala Pro Arg Tyr Gln His Val Gly Gln Val Leu
                420                     425                     430

Leu Phe Gln Ala Pro Glu Ala Gly Gly Arg Trp Asn Gln Thr Gln Lys
        435                     440                     445

Ile Glu Gly Thr Gln Ile Gly Ser Tyr Phe Gly Gly Glu Leu Cys Ser
        450                     455                     460

Val Asp Leu Asp Gln Asp Gly Glu Ala Glu Leu Leu Leu Ile Gly Ala
465                     470                     475                     480

Pro Leu Phe Phe Gly Glu Gln Arg Gly Gly Arg Val Phe Thr Tyr Gln
                485                     490                     495
```

```
Arg Arg Gln Ser Leu Phe Glu Met Val Ser Glu Leu Gln Gly Asp Pro
            500                 505             510

Gly Tyr Pro Leu Gly Arg Phe Gly Ala Ala Ile Thr Ala Leu Thr Asp
            515                 520             525

Ile Asn Gly Asp Arg Leu Thr Asp Val Ala Val Gly Ala Pro Leu Glu
        530                 535             540

Glu Gln Gly Ala Val Tyr Ile Phe Asn Gly Lys Pro Gly Gly Leu Ser
545                 550             555             560

Pro Gln Pro Ser Gln Arg Ile Gln Gly Ala Gln Val Phe Pro Gly Ile
            565                 570             575

Arg Trp Phe Gly Arg Ser Ile His Gly Val Lys Asp Leu Gly Gly Asp
            580                 585             590

Arg Leu Ala Asp Val Val Val Gly Ala Glu Gly Arg Val Val Val Leu
        595                 600             605

Ser Ser Arg Pro Val Val Asp Val Val Thr Glu Leu Ser Phe Ser Pro
    610                 615             620

Glu Glu Ile Pro Val His Glu Val Glu Cys Ser Tyr Ser Ala Arg Glu
625                 630             635             640

Glu Gln Lys His Gly Val Lys Leu Lys Ala Cys Phe Arg Ile Lys Pro
            645                 650             655

Leu Thr Pro Gln Phe Gln Gly Arg Leu Leu Ala Asn Leu Ser Tyr Thr
            660                 665             670

Leu Gln Leu Asp Gly His Arg Met Arg Ser Arg Gly Leu Phe Pro Asp
            675                 680             685

Gly Ser His Glu Leu Ser Gly Asn Thr Ser Ile Thr Pro Asp Lys Ser
        690                 695             700

Cys Leu Asp Phe His Phe His Phe Pro Ile Cys Ile Gln Asp Leu Ile
705                 710             715             720

Ser Pro Ile Asn Val Ser Leu Asn Phe Ser Leu Leu Glu Glu Glu Gly
            725                 730             735

Thr Pro Arg Asp Gln Lys Val Gly Arg Ala Met Gln Pro Ile Leu Arg
            740                 745             750

Pro Ser Ile His Thr Val Thr Lys Glu Ile Pro Phe Glu Lys Asn Cys
            755                 760             765

Gly Glu Asp Lys Lys Cys Glu Ala Asn Leu Thr Leu Ser Ser Pro Ala
        770                 775             780

Arg Ser Gly Pro Leu Arg Leu Met Ser Ser Ala Ser Leu Ala Val Glu
785                 790             795             800

Trp Thr Leu Ser Asn Ser Gly Glu Asp Ala Tyr Trp Val Arg Leu Asp
            805                 810             815

Leu Asp Phe Pro Arg Gly Leu Ser Phe Arg Lys Val Glu Met Leu Gln
            820                 825             830

Pro His Ser Arg Met Pro Val Ser Cys Glu Glu Leu Thr Glu Gly Ser
            835                 840             845

Ser Leu Leu Thr Lys Thr Leu Lys Cys Asn Val Ser Ser Pro Ile Phe
    850                 855             860

Lys Ala Gly Gln Glu Val Ser Leu Gln Val Met Phe Asn Thr Leu Leu
865                 870             875             880

Asn Ser Ser Trp Glu Asp Phe Val Glu Leu Asn Gly Thr Val His Cys
            885                 890             895

Glu Asn Glu Asn Ser Ser Leu Gln Glu Asp Asn Ser Ala Ala Thr His
            900                 905             910
```

```
Ile Pro Val Leu Tyr Pro Val Asn Ile Leu Thr Lys Glu Gln Glu Asn
        915             920             925

Ser Thr Leu Tyr Ile Ser Phe Thr Pro Lys Gly Pro Lys Thr Gln Gln
        930             935             940

Val Gln His Val Tyr Gln Val Arg Ile Gln Pro Ser Ala Tyr Asp His
945             950             955             960

Asn Met Pro Thr Leu Glu Ala Leu Val Gly Val Pro Trp Pro His Ser
                965             970             975

Glu Asp Pro Ile Thr Tyr Thr Trp Ser Val Gln Thr Asp Pro Leu Val
                980             985             990

Thr Cys His Ser Glu Asp Leu Lys  Arg Pro Ser Ser Glu  Ala Glu Gln
        995             1000            1005

Pro Cys  Leu Pro Gly Val Gln  Phe Arg Cys Pro Ile  Val Phe Arg
        1010            1015            1020

Arg Glu  Ile Leu Ile Gln Val  Thr Gly Thr Val Glu  Leu Ser Lys
        1025            1030            1035

Glu Ile  Lys Ala Ser Ser Thr  Leu Ser Leu Cys Ser  Ser Leu Ser
        1040            1045            1050

Val Ser  Phe Asn Ser Ser Lys  His Phe His Leu Tyr  Gly Ser Lys
        1055            1060            1065

Ala Ser  Glu Ala Gln Val Leu  Val Lys Val Asp Leu  Ile His Glu
        1070            1075            1080

Lys Glu  Met Leu His Val Tyr  Val Leu Ser Gly Ile  Gly Gly Leu
        1085            1090            1095

Val Leu  Leu Phe Leu Ile Phe  Leu Ala Leu Tyr Lys  Val Gly Phe
        1100            1105            1110

Phe Lys  Arg Asn Leu Lys Glu  Lys Met Glu Ala Asp  Gly Gly Val
        1115            1120            1125

Pro Asn  Gly Ser Pro Pro Glu  Asp Thr Asp Pro Leu  Ala Val Pro
        1130            1135            1140

Gly Glu  Glu Thr Lys Asp Met  Gly Cys Leu Glu Pro  Leu Arg Glu
        1145            1150            1155

Ser Asp  Lys Asp
        1160
```

```
<210> SEQ ID NO 70
<211> LENGTH: 532
<212> TYPE: PRT
<213> ORGANISM: Homo sapiens

<400> SEQUENCE: 70

Met Ala Pro Ser Ser Pro Arg Pro Ala Leu Pro Ala Leu Leu Val Leu
1               5               10              15

Leu Gly Ala Leu Phe Pro Gly Pro Gly Asn Ala Gln Thr Ser Val Ser
        20              25              30

Pro Ser Lys Val Ile Leu Pro Arg Gly Gly Ser Val Leu Val Thr Cys
        35              40              45

Ser Thr Ser Cys Asp Gln Pro Lys Leu Leu Gly Ile Glu Thr Pro Leu
        50              55              60

Pro Lys Lys Glu Leu Leu Leu Pro Gly Asn Asn Arg Lys Val Tyr Glu
65              70              75              80

Leu Ser Asn Val Gln Glu Asp Ser Gln Pro Met Cys Tyr Ser Asn Cys
                85              90              95

Pro Asp Gly Gln Ser Thr Ala Lys Thr Phe Leu Thr Val Tyr Trp Thr
        100             105             110
```

```
Pro Glu Arg Val Glu Leu Ala Pro Leu Pro Ser Trp Gln Pro Val Gly
    115                 120                 125

Lys Asn Leu Thr Leu Arg Cys Gln Val Glu Gly Gly Ala Pro Arg Ala
    130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg
                165                 170                 175

Arg Asp His His Gly Ala Asn Phe Ser Cys Arg Thr Glu Leu Asp Leu
                180                 185                 190

Arg Pro Gln Gly Leu Glu Leu Phe Glu Asn Thr Ser Ala Pro Tyr Gln
    195                 200                 205

Leu Gln Thr Phe Val Leu Pro Ala Thr Pro Pro Gln Leu Val Ser Pro
    210                 215                 220

Arg Val Leu Glu Val Asp Thr Gln Gly Thr Val Val Cys Ser Leu Asp
225                 230                 235                 240

Gly Leu Phe Pro Val Ser Glu Ala Gln Val His Leu Ala Leu Gly Asp
                245                 250                 255

Gln Arg Leu Asn Pro Thr Val Thr Tyr Gly Asn Asp Ser Phe Ser Ala
    260                 265                 270

Lys Ala Ser Val Ser Val Thr Ala Glu Asp Glu Gly Thr Gln Arg Leu
    275                 280                 285

Thr Cys Ala Val Ile Leu Gly Asn Gln Ser Gln Glu Thr Leu Gln Thr
    290                 295                 300

Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
                325                 330                 335

Arg Ala Lys Val Thr Leu Asn Gly Val Pro Ala Gln Pro Leu Gly Pro
                340                 345                 350

Arg Ala Gln Leu Leu Leu Lys Ala Thr Pro Glu Asp Asn Gly Arg Ser
    355                 360                 365

Phe Ser Cys Ser Ala Thr Leu Glu Val Ala Gly Gln Leu Ile His Lys
    370                 375                 380

Asn Gln Thr Arg Glu Leu Arg Val Leu Tyr Gly Pro Arg Leu Asp Glu
385                 390                 395                 400

Arg Asp Cys Pro Gly Asn Trp Thr Trp Pro Glu Asn Ser Gln Gln Thr
                405                 410                 415

Pro Met Cys Gln Ala Trp Gly Asn Pro Leu Pro Glu Leu Lys Cys Leu
                420                 425                 430

Lys Asp Gly Thr Phe Pro Leu Pro Ile Gly Glu Ser Val Thr Val Thr
                435                 440                 445

Arg Asp Leu Glu Gly Thr Tyr Leu Cys Arg Ala Arg Ser Thr Gln Gly
    450                 455                 460

Glu Val Thr Arg Lys Val Thr Val Asn Val Leu Ser Pro Arg Tyr Glu
465                 470                 475                 480

Ile Val Ile Ile Thr Val Val Ala Ala Ala Val Ile Met Gly Thr Ala
                485                 490                 495

Gly Leu Ser Thr Tyr Leu Tyr Asn Arg Gln Arg Lys Ile Lys Lys Tyr
                500                 505                 510

Arg Leu Gln Gln Ala Gln Lys Gly Thr Pro Met Lys Pro Asn Thr Gln
    515                 520                 525
```

```
Ala Thr Pro Pro
    530

<210> SEQ ID NO 71
<211> LENGTH: 537
<212> TYPE: PRT
<213> ORGANISM: Mus musculus

<400> SEQUENCE: 71

Met Ala Ser Thr Arg Ala Lys Pro Thr Leu Pro Leu Leu Leu Ala Leu
1               5                   10                  15

Val Thr Val Val Ile Pro Gly Pro Gly Asp Ala Gln Val Ser Ile His
            20                  25                  30

Pro Arg Glu Ala Phe Leu Pro Gln Gly Gly Ser Val Gln Val Asn Cys
        35                  40                  45

Ser Ser Ser Cys Lys Glu Asp Leu Ser Leu Gly Leu Glu Thr Gln Trp
    50                  55                  60

Leu Lys Asp Glu Leu Glu Ser Gly Pro Asn Trp Lys Leu Phe Glu Leu
65                  70                  75                  80

Ser Glu Ile Gly Glu Asp Ser Ser Pro Leu Cys Phe Glu Asn Cys Gly
                85                  90                  95

Thr Val Gln Ser Ser Ala Ser Ala Thr Ile Thr Val Tyr Ser Phe Pro
            100                 105                 110

Glu Ser Val Glu Leu Arg Pro Leu Pro Ala Trp Gln Gln Val Gly Lys
        115                 120                 125

Asp Leu Thr Leu Arg Cys His Val Asp Gly Gly Ala Pro Arg Thr Gln
    130                 135                 140

Leu Ser Ala Val Leu Leu Arg Gly Glu Glu Ile Leu Ser Arg Gln Pro
145                 150                 155                 160

Val Gly Gly His Pro Lys Asp Pro Lys Glu Ile Thr Phe Thr Val Leu
                165                 170                 175

Ala Ser Arg Gly Asp His Gly Ala Asn Phe Ser Cys Arg Thr Glu Leu
            180                 185                 190

Asp Leu Arg Pro Gln Gly Leu Ala Leu Phe Ser Asn Val Ser Glu Ala
        195                 200                 205

Arg Ser Leu Arg Thr Phe Asp Leu Pro Ala Thr Ile Pro Lys Leu Asp
    210                 215                 220

Thr Pro Asp Leu Leu Glu Val Gly Thr Gln Gln Lys Leu Phe Cys Ser
225                 230                 235                 240

Leu Glu Gly Leu Phe Pro Ala Ser Glu Ala Arg Ile Tyr Leu Glu Leu
            245                 250                 255

Gly Gly Gln Met Pro Thr Gln Glu Ser Thr Asn Ser Ser Asp Ser Val
            260                 265                 270

Ser Ala Thr Ala Leu Val Glu Val Thr Glu Glu Phe Asp Arg Thr Leu
            275                 280                 285

Pro Leu Arg Cys Val Leu Glu Leu Ala Asp Gln Ile Leu Glu Thr Gln
    290                 295                 300

Arg Thr Leu Thr Val Tyr Asn Phe Ser Ala Pro Val Leu Thr Leu Ser
305                 310                 315                 320

Gln Leu Glu Val Ser Glu Gly Ser Gln Val Thr Val Lys Cys Glu Ala
            325                 330                 335

His Ser Gly Ser Lys Val Val Leu Leu Ser Gly Val Glu Pro Arg Pro
            340                 345                 350

Pro Thr Pro Gln Val Gln Phe Thr Leu Asn Ala Ser Ser Glu Asp His
            355                 360                 365
```

```
Lys Arg Ser Phe Phe Cys Ser Ala Ala Leu Glu Val Ala Gly Lys Phe
    370             375             380

Leu Phe Lys Asn Gln Thr Leu Glu Leu His Val Leu Tyr Gly Pro Arg
385             390             395             400

Leu Asp Glu Thr Asp Cys Leu Gly Asn Trp Thr Trp Gln Glu Gly Ser
            405             410             415

Gln Gln Thr Leu Lys Cys Gln Ala Trp Gly Asn Pro Ser Pro Lys Met
            420             425             430

Thr Cys Arg Arg Lys Ala Asp Gly Ala Leu Leu Pro Ile Gly Val Val
            435             440             445

Lys Ser Val Lys Gln Glu Met Asn Gly Thr Tyr Val Cys His Ala Phe
    450             455             460

Ser Ser His Gly Asn Val Thr Arg Asn Val Tyr Leu Thr Val Leu Tyr
465             470             475             480

His Ser Gln Asn Asn Trp Thr Ile Ile Ile Leu Val Pro Val Leu Leu
            485             490             495

Val Ile Val Gly Leu Val Met Ala Ala Ser Tyr Val Tyr Asn Arg Gln
            500             505             510

Arg Lys Ile Arg Ile Tyr Lys Leu Gln Lys Ala Gln Glu Glu Ala Ile
            515             520             525

Lys Leu Lys Gly Gln Ala Pro Pro Pro
    530             535

<210> SEQ ID NO 72
<211> LENGTH: 231
<212> TYPE: PRT
<213> ORGANISM: Homo sapiens

<400> SEQUENCE: 72

Met Ser Lys Gln Arg Gly Thr Phe Ser Glu Val Ser Leu Ala Gln Asp
1               5               10              15

Pro Lys Arg Gln Gln Arg Lys Pro Lys Gly Asn Lys Ser Ser Ile Ser
            20              25              30

Gly Thr Glu Gln Glu Ile Phe Gln Val Glu Leu Asn Leu Gln Asn Pro
            35              40              45

Ser Leu Asn His Gln Gly Ile Asp Lys Ile Tyr Asp Cys Gln Gly Leu
    50              55              60

Leu Pro Pro Pro Glu Lys Leu Thr Ala Glu Val Leu Gly Ile Ile Cys
65              70              75              80

Ile Val Leu Met Ala Thr Val Leu Lys Thr Ile Val Leu Ile Pro Phe
            85              90              95

Leu Glu Gln Asn Asn Ser Ser Pro Asn Thr Arg Thr Gln Lys Ala Arg
            100             105             110

His Cys Gly His Cys Pro Glu Glu Trp Ile Thr Tyr Ser Asn Ser Cys
    115             120             125

Tyr Tyr Ile Gly Lys Glu Arg Arg Thr Trp Glu Glu Ser Leu Leu Ala
    130             135             140

Cys Thr Ser Lys Asn Ser Ser Leu Leu Ser Ile Asp Asn Glu Glu Glu
145             150             155             160

Met Lys Phe Leu Ala Ser Ile Leu Pro Ser Ser Trp Ile Gly Val Phe
            165             170             175

Arg Asn Ser Ser His His Pro Trp Val Thr Ile Asn Gly Leu Ala Phe
            180             185             190

Lys His Lys Ile Lys Asp Ser Asp Asn Ala Glu Leu Asn Cys Ala Val
```

-continued

```
              195                 200                 205
Leu Gln Val Asn Arg Leu Lys Ser Ala Gln Cys Gly Ser Ser Met Ile
    210                 215                 220

Tyr His Cys Lys His Lys Leu
225                 230

<210> SEQ ID NO 73
<211> LENGTH: 241
<212> TYPE: PRT
<213> ORGANISM: Homo sapiens

<400> SEQUENCE: 73

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
            35                  40                  45

Cys Cys Arg Val His Thr Thr Arg Cys Cys Arg Asp Tyr Pro Gly Glu
    50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
            115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
            195                 200                 205

Pro Pro Ser Thr Glu Asp Ala Arg Ser Cys Gln Phe Pro Glu Glu Glu
    210                 215                 220

Arg Gly Glu Arg Ser Ala Glu Glu Lys Gly Arg Leu Gly Asp Leu Trp
225                 230                 235                 240

Val

<210> SEQ ID NO 74
<211> LENGTH: 58
<212> TYPE: PRT
<213> ORGANISM: Homo sapiens

<400> SEQUENCE: 74

Gln Leu Gly Leu His Ile Trp Gln Leu Arg Ser Gln Cys Met Trp Pro
1               5                   10                  15

Arg Glu Thr Gln Leu Leu Leu Glu Val Pro Pro Ser Thr Glu Asp Ala
            20                  25                  30

Arg Ser Cys Gln Phe Pro Glu Glu Glu Arg Gly Glu Arg Ser Ala Glu
            35                  40                  45
```

-continued

```
Glu Lys Gly Arg Leu Gly Asp Leu Trp Val
    50                  55

<210> SEQ ID NO 75
<211> LENGTH: 228
<212> TYPE: PRT
<213> ORGANISM: Mus musculus

<400> SEQUENCE: 75

Met Gly Ala Trp Ala Met Leu Tyr Gly Val Ser Met Leu Cys Val Leu
1               5                   10                  15

Asp Leu Gly Gln Pro Ser Val Val Glu Glu Pro Gly Cys Gly Pro Gly
            20                  25                  30

Lys Val Gln Asn Gly Ser Gly Asn Asn Thr Arg Cys Cys Ser Leu Tyr
        35                  40                  45

Ala Pro Gly Lys Glu Asp Cys Pro Lys Glu Arg Cys Ile Cys Val Thr
    50                  55                  60

Pro Glu Tyr His Cys Gly Asp Pro Gln Cys Lys Ile Cys Lys His Tyr
65                  70                  75                  80

Pro Cys Gln Pro Gly Gln Arg Val Glu Ser Gln Gly Asp Ile Val Phe
                85                  90                  95

Gly Phe Arg Cys Val Ala Cys Ala Met Gly Thr Phe Ser Ala Gly Arg
            100                 105                 110

Asp Gly His Cys Arg Leu Trp Thr Asn Cys Ser Gln Phe Gly Phe Leu
        115                 120                 125

Thr Met Phe Pro Gly Asn Lys Thr His Asn Ala Val Cys Ile Pro Glu
    130                 135                 140

Pro Leu Pro Thr Glu Gln Tyr Gly His Leu Thr Val Ile Phe Leu Val
145                 150                 155                 160

Met Ala Ala Cys Ile Phe Phe Leu Thr Thr Val Gln Leu Gly Leu His
                165                 170                 175

Ile Trp Gln Leu Arg Arg Gln His Met Cys Pro Arg Glu Thr Gln Pro
            180                 185                 190

Phe Ala Glu Val Gln Leu Ser Ala Glu Asp Ala Cys Ser Phe Gln Phe
        195                 200                 205

Pro Glu Glu Glu Arg Gly Glu Gln Thr Glu Glu Lys Cys His Leu Gly
    210                 215                 220

Gly Arg Trp Pro
225

<210> SEQ ID NO 76
<211> LENGTH: 93
<212> TYPE: PRT
<213> ORGANISM: Homo sapiens

<400> SEQUENCE: 76

Met Ile His Leu Gly His Ile Leu Phe Leu Leu Leu Leu Pro Val Ala
1               5                   10                  15

Ala Ala Gln Thr Thr Pro Gly Glu Arg Ser Ser Leu Pro Ala Phe Tyr
            20                  25                  30

Pro Gly Thr Ser Gly Ser Cys Ser Gly Cys Gly Ser Leu Ser Leu Pro
        35                  40                  45

Leu Leu Ala Gly Leu Val Ala Ala Asp Ala Val Ala Ser Leu Leu Ile
    50                  55                  60

Val Gly Ala Val Phe Leu Cys Ala Arg Pro Arg Arg Ser Pro Ala Gln
65                  70                  75                  80
```

```
Glu Asp Gly Lys Val Tyr Ile Asn Met Pro Gly Arg Gly
                85                  90

<210> SEQ ID NO 77
<211> LENGTH: 24
<212> TYPE: PRT
<213> ORGANISM: Homo sapiens

<400> SEQUENCE: 77

Leu Cys Ala Arg Pro Arg Arg Ser Pro Ala Gln Glu Asp Gly Lys Val
1               5                   10                  15

Tyr Ile Asn Met Pro Gly Arg Gly
            20

<210> SEQ ID NO 78
<211> LENGTH: 79
<212> TYPE: PRT
<213> ORGANISM: Mus musculus

<400> SEQUENCE: 78

Met Asp Pro Pro Gly Tyr Leu Leu Phe Leu Leu Leu Pro Val Ala
1               5                   10                  15

Ala Ser Gln Thr Ser Ala Gly Ser Cys Ser Gly Cys Gly Thr Leu Ser
            20                  25                  30

Leu Pro Leu Leu Ala Gly Leu Val Ala Ala Asp Ala Val Met Ser Leu
        35                  40                  45

Leu Ile Val Gly Val Val Phe Val Cys Met Arg Pro His Gly Arg Pro
    50                  55                  60

Ala Gln Glu Asp Gly Arg Val Tyr Ile Asn Met Pro Gly Arg Gly
65                  70                  75

<210> SEQ ID NO 79
<211> LENGTH: 113
<212> TYPE: PRT
<213> ORGANISM: Homo sapiens

<400> SEQUENCE: 79

Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80

Lys Gln Arg Ile Thr Glu Thr Glu Ser Pro Tyr Gln Glu Leu Gln Gly
                85                  90                  95

Gln Arg Ser Asp Val Tyr Ser Asp Leu Asn Thr Gln Arg Pro Tyr Tyr
            100                 105                 110

Lys

<210> SEQ ID NO 80
<211> LENGTH: 52
<212> TYPE: PRT
<213> ORGANISM: Homo sapiens

<400> SEQUENCE: 80
```

-continued

```
Tyr Phe Leu Gly Arg Leu Val Pro Arg Gly Arg Gly Ala Ala Glu Ala
1               5                   10                  15

Ala Thr Arg Lys Gln Arg Ile Thr Glu Thr Glu Ser Pro Tyr Gln Glu
            20                  25                  30

Leu Gln Gly Gln Arg Ser Asp Val Tyr Ser Asp Leu Asn Thr Gln Arg
        35                  40                  45

Pro Tyr Tyr Lys
    50
```

<210> SEQ ID NO 81
<211> LENGTH: 114
<212> TYPE: PRT
<213> ORGANISM: Mus musculus

<400> SEQUENCE: 81

```
Met Gly Ala Leu Glu Pro Ser Trp Cys Leu Leu Phe Leu Pro Val Leu
1               5                   10                  15

Leu Thr Val Gly Gly Leu Ser Pro Val Gln Ala Gln Ser Asp Thr Phe
            20                  25                  30

Pro Arg Cys Asp Cys Ser Ser Val Ser Pro Gly Val Leu Ala Gly Ile
        35                  40                  45

Val Leu Gly Asp Leu Val Leu Thr Leu Leu Ile Ala Leu Ala Val Tyr
    50                  55                  60

Ser Leu Gly Arg Leu Val Ser Arg Gly Gln Gly Thr Ala Glu Gly Thr
65                  70                  75                  80

Arg Lys Gln His Ile Ala Glu Thr Glu Ser Pro Tyr Gln Glu Leu Gln
                85                  90                  95

Gly Gln Arg Pro Glu Val Tyr Ser Asp Leu Asn Thr Gln Arg Gln Tyr
            100                 105                 110

Tyr Arg
```

<210> SEQ ID NO 82
<211> LENGTH: 534
<212> TYPE: PRT
<213> ORGANISM: Homo sapiens

<400> SEQUENCE: 82

```
Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140
```

```
Pro Ser Met Thr Leu Glu Pro Asn Lys Asp Leu Arg Pro Gly Asp Thr
145             150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Ile Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
            245                 250                 255

Val Ala Leu Val Gly Thr Asp Ala Thr Leu Arg Cys Ser Phe Ser Pro
                260                 265                 270

Glu Pro Gly Phe Ser Leu Ala Gln Leu Asn Leu Ile Trp Gln Leu Thr
            275                 280                 285

Asp Thr Lys Gln Leu Val His Ser Phe Thr Glu Gly Arg Asp Gln Gly
    290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
            325                 330                 335

Ser Phe Thr Cys Phe Val Ser Ile Arg Asp Phe Gly Ser Ala Ala Val
            340                 345                 350

Ser Leu Gln Val Ala Ala Pro Tyr Ser Lys Pro Ser Met Thr Leu Glu
        355                 360                 365

Pro Asn Lys Asp Leu Arg Pro Gly Asp Thr Val Thr Ile Thr Cys Ser
370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
            405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
        435                 440                 445

Ala His Gly Ser Val Thr Ile Thr Gly Gln Pro Met Thr Phe Pro Pro
    450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
            500                 505                 510

Ser Lys Thr Ala Leu Gln Pro Leu Lys His Ser Asp Ser Lys Glu Asp
        515                 520                 525

Asp Gly Gln Glu Ile Ala
    530
```

<210> SEQ ID NO 83
<211> LENGTH: 113
<212> TYPE: PRT

```
<213> ORGANISM: Homo sapiens

<400> SEQUENCE: 83

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
        35                  40                  45

Lys Pro Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 84
<211> LENGTH: 339
<212> TYPE: DNA
<213> ORGANISM: Homo sapiens

<400> SEQUENCE: 84
ctgagagtga agttcagcag gagcgcagac gccccgcgt accagcaggg ccagaaccag      60
ctctataacg agctcaatct aggacgaaga gaggagtacg atgttttgga caagagacgt     120
ggccgggacc ctgagatggg gggaaagccg agaaggaaga accctcagga aggcctgtac     180
aatgaactgc agaaagataa gatggcggag gcctacagtg agattgggat gaaaggcgag     240
cgccggaggg gcaagggca cgatggcctt taccagggtc tcagtacagc caccaaggac     300
acctacgacg cccttcacat gcaggccctg cccccctcgc                          339

<210> SEQ ID NO 85
<211> LENGTH: 17
<212> TYPE: DNA
<213> ORGANISM: Artificial Sequence
<220> FEATURE:
<223> OTHER INFORMATION: Poly(A) sequence

<400> SEQUENCE: 85
aaataaaata cgaaatg                                                     17

<210> SEQ ID NO 86
<211> LENGTH: 62
<212> TYPE: PRT
<213> ORGANISM: Homo sapiens

<400> SEQUENCE: 86

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60
```

SINGLE- AND MULTI-CHAIN CHIMERIC ANTIGEN RECEPTORS

CROSS-REFERENCE TO RELATED APPLICATIONS

This application claims priority to U.S. Patent Application Ser. No. 62/609,895, filed Dec. 22, 2017, and U.S. Provisional Patent Application Ser. No. 62/767,212, filed Nov. 14, 2018, the entire contents of these two applications are herein incorporated by reference.

TECHNICAL FIELD

The present disclosure relates to the field of biotechnology, and more specifically, to single-chain and multi-chain chimeric antigen receptors.

BACKGROUND

Chimeric antigen receptors (CARs) are a subclass of single-chain and multi-chain polypeptides. Chimeric antigen receptors typically include, e.g., an antigen-binding domain, a transmembrane domain, and one or more signaling domains. CARs have been investigated for use in the clinical treatment of different cancers, e.g., hematological cancers, in mammals.

SUMMARY

The present disclosure is based, at least in part, on the discovery that chimeric antigen-receptors that have a specific combination of intracellular signaling domains, when expressed in a T-cell, demonstrated improved T-cell activation, improved target cell killing, and improved cytokine secretion including IL-2, interferon-gamma, and TNFα, as compared to a T-cell that expresses a chimeric antigen receptor that includes only includes the intracellular signaling domains from CD3 and CD3ζ.

Provided herein are single-chain chimeric antigen receptors that include: an extracellular antigen-binding domain; a transmembrane domain; a first intracellular signaling domain from DAP-10 or DAP12; a second intracellular signaling domain from a protein selected from the group of: 4-1BB, CD27, OX40, CD40, CD28, GITR, CD2, CD5, ICAM-1, CD11a, Lck, TNFR-I, TNFR-II, FasR, CD30, ICOS, LIGHT, NKG2C, and B7-H3; and an immunoreceptor tyrosine-based activation motif (ITAM). In some embodiments of any of the single-chain chimeric antigen receptors described herein, the extracellular antigen-binding domain is selected from the group of: a scFv, a (scFv)₂, a $V_HH$ domain, and a $V_{NAR}$ domain. In some embodiments of any of the single-chain chimeric antigen receptors described herein, the extracellular antigen-binding domain is a scFv.

In some embodiments of any of the single-chain chimeric antigen receptors described herein, the extracellular antigen-binding domain binds specifically to a single antigen. In some embodiments of any of the single-chain chimeric antigen receptors described herein, the single antigen is a tumor antigen. In some embodiments of any of the single-chain chimeric antigen receptors described herein, the tumor antigen is selected from the group of: MAGE, MUC16, CD19, WT-1, CD22, LI-CAM, ROR-1, CEA, 4-1BB, ETA, 5T4, adenocarcinoma antigen, alpha-fetoprotein (AFP), BAFF, B-lymphoma cell, C242 antigen, CA-125, carbonic anhydrase 9 (CA-IX), C-MET, CCR4, CD152, CD20, CD125 CD200, CD221, CD23 (IgE receptor), CD28, CD30

(TNFRSF8), CD33, CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgGl, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, and vimentin. In some embodiments of any of the single-chain chimeric antigen receptors described herein, the tumor antigen is CD19. In some embodiments of any of the single-chain chimeric antigen receptors described herein, the extracellular antigen-binding domain binds specifically to two different antigens.

In some embodiments of any of the single-chain chimeric antigen receptors described herein, the transmembrane domain is a transmembrane domain from: a chain of α T cell receptor, β chain of the T cell receptor, ζ chain of the T cell receptor, CD28, CD3ε, CD3δ, CD3γ, CD33, CD37, CD64, CD80, CD45, CD4, CD5, CD8α, CD9, CD16, CD22, CD86, or CD154. In some embodiments of any of the single-chain chimeric antigen receptors described herein, the ITAM comprises a cytoplasmic signaling sequence from CD3ζ.

In some embodiments of any of the single-chain chimeric antigen receptors described herein, when going in the N-terminal to the C-terminal direction or in the C-terminal to the N-terminal direction, the single-chain chimeric antigen receptor includes the extracellular antigen-binding domain, the transmembrane domain, the first intracellular signaling domain, the second intracellular signaling domain, and the ITAM. In some embodiments of any of the single-chain chimeric antigen receptors described herein, the transmembrane domain and the first intracellular signaling domain directly abut each other. In some embodiments of any of the single-chain chimeric antigen receptors described herein, the transmembrane domain and the first intracellular signaling domain are separated by 1 to 500 amino acids (e.g., 1 to 250 amino acids, or 1 to 50 amino acids). In some embodiments of any of the single-chain chimeric antigen receptors described herein, the first intracellular signaling domain and the second intracellular signaling domain directly abut each other. In some embodiments of any of the single-chain chimeric antigen receptors described herein, the first intracellular signaling domain and the second intracellular signaling domain are separated by 1 to 500 amino acids (e.g., 1 to 250 amino acids, or 1 to 50 amino acids). In some embodiments of any of the single-chain chimeric antigen receptors described herein, the second intracellular signaling domain and the ITAM directly abut each other. In some embodiments of any of the single-chain chimeric antigen receptors described herein, the second intracellular signaling domain and the ITAM are separated by 1 to 500 amino acids (e.g., 1 to 250 amino acids, or 1 to 50 amino acids).

In some embodiments of any of the single-chain chimeric antigen receptors described herein, when going in the N-terminal to the C-terminal direction or in the C-terminal to the N-terminal direction, the single-chain chimeric antigen receptor includes the extracellular antigen-binding domain, the transmembrane domain, the second intracellular signaling domain, the first intracellular signaling domain, and the ITAM.

In some embodiments of any of the single-chain chimeric antigen receptors described herein, when going in the N-terminal to the C-terminal direction or in the C-terminal to the N-terminal direction, the single-chain chimeric antigen receptor includes the extracellular antigen-binding domain, the transmembrane domain, the first intracellular signaling domain, the ITAM, and the second intracellular signaling domain.

In some embodiments of any of the single-chain chimeric antigen receptors described herein, when going in the N-terminal to the C-terminal direction or in the C-terminal to the N-terminal direction, the single-chain chimeric antigen receptor includes the extracellular antigen-binding domain, the transmembrane domain, the second intracellular signaling domain, the ITAM, and the first intracellular signaling domain.

In some embodiments of any of the single-chain chimeric antigen receptors described herein, when going to the N-terminal to the C-terminal direction or in the C-terminal to the N-terminal direction, the single-chain chimeric antigen receptor includes the extracellular antigen-binding domain, the transmembrane domain, the ITAM, the first intracellular signaling domain, and the second intracellular signaling domain.

In some embodiments of any of the single-chain chimeric antigen receptors described herein, when going to the N-terminal to the C-terminal direction or in the C-terminal to the N-terminal direction, the single-chain chimeric antigen receptor includes the extracellular antigen-binding domain, the transmembrane domain, the ITAM, the second intracellular signaling domain, and the first intracellular signaling domain.

In some embodiments of any of the single-chain chimeric antigen receptors described herein, the extracellular antigen-binding domain and the transmembrane domain directly abut each other. In some embodiments of any of the single-chain chimeric antigen receptors described herein, the extracellular antigen-binding domain and the transmembrane domain are separated by 1 to 500 amino acids (e.g., 1 to 250 amino acids, or 1 to 50 amino acids).

In some embodiments of any of the single-chain chimeric antigen receptors described herein, the first intracellular signaling domain is from DAP-10. In some embodiments of any of the single-chain chimeric antigen receptors described herein, the first intracellular signaling domain is from DAP-12.

Also provided herein are nucleic acids that include a nucleotide sequence encoding any of the single-chain chimeric antigen receptors described herein. Also provided herein are vectors that include any of the nucleic acids described herein that include a nucleotide sequence encoding any of the single-chain chimeric antigen receptors described herein.

Also provided herein are mammalian cells that include any of the vectors described herein. In some embodiments of any of the mammalian cells described herein, the mammalian cell is a T cell. In some embodiments of any of the mammalian cells described herein, the mammalian cell is selected from the group of: a CD8$^+$ T cell, a CD4$^+$ T cell, a memory T cell, a Treg cell, natural killer T cell, B cell, and a macrophage/monocyte. In some embodiments of any of the mammalian cells described herein, the mammalian cell is a mammalian cell obtained from a subject. In some embodiments of any of the mammalian cells described herein, the subject is diagnosed or identified as having a cancer. In some embodiments of any of the mammalian cells described herein, the subject is human.

Also provided herein are pharmaceutical compositions that include any of the mammalian cells described herein and a pharmaceutically acceptable carrier. Also provided herein are kits that include any of the pharmaceutical compositions described herein.

Also provided herein are pharmaceutical compositions that include any of the nucleic acids described herein or any of the vectors described herein, and a pharmaceutically acceptable carrier. Also provided herein are kits that include any of the pharmaceutical compositions described herein.

Also provided herein are methods of generating a chimeric antigen receptor-expressing cell, the method comprising introducing into a mammalian cell any of the nucleic acids described herein or any of the vectors described herein. In some embodiments of any of the methods described herein, the mammalian cell is a human cell. In some embodiments of any of the methods described herein, the mammalian cell is a cell selected from the group of: a CD8+ T cell, a CD4+ T cell, a memory T cell, a Treg cell, natural killer T cell, B cell, and a macrophage/monocyte. In some embodiments of any of the methods described herein, the mammalian cell is a mammalian cell obtained from a subject. In some embodiments of any of the methods described herein, the subject is diagnosed or identified as having a cancer. Some embodiments of any of the methods described herein further include, after the introducing step: culturing the cell in a liquid culture medium. Some embodiments of any of the methods described herein further include, before the introducing step: obtaining the mammalian cell from the subject.

Also provided herein are methods of treating a cancer in a subject that include administering a therapeutically effective amount of any of the mammalian cells described herein to the subject. Some embodiments of any of the methods described herein further include, prior to the administering step, obtaining an initial cell from the subject; and introducing any of the nucleic acids described herein or any of the vectors described herein into the initial cell, to yield the mammalian cell that is administered to the subject. Some embodiments of any of the methods described herein further include, between the introducing step and the administering step, a step of culturing the cell that is administered to the subject in a liquid culture medium. In some embodiments of any of the methods described herein, the subject is human.

Also provided herein are multi-chain chimeric antigen receptors that include at least one first polypeptide including: a transmembrane domain; a first intracellular signaling domain from DAP-10 or DAP-12; a second intracellular signaling domain from a protein selected from the group of: 4-1BB, CD27, OX40, CD40, CD28, GITR, CD2, CD5, ICAM-1, CD11a, Lck, TNFR-I, TNFR-II, FasR, CD30, ICOS, LIGHT, NKG2C, and B7-H3; and an immunoreceptor tyrosine-based activation motif (ITAM). In some embodiments of any of the multi-chain chimeric antigen receptors described herein, the transmembrane domain is a transmembrane domain from: α chain of a T cell receptor, β chain of the T cell receptor, ζ chain of the T cell receptor, CD28, CD3ε, CD3δ, CD3γ, CD33, CD37, CD64, CD80, CD45, CD4, CD5, CD8α, CD9, CD16, CD22, CD86, or CD154. In some embodiments of any of the multi-chain chimeric antigen receptors described herein, the ITAM includes a cytoplasmic signaling sequence from CD3ζ.

In some embodiments of any of the multi-chain chimeric antigen receptors described herein, when going in the N-terminal to the C-terminal direction or in the C-terminal to the N-terminal direction, the at least one first polypeptide includes the transmembrane domain, the first intracellular signaling domain, the second intracellular signaling domain, and the ITAM. In some embodiments of any of the multi-chain chimeric antigen receptors described herein, the transmembrane domain and the first intracellular signaling domain directly abut each other. In some embodiments of any of the multi-chain chimeric antigen receptors described herein, the transmembrane domain and the first intracellular signaling domain are separated by 1 to 500 amino acids (e.g., 1 to 250 amino acids, or 1 to 50 amino acids). In some embodiments of any of the multi-chain chimeric antigen receptors described herein, the first intracellular signaling domain and the second intracellular signaling domain directly abut each other. In some embodiments of any of the multi-chain chimeric antigen receptors described herein, the first intracellular signaling domain and the second intracellular signaling domain are separated by 1 to 500 amino acids (e.g., 1 to 250 amino acids, or 1 to 50 amino acids). In some embodiments of any of the multi-chain chimeric antigen receptors described herein, the second intracellular signaling domain and the ITAM directly abut each other. In some embodiments of any of the multi-chain chimeric antigen receptors described herein, the second intracellular signaling domain and the ITAM are separated by 1 to 500 amino acids (e.g., 1 to 250 amino acids, or 1 to 50 amino acids).

In some embodiments of any of the multi-chain chimeric antigen receptors described herein, when going in the N-terminal to the C-terminal direction or in the C-terminal to the N-terminal direction, the at least one first polypeptide includes the transmembrane domain, the second intracellular signaling domain, the first intracellular signaling domain, and the ITAM.

In some embodiments of any of the multi-chain chimeric antigen receptors described herein, when going in the N-terminal to the C-terminal direction or in the C-terminal to the N-terminal direction, the at least one first polypeptide includes the transmembrane domain, the first intracellular signaling domain, the ITAM, and the second intracellular signaling domain.

In some embodiments of any of the multi-chain chimeric antigen receptors described herein, when going in the N-terminal to the C-terminal direction or in the C-terminal to the N-terminal direction, the at least one first polypeptide includes the transmembrane domain, the second intracellular signaling domain, the ITAM, and the first intracellular signaling domain.

In some embodiments of any of the multi-chain chimeric antigen receptors described herein, when going to the N-terminal to the C-terminal direction or in the C-terminal to the N-terminal direction, the at least one first polypeptide includes the transmembrane domain, the ITAM, the first intracellular signaling domain, and the second intracellular signaling domain.

In some embodiments of any the multi-chain chimeric antigen receptors described herein, when going to the N-terminal to the C-terminal direction or in the C-terminal to the N-terminal direction, the at least one first polypeptide includes the transmembrane domain, the ITAM, the second intracellular signaling domain, and the first intracellular signaling domain.

In some embodiments of any of the multi-chain chimeric antigen receptors described herein, the first intracellular signaling domain is from DAP-10. In some embodiments of any of the multi-chain chimeric antigen receptors described herein, the first intracellular signaling domain is from DAP-12.

Also provided herein are nucleic acids that encode any of the multi-chain chimeric antigen receptors described herein. Also provided herein are sets of nucleic acids that together encode any of the multi-chain chimeric antigen receptors described herein.

Also provided herein are mammalian cells that include any of the nucleic acids described herein that encode any of the multi-chain chimeric antigen receptors described herein. Also provided herein are mammalian cells that include any of the sets of nucleic acids described herein that together encode any of the multi-chain chimeric antigen receptors described herein. In some embodiments of any of the mammalian cells described herein, the mammalian cell is a T cell. In some embodiments of any of the mammalian cells described herein, the mammalian cell is selected from the group of: a CD8$^+$ T cell, a CD4$^+$ T cell, a memory T cell, a Treg cell, natural killer T cell, B cell, and a macrophage/monocyte. In some embodiments of any of the mammalian cells described herein, the mammalian cell is a mammalian cell obtained from a subject. In some embodiments of any of the mammalian cells described herein, the subject is diagnosed or identified as having a cancer. In some embodiments of any of the mammalian cells described herein, the subject is human.

Also provided herein are pharmaceutical compositions that include any of the mammalian cells described herein and a pharmaceutically acceptable carrier. Also provided herein are kits that include any of the pharmaceutical compositions described herein.

Also provided herein are pharmaceutical compositions that include any of the nucleic acids described herein that encode any of the multi-chain chimeric antigen receptors described herein, or any of the sets of nucleic acids described herein that together encode any of the multi-chain chimeric antigen receptors described herein, and a pharmaceutically acceptable carrier. Also provided herein are kits that include any of the pharmaceutical compositions described herein.

Also provided herein are methods of generating a multi-chain chimeric antigen receptor-expressing cell that include introducing into a mammalian cell any of the nucleic acids described herein that encode any of the multi-chain chimeric antigen receptors described herein, or any of the sets of nucleic acids described herein that encode any of the multi-chain chimeric antigen receptors described herein. In some embodiments of any of the methods described herein, the mammalian cell is a human cell. In some embodiments of any of the methods described herein, the mammalian cell is a cell selected from the group consisting of: a CD8+ T cell, a CD4+ T cell, a memory T cell, a Treg cell, natural killer T cell, B cell, and a macrophage/monocyte. In some embodiments of any of the methods described herein, the mammalian cell is a mammalian cell obtained from a subject. In some embodiments of any of the methods described herein, the subject is diagnosed or identified as having a cancer. Some embodiments of any of the methods described herein further include, after the introducing step, culturing the cell in a liquid culture medium. Some embodiments of any of the methods described herein further include, before the introducing step, obtaining the mammalian cell from the subject.

Also provided herein are methods of treating cancer in a subject that include administering a therapeutically effective amount of any of the mammalian cell described herein to the subject. Some embodiments of any of the methods described herein further include, prior to the administering step, obtaining an initial cell from the subject; and introducing any of the nucleic acids descried herein that encode any of the multi-chain chimeric antigen receptors described herein or any of the sets of nucleic acids described herein that together encode any of the multi-chain chimeric antigen receptors described herein into the initial cell, to yield the mammalian cell that is administered to the subject.

Some embodiments of any of the methods described herein further include, between the introducing step and the administering step, a step of culturing the cell that is administered to the subject in a liquid culture medium. In some embodiments of any of the methods described herein, the subject is human.

Also provided herein are single-chain chimeric antigen receptors that include: an extracellular antigen-binding domain; a transmembrane domain; an intracellular signaling domain from a protein selected from the group of: 4-1BB, CD27, OX40, CD40, CD28, GITR, DAP-10, DAP-12, CD2, CD5, ICAM-1, CD11a, Lck, TNFR-I, TNFR-II, FasR, CD30, ICOS, LIGHT, NKG2C, and B7-H3; and an immunoreceptor tyrosine-based activation motif (ITAM). In some embodiments of any of the single-chain chimeric antigen receptors described herein, the extracellular antigen-binding domain is selected from the group consisting of: a scFv, a $(scFv)_2$, a $V_HH$ domain, and a $V_{NAR}$ domain. In some embodiments of any of the single-chain chimeric antigen receptors described herein, the extracellular antigen-binding domain is a scFv. In some embodiments of any of the single-chain chimeric antigen receptors described herein, the extracellular antigen-binding domain binds specifically to a single antigen. In some embodiments of any of the single-chain chimeric antigen receptors described herein, the single antigen is a tumor antigen. In some embodiments of any of the single-chain chimeric antigen receptors described herein, the tumor antigen is selected from the group of: MAGE, MUC16, CD19, WT-1, CD22, LI-CAM, ROR-1, CEA, 4-1BB, ETA, 5T4, adenocarcinoma antigen, alpha-fetoprotein (AFP), BAFF, B-lymphoma cell, C242 antigen, CA-125, carbonic anhydrase 9 (CA-IX), C-MET, CCR4, CD152, CD20, CD125 CD200, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgGl, IL-13, IL-6, insulin-like growth factor I receptor, integrin $\alpha5\beta1$, integrin $\alpha v\beta3$, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, SCH 900105, SDC1, SLAMF7, TAG-72, tenascin C, TGF beta 2, TGF-$\beta$, TRAIL-R1, TRAIL-R2, tumor antigen CTAA16.88, VEGF-A, VEGFR-1, VEGFR2, and vimentin. In some embodiments of any of the single-chain chimeric antigen receptors described herein, the tumor antigen is CD19. In some embodiments of any of the single-chain chimeric antigen receptors described herein, the extracellular antigen-binding domain binds specifically to two different antigens.

In some embodiments of any of the single-chain chimeric antigen receptors described herein, the transmembrane domain is a transmembrane domain from: a chain of a T cell receptor, $\beta$ chain of the T cell receptor, $\zeta$ chain of the T cell receptor, CD28, CD3$\epsilon$, CD3$\delta$, CD3$\gamma$, CD33, CD37, CD64, CD80, CD45, CD4, CD5, CD8$\alpha$, CD9, CD16, CD22, CD86, or CD154. In some embodiments of any of the single-chain chimeric antigen receptors described herein, the ITAM includes a cytoplasmic signaling sequence from CD3$\zeta$.

In some embodiments of any of the single-chain chimeric antigen receptors described herein, when going in the N-terminal to the C-terminal direction or in the C-terminal to the N-terminal direction, the single-chain chimeric antigen receptor include the extracellular antigen-binding domain, the transmembrane domain, the intracellular signaling domain, and the ITAM. In some embodiments of any of the single-chain chimeric antigen receptors described herein, the transmembrane domain and the intracellular signaling domain directly abut each other. In some embodiments of any of the single-chain chimeric antigen receptors described herein, the transmembrane domain and the intracellular signaling domain are separated by 1 to 500 amino acids (e.g., 1 to 250 amino acids, or 1 to 50 amino acids). In some embodiments of any of the single-chain chimeric antigen receptors described herein, the intracellular signaling domain and the ITAM directly abut each other. In some embodiments of any of the single-chain chimeric antigen receptors described herein, the intracellular signaling domain and the ITAM are separated by 1 to 500 amino acids (e.g., 1 to 250 amino acids, or 1 to 50 amino acids).

In some embodiments of any of the single-chain chimeric antigen receptors described herein, when going in the N-terminal to the C-terminal direction or in the C-terminal to the N-terminal direction, the single-chain chimeric antigen receptor includes the extracellular antigen-binding domain, the transmembrane domain, the ITAM, and the intracellular signaling domain. In some embodiments of any of the single-chain chimeric antigen receptors described herein, the extracellular antigen-binding domain and the transmembrane domain directly abut each other. In some embodiments of any of the single-chain chimeric antigen receptors described herein, the extracellular antigen-binding domain and the transmembrane domain are separated by 1 to 500 amino acids (e.g., 1 to 250 amino acids, or 1 to 50 amino acids).

Also provided herein are nucleic acids the include a nucleotide sequence encoding any of the single-chain chimeric antigen receptors described herein. Also provided herein are vectors that include any of the nucleic acids described herein that encode any of the single-chain chimeric antigen receptors described herein.

Also provided herein are mammalian cells that include any of the vectors described herein. In some embodiments of any of the mammalian cells described herein, the mammalian cell is a T cell. In some embodiments of any of the mammalian cells described herein, the mammalian cell is selected from the group of: a CD8$^+$ T cell, a CD4$^+$ T cell, a memory T cell, a Treg cell, natural killer T cell, B cell, and a macrophage/monocyte. In some embodiments of any of the mammalian cells described herein, the mammalian cell is a mammalian cell obtained from a subject. In some embodiments of any of the mammalian cells described herein, the subject is diagnosed or identified as having a cancer. In some embodiments of any of the mammalian cells described herein, the subject is human.

Also provided herein are pharmaceutical compositions that include any of the mammalian cells described herein and a pharmaceutically acceptable carrier. Also provided herein are kits that include any of the pharmaceutical compositions described herein.

Also provided herein are pharmaceutical compositions that include any of the nucleic acids described herein that encode any of the single-chain chimeric antigen receptors described herein, and a pharmaceutically acceptable carrier. Also provided herein are kits that include any of the pharmaceutical compositions described herein.

Also provided herein are methods of generating a chimeric antigen receptor-expressing cell that include introducing into a mammalian cell any of the nucleic acids described herein that encode any of the single-chain chimeric antigen receptors described herein or any of the vectors described herein. In some embodiments of any of the methods described herein, the mammalian cell is a human cell. In some embodiments of any of the methods described herein, the mammalian cell is a cell selected from the group of: a CD8+ T cell, a CD4+ T cell, a memory T cell, a Treg cell, natural killer T cell, B cell, and a macrophage/monocyte. In some embodiments of any of the methods described herein, the mammalian cell is a mammalian cell obtained from a subject. In some embodiments of any of the methods described herein, the subject is diagnosed or identified as having a cancer. Some embodiments of any of the methods described herein further include, after the introducing step, culturing the cell in a liquid culture medium. Some embodiments of any of the methods described herein further include, before the introducing step, obtaining the mammalian cell from the subject.

Also provided herein are methods of treating a cancer in a subject that include administering a therapeutically effective amount of any of the mammalian cells described herein. Some embodiments of any of the methods described herein further include, prior to the administering step, obtaining an initial cell from the subject; and introducing any of the nucleic acids described herein that encode any of the single-chain chimeric antigen receptors described herein or any of the vectors described herein into the initial cell, to yield the mammalian cell that is administered to the subject. Some embodiments of any of the methods described herein further include, between the introducing step and the administering step, a step of culturing the cell that is administered to the subject in a liquid culture medium. In some embodiments of any of the methods described herein, the subject is human.

Also provided herein are multi-chain chimeric antigen receptors that include at least one first polypeptide including: a transmembrane domain; an intracellular signaling domain from a protein selected from the group of: 4-1BB, CD27, OX40, CD40, CD28, GITR, DAP-10, DAP-12, CD2, CD5, ICAM-1, CD11a, Lck, TNFR-I, TNFR-II, FasR, CD30, ICOS, LIGHT, NKG2C, and B7-H3; and an immunoreceptor tyrosine-based activation motif (ITAM). In some embodiments of any of the multi-chain chimeric antigen receptors described herein, the transmembrane domain is a transmembrane domain from: α chain of a T cell receptor, β chain of the T cell receptor, ζ chain of the T cell receptor, CD28, CD3ε, CD3δ, CD3γ, CD33, CD37, CD64, CD80, CD45, CD4, CD5, CD8α, CD9, CD16, CD22, CD86, or CD154. In some embodiments of any of the multi-chain chimeric antigen receptors described herein, the ITAM includes a cytoplasmic signaling sequence from CD3ζ.

In some embodiments of any of the multi-chain chimeric antigen receptors described herein, when going in the N-terminal to the C-terminal direction or in the C-terminal to the N-terminal direction, the at least one first polypeptide includes the transmembrane domain, the intracellular signaling domain, and the ITAM. In some embodiments of any of the multi-chain chimeric antigen receptors described herein, the transmembrane domain and the intracellular signaling domain directly abut each other. In some embodiments of any of the multi-chain chimeric antigen receptors described herein, the transmembrane domain and the intracellular signaling domain are separated by 1 to 500 amino acids (e.g., 1 to 250 amino acids, or 1 to 50 amino acids). In some embodiments of any of the multi-chain chimeric antigen receptors described herein, the intracellular signaling domain and the ITAM directly abut each other. In some embodiments of any of the multi-chain chimeric antigen receptors described herein, the intracellular signaling domain and the ITAM are separated by 1 to 500 amino acids (e.g., 1 to 250 amino acids, or 1 to 50 amino acids).

In some embodiments of any of the multi-chain chimeric antigen receptors described herein, when going in the N-terminal to the C-terminal direction or in the C-terminal to the N-terminal direction, the at least one first polypeptide includes the transmembrane domain, the ITAM, and the intracellular signaling domain.

Also provided herein are nucleic acids that encode any of the multi-chain chimeric antigen receptors described herein. Also provided herein are sets of nucleic acids that together encode any of the multi-chain chimeric antigen receptors described herein.

Also provided herein are mammalian cells that include any of the nucleic acids described herein that encode any of the multi-chain chimeric antigen receptors described herein. Also provided herein are mammalian cells that include any of the sets of nucleic acids described herein that together encode any of the multi-chain chimeric antigen receptors described herein. In some embodiments of any of the mammalian cells described herein, the mammalian cell is a T cell. In some embodiments of any of the mammalian cells described herein, the mammalian cell is selected from the group of: a CD8+ T cell, a CD4+ T cell, a memory T cell, a Treg cell, natural killer T cell, B cell, and a macrophage/monocyte. In some embodiments of any of the mammalian cells described herein, the mammalian cell is a mammalian cell obtained from a subject. In some embodiments of any of the mammalian cells described herein, the subject is diagnosed or identified as having a cancer. In some embodiments of any of the mammalian cells described herein, the subject is human.

Also provided herein are pharmaceutical compositions that include any of the mammalian cells described herein and a pharmaceutically acceptable carrier. Also provided herein are kits that include any of the pharmaceutical compositions described herein.

Also provided herein are pharmaceutical compositions that include any of the nucleic acids described herein that encode any of the multi-chain chimeric antigen receptors described herein or any of the sets of nucleic acids described herein that together encode any of the multi-chain chimeric antigen receptors described herein, and a pharmaceutically acceptable carrier. Also provided are kits that include any of the pharmaceutical compositions described herein.

Also provided herein are methods of generating a chimeric antigen receptor-expressing cell that include introducing into a mammalian cell any of the nucleic acids described herein that encode any of the multi-chain chimeric antigen receptors described herein or any of the sets of nucleic acids described herein that encode any of the multi-chain chimeric antigen receptors described herein. In some embodiments of any of the methods described herein, the mammalian cell is a human cell. In some embodiments of any of the methods described herein, the mammalian cell is a cell selected from the group consisting of: a CD8+ T cell, a CD4+ T cell, a memory T cell, a Treg cell, natural killer T cell, B cell, and a macrophage/monocyte. In some embodiments of any of the methods described herein, the mammalian cell is a mammalian cell obtained from a subject. In some embodiments of any of the methods described herein, the subject is diagnosed or identified as having a cancer. Some embodiments of any of the methods described herein further include, after the introducing step, culturing the cell in a liquid culture medium. Some embodiments of any of the methods described herein further include, before the introducing step, obtaining the mammalian cell from the subject.

Also provided herein are methods of treating a cancer in a subject that include administering a therapeutically effective amount of any of the mammalian cells described herein. Some embodiments of any of the methods described herein further include, prior to the administering step, obtaining an initial cell from the subject; and introducing any of the nucleic acids described herein that encode any of the multi-chain chimeric antigen receptors described herein, of any of the sets of nucleic acids described herein that encode any of the multi-chain chimeric antigen receptors described herein into the initial cell, to yield the mammalian cell that is administered to the subject. Some embodiments of any of the methods described herein further include, between the introducing step and the administering step, a step of culturing the cell that is administered to the subject in a liquid culture medium. In some embodiments of any of the methods described herein, the subject is human.

The use of the term "a" before a noun is meant "one or more" of the particular noun. For example, the phrase "a mammalian cell" means "one or more mammalian cell."

The terms "chimeric antigen receptor" and "CAR" are used interchangeably herein, and refer to artificial multi-module molecules capable of triggering or inhibiting the activation of an immune cell which generally but not exclusively comprise an extracellular domain (e.g., a ligand/antigen binding domain), a transmembrane domain and one or more intracellular signaling domains. CAR molecules and derivatives thereof (e.g., CAR variants) are described, e.g., in PCT Application No. US2014/016527; Fedorov et al. *Sci Transl Med* (2013); 5(215):215ra172; Glienke et al. *Front Pharmacol* (2015) 6:21; Kakarla & Gottschalk 52 *Cancer J* (2014) 20(2):151-5; Riddell et al. *Cancer J* (2014) 20(2): 141-4; Pegram et al. *Cancer J* (2014) 20(2):127-33; Cheadle et al. *Immunol Rev* (2014) 257(1):91-106; Barrett et al. *Annu Rev Med* (2014) 65:333-47; Sadelain et al. *Cancer Discov* (2013) 3(4):388-98; Cartellieri et al., *J Biomed Biotechnol* (2010) 956304; the disclosures of which are incorporated herein by reference in their entirety. A CAR can be a single-chain chimeric antigen receptor or a multi-chain chimeric antigen receptor.

The term "single-chain chimeric antigen receptor" means a chimeric antigen receptor that is a single-chain polypeptide.

The term "multi-chain chimeric antigen receptor" means a chimeric antigen receptor including two or more single-chain polypeptides.

The term "transmembrane domain" means a domain of a polypeptide that includes at least one contiguous amino acid sequence that traverses a lipid bilayer when present in the corresponding endogenous polypeptide when expressed in a mammalian cell. For example, a transmembrane domain can include one, two, three, four, five, six, seven, eight, nine, or ten contiguous amino acid sequences that each traverse a lipid bilayer when present in the corresponding endogenous polypeptide when expressed in a mammalian cell. As is known in the art, a transmembrane domain can, e.g., include at least one (e.g., two, three, four, five, six, seven, eight, nine, or ten) contiguous amino acid sequence (that traverses a lipid bilayer when present in the corresponding endogenous polypeptide when expressed in a mammalian cell) that has α-helical secondary structure in the lipid bilayer. In some embodiments, a transmembrane domain can include two or more contiguous amino acid sequences (that each traverse a lipid bilayer when present in the corresponding endogenous polypeptide when expressed in a mammalian cell) that form a β-barrel secondary structure in the lipid bilayer. Non-limiting examples of transmembrane domains are described herein. Additional examples of transmembrane domains are known in the art.

The term "antigen-binding domain" means a domain that binds specifically to a target antigen. In some examples, an antigen-binding domain can be formed from the amino acids present within a single-chain polypeptide. In other examples, an antigen-binding domain can be formed from amino acids present within a first single-chain polypeptide and the amino acids present in one or more additional single-chain polypeptides (e.g., a second single-chain polypeptide). Non-limiting examples of antigen-binding domains are described herein, including, without limitation, scFvs, or LBDs of growth factors. Additional examples of antigen-binding domains are known in the art.

As used herein, the term "antigen" refers generally to a binding partner specifically recognized by an antigen-binding domain described herein. Exemplary antigens include different classes of molecules, such as, but not limited to, polypeptides and peptide fragments thereof, small molecules, lipids, carbohydrates, and nucleic acids. Non-limiting examples of antigen or antigens that can be specifically bound by any of the antigen-binding domains are described herein. Additional examples of antigen or antigens that can be specifically bound by any of the antigen-binding domains are known in the art.

The term "intracellular signaling domain" means an intracellular signaling domain from an endogenous signaling transmembrane polypeptide expressed in an immune cell (e.g., a T lymphocyte) that promotes downstream immune cell signaling (e.g., T-cell receptor signaling) and/or immune cell activation (e.g., T cell activation). Non-limiting examples of intracellular signaling domains are described herein. Additional examples of intracellular signaling domains are known in the art. See, e.g., Chen et al., *Nature Reviews Immunol.* 13:227-242, 2013.

The term "immunoreceptor tyrosine-based activation motif" or "ITAM)" means an amino acid motif that includes a four amino-acid consensus sequence of a tyrosine separated from a leucine or an isoleucine by two other amino acids (YxxL/I). The tyrosine residue in the four-amino acid consensus sequence becomes phosphorylated following interaction of a signaling pathway kinase (e.g., a lymphocyte signaling pathway kinase). Non-limiting examples of ITAMs are described herein. Additional examples of ITAMs are known in the art.

The phrase "treatment of cancer" means a reduction in the number, frequency, or severity of one or more (e.g., two, three, four, or five) symptoms of a cancer in a subject having a cancer. Non-limiting symptoms of cancer are described herein. Additional symptoms of cancer are known in the art.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIG. 3A shows TNF-alpha production. FIG. 3B shows interferon gamma production. FIG. 3C shows interleukin 2 production. The X axes of FIGS. 3 A-C show the intracellular signaling domain(s) and ITAM in each tested construct. The Y axes of FIGS. 3 A-C show the expression in pg/ml of TNF-alpha, interferon gamma, and interleukin 2 cytokines, respectively. The sequences of the various intracellular sequences of the CAR constructs are described in Example 1. UT=Untransduced.

DETAILED DESCRIPTION

Figure 1:
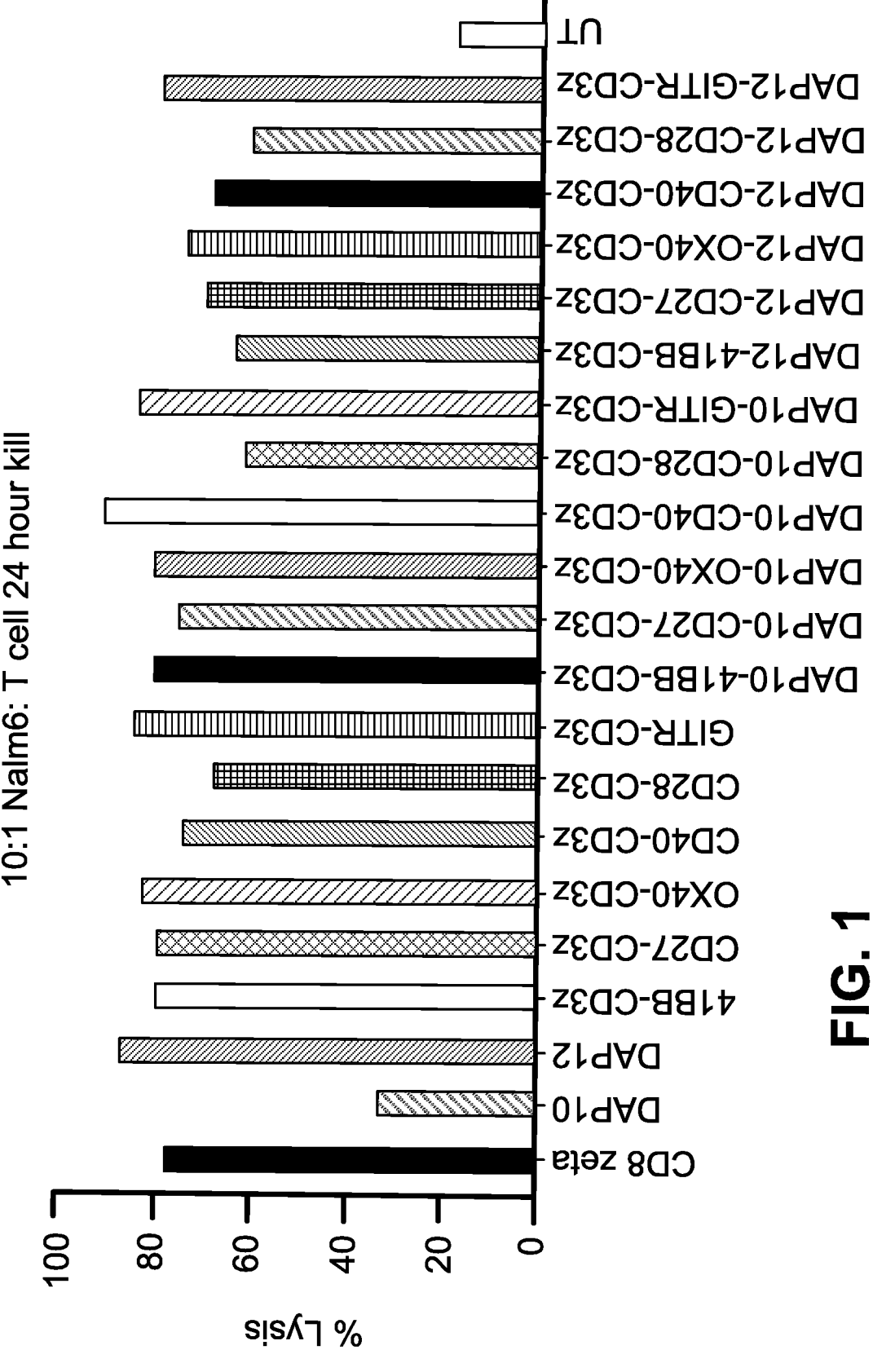
FIG. 1 shows the percent lysis of cell lines after co-culturing with CAR-T cells expressing various CAR constructs. The X axis shows the intracellular signaling domain (s) and ITAM in each tested construct. The Y axis shows the percentage of target cells that were lysed in the presence of the various CAR-T cells expressing the indicated CARs. The sequences of the various intracellular sequences of the CAR constructs are described in Example 1. UT=Untransduced.

Provided herein are single-chain chimeric antigen receptors that include: an extracellular antigen-binding domain; a transmembrane domain; a first intracellular signaling domain from DAP-10 or DAP-12, a second intracellular signaling domain from a protein selected from the group of 4-1BB, CD27, OX40, CD40, CD28, GITR, CD2, CD5, ICAM-1, CD11a, Lck, TNFR-I, TNFR-II, FasR, CD30, ICOS, LIGHT, NKG2C, and B7-H3; and an immunorecep-tor tyrosine-based activation motif (ITAM).

Also provided herein are multi-chain chimeric antigen receptors that comprise at least one first polypeptide includ-ing: a transmembrane domain; a first intracellular signaling domain from DAP-10 or DAP-12; a second intracellular signaling domain from a protein selected from the group of 4-1BB, CD27, OX40, CD40, CD28, GITR, CD2, CD5, ICAM-1, CD11a, Lck, TNFR-I, TNFR-II, FasR, CD30, ICOS, LIGHT, NKG2C, and B7-H3; and an ITAM.

Also provided herein are single-chain chimeric antigen receptors that include: an extracellular antigen-binding domain; a transmembrane domain; an intracellular signaling domain from a protein selected from the group of 4-1BB, CD27, OX40, CD40, CD28, GITR, DAP-10, DAP-12, CD2, CD5, ICAM-1, CD11a, Lck, TNFR-I, TNFR-II, FasR, CD30, ICOS, LIGHT, NKG2C, and B7-H3; and an ITAM. Some embodiments of any of the single-chain chimeric antigen receptors described herein can include, in addition to the extracellular antigen-binding domain, the transmem-brane domain, and the ITAM, one of the following combi-nations of intracellular signaling domains: (i) DAP12-OX40, (ii) DAP10-OX40, (iii) DAP12-CD40, (iv) DAP10-CD28, (v) DAP12-CD28, (vi) DAP10-41BB, (vii) DAP10-CD27, (viii) DAP10-CD40, (ix) DAP10-GITR, (x) DAP12-41BB, (xi) DAP12-CD27, (xii) DAP12-GITR, and (xiii) CD2-DAP12.

Also provided herein are multi-chain chimeric antigen receptors that comprise at least one first polypeptide includ-ing: an extracellular antigen-binding domain; a transmem-brane domain; an intracellular signaling domain from a protein selected from the group of 4-1BB, CD27, OX40, CD40, CD28, GITR, DAP-10, DAP-12, CD2, CD5, ICAM-1, CD11a, Lck, TNFR-I, TNFR-II, FasR, CD30, ICOS, LIGHT, NKG2C, and B7-H3; and an ITAM. Some embodi-ments of any of the multi-chain chimeric antigen receptors described herein comprise at least one first polypeptide that include, in addition to the extracellular antigen-binding domain, the transmembrane domain, and the ITAM, one of the following combinations of intracellular signaling domains: (i) DAP12-OX40, (ii) DAP10-OX40, (iii) DAP12-CD40, (iv) DAP10-CD28, (v) DAP12-CD28, (vi) DAP10-41BB, (vii) DAP10-CD27, (viii) DAP10-CD40, (ix) DAP10-GITR, (x) DAP12-41BB, (xi) DAP12-CD27, (xii) DAP12-GITR, and (xiii) CD2-DAP12.

Also provided herein are nucleic acids encoding any of the single-chain chimeric antigen receptors or any of the multi-chain chimeric antigen receptors described herein; vectors including any of these nucleic acids; mammalian cells including any of these vectors; and methods of treating a cancer in a subject by administering a mammalian cell (e.g., a T-cell) expressing any of the single-chain chimeric antigen receptors or any of the multi-chain chimeric antigen receptors described herein.

Non-limiting aspects of these single-chain chimeric anti-gen receptors, multi-chain chimeric antigen receptors, nucleic acids, vectors, mammalian cells, and methods are described below, and can be used in any combination without limitation. Additional aspects of these single-chain chimeric antigen receptors, multi-chain chimeric antigen receptors, nucleic acids, vectors, mammalian cells, and methods are known in the art.

In some embodiments, the compositions and/or methods disclosed herein can be used to selectively kill cancer cells in a subject. In some embodiments, a population of T-cells expressing any of the single-chain chimeric antigen recep-tors or any of the multi-chain chimeric antigen receptors described herein can have increased (e.g., a 1% to 300%, a 1% to 280%, a 1% to 260%, a 1% to 240%, a 1% to 220%, a 1% to 200%, a 1% to 190%, a 1% to 180%, a 1% to 170%, a 1% to 160%, a 1% to 150%, a 1% to 140%, a 1% to 130%, a 1% to 120%, a 1% to 110%, a 1% to 100%, a 1% to 95%, a 1% to 90%, a 1% to 85%, a 1% to 80%, a 1% to 75%, a 1% to 70%, a 1% to 65%, a 1% to 60%, a 1% to 55%, a 1% to 50%, a 1% to 45%, a 1% to 40%, a 1% to 35%, a 1% to 30%, a 1% to 25%, a 1% to 20%, a 1% to 15%, a 1% to 10%, a 1% to 5%, a 2% to 300%, a 2% to 280%, a 2% to 260%, a 2% to 240%, a 2% to 220%, a 2% to 200%, a 2% to 190%, a 2% to 180%, a 2% to 170%, a 2% to 160%, a 2% to 150%, a 2% to 140%, a 2% to 130%, a 2% to 120%, a 2% to 110%, a 2% to 100%, a 2% to 95%, a 2% to 90%, a 2% to 85%, a 2% to 80%, a 2% to 75%, a 2% to 70%, a 2% to 65%, a 2% to 60%, a 2% to 55%, a 2% to 50%, a 2% to 45%, a 2% to 40%, a 2% to 35%, a 2% to 30%, a 2% to 25%, a 2% to 20%, a 2% to 15%, a 2% to 10%, a 2% to 5%, a 3% to 300%, a 3% to 280%, a 3% to 260%, a 3% to 240%, a 3% to 220%, a 3% to 200%, a 3% to 190%, a 3% to 180%, a 3% to 170%, a 3% to 160%, a 3% to 150%, a 3% to 140%, a 3% to 130%, a 3% to 120%, a 3% to 110%, a 3% to 100%, a 3% to 95%, a 3% to 90%, a 3% to 85%, a 3% to 80%, a 3% to 75%, a 3% to 70%, a 3% to 65%, a 3% to 60%, a 3% to 55%, a 3% to 50%, a 3% to 45%, a 3% to 40%, a 3% to 35%, a 3% to 30%, a 3% to 25%, a 3% to 20%, a 3% to 15%, a 3% to 10%, a 3% to 5%, a 5% to 300%, a 5% to 280%, a 5% to 260%, a 5% to 240%, a 5% to 220%, a 5% to 200%, a 5% to 190%, a 5% to 180%, a 5% to 170%, a 5% to 160%, a 5% to 150%, a 5% to 140%, a 5% to 130%, a 5% to 120%, a 5% to 110%, a 5% to 100%, a 5% to 95%, a 5% to 90%, a 5% to 85%, a 5% to 80%, a 5% to 75%, a 5% to 70%, a 5% to 65%, a 5% to 60%, a 5% to 55%, a 5% to 50%, a 5% to 45%, a 5% to 40%, a 5% to 35%, a 5% to 30%, a 5% to 25%, a 5% to 20%, a 5% to 15%, a 5% to 10%, a 10% to 300%, a 10% to 280%, a 10% to 260%, a 10% to 240%, a 10% to 220%, a 10% to 200%, a 10% to 190%, a 10% to 180%, a 10% to 170%, a 10% to 160%, a 10% to 150%, a 10% to 140%, a 10% to 130%, a 10% to 120%, a 10% to 110%, a 10% to 100%, a 10% to 95%, a 10% to 90%, a 10% to 85%, a 10% to 80%, a 10% to 75%, a 10% to 70%, a 10% to 65%, a 10% to 60%, a 10% to 55%, a 10% to 50%, a 10% to 45%, a 10% to 40%, a 10% to 35%, a 10% to 30%, a 10% to 25%, a 10% to 20%, a 10% to 15%, a 15% to 300%, a 15% to 280%, a 15% to 260%, a 15% to 240%, a 15% to 220%, a 15% to 200%, a 15% to 190%, a 15% to 180%, a 15% to 170%, a 15% to 160%, a 15% to 150%, a 15% to 140%, a 15% to 130%, a 15% to 120%, a 15% to 110%, a 15% to 100%, a 15% to 95%, a 15% to 90%, a 15% to 85%, a 15% to 80%, a 15% to 75%, a 15% to 70%, a 15% to 65%, a 15% to 60%, a 15% to 55%, a 15% to 50%, a 15% to 45%, a 15% to 40%, a 15% to 35%, a 15% to 30%, a 15% to 25%, a 15% to 20%, a 20% to 300%, a 20% to 280%, a 20% to 260%, a 20% to 240%, a 20% to 220%, a 20% to 200%, a 20% to 190%, a 20% to 180%, a 20% to 170%, a 20% to 160%, a 20% to 150%, a 20% to 140%, a 20% to 130%, a 20% to 120%, a 20% to 110%, a 20% to 100%, a 20% to 95%, a 20% to 90%, a 20% to 85%, a 20% to 80%, a 20% to 75%, a 20% to 70%, a 20% to 65%, a 20% to 60%, a 20% to 55%, a 20% to 50%, a 20% to 45%, a 20% to 40%, a 20% to 35%, a 20% to 30%, a 20% to 25%, a 25% to 300%, a 25% to 280%, a 25% to 260%, a 25% to 240%, a 25% to 220%, a 25% to 200%, a 25% to 190%, a 25% to 180%, a 25% to 170%, a 25% to 160%, a 25% to 150%, a 25% to 140%, a 25% to 130%, a 25% to 120%, a 25% to 110%, a 25% to 100%, a 25% to 95%, a 25% to 90%, a 25% to 85%, a 25% to 80%, a 25% to 75%, a 25% to 70%, a 25% to 65%, a 25% to 60%, a 25% to 55%, a 25% to 50%, a 25% to 45%, a 25% to 40%, a 25% to 35%, a 25% to 30%, a 30% to 300%, a 30% to 280%, a 30% to 260%, a 30% to 240%, a 30% to 220%, a 30% to 200%, a 30% to 190%, a 30% to 180%, a 30% to 170%, a 30% to 160%, a 30% to 150%, a 30% to 140%, a 30% to 130%, a 30% to 120%, a 30% to 110%, a 30% to 100%, a 30% to 95%, a 30% to 90%, a 30% to 85%, a 30% to 80%, a 30% to 75%, a 30% to 70%, a 30% to 65%, a 30% to 60%, a 30% to 55%, a 30% to 50%, a 30% to 45%, a 30% to 40%, a 30% to 35%, a 35% to 300%, a 35% to 280%, a 35% to 260%, a 35% to 240%, a 35% to 220%, a 35% to 200%, a 35% to 190%, a 35% to 180%, a 35% to 170%, a 35% to 160%, a 35% to 150%, a 35% to 140%, a 35% to 130%, a 35% to 120%, a 35% to 110%, a 35% to 100%, a 35% to 95%, a 35% to 90%, a 35% to 85%, a 35% to 80%, a 35% to 75%, a 35% to 70%, a 35% to 65%, a 35% to 60%, a 35% to 55%, a 35% to 50%, a 35% to 45%, a 35% to 40%, a 40% to 300%, a 40% to 280%, a 40% to 260%, a 40% to 240%, a 40% to 220%, a 40% to 200%, a 40% to 190%, a 40% to 180%, a 40% to 170%, a 40% to 160%, a 40% to 150%, a 40% to 140%, a 40% to 130%, a 40% to 120%, a 40% to 110%, a 40% to 100%, a 40% to 95%, a 40% to 90%, a 40% to 85%, a 40% to 80%, a 40% to 75%, a 40% to 70%, a 40% to 65%, a 40% to 60%, a 40% to 55%, a 40% to 50%, a 40% to 45%, a 45% to 300%, a 45% to 280%, a 45% to 260%, a 45% to 240%, a 45% to 220%, a 45% to 200%, a 45% to 190%, a 45% to 180%, a 45% to 170%, a 45% to 160%, a 45% to 150%, a 45% to 140%, a 45% to 130%, a 45% to 120%, a 45% to 110%, a 45% to 100%, a 45% to 95%, a 45% to 90%, a 45% to 85%, a 45% to 80%, a 45% to 75%, a 45% to 70%, a 45% to 65%, a 45% to 60%, a 45% to 55%, a 45% to 50%, a 50% to 300%, a 50% to 280%, a 50% to 260%, a 50% to 240%, a 50% to 220%, a 50% to 200%, a 50% to 190%, a 50% to 180%, a 50% to 170%, a 50% to 160%, a 50% to 150%, a 50% to 140%, a 50% to 130%, a 50% to 120%, a 50% to 110%, a 50% to 100%, a 50% to 95%, a 50% to 90%, a 50% to 85%, a 50% to 80%, a 50% to 75%, a 50% to 70%, a 50% to 65%, a 50% to 60%, a 50% to 55%, a 55% to 300%, a 55% to 280%, a 55% to 260%, a 55% to 240%, a 55% to 220%, a 55% to 200%, a 55% to 190%, a 55% to 180%, a 55% to 170%, a 55% to 160%, a 55% to 150%, a 55% to 140%, a 55% to 130%, a 55% to 120%, a 55% to 110%, a 55% to 100%, a 55% to 95%, a 55% to 90%, a 55% to 85%, a 55% to 80%, a 55% to 75%, a 55% to 70%, a 55% to 65%, a 55% to 60%, a 60% to 300%, a 60% to 280%, a 60% to 260%, a 60% to 240%, a 60% to 220%, a 60% to 200%, a 60% to 190%, a 60% to 180%, a 60% to 170%, a 60% to 160%, a 60% to 150%, a 60% to 140%, a 60% to 130%, a 60% to 120%, a 60% to 110%, a 60% to 100%, a 60% to 95%, a 60% to 90%, a 60% to 85%, a 60% to 80%, a 60% to 75%, a 60% to 70%, a 60% to 65%, a 65% to 300%, a 65% to 280%, a 65% to 260%, a 65% to 240%, a 65% to 220%, a 65% to 200%, a 65% to 190%, a 65% to 180%, a 65% to 170%, a 65% to 160%, a 65% to 150%, a 65% to 140%, a 65% to 130%, a 65% to 120%, a 65% to 110%, a 65% to 100%, a 65% to 95%, a 65% to 90%, a 65% to 85%, a 65% to 80%, a 65% to 75%, a 65% to 70%, a 70% to 300%, a 70% to 280%, a 70% to 260%, a 70% to 240%, a 70% to 220%, a 70% to 200%, a 70% to 190%, a 70% to 180%, a 70% to 170%, a 70% to 160%, a 70% to 150%, a 70% to 140%, a 70% to 130%, a 70% to 120%, a 70% to 110%, a 70% to 100%, a 70% to 95%, a 70% to 90%, a 70% to 85%, a 70% to 80%, a 70% to 75%, a 75% to 300%, a 75% to 280%, a 75% to 260%, a 75% to 240%, a 75% to 220%, a 75% to 200%, a 75% to 190%, a 75% to 180%, a 75% to 170%, a 75% to 160%, a 75% to 150%, a 75% to 140%, a 75% to 130%, a 75% to 120%, a 75% to 110%, a 75% to 100%, a 75% to 95%, a 75% to 90%, a 75% to 85%, a 75% to 80%, a 80% to 300%, a 80% to 280%, a 80% to 260%, a 80% to 240%, a 80% to 220%, a 80% to 200%, a 80% to 190%, a 80% to 180%, a 80% to 170%, a 80% to 160%, a 80% to 150%, a 80% to 140%, a 80% to 130%, a 80% to 120%, a 80% to 110%, a 80% to 100%, a 80% to 95%, a 80% to 90%, a 80% to 85%, a 85% to 300%, a 85% to 280%, a 85% to 260%, a 85% to 240%, a 85% to 220%, a 85% to 200%, a 85% to 190%, a 85% to 180%, a 85% to 170%, a 85% to 160%, a 85% to 150%, a 85% to 140%, a 85% to 130%, a 85% to 120%, a 85% to 110%, a 85% to 100%, a 85% to 95%, a 85% to 90%, a 90% to 300%, a 90% to 280%, a 90% to 260%, a 90% to 240%, a 90% to 220%, a 90% to 200%, a 90% to 190%, a 90% to 180%, a 90% to 170%, a 90% to 160%, a 90% to 150%, a 90% to 140%, a 90% to 130%, a 90% to 120%, a 90% to 110%, a 90% to 100%, a 90% to 95%, a 95% to 300%, a 95% to 280%, a 95% to 260%, a 95% to 240%, a 95% to 220%, a 95% to 200%, a 95% to 190%, a 95% to 180%, a 95% to 170%, a 95% to 160%, a 95% to 150%, a 95% to 140%, a 95% to 130%, a 95% to 120%, a 95% to 110%, a 95% to 100%, a 100% to 300%, a 100% to 280%, a 100% to 260%, a 100% to 240%, a 100% to 220%, a 100% to 200%, a 100% to 190%, a 100% to 180%, a 100% to 170%, a 100% to 160%, a 100% to 150%, a 100% to 140%, a 100% to 130%, a 100% to 120%, a 100% to 110%, a 110% to 300%, a 110% to 280%, a 110% to 260%, a 110% to 240%, a 110% to 220%, a 110% to 200%, a 110% to 190%, a 110% to 180%, a 110% to 170%, a 110% to 160%, a 110% to 150%, a 110% to 140%, a 110% to 130%, a 110% to 120%, a 120% to 300%, a 120% to 280%, a 120% to 260%, a 120% to 240%, a 120% to 220%, a 120% to 200%, a 120% to 190%, a 120% to 180%, a 120% to 170%, a 120% to 160%, a 120% to 150%, a 120% to 140%, a 120% to 130%, a 130% to 300%, a 130% to 280%, a 130% to 260%, a 130% to 240%, a 130% to 220%, a 130% to 200%, a 130% to 190%, a 130% to 180%, a 130% to 170%, a 130% to 160%, a 130% to 150%, a 130% to 140%, a 140% to 300%, a 140% to 280%, a 140% to 260%, a 140% to 240%, a 140% to 220%, a 140% to 200%, a 140% to 190%, a 140% to 180%, a 140% to 170%, a 140% to 160%, a 140% to 150%, a 150% to 300%, a 150% to 280%, a 150% to 260%, a 150% to 240%, a 150% to 220%, a 150% to 200%, a 150% to 190%, a 150% to 180%, a 150% to 170%, a 150% to 160%, a 160% to 300%, a 160% to 280%, a 160% to 260%, a 160% to 240%, a 160% to 220%, a 160% to 200%, a 160% to 190%, a 160% to 180%, a 160% to 170%, a 170% to 300%, a 170% to 280%, a 170% to 260%, a 170% to 240%, a 170% to 220%, a 170% to 200%, a 170% to 190%, a 170% to 180%, a 180% to 300%, a 180% to 280%, a 180% to 260%, a 180% to 240%, a 180% to 220%, a 180% to 200%, a 180% to 190%, a 190% to 300%, a 190% to 280%, a 190% to 260%, a 190% to 240%, a 190% to 220%, a 190% to 200%, a 200% to 300%, a 200% to 280%, a 200% to 260%, a 200% to 240%, a 200% to 220%, a 220% to 300%, a 220% to 280%, a 220% to 260%, a 220% to 240%, a 240% to 300%, a 240% to 280%, a 240% to 260%, a 260% to 300%, a 260% to 280%, or a 280% to 300% increase) production of one or more cytokines (e.g., IL-2, interferon-gamma, and TNFα) as compared to a control T-cell (e.g., a T-cell including a CD28 costimulatory domain and a CD3 signaling domain) (e.g., when assessed using the same in vitro assay or in similar subjects in vivo).

In some embodiments, a population of T-cells expressing any of the single-chain chimeric antigen receptors or any of the multi-chain chimeric antigen receptors described herein can have increased (e.g., a 1% to 300%, or any of the subranges of this range described herein, increase) activation as compared a control population of T-cells (e.g., a T-cell including a CD28 costimulatory domain and a CD3 signaling domain) (e.g., when assessed using the same in vitro assay or in similar subjects in vivo).

In some embodiments, a population of T-cells expressing any of the single-chain chimeric antigen receptors or any of the multi-chain chimeric antigen receptors described herein can have increased (e.g., a 1% to 300%, or any of the subranges of this range described herein, increase) target cell killing as compared a control population of T-cells (e.g., a T-cell including a CD28 costimulatory domain and a CD3 signaling domain) (e.g., when assessed using the same in vitro assay or in similar subjects in vivo).

Single-Chain Chimeric Antigen Receptors
Single-Chain Chimeric Antigen Receptors Including a First Intracellular Signaling Domain, a Second Intracellular Signaling Domain, and an ITAM Provided herein are single-chain chimeric antigen receptors that include: an extracellular antigen-binding domain (e.g., any of the antigen-binding domains described herein or known in the art); a transmembrane domain (e.g., any of the transmembrane domains described herein or known in the art); a first intracellular signaling domain from DAP-10 or DAP-12, a second intracellular signaling domain from a protein selected from the group of 4-1BB, CD27, OX40, CD40, CD28, GITR, CD2, CD5, ICAM-1, CD11a, Lck, TNFR-I, TNFR-II, FasR, CD30, ICOS, LIGHT, NKG2C, and B7-H3; and an ITAM. The single-chain chimeric antigen receptors described herein can bind to any of the exemplary antigens described herein (e.g., any of MAGE, MUC16, CD19, WT-1, CD22, LI-CAM, ROR-1, CEA, 4-1BB, ETA, 5T4, adenocarcinoma antigen, alpha-fetoprotein (AFP), BAFF, B-lymphoma cell, C242 antigen, CA-125, carbonic anhydrase 9 (CA-IX), C-MET, CCR4, CD152, CD20, CD125 CD200, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgGl, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, and vimentin) or any other antigen known in the art. In some embodiments, the single-chain chimeric antigen receptor binds specifically to a single antigen (e.g., any of the exemplary antigens described herein). In some embodiments, the single-chain chimeric antigen receptor binds specifically to two different antigens (e.g., any combination of the exemplary antigens described herein). In some embodiments, the single-chain chimeric antigen receptor or the multi-chain chimeric antigen receptor can bind specifically to a tumor antigen.

Some embodiments of these single-chain chimeric antigen receptors can include one or more (e.g., two, three, four, or five) ITAMs (e.g., any of the ITAMs described herein or known in the art). In some embodiments of these single-chain chimeric antigen receptors, the ITAM includes a cytoplasmic signaling sequence from CD3ζ (e.g., human CD3ζ).

In some embodiments of any of these single-chain chimeric antigen receptors, any two neighboring domains can be separated by 1 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 15 amino acids, about 10 amino acids, about 8 amino acids, about 6 amino acids, about 4 amino acid, or about 3 amino acids (inclusive); about 2 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 15 amino acids, about 10 amino acids, about 8 amino acids, about 6 amino acids, or about 4 amino acid (inclusive); about 3 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 15 amino acids, about 10 amino acids, about 8 amino acids, about 6 amino acids, or about 5 amino acids (inclusive); about 4 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 15 amino acids, about 10 amino acids, about 8 amino acids, or about 6 amino acids (inclusive); about 5 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 15 amino acids, about 10 amino acids, about 8 amino acids, or about 7 amino acids (inclusive); about 6 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 15 amino acids, about 10 amino acids, or about 8 amino acids (inclusive); about 8 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, about 15 amino acids, or about 10 amino acids (inclusive); about 10 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, about 20 amino acids, or about 15 amino acids (inclusive); about 15 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, about 25 amino acids, or about 20 amino acids (inclusive); about 20 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, about 30 amino acids, or about 25 amino acids (inclusive); about 25 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, about 35 amino acids, or about 30 amino acids (inclusive); about 30 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids, or about 35 amino acids (inclusive); about 35 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, about 45 amino acids, about 40 amino acids (inclusive); about 40 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, about 50 amino acids, or about 45 amino acids (inclusive); about 45 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, about 55 amino acids, or about 50 amino acids (inclusive); about 50 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, about 60 amino acids, or about 55 amino acids (inclusive); about 55 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, about 65 amino acids, or about 60 amino acids (inclusive); about 60 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, about 70 amino acids, or about 65 amino acids (inclusive); about 65 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, about 75 amino acids, or about 70 amino acids (inclusive); about 70 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, or about 75 amino acids (inclusive); about 75 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, about 80 amino acids, or about 75 amino acids (inclusive); about 75 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, about 90 amino acids, about 85 amino acids, or about 80 amino acids (inclusive); about 80 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, about 110 amino acids, about 100 amino acids, about 95 amino acids, or about 90 amino acids (inclusive); about 100 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, about 120 amino acids, or about 110 amino acids (inclusive); about 110 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, or about 120 amino acids (inclusive); about 120 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, about 130 amino acids, or about 120 amino acids (inclusive); about 120 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, about 140 amino acids, or about 130 amino acids (inclusive); about 130 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, about 150 amino acids, or about 140 amino acids (inclusive); about 140 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, about 160 amino acids, or about 150 amino acids (inclusive); about 150 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, about 170 amino acids, or about 160 amino acids (inclusive); about 160 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, about 180 amino acids, or about 170 amino acids (inclusive); about 170 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, about 190 amino acids, or about 180 amino acids (inclusive); about 180 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, about 200 amino acids, or about 190 amino acids (inclusive); about 190 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, about 220 amino acids, or about 200 amino acids (inclusive); about 200 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, about 240 amino acids, or about 220 amino acids (inclusive); about 220 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, about 260 amino acids, or about 240 amino acids (inclusive); about 240 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, about 280 amino acids, or about 260 amino acids (inclusive); about 260 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, or about 280 amino acids (inclusive); about 280 amino acids to about 500 amino acids, about 480 amino acids, about 460 amino acids, about 440 amino acids, about 420 amino acids, about 400 amino acids, about 380 amino acids, about 360 amino acids, about 340 amino acids, about 320 amino acids, about 300 amino acids, or about 300 amino acids (inclusive); about 300 amino acids to about 500 amino acids, about 480 amino acids, about 460 amino acids, about 440 amino acids, about 420 amino acids, about 400 amino acids, about 380 amino acids, about 360 amino acids, about 340 amino acids, or about 320 amino acids (inclusive); about 320 amino acids to about 500 amino acids, about 480 amino acids, about 460 amino acids, about 440 amino acids, about 420 amino acids, about 400 amino acids, about 380 amino acids, about 360 amino acids, or about 340 amino acids (inclusive); about 340 amino acids to about 500 amino acids, about 480 amino acids, about 460 amino acids, about 440 amino acids, about 420 amino acids, about 400 amino acids, about 380 amino acids, or about 360 amino acids (inclusive); about 360 amino acids to about 500 amino acids, about 480 amino acids, about 460 amino acids, about 440 amino acids, about 420 amino acids, about 400 amino acids, or about 380 amino acids (inclusive); about 380 amino acids to about 500 amino acids, about 480 amino acids, about 460 amino acids, about 440 amino acids, about 420 amino acids, or about 400 amino acids (inclusive); about 400 amino acids to about 500 amino acids, about 480 amino acids, about 460 amino acids, about 440 amino acids, or about 420 amino acids (inclusive); about 420 amino acids to about 500 amino acids, about 480 amino acids, about 460 amino acids, or about 440 amino acids (inclusive); about 440 amino acids to about 500 amino acids, about 480 amino acids, or about 460 amino acids (inclusive); about 460 amino acids to about 500 amino acids or about 480 amino acids (inclusive); or about 480 amino acids to about 500 amino acids (inclusive).

In some embodiments, one or more amino acids between the extracellular antigen-binding domain and the transmembrane domain is a sequence from the same endogenous single-chain polypeptide from which the transmembrane domain is derived (e.g., a CD8a hinge region, e.g., SEQ ID NO: 1). In some embodiments, a sequence comprising SEQ ID NO: 1 or 3 is positioned between the extracellular antigen-binding domain and the transmembrane domain. In some embodiments, one or more amino acids between the extracellular antigen-binding domain and the transmembrane domain is or includes a hinge region sequence of an antibody such as, without limitation, a human antibody (e.g., IgG1, IgG2, IgG3, or IgG4). In some embodiments, one or more amino acids between the extracellular antigen-binding domain and the transmembrane domain is or comprises a linker peptide sequence (e.g., a non-naturally occurring linker sequence, e.g., GS or any of the other linker sequences described herein).

```
(CD8 alpha hinge)
                                 SEQ ID NO: 1
TTTPAPRPPTPAPTIASQPLSLRPEACRPAAGGAVHTRGLDFAC (DNA sequence encoding CD8 alpha hinge of SEQ ID
NO: 1)
                                 SEQ ID NO: 2
ACCACGACGCCAGCGCCGCGACCACCAACACCGGCGCCCACCATCGCGTC
GCAGCCCCTGTCCCTGCGCCCAGAGGCGTGCCGGCCAGCGGCGGGGGGCG
CAGTGCACACGAGGGGGCTGGACTTCGCCTGT (Dap10 extracellular domain)
                                 SEQ ID NO: 3
QTTPGERSSLPAFYPGTSGSCSGCGSLSLP (Dap10 extracellular domain)
                                 SEQ ID NO: 4
CAGACAACACCAGGCGAGAGATCTAGCCTGCCCGCCTTCTACCCTGGCAC
CAGCGGCTCTTGTTCTGGCTGTGGCAGCCTGTCTCTGCCC
```

In some embodiments of the single-chain chimeric antigen receptors, when going in the N-terminal to the C-terminal direction, or in the C-terminal to the N-terminal direction, the single-chain chimeric antigen receptor includes the extracellular antigen-binding domain, the transmembrane domain, the first intracellular signaling domain, the second intracellular signaling domain, and the ITAM. In some of these embodiments, one or more amino acids between the transmembrane domain and the first intracellular signaling domain is or includes a sequence from the same endogenous single chain polypeptide from which the first intracellular signaling domain or the transmembrane domain is derived. In some embodiments, one or more amino acids between the transmembrane domain and the first intracellular signaling domain is or includes a linker peptide sequence (e.g., any of the linker peptides sequences described herein or known in the art). In some of these embodiments, the transmembrane domain and the first intracellular signaling domain can directly abut each other. In some of these embodiments, one or more amino acids separating the first intracellular signaling domain and the second intracellular signaling domain is or includes a sequence from the same endogenous single chain polypeptide from which the first or second intracellular signaling domain is derived. In some embodiments, one or more amino acids between the first intracellular signaling domain and the second intracellular signaling domain is or includes a linker peptide sequence (e.g., any of the linker peptide sequences described herein or known in the art). In some of these embodiments, the first intracellular signaling domain and the second intracellular signaling domain directly abut each other. In some of these embodiments, one or more amino acids separating the second intracellular signaling domain and the ITAM is or includes a sequence from the same endogenous single chain polypeptide from which the second intracellular signaling domain or the ITAM is derived. In some embodiments, one or more amino acids between the second intracellular signaling domain and the ITAM is or includes a linker peptide sequence (e.g., any of the linker peptide sequences described herein or known in the art). In some of these embodiments, the second intracellular signaling domain and the ITAM directly abut each other.

In some embodiments of any of the single-chain chimeric antigen receptors, when going in the N-terminal to the C-terminal direction, or in the C-terminal to the N-terminal direction, include the extracellular antigen-binding domain, the transmembrane domain, the second intracellular signaling domain, the first intracellular signaling domain, and the ITAM. In some of these embodiments, one or more amino acids between the transmembrane domain and the second intracellular signaling domain is or includes a sequence from the same endogenous single chain polypeptide from which the second intracellular signaling domain or the transmembrane domain is derived. In some embodiments, one or more amino acids between the transmembrane domain and the second intracellular signaling domain is or includes a linker peptide sequence (e.g., any of the linker peptides sequences described herein or known in the art). In some of these embodiments, the transmembrane domain and the second intracellular signaling domain can directly abut each other. In some of these embodiments, one or more amino acids separating the second intracellular signaling domain and the first intracellular signaling domain is or includes a sequence from the same endogenous single chain polypeptide from which the second or first intracellular signaling domain is derived. In some embodiments, one or more amino acids between the second intracellular signaling domain and the first intracellular signaling domain is or includes a linker peptide sequence (e.g., any of the linker peptide sequences described herein or known in the art). In some of these embodiments, the second intracellular signaling domain and the first intracellular signaling domain directly abut each other. In some of these embodiments, one or more amino acids separating the first intracellular signaling domain and the ITAM is or includes a sequence from the same endogenous single chain polypeptide from which the first intracellular signaling domain or the ITAM is derived. In some embodiments, one or more amino acids between the first intracellular signaling domain and the ITAM is or includes a linker peptide sequence (e.g., any of the linker peptide sequences described herein or known in the art). In some of these embodiments, the first intracellular signaling domain and the ITAM directly abut each other.

In some embodiments of any of the single-chain chimeric antigen receptors, when going in the N-terminal to the C-terminal direction, or in the C-terminal to the N-terminal direction, include the extracellular antigen-binding domain, the transmembrane domain, the first intracellular binding domain, the ITAM, and the second intracellular signaling domain. In some of these embodiments, one or more amino acids between the transmembrane domain and the first intracellular signaling domain is or includes a sequence from the same endogenous single chain polypeptide from which the first intracellular signaling domain or the transmembrane domain is derived. In some embodiments, one or more amino acids between the transmembrane domain and the first intracellular signaling domain is or includes a linker peptide sequence (e.g., any of the linker peptides sequences described herein or known in the art). In some of these embodiments, the transmembrane domain and the first intracellular signaling domain can directly abut each other. In some of these embodiments, one or more amino acids separating the first intracellular signaling domain and the ITAM is or includes a sequence from the same endogenous single chain polypeptide from which the first intracellular signaling domain or the ITAM is derived. In some embodiments, one or more amino acids between the first intracellular signaling domain and the ITAM is or includes a linker peptide sequence (e.g., any of the linker peptide sequences described herein or known in the art). In some of these embodiments, the first intracellular signaling domain and the ITAM directly abut each other. In some of these embodiments, one or more amino acids separating the ITAM and the second intracellular signaling domain is or includes a sequence from the same endogenous single chain polypeptide from which the ITAM or the second intracellular signaling domain is derived. In some embodiments, one or more amino acids between the ITAM and the second intracellular signaling domain is or includes a linker peptide sequence (e.g., any of the linker peptide sequences described herein or known in the art). In some of these embodiments, the ITAM and the second intracellular signaling domain directly abut each other.

In some embodiments of any of the single-chain chimeric antigen receptors, when going in the N-terminal to the C-terminal direction, or in the C-terminal to the N-terminal direction, include the extracellular antigen-binding domain, the transmembrane domain, the second intracellular binding domain, the ITAM, and the first intracellular signaling domain. In some of these embodiments, one or more amino acids between the transmembrane domain and the second intracellular signaling domain is or includes a sequence from the same endogenous single chain polypeptide from which the second intracellular signaling domain or the transmembrane domain is derived. In some embodiments, one or more amino acids between the transmembrane domain and the second intracellular signaling domain is or includes a linker peptide sequence (e.g., any of the linker peptides sequences described herein or known in the art). In some of these embodiments, the transmembrane domain and the second intracellular signaling domain can directly abut each other. In some of these embodiments, one or more amino acids separating the second intracellular signaling domain and the ITAM is or includes a sequence from the same endogenous single chain polypeptide from which the second intracellular signaling domain or the ITAM is derived. In some embodiments, one or more amino acids between the second intracellular signaling domain and the ITAM is or includes a linker peptide sequence (e.g., any of the linker peptide sequences described herein or known in the art). In some of these embodiments, the second intracellular signaling domain and the ITAM directly abut each other.

In some of these embodiments, one or more amino acids separating the ITAM and the first intracellular signaling domain is or includes a sequence from the same endogenous single chain polypeptide from which the ITAM or the first intracellular signaling domain is derived. In some embodiments, one or more amino acids between the ITAM and the first intracellular signaling domain is or includes a linker peptide sequence (e.g., any of the linker peptide sequences described herein or known in the art). In some of these embodiments, the ITAM and the first intracellular signaling domain directly abut each other.

In some embodiments of any of the single-chain chimeric antigen receptors, when going in the N-terminal to the C-terminal direction, or in the C-terminal to the N-terminal direction, include the extracellular antigen-binding domain, the transmembrane domain, the ITAM, the first intracellular signaling domain, and the second intracellular signaling domain. In some of these embodiments, one or more amino acids between the transmembrane domain and the ITAM is or includes a sequence from the same endogenous single chain polypeptide from which the ITAM or the transmembrane domain is derived. In some embodiments, one or more amino acids between the transmembrane domain and the ITAM is or includes a linker peptide sequence (e.g., any of the linker peptides sequences described herein or known in the art). In some of these embodiments, the transmembrane domain and the ITAM can directly abut each other. In some of these embodiments, one or more amino acids separating the ITAM and the first intracellular signaling domain is or includes a sequence from the same endogenous single chain polypeptide from which the first intracellular signaling domain or the ITAM is derived. In some embodiments, one or more amino acids between the ITAM and the first intracellular signaling domain is or includes a linker peptide sequence (e.g., any of the linker peptide sequences described herein or known in the art). In some of these embodiments, the ITAM and the first intracellular signaling domain directly abut each other. In some of these embodiments, one or more amino acids separating the first intracellular signaling domain and the second intracellular signaling domain is or includes a sequence from the same endogenous single chain polypeptide from which the first intracellular signaling domain or the second intracellular signaling domain is derived. In some embodiments, one or more amino acids between the first intracellular signaling domain and the second intracellular signaling domain is or includes a linker peptide sequence (e.g., any of the linker peptide sequences described herein or known in the art). In some of these embodiments, the first intracellular signaling domain and the second intracellular signaling domain directly abut each other.

In some embodiments of any of the single-chain chimeric antigen receptors, when going in the N-terminal to the C-terminal direction, or in the C-terminal to the N-terminal direction, include the extracellular antigen-binding domain, the transmembrane domain, the ITAM, the second intracellular signaling domain, and the first intracellular signaling domain. In some of these embodiments, one or more amino acids between the transmembrane domain and the ITAM is or includes a sequence from the same endogenous single chain polypeptide from which the ITAM or the transmembrane domain is derived. In some embodiments, one or more amino acids between the transmembrane domain and the ITAM is or includes a linker peptide sequence (e.g., any of the linker peptides sequences described herein or known in the art). In some of these embodiments, the transmembrane domain and the ITAM can directly abut each other. In some of these embodiments, one or more amino acids separating the ITAM and the second intracellular signaling domain is or includes a sequence from the same endogenous single chain polypeptide from which the second intracellular signaling domain or the ITAM is derived. In some embodiments, one or more amino acids between the ITAM and the second intracellular signaling domain is or includes a linker peptide sequence (e.g., any of the linker peptide sequences described herein or known in the art). In some of these embodiments, the ITAM and the second intracellular signaling domain directly abut each other. In some of these embodiments, one or more amino acids separating the second intracellular signaling domain and the first intracellular signaling domain is or includes a sequence from the same endogenous single chain polypeptide from which the second intracellular signaling domain or the first intracellular signaling domain is derived. In some embodiments, one or more amino acids between the second intracellular signaling domain and the first intracellular signaling domain is or includes a linker peptide sequence (e.g., any of the linker peptide sequences described herein or known in the art). In some of these embodiments, the second intracellular signaling domain and the first intracellular signaling domain directly abut each other.

Some embodiments of any of the single-chain chimeric antigen receptors described herein can further include a dimerization domain and/or a peptide tag.

Single-Chain Chimeric Antigen Receptor Including an Intracellular Signaling Domain and an ITAM Also provided herein are single-chain chimeric antigen receptors that include: an extracellular antigen-binding domain (e.g., any of the antigen-binding domains described herein or known in the art); a transmembrane domain (e.g., any of the transmembrane domains described herein or known in the art); an intracellular signaling domain from a protein selected from the group of 4-1BB, CD27, OX40, CD40, CD28, GITR, DAP-10, DAP-12, CD2, CD5, ICAM-1, CD11a, Lck, TNFR-I, TNFR-II, FasR, CD30, ICOS, LIGHT, NKG2C, and B7-H3; and ITAM. The single-chain chimeric antigen receptors described herein can bind to any of the exemplary antigens described herein (e.g., any of MAGE, MUC16, CD19, WT-1, CD22, LI-CAM, ROR-1, CEA, 4-1BB, ETA, 5T4, adenocarcinoma antigen, alpha-fetoprotein (AFP), BAFF, B-lymphoma cell, C242 antigen, CA-125, carbonic anhydrase 9 (CA-IX), C-MET, CCR4, CD152, CD20, CD125 CD200, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgGl, IL-13, IL-6, insulin-like growth factor I receptor, integrin $\alpha5\beta1$, integrin $\alpha v\beta3$, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, SCH 900105, SDC1, SLAMF7, TAG-72, tenascin C, TGF beta 2, TGF-$\beta$, TRAIL-R1, TRAIL-R2, tumor antigen CTAA16.88, VEGF-A, VEGFR-1, VEGFR2, and vimentin) or any other antigen known in the art. In some embodiments, the single-chain chimeric antigen receptor binds specifically to a single antigen (e.g., any of the exemplary antigens described herein). In some embodiments, the single-chain chimeric antigen receptor binds specifically to two different antigens (e.g., any combination of the exemplary antigens described herein). In some embodiments, the single-chain chimeric antigen receptor or the multi-chain chimeric antigen receptor can bind specifically to a tumor antigen.

Some embodiments of these single-chain chimeric antigen receptors can include one or more (e.g., two, three, four, or five) ITAMs (e.g., any of the ITAMs described herein or known in the art). In some embodiments of these single-chain chimeric antigen receptors, the ITAM includes a cytoplasmic signaling sequence from CD3ζ (e.g., human CD3ζ). In some embodiments of any of these single-chain chimeric antigen receptors, any two neighboring domains can be separated by 1 amino acids to about 500 amino acids (or any of the subranges of this range described herein).

In some embodiments, one or more amino acids between the extracellular antigen-binding domain and the transmembrane domain is a sequence from the same endogenous single-chain polypeptide from which the transmembrane domain is derived (e.g., a CD8a hinge region, e.g., SEQ ID NO: 1). In some embodiments, a sequence comprising SEQ ID NO: 1 or 3 is positioned between the extracellular antigen-binding domain and the transmembrane domain. In some embodiments, one or more amino acids between the extracellular antigen-binding domain and the transmembrane domain is or includes a hinge region sequence of an antibody such as, without limitation, a human antibody (e.g., IgG1, IgG2, IgG3, or IgG4). In some embodiments, one or more amino acids between the extracellular antigen-binding domain and the transmembrane domain is or comprises a linker peptide sequence (e.g., a non-naturally occurring linker sequence, e.g., GS or any of the other linker sequences described herein).

Some embodiments of the single-chain chimeric antigen receptors described herein, when going in the N-terminal to the C-terminal or in the C-terminal to the N-terminal direction, include the extracellular antigen-binding domain, the transmembrane domain, the intracellular signaling domain, and the ITAM. In some of these embodiments, one or more amino acids between the transmembrane domain and the intracellular signaling domain is or includes a sequence from the same endogenous single chain polypeptide from which the intracellular signaling domain or the transmembrane domain is derived. In some embodiments, one or more amino acids between the transmembrane domain and the intracellular signaling domain is or includes a linker peptide sequence (e.g., any of the linker peptides sequences described herein or known in the art). In some of these embodiments, the transmembrane domain and the intracellular signaling domain can directly abut each other. In some of these embodiments, one or more amino acids separating the intracellular signaling domain and the ITAM is or includes a sequence from the same endogenous single chain polypeptide from which the intracellular signaling domain or the ITAM is derived. In some embodiments, one or more amino acids between the intracellular signaling domain and the ITAM is or includes a linker peptide sequence (e.g., any of the linker peptide sequences described herein or known in the art). In some of these embodiments, the intracellular signaling domain and the ITAM directly abut each other.

Some embodiments of the single-chain chimeric antigen receptors described herein, when going in the N-terminal to the C-terminal or in the C-terminal to the N-terminal direction, include the extracellular antigen-binding domain, the transmembrane domain, the ITAM, and the intracellular signaling domain. In some of these embodiments, one or more amino acids between the transmembrane domain and the ITAM is or includes a sequence from the same endogenous single chain polypeptide from which the transmembrane domain or the ITAM is derived. In some embodiments, one or more amino acids between the transmembrane domain and the ITAM is or includes a linker peptide sequence (e.g., any of the linker peptides sequences described herein or known in the art). In some of these embodiments, the transmembrane domain and the ITAM can directly abut each other. In some of these embodiments, one or more amino acids separating the ITAM and the intracellular signaling domain is or includes a sequence from the same endogenous single chain polypeptide from which the ITAM or the intracellular signaling domain is derived. In some embodiments, one or more amino acids between the ITAM and the intracellular signaling domain is or includes a linker peptide sequence (e.g., any of the linker peptide sequences described herein or known in the art). In some of these embodiments, the ITAM and the intracellular signaling domain directly abut each other.

Some embodiments of any of the single-chain chimeric antigen receptors described herein can further include a dimerization domain and/or a peptide tag.

Multi-Chain Chimeric Antigen Receptors

Multi-Chain Chimeric Antigen Receptors that Include at Least One First Polypeptide Including a First Intracellular Signaling Domain, a Second Intracellular Signaling Domain, and an ITAM Also provided herein are multi-chain chimeric antigen receptors that include at least one first polypeptide including: a transmembrane domain (e.g., any of the transmembrane domains described herein or known in the art); a first intracellular binding domain from DAP-10 or DAP-12, a second intracellular signaling domain from a protein selected from the group of 4-1BB, CD27, OX40, CD40, CD28, GITR, CD2, CD5, ICAM-1, CD11a, Lck, TNFR-I, TNFR-II, FasR, CD30, ICOS, LIGHT, NKG2C, and B7-H3; and an ITAM. In some embodiments, the at least one first polypeptide can further include an antigen-binding domain (e.g., any of the antigen-binding domains described herein or known in the art). In some embodiments, the multi-chain chimeric antigen receptor further includes a second polypeptide including an antigen-binding domain (e.g., any of the antigen-binding domains described herein or known in the art) and a transmembrane domain (e.g., any of the transmembrane domains described herein). The antigen specifically bound by the antigen-binding domain in any of these multi-chain chimeric antigen receptors can be any of the antigens described herein or known in the art. In some embodiments, the multi-chain chimeric antigen receptor only binds specifically to a single antigen (e.g., any of the exemplary antigens described herein). In some embodiments, the multi-chain chimeric antigen receptor binds specifically to two different antigens (e.g., any combination of any of the exemplary antigens described herein). In some embodiments, the multi-chain chimeric antigen receptor binds to a tumor antigen.

In some embodiments of the multi-chain chimeric antigen receptors, the extracellular antigen-binding domain and the transmembrane domain in the at least one first polypeptide and/or the second polypeptide directly abut each other. In some embodiments of the multi-chain chimeric antigen receptors, 1 to about 500 amino acids (e.g., any of the subranges of this range described herein) are between the extracellular antigen-binding domain and the transmembrane domain in the at least one first polypeptide and/or the second polypeptide. In some embodiments, one or more amino acids between the extracellular antigen-binding domain and the transmembrane domain in the at least one first polypeptide and/or the second polypeptide is a sequence from the same endogenous single-chain polypeptide from which the transmembrane domain is derived. In some embodiments, one or more amino acids between the extracellular antigen-binding domain and the transmembrane domain of the at least one first polypeptide and/or the second polypeptide is or includes a hinge region sequence of human antibody (e.g., IgG1, IgG2, IgG3, or IgG4). In some embodiments, one or more amino acids between the extracellular antigen-binding domain and the transmembrane domain in the at least one first polypeptide and/or the second polypeptide is or includes a linker sequence (e.g., a non-naturally occurring linker sequence).

In some embodiments, any two neighboring domains (e.g., the transmembrane domain, the first intracellular signaling domain, the second intracellular signaling domain, and the ITAM) in the at least one first polypeptide can directly abut each other. In some embodiments, any two neighboring domains in the at least one first polypeptide (e.g., the transmembrane domain, the first intracellular signaling domain, the second intracellular signaling domain, and the ITAM) can be separated by 1 to 500 amino acids (or any subrange of this range described herein).

In some embodiments of the multi-chain chimeric antigen receptors, when going in the N-terminal to the C-terminal direction, or in the C-terminal to the N-terminal direction, the at least one first polypeptide includes the transmembrane domain, the first intracellular signaling domain, the second intracellular signaling domain, and the ITAM. In some of these embodiments, one or more amino acids between the transmembrane domain and the first intracellular signaling domain is or includes a sequence from the same endogenous single chain polypeptide from which the first intracellular signaling domain or the transmembrane domain is derived. In some embodiments, one or more amino acids between the transmembrane domain and the first intracellular signaling domain is or includes a linker peptide sequence (e.g., any of the linker peptides sequences described herein or known in the art). In some of these embodiments, the transmembrane domain and the first intracellular signaling domain can directly abut each other. In some of these embodiments, one or more amino acids separating the first intracellular signaling domain and the second intracellular signaling domain is or includes a sequence from the same endogenous single chain polypeptide from which the first or second intracellular signaling domain is derived. In some embodiments, one or more amino acids between the first intracellular signaling domain and the second intracellular signaling domain is or includes a linker peptide sequence (e.g., any of the linker peptide sequences described herein or known in the art). In some of these embodiments, the first intracellular signaling domain and the second intracellular signaling domain directly abut each other. In some of these embodiments, one or more amino acids separating the second intracellular signaling domain and the ITAM is or includes a sequence from the same endogenous single chain polypeptide from which the second intracellular signaling domain or the ITAM is derived. In some embodiments, one or more amino acids between the second intracellular signaling domain and the ITAM is or includes a linker peptide sequence (e.g., any of the linker peptide sequences described herein or known in the art). In some of these embodiments, the second intracellular signaling domain and the ITAM directly abut each other.

In some embodiments of any of the multi-chain chimeric antigen receptors, when going in the N-terminal to the C-terminal direction, or in the C-terminal to the N-terminal direction, the at least one first polypeptide includes the transmembrane domain, the second intracellular signaling domain, the first intracellular signaling domain, and the ITAM. In some of these embodiments, one or more amino acids between the transmembrane domain and the second intracellular signaling domain is or includes a sequence from the same endogenous single chain polypeptide from which the second intracellular signaling domain or the transmembrane domain is derived. In some embodiments, one or more amino acids between the transmembrane domain and the second intracellular signaling domain is or includes a linker peptide sequence (e.g., any of the linker peptides sequences described herein or known in the art). In some of these embodiments, the transmembrane domain and the second intracellular signaling domain can directly abut each other. In some of these embodiments, one or more amino acids separating the second intracellular signaling domain and the first intracellular signaling domain is or includes a sequence from the same endogenous single chain polypeptide from which the second or first intracellular signaling domain is derived. In some embodiments, one or more amino acids between the second intracellular signaling domain and the first intracellular signaling domain is or includes a linker peptide sequence (e.g., any of the linker peptide sequences described herein or known in the art). In some of these embodiments, the second intracellular signaling domain and the first intracellular signaling domain directly abut each other. In some of these embodiments, one or more amino acids separating the first intracellular signaling domain and the ITAM is or includes a sequence from the same endogenous single chain polypeptide from which the first intracellular signaling domain or the ITAM is derived. In some embodiments, one or more amino acids between the first intracellular signaling domain and the ITAM is or includes a linker peptide sequence (e.g., any of the linker peptide sequences described herein or known in the art). In some of these embodiments, the first intracellular signaling domain and the ITAM directly abut each other.

In some embodiments of any of the multi-chain chimeric antigen receptors, when going in the N-terminal to the C-terminal direction, or in the C-terminal to the N-terminal direction, the at least one first polypeptide includes the transmembrane domain, the first intracellular binding domain, the ITAM, and the second intracellular signaling domain. In some of these embodiments, one or more amino acids between the transmembrane domain and the first intracellular signaling domain is or includes a sequence from the same endogenous single chain polypeptide from which the first intracellular signaling domain or the transmembrane domain is derived. In some embodiments, one or more amino acids between the transmembrane domain and the first intracellular signaling domain is or includes a linker peptide sequence (e.g., any of the linker peptides sequences described herein or known in the art). In some of these embodiments, the transmembrane domain and the first intracellular signaling domain can directly abut each other. In some of these embodiments, one or more amino acids separating the first intracellular signaling domain and the ITAM is or includes a sequence from the same endogenous single chain polypeptide from which the first intracellular signaling domain or the ITAM is derived. In some embodiments, one or more amino acids between the first intracellular signaling domain and the ITAM is or includes a linker peptide sequence (e.g., any of the linker peptide sequences described herein or known in the art). In some of these embodiments, the first intracellular signaling domain and the ITAM directly abut each other. In some of these embodiments, one or more amino acids separating the ITAM and the second intracellular signaling domain is or includes a sequence from the same endogenous single chain polypeptide from which the ITAM or the second intracellular signaling domain is derived. In some embodiments, one or more amino acids between the ITAM and the second intracellular signaling domain is or includes a linker peptide sequence (e.g., any of the linker peptide sequences described herein or known in the art). In some of these embodiments, the ITAM and the second intracellular signaling domain directly abut each other.

In some embodiments of any of the multi-chain chimeric antigen receptors, when going in the N-terminal to the C-terminal direction, or in the C-terminal to the N-terminal direction, the at least one first polypeptide includes the transmembrane domain, the second intracellular binding domain, the ITAM, and the first intracellular signaling domain. In some of these embodiments, one or more amino acids between the transmembrane domain and the second intracellular signaling domain is or includes a sequence from the same endogenous single chain polypeptide from which the second intracellular signaling domain or the transmembrane domain is derived. In some embodiments, one or more amino acids between the transmembrane domain and the second intracellular signaling domain is or includes a linker peptide sequence (e.g., any of the linker peptides sequences described herein or known in the art). In some of these embodiments, the transmembrane domain and the second intracellular signaling domain can directly abut each other. In some of these embodiments, one or more amino acids separating the second intracellular signaling domain and the ITAM is or includes a sequence from the same endogenous single chain polypeptide from which the second intracellular signaling domain or the ITAM is derived. In some embodiments, one or more amino acids between the second intracellular signaling domain and the ITAM is or includes a linker peptide sequence (e.g., any of the linker peptide sequences described herein or known in the art). In some of these embodiments, the second intracellular signaling domain and the ITAM directly abut each other. In some of these embodiments, one or more amino acids separating the ITAM and the first intracellular signaling domain is or includes a sequence from the same endogenous single chain polypeptide from which the ITAM or the first intracellular signaling domain is derived. In some embodiments, one or more amino acids between the ITAM and the first intracellular signaling domain is or includes a linker peptide sequence (e.g., any of the linker peptide sequences described herein or known in the art). In some of these embodiments, the ITAM and the first intracellular signaling domain directly abut each other.

In some embodiments of any of the multi-chain chimeric antigen receptors, when going in the N-terminal to the C-terminal direction, or in the C-terminal to the N-terminal direction, the at least one first polypeptide includes the transmembrane domain, the ITAM, the first intracellular signaling domain, and the second intracellular signaling domain. In some of these embodiments, one or more amino acids between the transmembrane domain and the ITAM is or includes a sequence from the same endogenous single chain polypeptide from which the ITAM or the transmembrane domain is derived. In some embodiments, one or more amino acids between the transmembrane domain and the ITAM is or includes a linker peptide sequence (e.g., any of the linker peptides sequences described herein or known in the art). In some of these embodiments, the transmembrane domain and the ITAM can directly abut each other. In some of these embodiments, one or more amino acids separating the ITAM and the first intracellular signaling domain is or includes a sequence from the same endogenous single chain polypeptide from which the first intracellular signaling domain or the ITAM is derived. In some embodiments, one or more amino acids between the ITAM and the first intracellular signaling domain is or includes a linker peptide sequence (e.g., any of the linker peptide sequences described herein or known in the art). In some of these embodiments, the ITAM and the first intracellular signaling domain directly abut each other. In some of these embodiments, one or more amino acids separating the first intracellular signaling domain and the second intracellular signaling domain is or includes a sequence from the same endogenous single chain polypeptide from which the first intracellular signaling domain or the second intracellular signaling domain is derived. In some embodiments, one or more amino acids between the first intracellular signaling domain and the second intracellular signaling domain is or includes a linker peptide sequence (e.g., any of the linker peptide sequences described herein or known in the art). In some of these embodiments, the first intracellular signaling domain and the second intracellular signaling domain directly abut each other.

In some embodiments of any of the multi-chain chimeric antigen receptors, when going in the N-terminal to the C-terminal direction, or in the C-terminal to the N-terminal direction, the at least one first polypeptide includes the transmembrane domain, the ITAM, the second intracellular signaling domain, and the first intracellular signaling domain. In some of these embodiments, one or more amino acids between the transmembrane domain and the ITAM is or includes a sequence from the same endogenous single chain polypeptide from which the ITAM or the transmembrane domain is derived. In some embodiments, one or more amino acids between the transmembrane domain and the ITAM is or includes a linker peptide sequence (e.g., any of the linker peptides sequences described herein or known in the art). In some of these embodiments, the transmembrane domain and the ITAM can directly abut each other. In some of these embodiments, one or more amino acids separating the ITAM and the second intracellular signaling domain is or includes a sequence from the same endogenous single chain polypeptide from which the second intracellular signaling domain or the ITAM is derived. In some embodiments, one or more amino acids between the ITAM and the second intracellular signaling domain is or includes a linker peptide sequence (e.g., any of the linker peptide sequences described herein or known in the art). In some of these embodiments, the ITAM and the second intracellular signaling domain directly abut each other. In some of these embodiments, one or more amino acids separating the second intracellular signaling domain and the first intracellular signaling domain is or includes a sequence from the same endogenous single chain polypeptide from which the second intracellular signaling domain or the first intracellular signaling domain is derived. In some embodiments, one or more amino acids between the second intracellular signaling domain and the first intracellular signaling domain is or includes a linker peptide sequence (e.g., any of the linker peptide sequences described herein or known in the art). In some of these embodiments, the second intracellular signaling domain and the first intracellular signaling domain directly abut each other.

In some embodiments of these multi-chain chimeric antigen receptors, the at least one first polypeptide can further include one or both of: a dimerizing domain (e.g., any dimerizing domain known in the art) and/or a peptide tag (e.g., any peptide tag known in the art).

The second polypeptide that can, e.g., include one or more (e.g., two, three, or four) of: an extracellular antigen-binding domain (e.g., any of the antigen-binding domains described herein), a transmembrane domain (e.g., any of the transmembrane domains described herein), a dimerizing domain (e.g., a dimerizing domain that can interact with a dimerizing domain in the at least one first polypeptide in a mammalian cell), one or more intracellular signaling domain (e.g., any of the intracellular signaling domains described herein), and one or more ITAM (e.g., any of the ITAMs described herein). As can be appreciated by those in the art, a pair or each pair of neighboring domains in the second polypeptide can abut each other or can be separated by 1 to about 500 amino acids (e.g., any of the subranges of this range described herein). The one or more amino acids between a pair of neighboring domains in the second polypeptide can be a sequence from an endogenous single-chain polypeptide from which a transmembrane, an intracellular signaling domain, or an ITAM present in the second polypeptide has been derived, or can be or include a linker peptide sequence. In some embodiments, any pair of neighboring domains in the second polypeptide can directly abut each other.

As can be appreciated in the art, the two or more polypeptides present in a multi-chain chimeric antigen receptor can associate via pair of domains that interact with each other (through dimerizing domains). In some embodiments, the interaction between dimerizing domains can be triggered by the addition of a small molecule. In some embodiments, the two or more polypeptides present in a multi-meric chimeric antigen receptor can associate through non-covalent interactions (e.g., between associations between dimerizing domains). In some embodiments, the two or more polypeptides present in a multi-meric chimeric antigen receptor can be through a covalent interaction (e.g., through a disulfide bond, through an ester bond, through an amide bond, through a thioester bond, or a combination thereof).

Multi-Chain Chimeric Antigen Receptors that Include at Least One First Polypeptide Including an Intracellular Signaling Domain and an ITAM Also provided herein are multi-chain chimeric antigen receptors that include at least one first polypeptide including: a transmembrane domain (e.g., any of the transmembrane domains described herein or known in the art); an intracellular signaling domain from a protein selected from the group of 4-1BB, CD27, OX40, CD40, CD28, GITR, DAP-10, DAP-12, CD2, CD5, ICAM-1, CD11a, Lck, TNFR-I, TNFR-II, FasR, CD30, ICOS, LIGHT, NKG2C, and B7-H3; and an ITAM. In some embodiments, the at least one first polypeptide can further include an antigen-binding domain (e.g., any of the antigen-binding domains described herein or known in the art). In some embodiments, the multi-chain chimeric antigen receptor further includes a second polypeptide including an antigen-binding domain (e.g., any of the antigen-binding domains described herein or known in the art) and a transmembrane domain (e.g., any of the transmembrane domains described herein). The antigen specifically bound by the antigen-binding domain in any of these multi-chain chimeric antigen receptors can be any of the antigens described herein or known in the art. In some embodiments, the multi-chain chimeric antigen receptor only binds specifically to a single antigen (e.g., any of the exemplary antigens described herein). In some embodiments, the multi-chain chimeric antigen receptor binds specifically to two different antigens (e.g., any combination of any of the exemplary antigens described herein). In some embodiments, the multi-chain chimeric antigen receptor binds to a tumor antigen.

In some embodiments of the multi-chain chimeric antigen receptors, the extracellular antigen-binding domain and the transmembrane domain in the at least one first polypeptide and/or the second polypeptide directly abut each other. In some embodiments of the multi-chain chimeric antigen receptors, 1 to about 500 amino acids (e.g., any of the subranges of this range described herein) are between the extracellular antigen-binding domain and the transmembrane domain in the at least one first polypeptide and/or the second polypeptide. In some embodiments, one or more amino acids between the extracellular antigen-binding domain and the transmembrane domain in the at least one first polypeptide and/or the second polypeptide is a sequence from the same endogenous single-chain polypeptide from which the transmembrane domain is derived. In some embodiments, one or more amino acids between the extracellular antigen-binding domain and the transmembrane domain of the at least one first polypeptide and/or the second polypeptide is or includes a hinge region sequence of human antibody (e.g., IgG1, IgG2, IgG3, or IgG4). In some embodiments, one or more amino acids between the extracellular antigen-binding domain and the transmembrane domain in the at least one first polypeptide and/or the second polypeptide is or includes a linker sequence (e.g., a non-naturally occurring linker sequence).

In some embodiments, any two neighboring domains (e.g., the transmembrane domain, the intracellular signaling domain, and the ITAM) in the at least one first polypeptide can directly abut each other. In some embodiments, any two neighboring domains in the at least one first polypeptide (e.g., the transmembrane domain, the intracellular signaling domain, and the ITAM) can be separated by 1 to 500 amino acids (or any subrange of this range described herein).

Some embodiments of the multi-chain chimeric antigen receptors described herein, when going in the N-terminal to the C-terminal or in the C-terminal to the N-terminal direction, the at least one first polypeptide includes the transmembrane domain, the intracellular signaling domain, and the ITAM. In some of these embodiments, one or more amino acids between the transmembrane domain and the intracellular signaling domain is or includes a sequence from the same endogenous single chain polypeptide from which the intracellular signaling domain or the transmembrane domain is derived. In some embodiments, one or more amino acids between the transmembrane domain and the intracellular signaling domain is or includes a linker peptide sequence (e.g., any of the linker peptides sequences described herein or known in the art). In some of these embodiments, the transmembrane domain and the intracellular signaling domain can directly abut each other. In some of these embodiments, one or more amino acids separating the intracellular signaling domain and the ITAM is or includes a sequence from the same endogenous single chain polypeptide from which the intracellular signaling domain or the ITAM is derived. In some embodiments, one or more amino acids between the intracellular signaling domain and the ITAM is or includes a linker peptide sequence (e.g., any of the linker peptide sequences described herein or known in the art). In some of these embodiments, the intracellular signaling domain and the ITAM directly abut each other.

Some embodiments of the multi-chain chimeric antigen receptors described herein, when going in the N-terminal to the C-terminal or in the C-terminal to the N-terminal direction, the at least one first polypeptide includes the transmembrane domain, the ITAM, and the intracellular signaling domain. In some of these embodiments, one or more amino acids between the transmembrane domain and the ITAM is or includes a sequence from the same endogenous single chain polypeptide from which the transmembrane domain or the ITAM is derived. In some embodiments, one or more amino acids between the transmembrane domain and the ITAM is or includes a linker peptide sequence (e.g., any of the linker peptides sequences described herein or known in the art). In some of these embodiments, the transmembrane domain and the ITAM can directly abut each other. In some of these embodiments, one or more amino acids separating the ITAM and the intracellular signaling domain is or includes a sequence from the same endogenous single chain polypeptide from which the ITAM or the intracellular signaling domain is derived. In some embodiments, one or more amino acids between the ITAM and the intracellular signaling domain is or includes a linker peptide sequence (e.g., any of the linker peptide sequences described herein or known in the art). In some of these embodiments, the ITAM and the intracellular signaling domain directly abut each other.

In some embodiments of these multi-chain chimeric antigen receptors, the at least one first polypeptide can further include one or both of: a dimerizing domain (e.g., any dimerizing domain known in the art) and/or a peptide tag (e.g., any peptide tag known in the art).

The second polypeptide that can, e.g., include one or more (e.g., two, three, or four) of: an extracellular antigen-binding domain (e.g., any of the antigen-binding domains described herein), a transmembrane domain (e.g., any of the transmembrane domains described herein), a dimerizing domain (e.g., a dimerizing domain that can interact with a dimerizing domain in the at least one first polypeptide in a mammalian cell), one or more intracellular signaling domain (e.g., any of the intracellular signaling domains described herein), and one or more ITAM (e.g., any of the ITAMs described herein). As can be appreciated by those in the art, a pair or each pair of neighboring domains in the second polypeptide can abut each other or can be separated by 1 to about 500 amino acids (e.g., any of the subranges of this range described herein). The one or more amino acids between a pair of neighboring domains in the second polypeptide can be a sequence from an endogenous single-chain polypeptide from which a transmembrane, an intracellular signaling domain, or an ITAM present in the second polypeptide has been derived, or can be or include a linker peptide sequence. In some embodiments, any pair of neighboring domains in the second polypeptide can directly abut each other.

As can be appreciated in the art, the two or more polypeptides present in a multi-chain chimeric antigen receptor can associate via pair of domains that interact with each other (through dimerizing domains). In some embodiments, the interaction between dimerizing domains can be triggered by the addition of a small molecule. In some embodiments, the two or more polypeptides present in a multi-meric chimeric antigen receptor can associate through non-covalent interactions (e.g., between associations between dimerizing domains). In some embodiments, the two or more polypeptides present in a multi-meric chimeric antigen receptor can be through a covalent interaction (e.g., through a disulfide bond, through an ester bond, through an amide bond, through a thioester bond, or a combination thereof).

Transmembrane Domains

In some embodiments, a single-chain chimeric antigen receptor or a multi-chain chimeric antigen receptor includes a transmembrane domain, or portion thereof, from an endogenous polypeptide, where the endogenous polypeptide is selected from the group of: an α chain of a T cell receptor, a β chain of the T cell receptor, a ζ chain of the T cell receptor, CD28 (also known as Tp44), CD3ε, CD3δ, CD3γ, CD33, CD37 (also known as GP52-40 or TSPAN26), CD64 (also known as FCGR1A), CD80 (also known as B7, B7-1, B7.1, BB1, CD28LG, CD28LG1, and LAB7), CD45 (also known as PTPRC, B220, CD45R, GP180, L-CA, LCA, LYS, T200, and protein tyrosine phosphatase, receptor type C), CD4, CD5 (also known as LEU1 and T1), CD8α (also known as Leu2, MAL, and p32), CD9 (also known as BTCC-1, DRAP-27, MIC3, MRP-1, TSPAN-29, and TSPAN29), CD16 (also known as FCGR3 andFCG3), CD22 (also known as SIGLEC-2 and SIGLEC2), CD86 (also known as B7-2, B7.2, B70, CD28LG2, and LAB72), CD134 (also known as TNFRSF4, ACT35, RP5-902P8.3, IMD16, OX40, TXGP1L, and tumor necrosis factor receptor superfamily member 4), CD137 (also known as TNFRSF9, 4-1BB, CDw137, ILA, and tumor necrosis factor receptor superfamily member 9), CD27 (also known as S152, S152.LPFS2, T14, TNFRSF7, and Tp55), CD152 (also known as CTLA4, ALPS5, CELIAC3, CTLA-4, GRD4, GSE, IDDM12, and cytotoxic T-lymphocyte associated protein 4), PD1 (also known as PDCD1, CD279, PD-1, SLEB2, hPD-1, hPD-1, hSLE1, and Programmed cell death 1), ICOS (also known as AILIM, CD278, and CVID1), CD272 (also known as BTLA and BTLA1), CD30 (also known as TNFRSF8, D1S166E, and Ki-1), GITR (also known as TNFRSF18, RP5-902P8.2, AITR, CD357, and GITR-D), HVEM (also known as TNFRSF14, RP3-395M20.6, ATAR, CD270, HVEA, HVEM, LIGHTR, and TR2), DAP10, and CD154 (also known as CD40LG, CD40L, HIGM1, IGM, IMD3, T-BAM, TNFSFS, TRAP, gp39, hCD40L, and CD40 ligand). The letters "CD" is the previous sentence stand for "Cluster of Differentiation." E.g., CD3 stands for "Cluster of Differentiation 3." In some embodiments, a single-chain chimeric antigen receptor or a multi-chain chimeric antigen receptor includes a transmembrane domain, or portion thereof, from an endogenous mammalian (e.g., human) polypeptide (e.g., a mammalian or human homolog of any of the polypeptides listed above).

Any transmembrane domain, or portion thereof, that serves to anchor an endogenous polypeptide in a lipid bilayer (e.g., plasma membrane) of a mammalian cell is suitable for use in accordance with compositions and methods disclosed herein. In some embodiments, a single-chain chimeric antigen receptor or a multi-chain chimeric antigen receptor includes a transmembrane domain, or portion thereof, from human CD28, e.g., Accession No. P01747, e.g., amino acids 153 to 179 of SEQ ID NO: 5. In some embodiments, a single-chain chimeric antigen receptor or a multi-chain chimeric antigen receptor includes a transmembrane domain that is at least 80% (e.g., at least 82%, at least 84%, at least 85%, at least 86%, at least 88%, at least 90%, at least 92%, at least 94%, at least 95%, at least 96%, at least 98%, or at least 99% identical) to amino acids 153 to 179 of SEQ ID NO: 5, or a portion thereof.

```
(Transmembrane domain of human CD28)
                                  SEQ ID NO: 5
MLRLLLALNLFPSIQVTGNKILVKQSPMLVAYDNAVNLSCKYSYNLFSRE

FRASLHKGLDSAVEVCVVYGNYSQQLQVYSKTGFNCDGKLGNESVTFYLQ

NLYVNQTDIYFCKIEVMYPPPYLDNEKSNGTIIHVKGKHLCPSPLFPGPS

KPFWVLVVVGGVLACYSLLVTVAFIIFWVRSKRSRLLHSDYMNMTPRRPG

PTRKHYQPYAPPRDFAAYRS
```

In some embodiments, transmembrane domain can comprise a sequence at least 80% (e.g., at least 82%, at least 84%, at least 86%, at least 88%, at least 90%, at least 92%, at least 94%, at least 96%, at least 98%, at least 99%, or 100% identical) to SEQ ID NO: 6 (or a portion thereof).

```
(CD8 alpha transmembrane domain)
                                  SEQ ID NO: 6
DIYIWAPLAGTCGVLLLSLVITLYC
```

In some embodiments, a single-chain chimeric antigen receptor or a multi-chain chimeric antigen receptor includes a transmembrane domain, or portion thereof, from human CD3, e.g., Accession No. P20963, e.g., amino acids 31 to 51 of SEQ ID NO: 7. In some embodiments, a single-chain chimeric antigen receptor or a multi-chain chimeric antigen receptor includes a transmembrane domain that is or includes a sequence that is at least 80% (e.g., at least 82%, at least 84%, at least 85%, at least 86%, at least 88%, at least 90%, at least 92%, at least 94%, at least 95%, at least 96%, at least 98%, or at least 99% identical) to amino acids 31 to 51 of SEQ ID NO: 7.

```
(Transmembrane domain of human CD3)
                                  SEQ ID NO: 7
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP

QRRKNPQEGLYNELQKDKMAEAYSEIGMKGERRRGKGHDGLYQGLSTATK

DTYDALHMQALPPR
```

In some embodiments, a single-chain chimeric antigen receptor or a multi-chain chimeric antigen receptor includes a transmembrane domain, or portion thereof, of any one of SEQ ID Nos. 8-14:

```
                                  (SEQ ID NO: 8)
LGLLVAGVLVLLVSLGVAIHLCC;

(SEQ ID NO: 9)
VAAILGLGLVLGLLGPLAILLALYLL;

(SEQ ID NO: 10)
ALIVLGGVAGLLLFIGLGIFFCVRC;

(SEQ ID NO: 11)
LCYLLDGILFIYGVILTALFLRV;

(SEQ ID NO: 12)
WVLVVVGGVLACYSLLVTVAFIIFWV;

(SEQ ID NO: 13)
IYIWAPLAGTCGVLLLSLVITLYC;
and (SEQ ID NO: 14)
ALPAALAVISFLLGLGLGVACVLA.
```

In some embodiments, a single-chain chimeric antigen receptor or a multi-chain chimeric antigen receptor includes a transmembrane domain that is or includes a sequence that is at least 80% (e.g., at least 82%, at least 84%, at least 85%, at least 86%, at least 88%, at least 90%, at least 92%, at least 94%, at least 95%, at least 96%, at least 98%, or at least 99% identical) to any one of SEQ ID Nos. 8-14.

In some embodiments, a single-chain chimeric antigen receptor or a multi-chain chimeric antigen receptor includes a transmembrane domain that is or includes a sequence that is at least 80% (e.g., at least 82%, at least 84%, at least 85%, at least 86%, at least 88%, at least 90%, at least 92%, at least 94%, at least 95%, at least 96%, at least 98%, or at least 99% identical, or 100% identical) to SEQ ID NO: 13.

```
(CD8 transmembrane domain)
                                  SEQ ID NO: 13
IYIWAPLAGTCGVLLLSLVITLYC (DNA sequence encoding CD8 transmembrane domain)
                                  SEQ ID NO: 15
atctatatttgggcacccctggctggaacctgcggagtgctgctgctgtc tctcgtgattacactgtattgc (DNA sequence encoding CD8 alpha transmembrane
domain)
                                  SEQ ID NO: 16
gatatctacatctgggcgcccttggccgggacttgtggggtccttctcct gtcactggttatcaccctttactgc
```

As will be appreciated by those of ordinary skill in the art, certain endogenous polypeptides have two or more isoforms that differ at least in their primary polypeptide sequence. A single-chain chimeric antigen receptor or a multi-chain chimeric antigen receptor disclosed herein can include a transmembrane domain that includes a sequence of amino acids from any isoform of an endogenous transmembrane protein (e.g., an endogenous mammalian, e.g., human, transmembrane protein) including, e.g., an isoform (e.g., a human isoform) of: an α chain of a T cell receptor, a β chain of the T cell receptor, a ζ chain of the T cell receptor, CD28, CD3ε, CD3δ, CD3γ, CD33, CD37, CD64, CD80, CD45, CD4, CD5, CD8α, CD9, CD16, CD22, CD86, CD27, CD152, PD1, or CD154.

In some embodiments, a transmembrane domain, or portion thereof, of a single-chain chimeric antigen receptor or a multi-chain chimeric antigen receptor includes a sequence of amino acids that exhibits at least 85%, 86%, 87%, 88%, 89%, 90%, 91%, 92%, 93%, 94%, 95%, 96%, 97%, 98%, 99% or more sequence identity to the transmembrane domains from one or more of the following endogenous mammalian (e.g., human) transmembrane proteins: an α chain of a T cell receptor, a β chain of the T cell receptor, a ζ chain of the T cell receptor, CD28, CD3ε, CD3δ, CD3γ, CD33, CD37, CD64, CD80, CD45, CD4, CD5, CD8α, CD9, CD16, CD22, CD86, CD27, CD152, PD1, or CD154. In some embodiments, a transmembrane domain, or portion thereof, of a single-chain chimeric antigen receptor or a multi-chain chimeric antigen receptor includes a sequence of amino acids having one or more amino acid substitutions, deletions, or additions as compared to the transmembrane domain of an endogenous mammalian (e.g., human) transmembrane protein: an α chain of a T cell receptor, a β chain of the T cell receptor, a ζ chain of the T cell receptor, CD28, CD3ε, CD3δ, CD3γ, CD33, CD37, CD64, CD80, CD45, CD4, CD5, CD8α, CD9, CD16, CD22, CD86, CD27, CD152, PD1, or CD154.

In some embodiments, a single-chain chimeric antigen receptor or a multi-chain chimeric antigen receptor includes a synthetic transmembrane domain. In some cases, a synthetic transmembrane domain can include predominantly hydrophobic residues such as, without limitation, leucine and valine. In some embodiments, a synthetic transmembrane domain includes a triplet of phenylalanine, tryptophan, and valine at each end of the domain.

In some embodiments, a single-chain chimeric antigen receptor or a multi-chain chimeric antigen receptor includes a transmembrane domain that is a chimeric transmembrane domain having portions of a transmembrane domain from two or more endogenous mammalian (e.g., human) transmembrane polypeptides such as, without limitation, an $\alpha$ chain of a T cell receptor, a $\beta$ chain of the T cell receptor, a $\zeta$ chain of the T cell receptor, CD28, CD3$\varepsilon$, CD3$\delta$, CD3$\gamma$, CD33, CD37, CD64, CD80, CD45, CD4, CD5, CD8$\alpha$, CD9, CD16, CD22, CD86, CD27, CD152, PD1, and CD154, such that the two or more portions of transmembrane domains together constitute a functional transmembrane domain. In some embodiments, such a portion of a chimeric transmembrane domain can include one or more amino acid substitutions, deletions, or additions as compared to a corresponding portion of a wild type transmembrane domain.

A transmembrane domain can include one, two, three, four, five, six, seven, eight, nine, or ten contiguous amino acid sequences that each traverse a lipid bilayer when present in the corresponding endogenous polypeptide when expressed in a mammalian cell. As is known in the art, a transmembrane domain can, e.g., include at least one (e.g., two, three, four, five, six, seven, eight, nine, or ten) contiguous amino acid sequence (that traverses a lipid bilayer when present in the corresponding endogenous polypeptide when expressed in a mammalian cell) that has $\alpha$-helical secondary structure in the lipid bilayer. In some embodiments, a transmembrane domain can include two or more contiguous amino acid sequences (that each traverse a lipid bilayer when present in the corresponding endogenous polypeptide when expressed in a mammalian cell) that form a $\beta$-barrel secondary structure in the lipid bilayer. Additional examples and features of transmembrane domains are known in the art.

Antigen-Binding Domains

In some embodiments of the single-chain chimeric antigen receptors or the multi-chain chimeric antigen receptors, the antigen-binding domain can be selected from a scFv, a scFv-Fc, a VHH domain, a VNAR domain, a (scFv)$_2$, and a BiTE. Additional examples of antigen-binding domains that can be used in a single-chain chimeric antigen receptor or a multi-chain chimeric antigen receptor are known in the art.

A single-chain Fv or scFv fragment includes a $V_H$ domain and a $V_L$ domain in a single polypeptide chain. The $V_H$ and $V_L$ are generally linked by a peptide linker. In other examples, the linker can be a single amino acid. In some examples, the linker can be a chemical bond. See, e.g., Pluckthun, Antibodies from *E. coli*. In Rosenberg M. & Moore GP. (Eds.), The Pharmacology of Monoclonal Antibodies, Vol. 113, pp. 269-315, Springer-Verlag, New York, 1994. An exemplary $V_L$ and $V_H$ sequences that can be used in a scFv are shown in SEQ ID NOs: 18 and 21. An exemplary linker that can be used between the $V_L$ and $V_H$ domains in an scFv can be any of the exemplary linkers described herein (e.g., a linker having the sequence of SEQ ID NO: 31).

Sc-Fv-Fc fragments include an scFv attached to an Fc domain. For example, an Fc domain can be attached, e.g., to the C-terminus of the scFv. The Fc domain can follow the $V_L$ or $V_H$, depending on the orientation of the variable domains in the scFv. The Fc domain can be any Fc domain known in the art. In some examples, the Fc domain is an IgG1, IgG2, IgG3, or IgG4 Fc domain (e.g., a human IgG1, IgG2, IgG3, or IgG4 Fc domain).

BiTEs are antigen-binding domains that include two $V_L$ and two $V_H$ in a single polypeptide that together form two scFvs, which can each bind to different epitopes on the same antigen or each bind to different antigens. See, e.g., Baeuerle et al., *Curr. Opin. Mol. Ther.* 11:22-30, 2009; Wolf et al., *Drug Discovery Today* 10:1237-1244, 2005; and Huehls et al., *Immunol. Cell Biol.* 93:290-296, 2015.

A $V_H$H domain is a single monomeric variable antibody domain found in camelids, and a $V_{NAR}$ domain is a single monomeric variable antibody domain found in cartilaginous fish. $V_H$H domains and $V_{NAR}$ domains are described in, e.g., Van Audenhove et al., *EBioMedicine* 8:40-48, 2016; Krah et al., *Immunopharmacol. Immunotoxicol.* 38:21-28, 2016; Cromie et al., *Curr. Top. Med. Chem.* 15:2543-2557, 2016; Kijanka et al., *Nanomedicine* 10:161-174, 2015; Kovaleva et al., *Expert. Opin. Biol. Ther.* 14:1527-1539, 2014; De Meyer et al., *Trends Biotechnol.* 32:263-270, 2014; Mujic-Delic et al., *Trends Pharmacol. Sci.* 35:247-255, 2014; Muyldermans, *Ann. Rev. Biochem.* 82:775-797, 2013; Vincke et al., *Methods Mol. Biol.* 911:15-26, 2012; Rahbarizadeh et al., *Immunol. Invest.* 40:299-338, 2011; Van Bockstaele et al., *Curr. Opin. Investig. Drugs* 10:1212-1224, 2009; Wesolowski et al., *Med. Microbiol. Immunol.* 198:157-174, 2009; De Genst et al., *Dev. Comp. Immunol.* 30:187-198, 2006; Muyldermans, *J. Biotechnol.* 74:277-302, 2001; and Muyldermans et al., *Trends Biochem. Sci.* 26:230-235, 2001.

In some embodiments of the multi-chain chimeric antigen receptors, at least two of the polypeptides that make up the multi-chain chimeric antigen receptor can interact together to form an antigen-binding domain. In such embodiments, the antigen-binding domain can be selected from the group of an antigen-binding antibody fragment, a dual-affinity re-targeting antibody (DART), Fab-scFv-Fc, a triomab, a crossmab, an ortho-Fab IgG, IgG-scFv, scFv$_2$-Fc, a bi-nanobody, tanden antibody, a DART-Fc, a scFv-HAS-scFv, DNL-Fab$_3$, DAF (two-in-one or four-in-one), DutaMab, DT-IgGs knobs-in-holes common LC, knobs-in-holes assembly, Fab-arm exchange antibody, SEEDbody, Triomab, LUZ-Y, scDiabody-Fc, Fcab, la-body, orthogonal Fab, DVD-IgG; IgG(H)-scFv, scFv-(H)IgG; IgG(L)-scFv, scFv-(L)-IgG; IgG (L,H)-Fc, IgG(H)-V, V(H)-IgG; IgG(L)-V, V(L)-IgG; KIH IgG-scFab, 2scFv-IgG; IgG-2scFv, scFv4-Ig, Zybody, DVI-NG; nanobody, nanobody-HSA, a diabody, a TandAb, scDiabody, scDiabody-CH3, charge pair antibody, diabody-CH3, Cov-X-Bod, Triple Body, miniantibody, a DVD-Ig, minibody, a 2-in-1-IgG TriBi minibody, scFv-CH3 KIH, Fab-scFv, scFv-CH-CL-scFv, F(ab')$_2$-scFV$_2$, scFv-KIH, tetravalent HCAb, diabody-Fc, tandem scFv-Fc, intrabody, dock and lock bispecific antibody, ImmTAC, HSAbody, scDiabody-HAS, tandem scFv, IgG-IgG; and scFv1-PEG-scFv$_2$.

Non-limiting examples of an antigen-binding antibody fragments include an FAT fragment, a Fab fragment, a F(ab')$_2$ fragment, and a Fab' fragment. Additional examples of an antigen-binding antibody fragment is an antigen-binding fragment of an IgG (e.g., an antigen-binding fragment of IgG1, IgG2, IgG3, or IgG4) (e.g., an antigen-binding fragment of a human or humanized NG; e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM).

Examples of DVD-Igs are described, e.g., in DiGiammarino et al., *Methods Mol. Biol.* 899:145-156, 2012; Jakob et al., *MABs* 5:358-363, 2013; and U.S. Pat. Nos. 7,612,181; 8,258,268; 8,586,714; 8,716,450; 8,722,855; 8,735,546; and 8,822,645. Examples of DARTs are described in, e.g., Garber, *Nature Reviews Drug Discovery* 13:799-801, 2014. Examples of triomabs, kih IgG with a common LCs, crossmabs, ortho-Fab IgGs, 2-in-1-IgGs, IgG-ScFvs, scFv2-Fcs, bi-nanobodies, tanden antibodies, DART-Fes, scFv-HAS-scFvs, and DNL-Fab3s are described in, e.g., Kontermann et al., *Drug Discovery Today* 20:838-847, 2015. Examples of DAFs (two-in-one or four-in-one), DutaMabs, DT-IgGs, knobs-in-holes common LCs, knobs-in-holes assemblies, charge pair antibodies, Fab-arm exchange antibodies, SEEDbodies, Triomabs, LUZ-Ys, Fcabs, kλ-bodies, orthogonal Fabs, DVD-IgGs, IgG(H)-scFvs, scFv-(H)IgGs, IgG(L)-scFvs, scFv-(L)-IgGs, IgG (L,H)-Fcs, IgG(H)-Vs, V(H)-IgGs, IgG(L)-Vs, V(L)-IgGs, KIH IgG-scFabs, 2scFv-IgGs, IgG-2scFvs, scFv4-Igs, Zybodies, DVI-IgGs, nanobodies, nanobody-HSAs, diabodies, TandAbs, scDia-bodies, scDiabody-CH3s, Diabody-CH3s, Triple Bodies, miniantibodies, minibodies, TriBi minibodies, scFv-CH3 KIHs, Fab-scFvs, scFv-CH-CL-scFvs, F(ab')₂-scFV2s, scFv-KIHs, Fab-scFv-Fcs, tetravalent HCAbs, scDiabody-Fcs, diabody-Fcs, tandem scFv-Fcs, intrabodies, dock and lock bispecific antibodies, ImmTACs, HSAbodies, scDia-body-HASs, tandem scFvs, IgG-IgGs, Cov-X-Bodies, and scFv1-PEG-scFv2s are described in, e.g., Spiess et al., *Mol. Immunol.* 67:95-106, 2015.

Exemplary sequences that encode an anti-CD19 scFv are shown below.

```
(FMC63 V_L)
                                        SEQ ID NO: 17
gacatccagatgacccagaccaccagcagcctgagcgccagcctgggcga tagagtgaccatcagctgcagagccagccaggacatcagcaagtacctga actggtatcagcagaaacccgacggcaccgtgaagctgctgatctaccac accagcagactgcacagcggcgtgcccagcagattttctggcagcggctc cggcaccgactacagcctgaccatctccaacctggaacaggaagatatcg ctacctacttctgtcagcaaggcaacaccctgccctacaccttcggcgga ggcaccaagctggaaatcaca (FMC63 V_L)
                                        SEQ ID NO: 18
DIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGG

GTKLEIT ((G4S)3 linker between V_L and V_H)
                                        SEQ ID NO: 19
ggcggcggaggatctggcggaggcggaagtggcggagggggatct (FMC63 V_H)
                                        SEQ ID NO: 20
gaagtgaaactgcaggaaagcggccctggcctggtggcccatctcagtc tctgagcgtgacctgtaccgtgtccggcgtgtccctgcctgactatggcg
```

```
tgtcctggatcagacagcccccagaaagggcctggaatggctgggagtg atctggggcagcgagacaacctactacaacagcgccctgaagtcccggct gaccatcatcaaggacaactccaagagccaggtgttcctgaagatgaaca gcctgcagaccgacgacaccgccatctactactgcgccaagcactactac tacggcggcagctacgccatggactactggggccagggcacaagcgtgac cgtgtctagc (FMC63 V_H)
                                        SEQ ID NO: 21
EVKLQESGPGLVAPSQSLSVTCTVSGVSLPDYGVSWIRQPPRKGLEWLGV

IWGSETTYYNSALKSRLTIIKDNSKSQVFLKMNSLQTDDTAIYYCAKHYY

YGGSYAMDYWGQGTSVTVSS
```

Any of the antigen-binding domains described herein can bind to an antigen with a dissociation equilibrium constant ($K_D$) of less than $1\times10^{-7}$ M, less than $1\times10^{-8}$M, less than $1\times10^{-9}$ M, less than $1\times10^{-10}$M, less than $1\times10^{-11}$ M, less than $1\times10^{-12}$ M, or less than $1\times10^{-13}$ M. In some embodiments, the antigen-binding protein complexes provided herein can bind to a first and/or second antigen with a $K_D$ of about $1\times10^{-4}$ M to about $1\times10^{-6}$ M, about $1\times10^{-5}$ M to about $1\times10^{-7}$M, about $1\times10^{-6}$ M to about $1\times10^{-8}$M, about $1\times10^{-7}$ M to about $1\times10^{-9}$ M, about $1\times10^{-8}$ M to about $1\times10^{-10}$ M, or about $1\times10^{-9}$ M to about $1\times10^{-11}$ M (inclusive). A variety of different methods known in the art can be used to determine the $K_D$ value of an antigen-binding domain (e.g., an electrophoretic mobility shift assay, a filter binding assay, surface plasmon resonance, and a biomolecular binding kinetics assay, etc.).

Linker Peptide Sequences

In some embodiments, any two domains of single-chain chimeric antigen receptor, or any two neighboring domains within of a single-chain polypeptide that makes up a multi-chain chimeric antigen receptor (e.g., the at least one first polypeptide and second polypeptide) can be separated by a sequence that includes one or more (e.g., one, two, three, four, or five) linker peptide sequences. The length of a linker peptide sequence can be about 2 amino acids to about 100 amino acids, about 2 amino acids to about 95 amino acids, about 2 amino acids to about 90 amino acids, about 2 amino acids to about 85 amino acids, about 2 amino acids to about 80 amino acids, about 2 amino acids to about 75 amino acids, about 2 amino acids to about 70 amino acids, about 2 amino acids to about 65 amino acids, about 2 amino acids to about 60 amino acids, about 2 amino acids to about 55 amino acids, about 2 amino acids to about 50 amino acids, about 2 amino acids to about 45 amino acids, about 2 amino acids to about 40 amino acids, about 2 amino acids to about 35 amino acids, about 2 amino acids to about 30 amino acids, about 2 amino acids to about 25 amino acids, about 2 amino acids to about 20 amino acids, about 2 amino acids to about 15 amino acids, about 2 amino acids to about 14 amino acids, about 2 amino acids to about 12 amino acids, about 2 amino acids to about 10 amino acids, about 2 amino acids to about 8 amino acids, about 2 amino acids to about 6 amino acids, about 2 amino acids to about 4 amino acids, about 4 amino acids to about 100 amino acids, about 4 amino acids to about 95 amino acids, about 4 amino acids to about 90 amino acids, about 4 amino acids to about 85 amino acids, about 4 amino acids to about 80 amino acids, about 4 amino acids to about 75 amino acids, about 4 amino acids to about 70 amino acids, about 4 amino acids to about 65 amino acids, about 4 amino acids to about 60 amino acids, about 4 amino acids to about 55 amino acids, about 4 amino acids to about 50 amino acids, about 4 amino acids to about 45 amino acids, about 4 amino acids to about 40 amino acids, about 4 amino acids to about 35 amino acids, about 4 amino acids to about 30 amino acids, about 4 amino acids to about 25 amino acids, about 4 amino acids to about 20 amino acids, about 4 amino acids to about 15 amino acids, about 4 amino acids to about 14 amino acids, about 4 amino acids to about 12 amino acids, about 4 amino acids to about 10 amino acids, about 4 amino acids to about 8 amino acids, about 4 amino acids to about 6 amino acids, about 6 amino acids to about 100 amino acids, about 6 amino acids to about 95 amino acids, about 6 amino acids to about 90 amino acids, about 6 amino acids to about 85 amino acids, about 6 amino acids to about 80 amino acids, about 6 amino acids to about 75 amino acids, about 6 amino acids to about 70 amino acids, about 6 amino acids to about 65 amino acids, about 6 amino acids to about 60 amino acids, about 6 amino acids to about 55 amino acids, about 6 amino acids to about 50 amino acids, about 6 amino acids to about 45 amino acids, about 6 amino acids to about 40 amino acids, about 6 amino acids to about 35 amino acids, about 6 amino acids to about 30 amino acids, about 6 amino acids to about 25 amino acids, about 6 amino acids to about 20 amino acids, about 6 amino acids to about 15 amino acids, about 6 amino acids to about 14 amino acids, about 6 amino acids to about 12 amino acids, about 6 amino acids to about 10 amino acids, about 6 amino acids to about 8 amino acids, about 8 amino acids to about 100 amino acids, about 8 amino acids to about 95 amino acids, about 8 amino acids to about 90 amino acids, about 8 amino acids to about 85 amino acids, about 8 amino acids to about 80 amino acids, about 8 amino acids to about 75 amino acids, about 8 amino acids to about 70 amino acids, about 8 amino acids to about 65 amino acids, about 8 amino acids to about 60 amino acids, about 8 amino acids to about 55 amino acids, about 8 amino acids to about 50 amino acids, about 8 amino acids to about 45 amino acids, about 8 amino acids to about 40 amino acids, about 8 amino acids to about 35 amino acids, about 8 amino acids to about 30 amino acids, about 8 amino acids to about 25 amino acids, about 8 amino acids to about 20 amino acids, about 8 amino acids to about 15 amino acids, about 8 amino acids to about 14 amino acids, about 8 amino acids to about 12 amino acids, about 8 amino acids to about 10 amino acids, about 10 amino acids to about 100 amino acids, about 10 amino acids to about 95 amino acids, about 10 amino acids to about 90 amino acids, about 10 amino acids to about 85 amino acids, about 10 amino acids to about 80 amino acids, about 10 amino acids to about 75 amino acids, about 10 amino acids to about 70 amino acids, about 10 amino acids to about 65 amino acids, about 10 amino acids to about 60 amino acids, about 10 amino acids to about 55 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 20 amino acids, about 10 amino acids to about 15 amino acids, about 10 amino acids to about 14 amino acids, about 10 amino acids to about 12 amino acids, about 12 amino acids to about 100 amino acids, about 12 amino acids to about 95 amino acids, about 12 amino acids to about 90 amino acids, about 12 amino acids to about 85 amino acids, about 12 amino acids to about 80 amino acids, about 12 amino acids to about 75 amino acids, about 12 amino acids to about 70 amino acids, about 12 amino acids to about 65 amino acids, about 12 amino acids to about 60 amino acids, about 12 amino acids to about 55 amino acids, about 12 amino acids to about 50 amino acids, about 12 amino acids to about 45 amino acids, about 12 amino acids to about 40 amino acids, about 12 amino acids to about 35 amino acids, about 12 amino acids to about 30 amino acids, about 12 amino acids to about 25 amino acids, about 12 amino acids to about 20 amino acids, about 12 amino acids to about 15 amino acids, about 12 amino acids to about 14 amino acids, about 15 amino acids to about 100 amino acids, about 15 amino acids to about 95 amino acids, about 15 amino acids to about 90 amino acids, about 15 amino acids to about 85 amino acids, about 15 amino acids to about 80 amino acids, about 15 amino acids to about 75 amino acids, about 15 amino acids to about 70 amino acids, about 15 amino acids to about 65 amino acids, about 15 amino acids to about 60 amino acids, about 15 amino acids to about 55 amino acids, about 15 amino acids to about 50 amino acids, about 15 amino acids to about 45 amino acids, about 15 amino acids to about 40 amino acids, about 15 amino acids to about 35 amino acids, about 15 amino acids to about 30 amino acids, about 15 amino acids to about 25 amino acids, about 15 amino acids to about 20 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 65 amino acids, about 20 amino acids to about 60 amino acids, about 20 amino acids to about 55 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 65 amino acids, about 20 amino acids to about 60 amino acids, about 20 amino acids to about 55 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 25 amino acids to about 100 amino acids, about 25 amino acids to about 95 amino acids, about 25 amino acids to about 90 amino acids, about 25 amino acids to about 85 amino acids, about 25 amino acids to about 80 amino acids, about 25 amino acids to about 75 amino acids, about 25 amino acids to about 70 amino acids, about 25 amino acids to about 65 amino acids, about 25 amino acids to about 60 amino acids, about 25 amino acids to about 55 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 65 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 35 amino acids, about 35 amino acids to about 100 amino acids, about 35 amino acids to about 95 amino acids, about 35 amino acids to about 90 amino acids, about 35 amino acids to about 85 amino acids, about 35 amino acids to about 80 amino acids, about 35 amino acids to about 75 amino acids, about 35 amino acids to about 70 amino acids, about 35 amino acids to about 65 amino acids, about 35 amino acids to about 60 amino acids, about 35 amino acids to about 55 amino acids, about 35 amino acids to about 50 amino acids, about 35 amino acids to about 45 amino acids, about 35 amino acids to about 40 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 65 amino acids, about 40 amino acids to about 60 amino acids, about 40 amino acids to about 55 amino acids, about 40 amino acids to about 50 amino acids, about 40 amino acids to about 45 amino acids, about 45 amino acids to about 100 amino acids, about 45 amino acids to about 95 amino acids, about 45 amino acids to about 90 amino acids, about 45 amino acids to about 85 amino acids, about 45 amino acids to about 80 amino acids, about 45 amino acids to about 75 amino acids, about 45 amino acids to about 70 amino acids, about 45 amino acids to about 65 amino acids, about 45 amino acids to about 60 amino acids, about 45 amino acids to about 55 amino acids, about 45 amino acids to about 50 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 65 amino acids, about 50 amino acids to about 60 amino acids, about 50 amino acids to about 55 amino acids, about 55 amino acids to about 100 amino acids, about 55 amino acids to about 95 amino acids, about 55 amino acids to about 90 amino acids, about 55 amino acids to about 85 amino acids, about 55 amino acids to about 80 amino acids, about 55 amino acids to about 75 amino acids, about 55 amino acids to about 70 amino acids, about 55 amino acids to about 65 amino acids, about 55 amino acids to about 60 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 60 amino acids to about 65 amino acids, about 65 amino acids to about 100 amino acids, about 65 amino acids to about 95 amino acids, about 65 amino acids to about 90 amino acids, about 65 amino acids to about 85 amino acids, about 65 amino acids to about 80 amino acids, about 65 amino acids to about 75 amino acids, about 65 amino acids to about 70 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 70 amino acids to about 75 amino acids, about 75 amino acids to about 100 amino acids, about 75 amino acids to about 95 amino acids, about 75 amino acids to about 90 amino acids, about 75 amino acids to about 85 amino acids, about 75 amino acids to about 80 amino acids, about 80 amino acids to about 100 amino acids, about 80 amino acids to about 95 amino acids, about 80 amino acids to about 90 amino acids, about 80 amino acids to about 85 amino acids, about 85 amino acids to about 100 amino acids, about 85 amino acids to about 95 amino acids, about 85 amino acids to about 90 amino acids, about 90 amino acids to about 100 amino acids, about 90 amino acids to about 95 amino acids, or about 95 amino acids to about 100 amino acids.

A linker peptide sequence can be or include a non-naturally occurring sequence (e.g., a synthetic sequence). In some embodiments, a linker peptide sequence can include a sequence from a naturally occurring polypeptide (e.g., a domain). In some embodiments of any of the linker peptide sequences described herein, the linker peptide sequence is a flexible sequence (e.g., does not form an alpha alpha-helix or a beta-strand). In some embodiments of any of the linker peptide sequences described herein, the linker peptide sequence (or a portion thereof) forms an alpha-helix. In some embodiments of any of the linker peptides sequences described herein, the linker peptide sequence (or a portion thereof) forms a beta-strand.

In some embodiments, a linker peptide sequence can include one or more of the following amino acid sequences: GSGSGSGSGS (SEQ ID NO: 22), GSGSGSGS (SEQ ID NO: 23), or RSGSGSGS (SEQ ID NO: 24). In some embodiments, linker peptide sequence can be encoded by one or more of the following nucleic acid sequences:

```
                                 (SEQ ID NO: 25)
          GGATCCGGCAGCGGATCTGGCAGTGGAAGC, (SEQ ID NO: 26)
          GGATCTGGCTCTGGAAGCGGCAGC, (SEQ ID NO: 27)
          AGATCCGGATCTGGAAGTGGCTCC,
          or (SEQ ID NO: 28)
          GGAAGTGGATCTGGGAGCGGCTCT.
```

In some embodiments, a linker peptide sequence can include one or more (e.g., two, three, or four) copies of any one of SEQ ID NOs: 22-24, e.g., in tandem.

In some embodiments, a linker peptide sequence can be or can include one or more of SEQ ID NO: 23, 24, or 31. In some embodiments, a linker peptide sequence can be or include GS (which can, e.g., be encoded by the DNA sequence of ggatcc).

```
(DNA sequence encoding the exemplary linker
peptide sequence of SEQ ID NO: 23)
                                 SEQ ID NO: 29
ggatcaggcagtggctctggcagc (DNA sequence encoding the exemplary linker
peptide sequence of SEQ ID NO: 24)
                                 SEQ ID NO: 30
ggatctggaagtggctcc (DNA sequence encoding the exemplary linker
peptide sequence of SEQ ID NO: 23)
                                 SEQ ID NO: 28
ggaagtggatctgggagcggctct ((G4S)3 linker peptide sequence)
                                 SEQ ID NO: 31
GGGGSGGGGSGGGGS
```

Additional examples of linker peptide sequences that can be used in the present single-chain chimeric antigen receptors and multi-chain chimeric antigen receptors are known in the art.

Antigens

In some embodiments, an antigen-binding domain described herein can bind to a single antigen (e.g., any of the exemplary antigens described herein or known in the art). In some embodiments, an antigen-binding domain described herein can bind to two or more different antigens (e.g., two or more of any of the exemplary antigens described herein or known in the art). Non-limiting examples of antigens include: HER2, A33 antigen, 9-0-acetyl-GD3, CA19-9 marker, BhCG CA-125 marker, carboanhydrase IX (MN/CA IX), calreticulin, CCR5, CCR8, CD2, CD3, CD5, CD16, CD19, CD20, CD22, CD24, CD25, CD27, CD28, CD30, CD33, CD38, CD40L, CD44, CD44V6, CD63, CD70, CD84, CD96, CD100, CC123, CD133, CD138, CD150, CD152 (CTLA-4), CD160, CRTAM, CS1 (CD319), DNAM-1 (CD226), CD229, CD244, CD272 (BTLA), CD274 (PDL-1, B7H1), CD279 (PD-1), CD319, CD352, CRTAM (CD355), CD358, DR3, GITR (TNFRSF 18), HVEM, ICOS, LIGHT, LTBR, OX40, activating forms of KIR, NKG2C, NKG2D, NKG2E, one or more natural cytotoxicity receptors, NTB-A, PEN-5, carcinoma embryonic antigen (CEA; CD66e), desmoglein 4, E-cadherin neoepitope, endosialin, ephrin A2 (EphA2), epidermal growth factor receptor (EGFR), epithelial cell adhesion molecule (EpCAM), fucosyl GM1, GD2, GD3, GM2, ganglioside GM3, Globo H, glycoprotein 100, HER2/neu, HER3, HER4, insulin-like growth factor receptor 1, Lewis-Y, LG, Ly-6, melanoma-specific chondroitin-sulfate proteoglycan (MCSCP), mesothelin, MUC1, MUC2, MUC3, MUC4, MUC5AC, MUC5$_b$, MUC7, MUC16, Mullerian inhibitory substance (MIS) receptor type II, plasma cell antigen, poly SA, PSCA, PSMA, sonic hedgehog (SHH), SAS, STEAP, sTn antigen, TNF-α precursor, 2B4 (CD244), β2-integrins, KIR, KIR2DL1, KIR2DL2, KIR2DL3, KIR3DL2, KIR-L, KLRGI, LAIR-1, NKG2A, NKR-P IA, Siglec-3, Siglec-7, Siglec-9, TCRa, TCRB, TCR5y, TIM1, LAG3, LAIR1, PD-1H, TIGIT, TIM2, and TIM3.

In some embodiments, the antigen-binding domain described herein can specifically bind to antigen selected from the group of: MAGE, MUC16, CD19, WT-1, CD22, LI-CAM, ROR-1, CEA, 4-1BB, ETA, 5T4, adenocarcinoma antigen, alpha-fetoprotein (AFP), BAFF, B-lymphoma cell, C242 antigen, CA-125, carbonic anhydrase 9 (CA-IX), C-MET, CCR4, CD152, CD20, CD125 CD200, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, and vimentin.

Additional examples of antigens are known in the art.

Intracellular Signaling Domains

An example of an intracellular signaling domain is the intracellular signaling domain of Lck (also variously known as lymphocyte-specific protein tyrosine kinase, LCK protooncogene, Src family tyrosine kinase, IMD22, LSK, YT16, p561ck, or pp581ck). Lck is a member of the Src family of tyrosine kinases that is found in lymphocytes. Lck phosphorylates tyrosine residues of various proteins involved in the intracellular signaling pathways of lymphocytes. In some embodiments, an intracellular signaling domain can be an intracellular signaling domain from human Lck polypeptide. An exemplary polypeptide sequence of a human Lck (e.g., UniProt Protein Accession: P06239, found at URL www.uniprot.org/uniprot/P06239) with an exemplary intracellular signaling domain underlined is SEQ ID NO: 32. An intracellular signaling domain can be a portion of the exemplary intracellular signaling domain underlined in SEQ ID NO: 32, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 32.

```
(Human Lck with an exemplary intracellular
signaling domain underlined)
                              SEQ ID NO: 32
MGCGCSSHPEDDWMENIDVCENCHYPIVPLDGKGTLLIRNGSEVRDPLVT

YEGSNPPASPLQDNLVIALHSYEPSHDGDLGFEKGEQLRILEQSGEWWKA

QSLTTGQEGFIPFNFVAKANSLEPEPWFFKNLSRKDAERQLLAPGNTHGS

FLIRESESTAGSFSLSVRDFDQNQGEVVKHYKIRNLDNGGFYISPRITFP

GLHELVRHYTNASDGLCTRLSRPCQTQKPQKPWWEDEWEVPRETLKLVER

LGAGQFGEVWMGYYNGHTKVAVKSLKQGSMSPDAFLAEANLMKQLQHQRL

VRLYAVVTQEPIYIITEYMENGSLVDFLKTPSGIKLTINKLLDMAAQIAE

GMAFIEERNYIHRDLRAANILVSDTLSCKIADFGLARLIEDNEYTAREGA

KFPIKWTAPEAINYGTFTIKSDVWSFGILLTEIVTHGRIPYPGMTNPEVI

QNLERGYRMVRPDNCPEELYQLMRLCWKERPEDRPTFDYLRSVLEDFFTA

TEGQYQPQP
```

In some embodiments, an intracellular signaling domain can be an intracellular signaling domain from mouse Lck polypeptide. An exemplary polypeptide sequence of a mouse Lck (e.g., a polypeptide as shown in UniProt Protein Accession: P06240, found at URL www.uniprot.org/uniprot/P06240) with an exemplary intracellular signaling domain underlined is SEQ ID NO: 33. An intracellular signaling domain can be a portion of the exemplary intracellular signaling domain underlined in SEQ ID NO: 33, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 33.

```
(Mouse Lck polypeptide with an exemplary
intracellular signaling domain underlined)
                              SEQ ID NO: 33
MGCVCSSNPEDDWMENIDVCENCHYPIVPLDSKISLPIRNGSEVRDPLVT

YEGSLPPASPLQDNLVIALHSYEPSHDGDLGFEKGEQLRILEQSGEWWKA

QSLTTGQEGFIPFNFVAKANSLEPEPWFFKNLSRKDAERQLLAPGNTHGS

FLIRESESTAGSFSLSVRDFDQNQGEVVKHYKIRNLDNGGFYISPRITFP

GLHDLVRHYTNASDGLCTKLSRPCQTQKPQKPWWEDEWEVPRETLKLVER
```

-continued

LGAGQFGEVWMGYYNGHTKVAVKSLKQGSMSPDAFLAEANLMKQLQHPRL

VRLYAVVTQEPIYIITEYMENGSLVDFLKTPSGIKLNVNKLLDMAAQIAE

GMAFIEEQNYIHRDLRAANILVSDTLSCKIADFGLARLIEDNEYTAREGA

KFPIKWTAPEAINYGTFTIKSDVWSFGILLTEIVTHGRIPYPGMTNPEVI

QNLERGYRMVRPDNCPEELYHLMMLCWKERPEDRPTFDYLRSVLDDFFTA

TEGQYQPQP

In some embodiments, an intracellular signaling domain can be an intracellular signaling domain from FasR polypeptide (also variously known as Fas receptor, ALPS1A, APO-1, APT1, CD95, FAS1, FASTM, TNFRSF6, or Fas cell surface death receptor). The Fas receptor is encoded by the FasR gene, and is a death receptor on the surface of cells that leads to apoptosis.

In some embodiments, an intracellular signaling domain can be an intracellular signaling domain from human FasR polypeptide. An exemplary polypeptide sequence of a human FasR (e.g., UniProt Protein Accession: P25445, found at URL www.uniprot.org/uniprot/P25445) with an exemplary cytoplasmic signaling domain underlined is SEQ ID NO: 34. An intracellular signaling domain can be a portion of the exemplary intracellular signaling domain underlined in SEQ ID NO: 34, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 34.

(Human FasR polypeptide with an exemplary
intracellular signaling domain underlined)
                                    SEQ ID NO: 34
MLGIWTLLPLVLTSVARLSSKSVNAQVTDINSKGLELRKTVTTVETQNLE

GLHHDGQFCHKPCPPGERKARDCTVNGDEPDCVPCQEGKEYTDKAHFSSK

CRRCRLCDEGHGLEVEINCTRTQNTKCRCKPNFFCNSTVCEHCDPCTKCE

HGIIKECTLTSNTKCKEEGSRSNLGWLCLLLLPIPLIVWVKRKEVQKTCR

KHRKENQGSHESPTLNPETVAINLSDVDLSKYITTIAGVMTLSQVKGFVR

KNGVNEAKIDEIKNDNVQDTAEQKVQLLRNWHQLHGKKEAYDTLIKDLKK

ANLCTLAEKIQTIILKDITSDSENSNFRNEIQSLV

In some embodiments, an intracellular signaling domain can be an intracellular signaling domain of mouse FasR polypeptide. An exemplary polypeptide sequence of a mouse FasR (e.g., a polypeptide as shown in UniProt Protein Accession: P25446, found at URL www.uniprot.org/uniprot/P25446) with an exemplary cytoplasmic signaling domain underlined is SEQ ID NO: 35. An intracellular signaling domain can be a portion of the exemplary intracellular signaling domain underlined in SEQ ID NO: 35, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 35.

(Mouse FasR polypeptide with an exemplary
intracellular signaling domain underlined)
                                    SEQ ID NO: 35
MLWIWAVLPLVLAGSQLRVHTQGTNSISESLKLRRRVRETDKNCSEGLYQ

GGPFCCQPCQPGKKKVEDCKMNGGTPTCAPCTEGKEYMDKNHYADKCRRC

TLCDEEHGLEVETNCTLTQNTKCKCKPDFYCDSPGCEHCVRCASCEHGTL

EPCTATSNTNCRKQSPRNRLWLLTILVLLIPLVFIYRKYRKRKCWKRRQD

DPESRTSSRETIPMNASNLSLSKYIPRIAEDMTIQEAKKFARENNIKEGK

IDEIMHDSIQDTAEQKVQLLLCWYQSHGKSDAYQDLIKGLKKAECRRTLD

KFQDMVQKDLGKSTPDTGNENEGQCLE

In some embodiments, an intracellular signaling domain that is a domain from TNFR-I (also variously known as tumor necrosis factor receptor 1, TNFRSF1A, CD120a, FPF, MS5, TBP1, TNF-R, TNF-R-I, TNF-R55, TNFAR, TNFR1, TNFR1-d2, TNFR55, TNFR60, p55, p55-R, p60, tumor necrosis factor receptor superfamily member 1A, or TNF receptor superfamily member 1A). TNFR-I is a membrane receptor that binds tumor necrosis factor-alpha (TNFα). In some embodiments, an intracellular signaling domain can be an intracellular signaling domain of human TNFR-I polypeptide. An exemplary polypeptide sequence of a human TNFR-I (e.g., UniProt Protein Accession: P19438, found at URL www.uniprot.org/uniprot/P19438) with an exemplary cytoplasmic signaling domain underlined is SEQ ID NO: 36. An intracellular signaling domain can be a portion of the exemplary intracellular signaling domain underlined in SEQ ID NO: 36, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 36.

(Human TNFR-I polypeptide with an exemplary
intracellular signaling domain underlined)
                                    SEQ ID NO: 36
MGLSTVPDLLLPLVLLELLVGIYPSGVIGLVPHLGDREKRDSVCPQGKYI

HPQNNSICCTKCHKGTYLYNDCPGPGQDTDCRECESGSFTASENHLRHCL

SCSKCRKEMGQVEISSCTVDRDTVCGCRKNQYRHYWSENLFQCFNCSLCL

NGTVHLSCQEKQNTVCTCHAGFFLRENECVSCSNCKKSLECTKLCLPQIE

NVKGTEDSGTTVLLPLVIFFGLCLLSLLFIGLMYRYQRWKSKLYSIVCGK

STPEKEGELEGTTTKPLAPNPSFSPTPGFTPTLGFSPVPSSTFTSSSTYT

PGDCPNFAAPRREVAPPYQGADPILATALASDPIPNPLQKWEDSAHKPQS

LDTDDPATLYAVVENVPPLRWKEFVRRLGLSDHEIDRLELQNGRCLREAQ

YSMLATWRRRTPRREATLELLGRVLRDMDLLGCLEDIEEALCGPAALPPA

PSLLR

In some embodiments, an intracellular signaling domain can be an intracellular domain from a mouse TNFR-I polypeptide. An exemplary polypeptide sequence of a mouse TNFR-I (e.g., a polypeptide as shown in UniProt Protein Accession: P25118, found at URL www.uniprot.org/uniprot/P25118) with an exemplary cytoplasmic signaling domain underlined is SEQ ID NO: 37. An intracellular signaling domain can be a portion of the exemplary intracellular signaling domain underlined in SEQ ID NO: 37, or a sequence that is at least 50% identical (e.g., at least 55%, at least 60%, at least 70%, at least 75%, at least 80%, at least 85%, at least 90%, at least 95%, or at least 99% identical)

to the portion of the exemplary intracellular signaling domain underlined in SEQ ID NO: 37.

```
(Mouse TNFR-I polypeptide with an exemplary
intracellular signaling domain underlined)
                                  SEQ ID NO: 37
MGLPTVPGLLLSLVLLALLMGIHPSGVTGLVPSLGDREKRDSLCPQGKYV

HSKNNSICCTKCHKGTYLVSDCPSPGRDTVCRECEKGTFTASQNYLRQCL

SCKTCRKEMSQVEISPCQADKDTVCGCKENQFQRYLSETHFQCVDCSPCF

NGTVTIPCKETQNTVCNCHAGFFLRESECVPCSHCKKNEECMKLCLPPPL

ANVTNPQDSGTAVLLPLVILLGLCLLSFIFISLMCRYPRWRPEVYSIICR

DPVPVKEEKAGKPLTPAPSPAFSPTSGFNPTLGFSTPGFSSPVSSTPISP

IFGPSNWHFMPPVSEVVPTQGADPLLYESLCSVPAPTSVQKWEDSAHPQR

PDNADLAILYAVVDGVPPARWKEFMRFMGLSEHEIERLEMQNGRCLREAQ

YSMLEAWRRRTPRHEDTLEVVGLVLSKMNLAGCLENILEALRNPAPSSTT

RLPR
```

In some embodiments, an intracellular signaling domain can be an intracellular signaling domain from TNFR-II (also variously known as tumor necrosis factor receptor 2, TNFRSF1B, CD120b, TBPII, TNF-R-II, TNF-R75, TNFBR, TNFR1B, TNFR2, TNFR80, p75, p75TNFR, tumor necrosis factor receptor superfamily member 1B, or TNF receptor superfamily member 1B). TNFR-II is a membrane receptor that binds tumor necrosis factor-alpha (TNFα). In some embodiments, an intracellular signaling domain can be an intracellular signaling domain from a human TNFR-II polypeptide. An exemplary polypeptide sequence of a human TNFR-II (e.g., UniProt Protein Accession: P20333, found at URL www.uniprot.org/uniprot/P20333) with an exemplary cytoplasmic signaling domain underlined is SEQ ID NO: 38. An intracellular signaling domain can be a portion of the exemplary intracellular signaling domain underlined in SEQ ID NO: 38, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 38.

```
(Human TNFR-II polypeptide with an exemplary
intracellular signaling domain underlined)
                                  SEQ ID NO: 38
MAPVAVWAALAVGLELWAAAHALPAQVAFTPYAPEPGSTCRLREYYDQTA

QMCCSKCSPGQHAKVFCTKTSDTVCDSCEDSTYTQLWNWVPECLSCGSRC

SSDQVETQACTREQNRICTCRPGWYCALSKQEGCRLCAPLRKCRPGFGVA

RPGTETSDVVCKPCAPGTFSNTTSSTDICRPHQICNVVAIPGNASMDAVC

TSTSPTRSMAPGAVHLPQPVSTRSQHTQPTPEPSTAPSTSFLLPMGPSPP

AEGSTGDFALPVGLIVGVTALGLLIIGVVNCVIMTQVKKKPLCLQREAKV

PHLPADKARGTQGPEQQHLLITAPSSSSSSLESSASALDRRAPTRNQPQA

PGVEASGAGEARASTGSSDSSPGGHGTQVNVTCIVNVCSSSDHSSQCSSQ

ASSTMGDTDSSPSESPKDEQVPFSKEECAFRSQLETPETLLGSTEEKPLP

LGVPDAGMKPS
```

In some embodiments, an intracellular signaling domain is an intracellular signaling domain from a mouse TNFR-II polypeptide. An exemplary polypeptide sequence of a mouse TNFR-II (e.g., a polypeptide as shown in UniProt Protein Accession: P25119, found at URL www.uniprot.org/uniprot/P25119) with an exemplary cytoplasmic signaling domain underlined is SEQ ID NO: 39. An intracellular signaling domain can be a portion of the exemplary intracellular signaling domain underlined in SEQ ID NO: 39, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 39.

```
(Mouse TNFR-II polypeptide with an exemplary
intracellular signaling domain underlined)
                                  SEQ ID NO: 39
MAPAALWVALVFELQLWATGHTVPAQVVLTPYKPEPGYECQISQEYYDRK

AQMCCAKCPPGQYVKHFCNKTSDTVCADCEASMYTQVWNQFRTCLSCSSS

CTTDQVEIRACTKQQNRVCACEAGRYCALKTHSGSCRQCMRLSKCGPGFG

VASSRAPNGNVLCKACAPGTFSDTTSSTDVCRPHRICSILAIPGNASTDA

VCAPESPTLSAIPRTLYVSQPEPTRSQPLDQEPGPSQTPSILTSLGSTPI

IEQSTKGGISLPIGLIVGVTSLGLLMLGLVNCIILVQRKKKPSCLQRDAK

VPHVPDEKSQDAVGLEQQHLLTTAPSSSSSSLESSASAGDRRAPPGGHPQ

ARVMAEAQGFQEARASSRISDSSHGSHGTHVNVTCIVNVCSSSDHSSQCS

SQASATVGDPDAKPSASPKDEQVPFSQEECPSQSPCETTETLQSHEKPLP

LGVPDMGMKPSQAGWFDQIAVKVA
```

In some embodiments, an intracellular signaling domain is an intracellular signaling domain is from LIGHT (also variously known as tumor necrosis factor superfamily member 14, TNFSF14, CD258, HVEML, LIGHT, LTg, TR2, TNLG1D, tumor necrosis factor superfamily member 14, or TNF superfamily member 14). LIGHT is a secreted protein of the TNF superfamily, has been shown to stimulate the proliferation of T cells, and trigger apoptosis of various tumor cells, and has been shown to interact with TNFRSF14, TNFRSF6B, BIRC2, TRAF2, and TRAF3. In some embodiments, an intracellular signaling domain is an intracellular signaling domain from a human LIGHT polypeptide. An exemplary polypeptide sequence of a human LIGHT (e.g., UniProt Protein Accession: O43557, found at URL www.uniprot.org/uniprot/O43557) with an exemplary cytoplasmic signaling domain underlined is SEQ ID NO: 40. An intracellular signaling domain can be a portion of the exemplary intracellular signaling domain underlined in SEQ ID NO: 40, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 40.

```
(Human LIGHT polypeptide with an exemplary
intracellular signaling domain underlined)
                                  SEQ ID NO: 40
MEESVVRPSVFVVDGQTDIPFTRLGRSHRRQSCSVARVGLGLLLLLMGAG

LAVQGWFLLQLHWRLGEMVTRLPDGPAGSWEQLIQERRSHEVNPAAHLTG

ANSSLTGSGGPLLWETQLGLAFLRGLSYHDGALVVTKAGYYYIYSKVQLG

GVGCPLGLASTITHGLYKRTPRYPEELELLVSQQSPCGRATSSSRVWWDS
```

-continued

SFLGGVVHLEAGEKVVVRVLDERLVRLRDGTRSYFGAFMV

In some embodiments, an intracellular signaling domain is an intracellular signaling domain from a mouse LIGHT polypeptide. An exemplary polypeptide sequence of a mouse LIGHT (e.g., a polypeptide as shown in UniProt Protein Accession: Q9QYH9, found at URL www.uniprot.org/uniprot/Q9QYH9) with an exemplary cytoplasmic signaling domain underlined is SEQ ID NO: 41. An intracellular signaling domain can be a portion of the exemplary intracellular signaling domain underlined in SEQ ID NO: 41, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 41.

(Mouse LIGHT polypeptide with an exemplary
intracellular signaling domain underlined)
                                SEQ ID NO: 41
*MESVVQPSVFVVDGQTDIPFRRLEQNHRRRRCGTVQVS*LALVLLLGAGLA

TQGWFLLRLHQRLGDIVAHLPDGGKGSWEKLIQDQRSHQANPAAHLTGAN

ASLIGIGGPLLWETRLGLAFLRGLTYHDGALVTMEPGYYYVYSKVQLSGV

GCPQGLANGLPITHGLYKRTSRYPKELELLVSRRSPCGRANSSRVWWDSS

FLGGVVHLEAGEEVVVRVPGNRLVRPRDGTRSYFGAFMV

In some embodiments, an intracellular signaling domain can be an intracellular signaling domain from ICOS (also variously known as CD278, AILIM, CVID1, inducible T-cell costimulator, or inducible T-cell costimulator). ICOS is an immune checkpoint protein that is a member of the CD28-superfamily costimulatory molecule and is expressed on activated T cells. In some embodiments, an intracellular signaling domain is an intracellular signaling domain from a human ICOS polypeptide. An exemplary polypeptide sequence of a human ICOS (e.g., UniProt Protein Accession: Q9Y6W8, found at URL www.uniprot.org/uniprot/Q9Y6W8) with an exemplary intracellular signaling domain underlined is SEQ ID NO: 42. An intracellular to signaling domain can be a portion of the exemplary intracellular signaling domain underlined in SEQ ID NO: 42, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 42.

(Human ICOS polypeptide with an exemplary
intracellular signaling domain underlined)
                                SEQ ID NO: 42
MKSGLWYFFLFCLRIKVLTGEINGSANYEMFIFHNGGVQILCKYPDIVQQ

FKMQLLKGGQILCDLTKTKGSGNTVSIKSLKFCHSQLSNNSVSFFLYNLD

HSHANYYFCNLSIFDPPPFKVTLTGGYLHIYESQLCCQLKFWLPIGCAAF

VVVCILGCILI*CWLTKKKYSSSVHDPNGEYMFMRAVNTAKKSRLTDVTL*

In some embodiments, an intracellular signaling domain is an intracellular signaling domain from a mouse ICOS polypeptide. An exemplary polypeptide sequence of a mouse ICOS (e.g., a polypeptide as shown in UniProt Protein Accession: Q9WVS0, found at URL www.uniprot.org/uniprot/Q9WVS0) with an exemplary intracellular signaling domain underlined is SEQ ID NO: 43. An intracellular signaling domain can be a portion of the exemplary intracellular signaling domain underlined in SEQ ID NO: 43, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 43.

(Mouse ICOS polypeptide with an exemplary
intracellular signaling domain underlined)
                                SEQ ID NO: 43
MKPYFCRVFVFCFLIRLLTGEINGSADHRMFSFHNGGVQISCKYPETVQQ

LKMRLFREREVLCELTKTKGSGNAVSIKNPMLCLYHLSNNSVSFFLNNPD

SSQGSYYFCSLSIFDPPPFQERNLSGGYLHIYESQLCCQLKLWLPVGCAA

FVVVLLFGCILIIWF*SKKKYGSSVHDPNSEYMFMAAVNTNKKSRLAGVTS*

In some embodiments, an intracellular signaling domain can be an intracellular signaling domain from 4-1BB (also variously known as TNFRSF9, CD137, CDw137, ILA, tumor necrosis factor receptor superfamily member 9, or TNF receptor superfamily member 9). 4-1BB is a member of the tumor necrosis factor (TNF) receptor family that contributes to costimulatory activity for activated T cells. In some embodiments, an intracellular signaling domain is an intracellular signaling domain from a human 4-1BB polypeptide. An exemplary polypeptide sequence of a human 4-1BB (e.g., UniProt Protein Accession: Q07011, found at URL www.uniprot.org/uniprot/Q07011) with an exemplary intracellular signaling domain underlined is SEQ ID NO: 44. An intracellular signaling domain can be a portion of the exemplary intracellular signaling domain underlined in SEQ ID NO: 44, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 44.

(Human 4-1BB polypeptide with an exemplary
intracellular signaling domain underlined)
                                SEQ ID NO: 44
MGNSCYNIVATLLLVLNFERTRSLQDPCSNCPAGTFCDNNRNQICSPCPP

NSFSSAGGQRTCDICRQCKGVFRTRKECSSTSNAECDCTPGFHCLGAGCS

MCEQDCKQGQELTKKGCKDCCFGTFNDQKRGICRPWTNCSLDGKSVLVNG

TKERDVVCGPSPADLSPGASSVTPPAPAREPGHSPQIISFFLALTSTALL

FLLFFLTLRFSVV*KRGRKKLLYIFKQPFMRPVQTTQEEDGCSCRFPEEEE*

*GGCEL*

In some embodiments, an intracellular signaling domain can be or can include a sequence that is at least 50% (at least 55%, at least 60%, at least 65%, at least 70%, at least 75%, at least 80%, at least 85%, at least 90%, at least 95%, at least 99%, or 100%) identical to SEQ ID NO: 45.

(4-1BB intracellular signaling domain)
                                SEQ ID NO: 45
KRGRKKLLYIFKQPFMRPVQTTQEEDGCSCRFPEEEEGGCEL (DNA sequence encoding the 4-1BB intracellular
signaling domain of SEQ ID NO: 45)
                                SEQ ID NO: 46
AAAAGGGGCCGGAAAAAGCTGCTGTATATTTTCAAACAGCCTTTTATGAG -continued

GCCTGTGCAGACAACACAGGAAGAGGACGGCTGTAGCTGTCGGTTCCCCG

AAGAGGAAGAGGGGGGCTGCGAACTG

In some embodiments, an intracellular signaling domain can be an intracellular domain from amino acids 214 to 255 of SEQ ID NO: 44 (human 4-1BB). In some embodiments, a costimulatory domain is or includes a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to amino acids 214 to 255 of SEQ ID NO: 44, or a portion thereof.

(Human 4-1BB polypeptide)
SEQ ID NO: 44
MGNSCYNIVATLLLVLNFERTRSLQDPCSNCPAGTFCDNNRNQICSPCPP

NSFSSAGGQRTCDICRQCKGVFRTRKECSSTSNAECDCTPGFHCLGAGCS

MCEQDCKQGQELTKKGCKDCCFGTFNDQKRGICRPWTNCSLDGKSVLVNG

TKERDVVCGPSPADLSPGASSVTPPAPAREPGHSPQIISFFLALTSTALL

FLLFFLTLRFSVVKRGRKKLLYIFKQPFMRPVQTTQEEDGCSCRFPEEEE

GGCEL

In some embodiments, an intracellular signaling domain can be or can include a sequence that is at least 50% (at least 55%, at least 60%, at least 65%, at least 70%, at least 75%, at least 80%, at least 85%, at least 90%, at least 95%, at least 99%, or 100%) identical to SEQ ID NO: 47.

(Human 4-1BB intracellular signaling domain)
SEQ ID NO: 47
KRGRKKLLYIFKQPFMRPVQTTQEEDGCSCRFPEEEEGGCE (DNA encoding the 4-1BB intracellular signaling
domain of SEQ ID NO: 47)
SEQ ID NO: 48
aaacggggcagaaagaaactcctgtatatattcaaacaaccatttatgag accagtacaaactactcaagaggaagatggctgtagctgccgatttccag aagaagaagaaggaggatgtgaa In some embodiments, an intracellular signaling domain can be an intracellular signaling domain from a mouse 4-1BB polypeptide. An exemplary polypeptide sequence of a mouse 4-1BB (e.g., a polypeptide as shown in UniProt Protein Accession: P20334, found at URL www.uniprot.org/uniprot/P20334) with an exemplary intracellular signaling domain underlined is SEQ ID NO: 49. An intracellular signaling domain can be a portion of the exemplary intracellular signaling domain underlined in SEQ ID NO: 49, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 49.

(Mouse 4-1BB polypeptide with an exemplary
intracellular signaling domain underlined)
SEQ ID NO: 49
MGNNCYNVVVIVLLLVGCEKVGAVQNSCDNCQPGTFCRKYNPVCKSCPPS

TFSSIGGQPNCNICRVCAGYFRFKKFCSSTHNAECECIEGFHCLGPQCTR

CEKDCRPGQELTKQGCKTCSLGTFNDQNGTGVCRPWTNCSLDGRSVLKTG

-continued

TTEKDVVCGPPVVSFSPSTTISVTPEGGPGGHSLQVLTLFLALTSALLLA

LIFITLLF*SVLKWIRKKFPHIFKQPFKKTTGAAQEEDACSCRCPQEEEGG*

*GGGYEL*

In some embodiments, an intracellular signaling domain can be a domain from CD27 (also variously known as S152, S152. LPFS2, T14, TNFRSF7, Tp55, or CD27 molecule). CD27 is a member of the tumor necrosis factor (TNF) receptor superfamily and plays a role in the generation and long-term maintenance of T cell immunity. In some embodiments, an intracellular signaling domain can be an intracellular signaling domain from a human CD27 polypeptide. An exemplary polypeptide sequence of a human CD27 (e.g., UniProt Protein Accession: P26842, found at URL www.uniprot.org/uniprot/P26842) with an intracellular signaling domain underlined is SEQ ID NO: 50. An intracellular signaling domain can be a portion of the exemplary intracellular signaling domain underlined in SEQ ID NO: 50, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 50.

(Human CD27 polypeptide with an exemplary
intracellular signaling domain underlined)
SEQ ID NO: 50
MARPHPWWLCVLGTLVGLSATPAPKSCPERHYWAQGKLCCQMCEPGTFLV

KDCDQHRKAAQCDPCIPGVSFSPDHHTRPHCESCRHCNSGLLVRNCTITA

NAECACRNGWQCRDKECTECDPLPNPSLTARSSQALSPHPQPTHLPYVSE

MLEARTAGHMQTLADFRQLPARTLSTHWPPQRSLCSSDFIRILVIFSGMF

LVFTLAGALFLH*QRRKYRSNKGESPVEPAEPCHYSCPREEEGSTIPIQED*

*YRKPEPACSP*

In some embodiments, an intracellular signaling domain can be or can include a sequence that is at least 50% (at least 55%, at least 60%, at least 65%, at least 70%, at least 75%, at least 80%, at least 85%, at least 90%, at least 95%, at least 99%, or 100%) identical to SEQ ID NO: 51.

(CD27 Intracellular Signaling Domain)
SEQ ID NO: 51
QRRKYRSNKGESPVEPAEPCHYSCPREEEGSTIPIQEDYRKPEPACSP In some embodiments, an intracellular signaling domain can be an intracellular signaling domain from a mouse CD27 polypeptide. An exemplary polypeptide sequence of a mouse CD27 (e.g., a polypeptide as shown in UniProt Protein Accession: P41272, found at URL www.uniprot.org/uniprot/P41272) with an exemplary intracellular signaling domain underlined is SEQ ID NO: 52. An intracellular signaling domain can be a portion of the exemplary intracellular signaling domain underlined in SEQ ID NO: 52, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 52.

(Mouse CD27 polypeptide with an exemplary
intracellular signaling domain underlined)
                                  SEQ ID NO: 52
MAWPPPYWLCMLGTLVGLSATLAPNSCPDKHYWTGGGLCCRMCEPGTFFV

KDCEQDRTAAQCDPCIPGTSFSPDYHTRPHCESCRHCNSGFLIRNCTVTA

NAECSCSKNWQCRDQECTECDPPLNPALTRQPSETPSPQPPPTHLPHGTE

KPSWPLHRQLPNSTVYSQRSSHRPLCSSDCIRIFVTFSSMFLIFVLGAIL

FFH*QRRNHGPNEDRQAVPEEPCPYSCPREEEGSAIPIQEDYRKPEPAFYP*

In some embodiments, an intracellular signaling domain can be a domain from OX40 (also variously known as CD134, TNFRSF4, ACT35, IMD16, OX40, TXGP1L, tumor necrosis factor receptor superfamily member 4, or TNF receptor superfamily member 4). OX40 is a member of the tumor necrosis factor (TNF) receptor superfamily and is a secondary co-stimulatory immune checkpoint molecule. OX40 binds to its ligand OX40L. In some embodiments, an intracellular signaling domain can be an intracellular signaling domain from a human OX40 polypeptide. An exemplary polypeptide sequence of a human OX40 (e.g., UniProt Protein Accession: P43489, found at URL www.uniprot.org/uniprot/P43489) with an exemplary intracellular signaling domain underlined is SEQ ID NO: 53. An intracellular signaling domain can be a portion of the exemplary intracellular signaling domain underlined in SEQ ID NO: 53, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 53.

(Human OX40 polypeptide with an exemplary
intracellular signaling domain underlined)
                                  SEQ ID NO: 53
MCVGARRLGRGPCAALLLLGLGLSTVTGLHCVGDTYPSNDRCCHECRPGN

GMVSRCSRSQNTVCRPCGPGFYNDVVSSKPCKPCTWCNLRSGSERKQLCT

ATQDTVCRCRAGTQPLDSYKPGVDCAPCPPGHFSPGDNQACKPWTNCTLA

GKHTLQPASNSSDAICEDRDPPATQPQETQGPPARPITVQPTEAWPRTSQ

GPSTRPVEVPGGRAVAAILGLGLVLGLLGPLAILL*ALYLLRRDQRLPPDA*

*HKPPGGGSFRTPIQEEQADAHSTLAKI*

In some embodiments, an intracellular signaling domain can be or can include a sequence that is at least 50% (at least 55%, at least 60%, at least 65%, at least 70%, at least 75%, at least 80%, at least 85%, at least 90%, at least 95%, at least 99%, or 100%) identical to SEQ ID NO: 54.

(OX40 intracellular signaling domain)
                                  SEQ ID NO: 54
    ALYLLRRDQRLPPDAHKPPGGGSFRTPIQEEQADAHSTLAKI In some embodiments, an intracellular signaling domain can be an intracellular signaling domain from a mouse OX40 polypeptide. An exemplary polypeptide sequence of a mouse OX40 (e.g., a polypeptide as shown in UniProt Protein Accession: P47741, found at URL www.uniprot.org/uniprot/P47741) with an exemplary intracellular signaling domain underlined is SEQ ID NO: 55. An intracellular signaling domain can be a portion of the exemplary intracellular signaling domain underlined in SEQ ID NO: 55, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 55.

(Mouse OX40 polypeptide with an exemplary
intracellular signaling domain underlined)
                                  SEQ ID NO: 55
MYVWVQQPTALLLLALTLGVTARRLNCVKHTYPSGHKCCRECQPGHGMVS

RCDHTRDTLCHPCETGFYNEAVNYDTCKQCTQCNHRSGSELKQNCTPTQD

TVCRCRPGTQPRQDSGYKLGVDCVPCPPGHFSPGNNQACKPWTNCTLSGK

QTRHPASDSLDAVCEDRSLLATLLWETQRPTFRPTTVQSTTVWPRTSELP

SPPTLVTPEGPAFAVLLGLGLGLLAPLTVLLALYLL*RKAWRLPNTPKPCW*

*GNSFRTPIQEEHTDAHFTLAKI*

In some embodiments, an intracellular signaling domain can be an intracellular signaling domain from CD2 (also variously known as cluster of differentiation 2, LFA-2, SRBC, T11, or CD2 molecule). CD2 is a cell adhesion molecule found on the surface of T cells and natural killer (NK) cells, and acts as a co-stimulatory molecule on these cells. In some embodiments, an intracellular signaling domain can be an intracellular signaling domain from a human CD2 polypeptide. An exemplary polypeptide sequence of a human CD2 (e.g., UniProt Protein Accession: P06729, found at URL www.uniprot.org/uniprot/P06729) with an exemplary intracellular signaling domain underlined is SEQ ID NO: 56. An intracellular signaling domain can be a portion of the exemplary intracellular signaling domain underlined in SEQ ID NO: 56, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 56.

(Human CD2 polypeptide with an exemplary
intracellular signaling domain underlined)
                                  SEQ ID NO: 56
MSFPCKFVASFLLIFNVSSKGAVSKEITNALETWGALGQDINLDIPSFQM

SDDIDDIKWEKTSDKKKIAQFRKEKETFKEKDTYKLFKNGTLKIKHLKTD

DQDIYKVSIYDTKGKNVLEKIFDLKIQERVSKPKISWTCINTTLTCEVMN

GTDPELNLYQDGKHLKLSQRVITHKWTTSLSAKFKCTAGNKVSKESSVEP

VSCPEKGLDIYLIIGICGGGSLLMVFVALLVFYIT*KRKKQRSRRNDEELE*

*TRAHRVATEERGRKPHQIPASTPQNPATSQHPPPPPGHRSQAPSHRPPPP*

*GHRVQHQPQKRPPAPSGTQVHQQKGPPLPRPRVQPKPPHGAAENSLSPSS*

*N*

In some embodiments, an intracellular signaling domain can be an intracellular signaling domain from a mouse CD2 polypeptide. An exemplary polypeptide sequence of a mouse CD2 (e.g., a polypeptide as shown in UniProt Protein Accession: P08920, found at URL www.uniprot.org/uniprot/P08920) with an exemplary intracellular signaling domain underlined is SEQ ID NO: 57. An intracellular signaling domain can be a portion of the exemplary intracellular signaling domain underlined in SEQ ID NO: 57, or a sequence that is at least 50% identical (e.g., at least 55%, at least 60%, at least 70%, at least 75%, at least 80%, at least 85%, at least 90%, at least 95%, or at least 99% identical)

to the portion of the exemplary intracellular signaling domain underlined in SEQ ID NO: 57.

```
(Mouse CD2 polypeptide with an exemplary
intracellular signaling domain underlined)
                                SEQ ID NO: 57
MKCKFLGSFFLLFSLSGKGADCRDNETIWGVLGHGITLNIPNFQMTDDID

EVRWVRRGTLVAEFKRKKPPFLISETYEVLANGSLKIKKPMMRNDSGTYN

VMVYGTNGMTRLEKDLDVRILERVSKPMIHWECPNTTLTCAVLQGTDFEL

KLYQGETLLNSLPQKNMSYQWTNLNAPFKCEAINPVSKESKMEVVNCPEK

GLSFYVTVGVGAGGLLLVLLVALFIFCICKRRKRNRRRKDEELEIKASRT

STVERGPKPHSTPAAAAQNSVALQAPPPPGHHLQTPGHRPLPPGHRTREH

QQKKRPPPSGTQIHQQKGPPLPRPRVQPKPPCGSGDGVSLPPPN
```

In some embodiments, an intracellular signaling domain can be an intracellular signaling domain from CD5 (also variously known as cluster of differentiation 5, LEU1, T1, or CD5 molecule). CD5 is expressed on the surface of T cells and is upregulated on T cells upon strong activation. In some embodiments, an intracellular signaling domain can be an intracellular signaling domain from a human CD5 polypeptide. An exemplary polypeptide sequence of a human CD5 (e.g., UniProt Protein Accession: P06127, found at URL www.uniprot.org/uniprot/P06127) with an exemplary intracellular signaling domain underlined is SEQ ID NO: 58. An intracellular signaling domain can be a portion of the exemplary intracellular signaling domain underlined in SEQ ID NO: 58, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 58.

```
(Human CD5 polypeptide with an exemplary
intracellular signaling domain underlined)
                                SEQ ID NO: 58
MPMGSLQPLATLYLLGMLVASCLGRLSWYDPDFQARLTRSNSKCQGQLEV

YLKDGWHMVCSQSWGRSSKQWEDPSQASKVCQRLNCGVPLSLGPFLVTYT

PQSSIICYGQLGSFSNCSHSRNDMCHSLGLTCLEPQKTTPPTTRPPPTTT

PEPTAPPRLQLVAQSGGQHCAGVVEFYSGSLGGTISYEAQDKTQDLENFL

CNNLQCGSFLKHLPETEAGRAQDPGEPREHQPLPIQWKIQNSSCTSLEHC

FRKIKPQKSGRVLALLCSGFQPKVQSRLVGGSSICEGTVEVRQGAQWAAL

CDSSSARSSLRWEEVCREQQCGSVNSYRVLDAGDPTSRGLFCPHQKLSQC

HELWERNSYCKKVFVTCQDPNPAGLAAGTVASIILALVLLVVLLVVCGPL

AYKKLVKKFRQKKQRQWIGPTGMNQNMSFHRNHTATVRSHAENPTASHVD

NEYSQPPRNSHLSAYPALEGALHRSSMQPDNSSDSDYDLHGAQRL
```

In some embodiments, an intracellular signaling domain can be an intracellular signaling domain from a mouse CD5 polypeptide. An exemplary polypeptide sequence of a mouse CD5 (e.g., a polypeptide as shown in UniProt Protein Accession: P13379, found at URL www.uniprot.org/uniprot/P13379) with an intracellular signaling domain underlined is SEQ ID NO: 59. An intracellular signaling domain can be a portion of the exemplary intracellular signaling domain underlined in SEQ ID NO: 59, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 59.

```
(Mouse CD5 polypeptide with an exemplary
intracellular signaling domain underlined)
                                SEQ ID NO: 59
MDSHEVLLAATYLLGTLAAFCLGQSGRGGLDIQVMLSGSNSKCQGQVEIQ

MENKWKTVCSSSWRLSQDHSKNAQQASAVCKQLRCGDPLALGPFPSLNRP

QNQVFCQGSPWSISNCNNTSSQDQCLPLSLICLEPQRTTPPPTTTPPTTV

PEPTAPPRLQLVPGHEGLRCTGVVEFYNGSWGGTILYKAKDRPLGLGNLI

CKSLQCGSFLTHLSGTEAAGTPAPAELRDPRPLPIRWEAPNGSCVSLQQC

FQKTTAQEGGQALTVICSDFQPKVQSRLVGGSSVCEGIAEVRQRSQWEAL

CDSSAARGRGRWEELCREQQCGDLISFHTVDADKTSPGFLCAQEKLSQCY

HLQKKKHCNKRVFVTCQDPNPAGLAPGTVASIILTLVLLVVLLAMCGPLV

YKKLVKKFRQKKQRQWIGPTGVNQNMSFHRSHTATVRSQVENPTASHVDN

EYSQPPRNSHLSAYPALEGALHRSSTQPDNSSDSDYDLQVAQRL
```

In some embodiments, an intracellular signaling domain can be an intracellular signaling domain from CD30 (also variously known as TNFRSF8, D1S166E, Ki-1, tumor necrosis factor receptor superfamily member 8, or TNF receptor superfamily member 8). CD30 is expressed by activated T and B cells and is involved with the activation of NF-kappaB. In some embodiments, an intracellular signaling domain can be an intracellular signaling domain from a human CD30 polypeptide. An exemplary polypeptide sequence of a human CD30 (e.g., UniProt Protein Accession: P28908, found at URL www.uniprot.org/uniprot/P28908) with an exemplary intracellular signaling domain underlined is SEQ ID NO: 60. An intracellular signaling domain can be a portion of the exemplary intracellular signaling domain underlined in SEQ ID NO: 60, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 60.

```
(Human CD30 polypeptide with an exemplary
intracellular signaling domain underlined)
                                SEQ ID NO: 60
MRVLLAALGLLFLGALRAFPQDRPFEDTCHGNPSHYYDKAVRRCCYRCPM

GLFPTQQCPQRPTDCRKQCEPDYYLDEADRCTACVTCSRDDLVEKTPCAW

NSSRVCECRPGMFCSTSAVNSCARCFFHSVCPAGMIVKFPGTAQKNTVCE

PASPGVSPACASPENCKEPSSGTIPQAKPTPVSPATSSASTMPVRGGTRL

AQEAASKLTRAPDSPSSVGRPSSDPGLSPTQPCPEGSGDCRKQCEPDYYL

DEAGRCTACVSCSRDDLVEKTPCAWNSSRTCECRPGMICATSATNSCARC

VPYPICAAETVTKPQDMAEKDTTFEAPPLGTQPDCNPTPENGEAPASTSP

TQSLLVDSQASKTLPIPTSAPVALSSTGKPVLDAGPVLFWVILVLVVVVG

SSAFLLCHRRACRKRIRQKLHLCYPVQTSQPKLELVDSRPRRSSTQLRSG

ASVTEPVAEERGLMSQPLMETCHSVGAAYLESLPLQDASPAGGPSSPRDL

PEPRVSTEHTNNKIEKIYIMKADTVIVGTVKAELPEGRGLAGPAEPELEE

ELEADHTPHYPEQETEPPLGSCSDVMLSVEEEGKEDPLPTAASGK
```

In some embodiments, an intracellular signaling domain can be an intracellular signaling domain from a mouse CD30 polypeptide. An exemplary polypeptide sequence of a mouse CD30 (e.g., a polypeptide as shown in UniProt Protein Accession: Q60846, found at URL www.uniprot.org/uniprot/Q60846) with an exemplary intracellular signaling domain underlined is SEQ ID NO: 61. An intracellular signaling domain can be a portion of the exemplary intracellular signaling domain underlined in SEQ ID NO: 61, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 61.

```
(Mouse CD30 polypeptide with an exemplary
intracellular signaling domain underlined)
                               SEQ ID NO: 61
MSALLTAAGLLFLGMLQAFPTDRPLKTTCAGDLSHYPGEAARNCCYQCPS

GLSPTQPCPRGPAHCRKQCAPDYYVNEDGKCTACVTCLPGLVEKAPCSGN

SPRICECQPGMHCCTPAVNSCARCKLHCSGEEVVKSPGTAKKDTICELPS

SGSGPNCSNPGDRKTLTSHATPQAMPTLESPANDSARSLLPMRVTNLVQE

DATELVKVPESSSSKAREPSPDPGNAEKNMTLELPSPGTLPDISTSENSK

EPASTASTLSLVVDAWTSSRMQPTSPLSTGTPFLDPGPVLFWVAMVVLLV

GSGSFLLCYWKACRRRFQQKFHLDYLVQTFQPKMEQTDSCPTEKLTQPQR

SGSVTDPSTGHKLSPVSPPPAVETCASVGATYLENLPLLDDSPAGNPFSP

REPPEPRVSTEHTNNRIEKIYIMKADTVIVGSVKTEVPEGRAPAGSTESE

LEAELEVDHAPHYPEQETEPPLGSCTEVMFSVEEGGKEDHGPTTVSEK
```

In some embodiments, an intracellular signaling domain can be an intracellular signaling domain from CD40 (also variously known as Bp50, CDW40, TNFRSF5, p50, or CD40 molecule). CD40 is a costimulatory protein found on antigen presenting cells and plays a role in their activation. In some embodiments, an intracellular signaling domain can be an intracellular signaling domain from a human CD40 polypeptide. An exemplary polypeptide sequence of a human CD40 (e.g., UniProt Protein Accession: P25942, found at URL www.uniprot.org/uniprot/P25942) with an exemplary intracellular signaling domain underlined is SEQ ID NO: 62. An intracellular signaling domain can be a portion of the exemplary intracellular signaling domain underlined in SEQ ID NO: 62, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 62.

```
(Human CD40 polypeptide with an exemplary
intracellular signaling domain underlined)
                               SEQ ID NO: 62
MVRLPLQCVLWGCLLTAVHPEPPTACREKQYLINSQCCSLCQPGQKLVSD

CTEFTETECLPCGESEFLDTWNRETHCHQHKYCDPNLGLRVQQKGTSETD

TICTCEEGWHCTSEACESCVLHRSCSPGFGVKQIATGVSDTICEPCPVGF

FSNVSSAFEKCHPWTSCETKDLVVQQAGTNKTDVVCGPQDRLRALVVIPI
```

```
IFGILFAILLVLVFIKKVAKKPTNKAPHPKQEPQEINFPDDLPGSNTAAP

VQETLHGCQPVTQEDGKESRISVQERQ
```

In some embodiments, an intracellular signaling domain can be or can include a sequence that is at least 50% (at least 55%, at least 60%, at least 65%, at least 70%, at least 75%, at least 80%, at least 85%, at least 90%, at least 95%, at least 99%, or 100%) identical to SEQ ID NO: 63.

SEQ ID NO: 63 (CD40 Intracellular Signaling Sequence) KKVAKKPTNKAPHPKQEPQEINFPDDLPGSN-
TAAPVQETLHGCQPVTQ(A) EDGKESRISVQERQ In some embodiments, an intracellular signaling domain can be an intracellular signaling domain from a mouse CD40 polypeptide. An exemplary polypeptide sequence of a mouse CD40 (e.g., a polypeptide as shown in UniProt Protein Accession: P27512, found at URL www.uniprot.org/uniprot/P27512) with an exemplary intracellular signaling domain underlined is SEQ ID NO: 64. An intracellular signaling domain can be a portion of the exemplary intracellular signaling domain underlined in SEQ ID NO: 64, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 64.

```
(Mouse CD40 polypeptide with an exemplary
intracellular signaling domain underlined)
                               SEQ ID NO: 64
MVSLPRLCALWGCLLTAVHLGQCVTCSDKQYLHDGQCCDLCQPGSRLTSH

CTALEKTQCHPCDSGEFSAQWNREIRCHQHRHCEPNQGLRVKKEGTAESD

TVCTCKEGQHCTSKDCEACAQHTPCIPGFGVMEMATETTDTVCHPCPVGF

FSNQSSLFEKCYPWTSCEDKNLEVLQKGTSQTNVICGLKSRMRALLVIPV

VMGILITIFGVFLYIKKVVKKPKDNEILPPAARRQDPQEMEDYPGHNTAA

PVQETLHGCQPVTQEDGKESRISVQERQVTDSIALRPLV
```

In some embodiments, an intracellular signaling domain can be an intracellular signaling domain from CD28 (also variously known as cluster of differentiation 28, Tp44, or CD28 molecule). CD28 is a costimulatory protein expressed on T cells and provides co-stimulatory signals involved in T cell activation and survival. CD28 is the receptor for CD80 and CD86. In some embodiments, an intracellular signaling domain can be an intracellular signaling domain from a human CD28 polypeptide. An exemplary polypeptide sequence of a human CD28 (e.g., UniProt Protein Accession: P10747, found at URL www.uniprot.org/uniprot/P10747) with an exemplary intracellular signaling domain underlined is SEQ ID NO: 5. An intracellular signaling domain can be a portion of the exemplary intracellular signaling domain underlined in SEQ ID NO: 5, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 5.

```
(Human CD28 polypeptide with an exemplary
intracellular signaling domain underlined)
                               SEQ ID NO: 5
MLRLLLALNLFPSIQVTGNKILVKQSPMLVAYDNAVNLSCKYSYNLFSRE
```

-continued

FRASLHKGLDSAVEVCVVYGNYSQQLQVYSKTGFNCDGKLGNESVTFYLQ

NLYVNQTDIYFCKIEVMYPPPYLDNEKSNGTIIHVKGKHLCPSPLFPGPS

KPFWVLVVVGGVLACYSLLVTVAFIIFWV*RSKRSRLLHSDYMNMTPRRPG*

*PTRKHYQPYAPPRDFAAYRS*

In some embodiments, an intracellular signaling domain can be or can include a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical (or is identical) to amino acids 180 to 220 of SEQ ID NO: 5, or a fragment thereof.

In some embodiments, an intracellular signaling domain can be or can include a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical (or is identical) to amino acids 180 to 220 of SEQ ID NO: 65, or a fragment thereof.

(CD28 Intracellular Signaling Domain)
SEQ ID NO: 65
RSKRSRLLHSDYMNMTPRRPGPTRKHYQPYAPPRDFAAYRS In some embodiments, an intracellular signaling domain can be an intracellular signaling domain from a mouse CD28 polypeptide. An exemplary polypeptide sequence of a mouse CD28 (e.g., a polypeptide as shown in UniProt Protein Accession: P31041, found at URL www.uniprot.org/uniprot/P31041) with an exemplary intracellular signaling domain underlined is SEQ ID NO: 66. An intracellular signaling domain can be a portion of the exemplary intracellular signaling domain underlined in SEQ ID NO: 66, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 66.

(Mouse CD28 polypeptide with an exemplary
intracellular signaling domain underlined)
SEQ ID NO: 66
MTLRLLFLALNFFSVQVTENKILVKQSPLLVVDSNEVSLSCRYSYNLLAK

EFRASLYKGVNSDVEVCVGNGNFTYQPQFRSNAEFNCDGDFDNETVTFRL

WNLHVNHTDIYFCKIEFMYPPPYLDNERSNGTIIHIKEKHLCHTQSSPKL

FWALVVVAGVLFCYGLLVTVALCVIWT*NSRRNRLLQSDYMNMTPRRPGLT*

*RKPYQPYAPARDFAAYRP*

In some embodiments, an intracellular signaling domain can be an intracellular signaling domain that from CD11a. CD11a is found on T-cells, B-cells, macrophages, neutrophils, and NK cells, and binds to CD11a on antigen-presenting cells. In some embodiments, an intracellular signaling domain can be an intracellular signaling domain from human CD11a polypeptide. In some embodiments, an intracellular signaling domain can be an intracellular signaling domain from a human CD11a polypeptide.

An exemplary polypeptide sequence of a human CD11a with an exemplary intracellular signaling domain underlined is SEQ ID NO: 67. An intracellular signaling domain can be a portion of the exemplary intracellular signaling domain underlined in SEQ ID NO: 67, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 67.

(Human CD11a with exemplary intracellular
signaling domain underlined)
SEQ ID NO: 67
mkdscitvma mallsgffff apassynldv rgarsfsppr agrhfgyrvl qvgngvivga pgegnstgsl yqcqsgtghc lpvtlrgsny tskylgmtla tdptdgsila cdpglsrtcd qntylsglcy lfrqnlqgpm lqgrpgfqec ikgnvdlvfl fdgsmslqpd efqkildfmk dvmkklsnts yqfaavqfst syktefdfsd yvkrkdpdal lkhvkhmlll tntfgainyv atevfreelg arpdatkvli iitdgeatds gnidaakdii ryiigigkhf qtkesqetlh kfaskpasef vkildtfekl kdlftelqkk iyviegtskq dltsfnmels ssgisadlsr ghavvgavga kdwaggfldl kadlqddtfi gnepltpevr agylgytvtw lpsrqktsll asgapryqhm grvllfqepq ggghwsqvqt ihgtqigsyf ggelcgvdvd qdgetellli gaplfygeqr ggrvfiyqrr qlgfeevsel qgdpgyplgr fgeaitaltd ingdglvdva vgapleeqga vyifngrhgg lspqpsqrie gtqvlsgiqw fgrsihgvkd legdgladva vgaesqmivl ssrpvvdmvt lmsfspaeip vhevecsyst snkmkegvni ticfqiksli pqfqgrlvan ltytlqldgh rtrrrglfpg grhelrmia vttsmsctdf sfhfpvcvqd lispinvsln fslweeegtp rdqraqgkdi ppilrpslhs etweipfekn cgedkkcean lrvsfspars ralrltafas lsvelslsnl eedaywvqld lhfppglsfr kvemlkphsq ipvsceelpe esrllsrals cnvsspifka ghsvalqmmf ntlvnsswgd svelhanvtc nnedsdlled nsattiipil ypiniliqdq edstlyvsft pkgpkihqvk hmyqvriqps ihdhniptle avvgvpqpps egpithqwsv qmeppvpchy edlerlpdaa epclpgalfr cpvvfrqeil vqvigtlelv geieassmfs lcsslsisfn sskhfhlygs naslaqvvmk vdvvyekqml ylyvlsgigg lllllifiv *lykvgffkrn*

*lkekmeagrg vpngipaeds eqlasgqeag dpgclkplhe*

*kdsesgggkd*

In some embodiments, an intracellular signaling domain can be or can include a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical (or is identical) to amino acids 180 to 220 of SEQ ID NO: 68, or a fragment thereof.

(Exemplary CD11a intracellular signaling domain)

SEQ ID NO: 68

YKVGFFKRNLKEKMEAGRGVPNGIPAEDSEQLASGQEAGDPGCLKPLHEK

DSESGGGKD

An exemplary polypeptide sequence of a mouse CD11a with an exemplary intracellular signaling domain underlined is SEQ ID NO: 69. An intracellular signaling domain can be a portion of the exemplary intracellular signaling domain underlined in SEQ ID NO: 69, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 69.

(mouse CD11a with exemplary intracellular signaling domain underlined)

SEQ ID NO: 69 msfriagprl lllglqlfak awsynldtrp tqsflaqagr hfgyqvlqie dgvvvgapge gdntgglyhc rtssefcqpv slhgsnhtsk ylgmtlatda akgsllacdp glsrtcdqnt ylsglcylfp qslegpmlqn rpayqecmkg kvdlvflfdg sqsldrkdfe kilefmkdvm rklsntsyqf aavqfstdcr teftfldyvk qnknpdvllg svqpmflltn tfrainyvva hvfkeesgar pdatkvlvii tdgeasdkgn isaahditry iigigkhfvs vqkqktlhif asepveefvk ildtfeklkd lftdlqrriy aiegtnrqdl tsfnmelsss gisadlskgh avvgavgakd waggfldlre dlqgatfvgq epltsdvrgg ylgytvawmt srssrpllaa gapryqhvgq vllfqapeag grwnqtqkie gtqigsyfgg elcsvdldqd geaellliga plffgeqrgg rvftyqrrqs lfemvselqg dpgyplgrfg aaitaltdin gdrltdvavg apleeqgavy ifngkpggls pqpsqriqga qvfpgirwfg rsihgvkdlg gdrladvvvg aegrvvvlss rpvvdvvtel sfspeeipvh evecsysare eqkhgvklka cfrikpltpq fqgrllanls ytlqldghrm rsrglfpdgs helsgntsit pdkscldfhf hfpiciqdli spinvslnfs lleeegtprd qkvgramqpi lrpsihtvtk eipfekncge dkkceanltl ssparsgplr lmssaslave wtlsnsgeda ywvrldldfp rglsfrkvem lqphsrmpvs ceeltegssl ltktlkcnvs spifkagqev slqvmfntll nsswedfvel ngtvhcenen sslqednsaa thipvlypvn iltkeqenst lyisftpkgp ktqqvqhvyq vriqpsaydh nmptlealvg vpwphsedpi tytwsvqtdp lvtchsedl*k*

*rpsseaeqpc lpgvqfrcpi vfrreiliqv tgtvelskei*

*kasstlslcs slsvsfnssk hfhlygskas eaqvlvkvdl*

*ihekemlhvy vlsgigglvl lfliflalyk vgffkrnlke*

*kmeadggvpn gsppedtdpl avpgeetkdm gcleplresd*

*kd*

In some embodiments, an intracellular signaling domain can be an intracellular signaling domain from ICAM-1 (also variously known as BB2, CD54, cluster of differentiation 54, P3.58, or intercellular adhesion molecule 1). ICAM-1 is a cell surface glycoprotein that is expressed on endothelial cells and cells of the immune system. It binds to integrins of type CD11a/CD18, or CD11b/CD18. In some embodiments, an intracellular signaling domain can be an intracellular signaling domain from a human ICAM-1 polypeptide. An exemplary polypeptide sequence of a human ICAM-1 (e.g., UniProt Protein Accession: P05362, found at URL www.uniprot.org/uniprot/P05362) with an intracellular signaling domain underlined is SEQ ID NO: 70. An intracellular signaling domain can be a portion of the exemplary intracellular signaling domain underlined in SEQ ID NO: 70, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 70.

(Human ICAM-1 polypeptide with an exemplary intracellular signaling domain underlined)

SEQ ID NO: 70

MAPSSPRPALPALLVLLGALFPGPGNAQTSVSPSKVILPRGGSVLVTCST

SCDQPKLLGIETPLPKKELLLPGNNRKVYELSNVQEDSQPMCYSNCPDGQ

STAKTFLTVYWTPERVELAPLPSWQPVGKNLTLRCQVEGGAPRANLTVVL

LRGEKELKREPAVGEPAEVTTTVLVRRDHHGANFSCRTELDLRPQGLELF

ENTSAPYQLQTFVLPATPPQLVSPRVLEVDTQGTVVCSLDGLFPVSEAQV

HLALGDQRLNPTVTYGNDSFSAKASVSVTAEDEGTQRLTCAVILGNQSQE

TLQTVTIYSFPAPNVILTKPEVSEGTEVTVKCEAHPRAKVTLNGVPAQPL

GPRAQLLLKATPEDNGRSFSCSATLEVAGQLIHKNQTRELRVLYGPRLDE

RDCPGNWTWPENSQQTPMCQAWGNPLPELKCLKDGTFPLPIGESVTVTRD

LEGTYLCRARSTQGEVTRKVTVNVLSPRYEIVIITVVAAAVIMGTAGLST

YLY*NRQRKIKKYRLQQAQKGTPMKPNTQATPP*

In some embodiments, an intracellular signaling domain can be an intracellular signaling domain from a mouse ICAM-1 polypeptide. An exemplary polypeptide sequence of a mouse ICAM-1 (e.g., a polypeptide as shown in UniProt Protein Accession: P13597, found at URL www.uniprot.org/uniprot/P13597) with an exemplary intracellular signaling domain underlined is SEQ ID NO: 71. An intracellular signaling domain can be a portion of the exemplary intracellular signaling domain underlined in SEQ ID NO: 71, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 71.

(Mouse ICAM-1 polypeptide with an exemplary intracellular signaling domain underlined)

SEQ ID NO: 71

MASTRAKPTLPLLLALVTVVIPGPGDAQVSIHPREAFLPQGGSVQVNCSS

-continued

```
SCKEDLSLGLETQWLKDELESGPNWKLFELSEIGEDSSPLCFENCGTVQS

SASATITVYSFPESVELRPLPAWQQVGKDLTLRCHVDGGAPRTQLSAVLL

RGEEILSRQPVGGHPKDPKEITFTVLASRGDHGANFSCRTELDLRPQGLA

LFSNVSEARSLRTFDLPATIPKLDTPDLLEVGTQQKLFCSLEGLFPASEA

RIYLELGGQMPTQESTNSSDSVSATALVEVTEEFDRTLPLRCVLELADQI

LETQRTLTVYNFSAPVLTLSQLEVSEGSQVTVKCEAHSGSKVVLLSGVEP

RPPTPQVQFTLNASSEDHKRSFFCSAALEVAGKFLFKNQTLELHVLYGPR

LDETDCLGNWTWQEGSQQTLKCQAWGNPSPKMTCRRKADGALLPIGVVKS

VKQEMNGTYVCHAFSSHGNVTRNVYLTVLYHSQNNWTIIILVPVLLVIVG

LVMAASYVYNRQRKIRIYKLQKAQEEAIKLKGQAPPP
```

In some embodiments, an intracellular signaling domain can be an intracellular signaling domain from NKG2C (also variously known as CD159c, NKG2-C, NKG2C, or killer cell lectin like receptor C2). NKG2C is expressed primarily in natural killer (NK) cells and acts as a receptor for the recognition of MHC class I HLA-E molecules. In some embodiments, an intracellular signaling domain can be an intracellular signaling domain from a human NKG2C polypeptide. An exemplary polypeptide sequence of a human NKG2C (e.g., UniProt Protein Accession: P26717, found at URL www.uniprot.org/uniprot/P26717) with an exemplary intracellular signaling domain underlined is SEQ ID NO: 72. An intracellular signaling domain can be a portion of the exemplary intracellular signaling domain underlined in SEQ ID NO: 72, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 72.

```
(Human NKG2C polypeptide with an exemplary
intracellular signaling domain underlined)
                              SEQ ID NO: 72
MSKQRGTFSEVSLAQDPKRQQRKPKGNKSSISGTEQEIFQVELNLQNPSL

NHQGIDKIYDCQGLLPPPEKLTAEVLGIICIVLMATVLKTIVLIPFLEQN

NSSPNTRTQKARHCGHCPEEWITYSNSCYYIGKERRTWEESLLACTSKNS

SLLSIDNEEEMKFLASILPSSWIGVFRNSSHHPWVTINGLAFKHKIKDSD

NAELNCAVLQVNRLKSAQCGSSMIYHCKHKL
```

In some embodiments, an intracellular signaling domain can be an intracellular signaling domain from GITR (also variously known as glucocorticoid-induced tumor necrosis factor receptor, tumor necrosis factor receptor superfamily member 18, TNFRSF18, activation-inducible TNFR family receptor, AITR, CD357, GITR-D, or TNF receptor superfamily member 18). GITR is a member of the tumor necrosis factor receptor (TNF-R) superfamily and is involved in inhibiting the suppressive activity of T-regulatory cells and extending the survival of T-effector cells. In some embodiments, an intracellular signaling domain can be an intracellular signaling domain from a human GITR polypeptide. An exemplary polypeptide sequence of a human GITR (e.g., UniProt Protein Accession: Q9Y5U5, found at URL www.uniprot.org/uniprot/Q9Y5U5) with an exemplary intracellular signaling domain underlined is SEQ ID NO: 73. An intracellular signaling domain can be a portion of the exemplary intracellular signaling domain underlined in SEQ ID NO: 73, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 73.

```
(Human GITR polypeptide with an exemplary
intracellular signaling domain underlined)
                              SEQ ID NO: 73
MAQHGAMGAFRALCGLALLCALSLGQRPTGGPGCGPGRLLLGTGTDARCC

RVHTTRCCRDYPGEECCSEWDCMCVQPEFHCGDPCCTTCRHHPCPPGQGV

QSQGKFSFGFQCIDCASGTFSGGHEGHCKPWTDCTQFGFLTVFPGNKTHN

AVCVPGSPPAEPLGWLTVVLLAVAACVLLLTSAQLGLHIWQLRSQCMWPR

ETQLLLEVPPSTEDARSCQFPEEERGERSAEEKGRLGDLWV
```

In some embodiments, an intracellular signaling domain can be or can include a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical (or is identical) to amino acids 180 to 220 of SEQ ID NO: 74, or a fragment thereof.

```
(GITR intracellular signaling domain)
                              SEQ ID NO: 74
QLGLHIWQLRSQCMWPRETQLLLEVPPSTEDARSCQFPEEERGERSAEEK

GRLGDLWV
```

In some embodiments, an intracellular signaling domain can be an intracellular signaling domain from a mouse GITR polypeptide. An exemplary polypeptide sequence of a mouse GITR (e.g., a polypeptide as shown in UniProt Protein Accession: O35714, found at URL www.uniprot.org/uniprot/O35714) with an intracellular signaling domain underlined is SEQ ID NO: 75. An intracellular signaling domain can be a portion of the exemplary intracellular signaling domain underlined in SEQ ID NO: 75, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 75.

```
(Mouse GITR polypeptide with an exemplary
intracellular signaling domain underlined)
                              SEQ ID NO: 75
MGAWAMLYGVSMLCVLDLGQPSVVEEPGCGPGKVQNGSGNNTRCCSLYAP

GKEDCPKERCICVTPEYHCGDPQCKICKHYPCQPGQRVESQGDIVFGFRC

VACAMGTFSAGRDGHCRLWTNCSQFGFLTMFPGNKTHNAVCIPEPLPTEQ

YGHLTVIFLVMAACIFFLTTVQLGLHIWQLRRQHMCPRETQPFAEVQLSA

EDACSFQFPEEERGEQTEEKCHLGGRWP
```

In some embodiments, an intracellular signaling domain can be an intracellular signaling domain is from DAP-10 (also variously known as hematopoietic cell signal transducer, HCST, KAP10, DAP10, PIK3AP, or hematopoietic cell signal transducer). See e.g., Lanier, DAP10- and DAP12-associated receptors in innate immunity, *Immunol Rev.*, January; 227(1):150-60. doi: 10.1111/j.1600-065X.2008.00720.x, 2009, incorporated by reference herein in its entirety. DAP-10 is a transmembrane signaling adaptor that contains a YxxM ITAM motif in its cytoplasmic domain. In some embodiments, an intracellular signaling domain is an intracellular signaling domain from a human DAP-10 polypeptide. An exemplary polypeptide sequence of a human DAP-10 (e.g., UniProt Protein Accession: Q9UBK5, found at URL www.uniprot.org/uniprot/ Q9UBK5) an exemplary intracellular signaling domain underlined is SEQ ID NO: 76. An intracellular signaling domain can be a portion of the exemplary to intracellular signaling domain underlined in SEQ ID NO: 76, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 76.

(Human DAP-10 polypeptide with an exemplary
intracellular signaling domain underlined)
                                  SEQ ID NO: 76
MIHLGHILFLLLLPVAAAQTTPGERSSLPAFYPGTSGSCSGCGSLSLPLL

AGLVAADAVASLLIVGAVF*LCARPRRSPAQEDGKVYINMPGRG*

In some embodiments, an intracellular signaling domain can be or can include a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical (or is identical) to amino acids 180 to 220 of SEQ ID NO: 77, or a fragment thereof.

(DAP-10 intracellular signaling domain)
                                  SEQ ID NO: 77
    LCARPRRSPAQEDGKVYINMPGRG In some embodiments, an intracellular signaling domain is an intracellular signaling domain from a mouse DAP-10 polypeptide. An exemplary polypeptide sequence of a mouse DAP-10 (e.g., a polypeptide as shown in UniProt Protein Accession: Q9QUJ0, found at URL www.unipro-t.org/uniprot/Q9QUJ0) with an intracellular signaling domain underlined is SEQ ID NO: 78. An intracellular signaling domain can be a portion of the exemplary intracellular signaling domain underlined in SEQ ID NO: 78, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 78.

(Mouse DAP-10 polypeptide with an exemplary
intracellular signaling domain underlined)
                                  SEQ ID NO: 78
MDPPGYLLFLLLLPVAASQTSAGSCSGCGTLSLPLLAGLVAADAVMSLLI

VGVVFV*CMRPHGRPAQEDGRVYINMPGRG*

In some embodiments, an intracellular signaling domain can be an intracellular signaling domain from DAP-12 (also variously known as TYROBP, DAP12, KARAP, PLOSL, and TYRO protein tyrosine kinase binding protein). See e.g., Lanier, *Immunol Rev.*, January; 227(1):150-60. doi: 10.1111/ j.1600-065X.2008.00720.x, 2009, incorporated by reference herein in its entirety. DAP-12 is a transmembrane signaling adaptor that contains a YxxM ITAM motif in its cytoplasmic domain. In some embodiments, an intracellular signaling domain can be an intracellular signaling domain from a human DAP-12 polypeptide. An exemplary polypeptide sequence of a human DAP-12 (e.g., UniProt Protein Accession: O43914, found at URL www.uniprot.org/uniprot/ O43914) with an exemplary intracellular signaling domain underlined is SEQ ID NO: 79. An intracellular signaling domain can be a portion of the exemplary intracellular signaling domain underlined in SEQ ID NO: 79, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 79.

(Human DAP-12 polypeptide with an exemplary
intracellular signaling domain underlined)
                                  SEQ ID NO: 79
MGGLEPCSRLLLLPLLLAVSGLRPVQAQAQSDCSCSTVSPGVLAGIVMGD

LVLTVLIALAV*YFLGRLVPRGRGAAEAATRKQRITETESPYQELQGQRSD*

*VYSDLNTQRPYYK*

In some embodiments, an intracellular signaling domain can be or can include a sequence that is at least 80%, 81%, 82%, 83%, 84%, 85%, 86%, 87%, 88%, 89%, 90%, 91%, 92%, 93%, 94%, 95%, 96%, 97%, 98%, or 99% identical (or is identical) to amino acids 180 to 220 of SEQ ID NO: 80, or a fragment thereof.

(DAP-12 intracellular signaling domain)
                                  SEQ ID NO: 80
YFLGRLVPRGRGAAEAATRKQRITETESPYQELQGQRSDVYSDLNTQRPY

YK

In some embodiments, an intracellular signaling domain can be an intracellular signaling domain from a mouse DAP-12 polypeptide. An exemplary polypeptide sequence of a mouse DAP-12 (e.g., a polypeptide as shown in UniProt Protein Accession: 054885, found at URL www.uniprot.org/ uniprot/054885) with an exemplary intracellular signaling domain underlined is SEQ ID NO: 81. An intracellular signaling domain can be a portion of the exemplary intracellular signaling domain underlined in SEQ ID NO: 81, or a sequence that is at least 50% identical (e.g., at least 55%, at least 60%, at least 70%, at least 75%, at least 80%, at least 85%, at least 90%, at least 95%, or at least 99% identical) to the portion of the exemplary intracellular signaling domain underlined in SEQ ID NO: 81.

(Mouse DAP-12 polypeptide with an exemplary
intracellular signaling domain underlined)
                                  SEQ ID NO: 81
MGALEPSWCLLFLPVLLTVGGLSPVQAQSDTFPRCDCSSVSPGVLAGIVL

GDLVLTLLIALAV*YSLGRLVSRGQGTAEGTRKQHIAETESPYQELQGQRP*

*EVYSDLNTQRQYYR*

In some embodiments, an intracellular signaling domain can be an intracellular signaling domain of B7-H3 (also called CD276). An exemplary sequence of human B7-H3 polypeptide is SEQ ID NO: 82. An exemplary intracellular signaling domain can be amino acids 488 to 534 of SEQ ID NO: 82. An intracellular signaling domain can be a sequence that is at least 50% identical (e.g., at least 55%, at least 60%, at least 70%, at least 75%, at least 80%, at least 85%, at least 90%, at least 95%, or at least 99% identical) to amino acids 488 to 534 of SEQ ID NO: 82.

(Human B7-H3 polypeptide)

SEQ ID NO: 82

```
mlrrrgspgm gvhvgaalga lwfcltgale vqvpedpvva lvgtdatlcc sfspepgfsl aqlnliwqlt dtkqlvhsfa egqdqgsaya nrtalfpdll aqgnaslrlq rvrvadegsf tcfvsirdfg saavslqvaa pyskpsmtle pnkdlrpgdt vtitcssyqg ypeaevfwqd gqgvpltgnv ttsqmaneqg lfdvhsilrv vlgangtysc lvrnpvlqqd ahssvtitpq rsptgavevq vpedpvvalv gtdatlrcsf spepgfslaq lnliwqltdt kqlvhsfteg rdqgsayanr talfpdllaq gnaslrlqrv rvadegsftc fvsirdfgsa avslqvaapy skpsmtlepn kdlrpgdtvt itcssyrgyp eaevfwqdgq gvpltgnvtt sqmaneqglf dvhsvlrvvl gangtysclv rnpvlqqdah gsvtitgqpm tfppealwvt vglsvclial lvalafvcwr kikqsceeen agaedqdgeg egsktalqpl khsdskeddg qeia
```

In some embodiments, an intracellular signaling domain (e.g., one or more intracellular signaling domains) can be a variant polypeptide sequence that differs by at least one amino acid from an intracellular signaling domain of a wildtype protein selected from the group consisting of: Lck, FasR, TNFR-I, TNFR-II, LIGHT, ICOS, 4-1BB, CD27, OX40, CD2, CD5, CD30, CD40, CD27, CD28, CD11a, ICAM-1, B7-H3, NKG2C, GITR, DAP-10, and DAP-12. A variant polypeptide sequence, as used herein (e.g., in reference to an intracellular signaling domain) is an intracellular signaling domain having a polypeptide sequence that is at least about 80% (e.g., at least about 85%, at least about 90%, at least about 95%, at least about 96%, at least about 97%, at least about 98%, or at least about 99%) identical to the wild type polypeptide sequence of an intracellular signaling domain (e.g., of a protein selected from the group consisting of: Lck, FasR, TNFR-I, TNFR-II, LIGHT, ICOS, 4-1BB, CD27, OX40, CD2, CD5, CD30, CD40, CD27, CD28, CD11a, ICAM-1, B7-H3, NKG2C, GITR, DAP-10, and DAP-12). In some embodiments, a single-chain or a multi-chain CAR comprises two or more intracellular signaling domains, at least one of which comprises a wild type intracellular signaling domain polypeptide sequence, and at least one of which comprises a variant intracellular signaling domain polypeptide sequence. In some embodiments, a CAR comprises two or more variant intracellular signaling domains. In some embodiments, a CAR comprises a variant intracellular signaling domain comprising at least the amino acid residues that play a role in mediating signaling. For example, a CAR can comprise a variant intracellular signaling domain comprising at least the amino acid residues that play a role in interacting with various tumor necrosis factor receptor (TNF-R)-associated factor (TRAF) proteins including, but not limited to, TRAF1, TRAF2, TRAF3, and/or TRAF 5. See, e.g., Xie, TRAF molecules in cell signaling and in human diseases, *J. Mol. Signal.*, 8(1):7. doi: 10.1186/1750-2187-8-7, 2013. Those of ordinary skill in the art will be aware of known structural and functional features of individual intracellular signaling domains and their partners that play a role in mediating signaling, will be able to select appropriate amino acid residues of endogenous intracellular signaling domains for use in designing variant intracellular signaling domains for use in the single-chain and multi-chain CARs described herein.

Immunoreceptor Tyrosine-Based Activation Motifs (ITAMs)

ITAMs include a tyrosine separated from a leucine or isoleucine by any two other amino acids, and can thus be represented as, e.g., Tyr-X-X-Leu/Ile. ITAMs are typically repeated (e.g., two or more times) in the cytoplasmic tails of certain cell surface proteins of the immune system, and are typically separated by between six and eight amino acids.

In some embodiments, a single-chain chimeric antigen receptor or a multi-chain chimeric antigen receptor includes an ITAM, or portion thereof, from an endogenous mammalian (e.g., human) polypeptide, wherein endogenous mammalian (e.g., human) polypeptide is selected from the group of: CD3ζ (also referred to as CD3 zeta), CD3–(CD3 delta), CD3ε (CD3 epsilon), CD3γ (CD3 gamma), DAP12, FCεR1γ (Fc epsilon receptor I gamma chain), FcRy, FcRft, CD35, CD22, CD79A (antigen receptor complex-associated protein alpha chain), CD79B (antigen receptor complex-associated protein beta chain), and CD66d. The letters "CD" is the previous sentence stand for "Cluster of Differentiation." For example, CD3 stands for "Cluster of Differentiation 3."

Any ITAM, or portion thereof, that serves to mediate signaling in an endogenous mammalian (e.g., human) transmembrane protein suitable for use in accordance with compositions and methods disclosed herein. In some embodiments, a single-chain chimeric antigen receptor or a multi-chain chimeric antigen receptor includes an ITAM, or portion thereof, from human CD3 zeta (e.g. Accession No. P20963, e.g., an ITAM present in amino acids 52-164 of SEQ ID NO: 7, or a portion thereof; or SEQ ID NO: 83 or a portion thereof). In some embodiments, an ITAM comprises a sequence that is at least 80% (e.g., at least 82%, at least 84%, at least 86%, at least 88%, at least 90%, at least 92%, at least 94%, at least 96%, at least 98%, at least 99%, or 100% identical to: the sequence of amino acids 52-165 of SEQ ID NO: 7 (or a portion thereof), or the sequence of SEQ ID NO: 83 (or a portion thereof).

SEQ ID NO: 7

```
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP

QRRKNPQEGLYNELQKDKMAEAYSEIGMKGERRRGKGHDGLYQGLSTATK

DTYDALHMQALPPR
```

(Human CD3 zeta signaling domain)

SEQ ID NO: 83

```
LRVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATKD

TYDALHMQALPPR
```

(cDNA encoding human CD3 zeta signaling domain of SEQ ID NO: 83)

SEQ ID NO: 84

```
ctgagagtgaagttcagcaggagcgcagacgcccccgcgtaccagcaggg ccagaaccagctctataacgagctcaatctaggacgaagagaggagtacg atgttttggacaagagacgtggccgggaccctgagatggggggaaagccg agaaggaagaaccctcaggaaggcctgtacaatgaactgcagaaagataa gatggcggaggcctacagtgagattgggatgaaaggcgagcgccggaggg
```

-continued

```
gcaaggggcacgatggcctttaccagggtctcagtacagccaccaaggac acctacgacgcccttcacatgcaggccctgccccctcgc
```

As will be appreciated by those of ordinary skill in the art, certain polypeptides have two or more isoforms that differ at least in their primary polypeptide sequence. For example, different isoforms can be generated as a result of alternative splicing. A single-chain chimeric antigen receptor or a multi-chain chimeric antigen receptor disclosed herein can include an ITAM that includes a sequence of amino acids from any isoform of an endogenous mammalian transmembrane polypeptide having an ITAM including, e.g., a mammalian (e.g., human) isoform of: CD3ζ, CD3D, CD3E, CD3G, DAP12, FCER1G, FcRy, FcRft, CD35, CD22, CD79A, CD79B, or CD66d.

In some embodiments, an ITAM, or portion thereof, of a single-chain chimeric antigen receptor or a multi-chain chimeric antigen receptor includes a sequence of amino acids having one or more (e.g., two, three, four, or five) amino acid substitutions, deletions, or additions as compared to an ITAM of one or more of an ITAM in an endogenous mammalian (e.g., human) transmembrane protein, such as, CD3ζ, CD3D, CD3E, CD3G, DAP12, FCER1G, FcRy, FcRft, CD35, CD22, CD79A, CD79B, or CD66d. For example, the tyrosine and leucine or isoleucine of an ITAM could be retained, while the two amino acids separating them could be replaced with different amino acids.

In some embodiments, a single-chain chimeric antigen receptor or a multi-chain chimeric antigen receptor includes an ITAM that is a chimeric ITAM having portions of an ITAM from two or more endogenous mammalian (e.g., human) transmembrane polypeptides including, without limitation, CD3ζ, CD3D, CD3E, CD3G, DAP12, FCER1G, FcRy, FcRft, CD35, CD22, CD79A, CD79B, or CD66d (including, without limitation, a mammalian or human homolog of any of these polypeptides), such that the two or more ITAM portions together constitute a functional ITAM. In some embodiments, such a portion of a chimeric ITAM can include one or more amino acid substitutions, deletions, or additions as compared to a corresponding portion of a wild type ITAM.

In some embodiments, a single-chain chimeric antigen receptor or a multi-chain chimeric antigen receptor includes two or more ITAMs, e.g., two, three, four, or five, or more ITAMs. In some embodiments, the two or more ITAMs are identical (e.g., they have the same amino acid sequence). In some embodiments, the two or more ITAMs are not identical. For example, the ITAMs can be selected from different endogenous mammalian (e.g., human) transmembrane polypeptides including, without limitation, CD3, CD3D, CD3E, CD3G, DAP12, FCER1G, FcRy, FcRft, CD35, CD22, CD79A, CD79B (including, without limitation, a mammalian or human homolog of any of these polypeptides). In some embodiments, the two or more ITAMs can differ from each other by one or more amino acid substitutions, deletions, or additions.

Nucleic Acids

Also provided herein are nucleic acids that encode any of the single-chain chimeric antigen receptors and multi-chain chimeric antigen receptors described herein. Also provided herein are a set of nucleic acids that encode one or more single-chain polypeptides that make up a multi-chain chimeric antigen receptor described herein (e.g., where at least one single-chain polypeptide that makes up the multi-chain chimeric antigen receptor is encoded by each nucleic acid in the set).

Vectors

Provided herein are vectors that include any of the nucleic acids provided herein. A "vector" according to the present disclosure is a polynucleotide capable of inducing the expression of a recombinant protein (e.g., a single-chain chimeric antigen receptor or a multi-chain chimeric antigen receptor) in a mammalian cell. A vector provided herein can be, e.g., in circular or linearized form. Non-limiting examples of vectors include plasmids, SV40 vectors, adenoviral viral vectors, and adeno-associated virus (AAV) vectors. Non-limiting examples of vectors include lentiviral vectors or retroviral vectors, e.g., gamma-retroviral vectors. See, e.g., Carlens et al., *Exp. Hematol.* 28(10:1137-1146, 2000; Park et al., *Trends Biotechnol.* 29(11):550-557, 2011; and Alonso-Camino et al., *Mol. Ther. Nucleic Acids* 2:e93, 2013. Non-limiting examples of retroviral vectors include those derived from Moloney murine leukemia virus, myeloproliferative sarcoma virus, murine embryonic stem cell virus, murine stem cell virus, spleen focus forming virus, or adeno-associated virus. Non-limiting examples of retroviral vectors are described in, e.g., U.S. Pat. Nos. 5,219,740 and 6,207,453; Miller et al., *BioTechniques* 7:980-990, 1989; Miller, *Human Gene Therapy* 1:5-14, 1990; Scarpa et al., *Virology* 180:849-852, 1991; Burns et al., *Proc. Natl. Acad. Sci. U.S.A.* 90:8033-8037, 1993; and Boris-Lawrie et al., *Cur. Opin. Genet. Develop.* 3:102-109, 1993. Exemplary lentiviral vectors are described in, e.g., Wang et al., *J. Immunother.* 35(9):689-701, 2003; Cooper et al., *Blood* 101:1637-1644, 2003; Verhoeyen et al., *Methods Mol. Biol.* 506:97-114, 2009; and Cavalieri et al., *Blood* 102(2):497-505, 2003.

Exemplary vectors, in which any of the nucleic acids provided herein can be inserted, are described in, e.g., Ausubel et al., Eds. "Current Protocols in Molecular Biology" Current Protocols, 1993; and Sambrook et al., Eds. "Molecular Cloning: A Laboratory Manual," 2nd ed., Cold Spring Harbor Press, 1989.

In some embodiments, the vectors further include a promoter and/or enhancer operably linked to any of the nucleic acids described herein. Non-limiting examples of promoters include promoters from human cytomegalovirus (CMV), mouse phosphoglycerate kinase 1, polyoma adenovirus, thyroid stimulating hormone α, vimentin, simian virus 40 (SV40), tumor necrosis factor, β-globin, α-fetoprotein, γ-globin, β-interferon, γ-glutamyl transferase, human ubiquitin C (UBC), mouse mammary tumor virus (MMTV), Rous sarcoma virus, glyceraldehyde-3-phosphate dehydrogenase, β-actin, metallothionein II (MT II), amylase, human EF1α, cathepsin, MI muscarinic receptor, retroviral LTR (e.g. human T-cell leukemia virus HTLV), AAV ITR, interleukin-2, collagenase, platelet-derived growth factor, adenovirus E2, stromelysin, murine MX, rat insulin, glucose regulated protein 78, human immunodeficiency virus, glucose regulated protein 94, α-2-macroglobulin, MHC class I, HSP70, proliferin, immunoglobulin light chain, T-cell receptor, HLA DQα, HLA DQβ, interleukin-2 receptor, MHC class II, prealbumin (transthyretin), elastase I, albumin, c-fos, neural cell adhesion molecule (NCAM), H2B histone, rat growth hormone, human serum amyloid (SAA), muscle creatinine kinase, troponin I (TN I), and Gibbon Ape Leukemia Virus (GALV). In some embodiments, the promoter may be an inducible promoter or a constitutive promoter. Additional examples of promoters are known in the art.

In some examples, the vectors provided herein further include a poly(A) sequence, which is operably linked and positioned 3' to the sequence encoding the single-chain chimeric antigen receptor or any of the polypeptides that make up the multi-chain chimeric antigen receptor. Non-limiting examples of a poly(A) sequence include those derived from bovine growth hormone (Woychik et al., *Proc. Natl. Acad. Sci. U.S.A.* 81(13): 3944-3948, 1984, and U.S. Pat. No. 5,122,458), mouse-β-globin, mouse-α-globin (Orkin et al., *EMBO J.* 4(2): 453-456, 1985), human collagen, polyoma virus (Batt et al., *Mol. Cell Biol.* 15(9):4783-4790, 1995), the Herpes simplex virus thymidine kinase gene (HSV TK), IgG heavy chain gene polyadenylation signal (U.S. Patent Application Publication No. 2006/0040354), human growth hormone (hGH) (Szymanski et al., *Mol. Therapy* 15(7):1340-1347, 2007), SV40 poly(A) site, e.g., SV40 late and early poly(A) site (Schek et al., *Mol. Cell Biol.* 12(12):5386-5393, 1992). In some embodiments, the poly(A) sequence includes a highly conserved upstream element (AATAAA). The this AATAAA sequence can, e.g., be substituted with other hexanucleotide sequences with homology to AATAAA which are capable of signaling polyadenylation, including, e.g., ATTAAA, AGTAAA, CATAAA, TATAAA, GATAAA, ACTAAA, AATATA, AAGAAA, AATAAT, AAAAAA, AATGAA, AATCAA, AACAAA, AATCAA, AATAAC, AATAGA, AATTAA, and AATAAG. See, e.g., WO 06012414 A2).

A poly(A) sequence can, e.g., be a synthetic polyadenylation site. See, e.g., Levitt el al, *Genes Dev.* 3(7): 1019-1025, 1989). In some examples, a poly(A) sequence can be the polyadenylation signal of soluble neuropilin-1: AAATAAAATACGAAATG (SEQ ID NO: 85). Additional examples of poly(A) sequences are known in the art. Additional examples and aspects of vectors are also known in the art.

Methods of Introducing a Nucleic Acid or Vectors into a Mammalian Cell

A variety of different methods known in the art can be used to introduce any of the nucleic acids and vectors disclosed herein into a mammalian cell (e.g., any of the mammalian cells described herein, e.g., any of the T cells (e.g., human T cells) described herein). Non-limiting examples of methods that can be used to introduce a nucleic acid or vector into a mammalian cell include lipofection, transfection, electroporation, microinjection, calcium phosphate transfection, dendrimer-based transfection, cationic polymer transfection, cell squeezing, sonoporation, optical transfection, impalection, hydrodynamic delivery, magnetofection, viral transduction (e.g., adenoviral and lentiviral transduction), and nanoparticle transfection. Additional methods of introducing a nucleic acid or vector into a mammalian cell are known in the art.

Mammalian Cells

Also provided herein are mammalian cells that include any of the nucleic acids or vectors described herein. In some embodiments, the mammalian cell is previously obtained from a subject (e.g., a human subject, e.g., a human subject identified or diagnosed as having a cancer).

Non-limiting examples of mammalian cells include a T cell (e.g., a human T cell). Non limiting examples of T cells (e.g., human T cells) include, e.g., an immature thymocyte, a peripheral blood lymphocyte, a naïve T cell, a pluripotent $T_H$ cell precursor, a lymphoid progenitor cell, a $T_{reg}$ cell, a memory T cell, a $T_H17$ cell, a $T_H22$ cell, a $T_H9$ cell, a $T_H2$ cell, a $T_H1$ cell, a $T_H3$ cell, γδ T cell, an αβ T cell, a Treg cell, and a tumor-infiltrating T cell. Additional examples of a T cell (e.g., a human T cell) include a CD8$^+$ T cell, a CD4$^+$ T cell, a memory T cell, a Treg cell, natural killer T cell, B cell, and a monocyte. Additional examples of mammalian cells include a mast cell, a macrophage, a neutrophil, a dendritic cell, a basophil, an eosinophil, and a natural killer cell.

Compositions and Kits

Also provided herein are compositions (e.g., pharmaceutical compositions) that include any of the nucleic acids, vectors, sets of nucleic acids, sets of vectors, or mammalian cells described herein. For example, provided herein is a composition that includes any of the nucleic acids or sets of nucleic acids described herein, or any of the vectors or sets of vectors provided herein and a pharmaceutically acceptable solvent or carrier.

In some embodiments, a composition can be any of the mammalian cells described herein (e.g., any of the mammalian cells described herein previously obtained from a subject, e.g., a subject identified or diagnosed as having a cancer) comprising a nucleic acid encoding any of the single-chain chimeric antigen receptors or multi-chain chimeric antigen receptors described herein. In a composition including any of the mammalian cells described herein, the composition can further include a cell culture medium or a pharmaceutically acceptable buffer (e.g., phosphate-buffered saline). A composition that includes any of the mammalian cells described herein can be formulated for intravenous or intraarterial administration.

Also provided are kits that include one or more of any of the compositions described herein. In some embodiments, a kit can further include instructions for performing any of the methods described herein.

Methods of Treating a Cancer in a Subject

Also provided herein are methods of treating a cancer in a subject (e.g., a human, a mouse, a rabbit, a rat, a horse, a dog, a monkey, or an ape) that include administering a therapeutically effective amount of any of the mammalian cells including a nucleic acid encoding any of the single-chain chimeric antigen receptors described herein or any of the multi-chain chimeric antigen receptors described herein. In some examples of these methods, the mammalian cell is a T cell (e.g., a CD8+ T cell, a CD4+ T cell, a memory T cell, a Treg cell, and a natural killer T cell). In some examples, the mammalian cell (e.g., any of the mammalian cells described herein) is a mammalian cell previously obtained from a subject (e.g., a subject that has been identified or diagnosed as having a cancer, e.g., any of the cancers described herein). Some embodiments of these methods further include obtaining the mammalian cell from the subject.

Some embodiments of these methods further include introducing a nucleic acid encoding the single-chain chimeric antigen receptor described herein or the multi-chain chimeric antigen receptor described into a mammalian cell (e.g., any of the mammalian cells described herein or known in the art) to generate the mammalian cell that is administered to the subject.

Non-limiting examples of cancer that can be treated using any of the methods provided herein include: acute lymphoblastic leukemia, acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, bile duct cancer, endometrial cancer, ependymoma, esophageal cancer, esthesioneuroblastoma, Ewing sarcoma, eye cancer, fallopian tube cancer, gallbladder cancer, gastric cancer, gastrointestinal carcinoid tumor, gastrointestinal stromal tumor, germ cell tumor, hairy cell leukemia, head and neck cancer, heart cancer, liver cancer, hypopharyngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, gastric cancer, testicular cancer, throat cancer, thyroid cancer, urethral cancer, uterine cancer, vaginal cancer, and vulvar cancer.

In some embodiments of any of these methods, the methods result in a decrease in the tumor burden (e.g., tumor mass and/or volume) in a subject. For example, any of the methods described herein can result in at least about 1% to about 99% (e.g., about 1% to about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 2% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 3% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 5% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, or about 10% (inclusive); about 10% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, or about 15% (inclusive); about 15% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, or about 20% (inclusive); about 20% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, or about 25% (inclusive); about 25% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, or about 30% (inclusive); about 30% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, or about 35% (inclusive); about 35% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, or about 40% (inclusive); about 40% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, or about 45% (inclusive); about 45% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, or about 50% (inclusive); about 50% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, or about 55% (inclusive); about 55% to about 99%, about 98%, about 96%, about 94%, about 92%, about 90%, about 88%, about 86%, about 84%, about 82%, about 80%, about 78%, about 76%, about 74%, about 72%, about 70%, about 65%, or about 60% (inclusive); about 60% to about 99%, about 98%, about 96%, about 94%, about 92%, about 90%, about 88%, about 86%, about 84%, about 82%, about 80%, about 78%, about 76%, about 74%, about 72%, about 70%, or about 65% (inclusive); about 65% to about 99%, about 98%, about 96%, about 94%, about 92%, about 90%, about 88%, about 86%, about 84%, about 82%, about 80%, about 78%, about 76%, about 74%, about 72%, or about 70% (inclusive); about 70% to about 99%, about 98%, about 96%, about 94%, about 92%, about 90%, about 88%, about 86%, about 84%, about 82%, about 80%, about 78%, about 76%, about 74%, or about 72% (inclusive); about 72% to about 99%, about 98%, about 96%, about 94%, about 92%, about 90%, about 88%, about 86%, about 84%, about 82%, about 80%, about 78%, about 76%, or about 74% (inclusive); about 74% to about 99%, about 98%, about 96%, about 94%, about 92%, about 90%, about 88%, about 86%, about 84%, about 82%, about 80%, about 78%, or about 76% (inclusive); about 76% to about 99%, about 98%, about 96%, about 94%, about 92%, about 90%, about 88%, about 86%, about 84%, about 82%, about 80%, or about 78% (inclusive); about 78% to about 99%, about 98%, about 96%, about 94%, about 92%, about 90%, about 88%, about 86%, about 84%, about 82%, or about 80% (inclusive); about 80% to about 99%, about 98%, about 96%, about 94%, about 92%, about 90%, about 88%, about 86%, about 84%, or about 82% (inclusive); about 82% to about 99%, about 98%, about 96%, about 94%, about 92%, about 90%, about 88%, about 86%, or about 84% (inclusive); about 84% to about 99%, about 98%, about 96%, about 94%, about 92%, about 90%, about 88%, or about 86% (inclusive); about 86% to about 99%, about 98%, about 96%, about 94%, about 92%, about 90%, or about 88% (inclusive); about 88% to about 99%, about 98%, about 96%, about 94%, about 92%, or about 90% (inclusive); about 90% to about 99%, about 98%, about 96%, about 94%, or about 92% (inclusive); about 92% to about 99%, about 98%, about 96%, or about 94% (inclusive); about 94% to about 99%, about 98%, or about 96% (inclusive); or about 96% to about 99% or about 98% (inclusive)) reduction in the tumor burden in a subject (e.g., as compared to the tumor burden in the subject prior to treatment).

In some embodiments, the methods result in a decrease in the rate of progression of a cancer in the subject. For example, any of the methods described herein can result in at least about 1% to about 99% (e.g., about 1% to about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 2% to about 99%, about 98% about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 3% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, about 10%, or about 5% (inclusive); about 5% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, about 15%, or about 10% (inclusive); about 10% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, about 20%, or about 15% (inclusive); about 15% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, about 25%, or about 20% (inclusive); about 20% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, about 30%, or about 25% (inclusive); about 25% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, about 35%, or about 30% (inclusive); about 30% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, about 40%, or about 35% (inclusive); about 35% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, about 45%, or about 40% (inclusive); about 40% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, about 50%, or about 45% (inclusive); about 45% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, about 55%, or about 50% (inclusive); about 50% to about 99%, about 98%, about 96%, about 94%, about 92%, about 90%, about 88%, about 86%, about 84%, about 82%, about 80%, about 78%, about 76%, about 74%, about 72%, about 70%, about 65%, about 60%, or about 55% (inclusive); about 55% to about 99%, about 98%, about 96%, about 94%, about 92%, about 90%, about 88%, about 86%, about 84%, about 82%, about 80%, about 78%, about 76%, about 74%, about 72%, about 70%, about 65%, or about 60% (inclusive); about 60% to about 99%, about 98%, about 96%, about 94%, about 92%, about 90%, about 88%, about 86%, about 84%, about 82%, about 80%, about 78%, about 76%, about 74%, about 72%, about 70%, or about 65% (inclusive); about 65% to about 99%, about 98%, about 96%, about 94%, about 92%, about 90%, about 88%, about 86%, about 84%, about 82%, about 80%, about 78%, about 76%, about 74%, about 72%, or about 70% (inclusive); about 70% to about 99%, about 98%, about 96%, about 94%, about 92%, about 90%, about 88%, about 86%, about 84%, about 82%, about 80%, about 78%, about 76%, about 74%, or about 72% (inclusive); about 72% to about 99%, about 98%, about 96%, about 94%, about 92%, about 90%, about 88%, about 86%, about 84%, about 82%, about 80%, about 78%, about 76%, or about 74% (inclusive); about 74% to about 99%, about 98%, about 96%, about 94%, about 92%, about 90%, about 88%, about 86%, about 84%, about 82%, about 80%, about 78%, or about 76% (inclusive); about 76% to about 99%, about 98%, about 96%, about 94%, about 92%, about 90%, about 88%, about 86%, about 84%, about 82%, about 80%, or about 78% (inclusive); about 78% to about 99%, about 98%, about 96%, about 94%, about 92%, about 90%, about 88%, about 86%, about 84%, about 82%, or about 80% (inclusive); about 80% to about 99%, about 98%, about 96%, about 94%, about 92%, about 90%, about 88%, about 86%, about 84%, or about 82% (inclusive); about 82% to about 99%, about 98%, about 96%, about 94%, about 92%, about 90%, about 88%, about 86%, or about 84% (inclusive); about 84% to about 99%, about 98%, about 96%, about 94%, about 92%, about 90%, about 88%, or about 86% (inclusive); about 86% to about 99%, about 98%, about 96%, about 94%, about 92%, about 90%, or about 88% (inclusive); about 88% to about 99%, about 98%, about 96%, about 94%, about 92%, or about 90% (inclusive); about 90% to about 99%, about 98%, about 96%, about 94%, or about 92% (inclusive); about 92% to about 99%, about 98%, about 96%, or about 94% (inclusive); about 94% to about 99%, about 98%, or about 96% (inclusive); or about 96% to about 99% or about 98% (inclusive)) reduction in the rate of progression of a cancer in a subject (e.g., as compared to the rate of progression of a cancer in the subject prior to treatment or in a control subject or a control population of subjects having the same cancer and administered no treatment or a different treatment).

In some embodiments of any of these methods, the methods result in an increase in the time of survival of a cancer in a subject. For example, any of the methods described herein can result in an about 1% to about 800% (e.g., about 1% to about 750%, about 700%, about 650%, about 600%, about 550%, about 500%, about 450%, about 400%, about 350%, about 300%, about 250%, about 200%, about 150%, about 100%, about 80%, about 60%, about 40%, about 20%, about 10%, or about 5% (inclusive); about 5% to about 800%, about 750%, about 700%, about 650%, about 600%, about 550%, about 500%, about 450%, about 400%, about 350%, about 300%, about 250%, about 200%, about 150%, about 100%, about 80%, about 60%, about 40%, about 20%, or about 10% (inclusive); about 10% to about 800%, about 750%, about 700%, about 650%, about 600%, about 550%, about 500%, about 450%, about 400%, about 350%, about 300%, about 250%, about 200%, about 150%, about 100%, about 80%, about 60%, about 40%, or about 20% (inclusive); about 20% to about 800%, about 750%, about 700%, about 650%, about 600%, about 550%, about 500%, about 450%, about 400%, about 350%, about 300%, about 250%, about 200%, about 150%, about 100%, about 80%, about 60%, or about 40% (inclusive); about 40% to about 800%, about 750%, about 700%, about 650%, about 600%, about 550%, about 500%, about 450%, about 400%, about 350%, about 300%, about 250%, about 200%, about 150%, about 100%, about 80%, or about 60% (inclusive); about 60% to about 800%, about 750%, about 700%, about 650%, about 600%, about 550%, about 500%, about 450%, about 400%, about 350%, about 300%, about 250%, about 200%, about 150%, about 100%, about 80% (inclusive); about 80% to about 800%, about 750%, about 700%, about 650%, about 600%, about 550%, about 500%, about 450%, about 400%, about 350%, about 300%, about 250%, about 200%, about 150%, or about 100% (inclusive); about 100% to about 800%, about 750%, about 700%, about 650%, about 600%, about 550%, about 500%, about 450%, about 400%, about 350%, about 300%, about 250%, about 200%, or about 150% (inclusive); about 150% to about 800%, about 750%, about 700%, about 650%, about 600%, about 550%, about 500%, about 450%, about 400%, about 350%, about 300%, about 250%, or about 200% (inclusive); about 200% to about 800%, about 750%, about 700%, about 650%, about 600%, about 550%, about 500%, about 450%, about 400%, about 350%, about 300%, or about 250% (inclusive); about 250% to about 800%, about 750%, about 700%, about 650%, about 600%, about 550%, about 500%, about 450%, about 400%, about 350%, or about 300% (inclusive); about 300% to about 800%, about 750%, about 700%, about 650%, about 600%, about 550%, about 500%, about 450%, about 400%, or about 350% (inclusive); about 350% to about 800%, about 750%, about 700%, about 650%, about 600%, about 550%, about 500%, about 450%, or about 400% (inclusive); about 400% to about 800%, about 750%, about 700%, about 650%, about 600%, about 550%, about 500%, or about 450% (inclusive); about 450% to about 800%, about 750%, about 700%, about 650%, about 600%, about 550%, or about 500% (inclusive); about 500% to about 800%, about 750%, about 700%, about 650%, about 600%, or about 550% (inclusive); about 550% to about 800%, about 750%, about 700%, about 650%, or about 600% (inclusive); about 600% to about 800%, about 750%, about 700%, or about 650% (inclusive); about 650% to about 800%, about 750%, or about 700% (inclusive); about 700% to about 800% or about 750% (inclusive); or about 750% to about 800% (inclusive)) increase in the time of survival of a cancer in a subject (e.g., as compared to the time of survival for a control subject or a population of control subjects having the same cancer and receiving no treatment or a different treatment).

EXAMPLES

The invention is further described in the following examples, which do not limit the scope of the invention described in the claims.

Example 1: Percent Lysis of Cell Lines After Co-culturing with CAR-T Cells Expressing Various CAR Constructs CAR-T cells were generated to express CARs that include the anti-CD19 FMC63 ScFv, the CD8 hinge region, the CD8 transmembrane region, and various co-stimulatory domains. The X axis of FIG. 1 shows the intracellular signaling domain(s) and immunoreceptor tyrosine-based activation motifs in each tested construct. The Y axis of FIG. 1 shows the percentage of target cells that were lysed in the presence of the various CAR-T cells expressing the indicated CARs.

For the various CAR constructs tested and shown in FIG. 1, the following intracellular sequences were used:

```
4-1BB
                                (SEQ ID NO: 45)
KRGRKKLLYIFKQPFMRPVQTTQEEDGCSCRFPEEEEGGCEL

GITR
                                (SEQ ID NO: 74)
QLGLHIWQLRSQCMWPRETQLLLEVPPSTEDARSCQFPEEERGERSAEEK

GRLGDLWV

OX40
                                (SEQ ID NO: 54)
ALYLLRRDQRLPPDAHKPPGGGSFRTPIQEEQADAHSTLAKI

CD27
                                (SEQ ID NO: 51)
QRRKYRSNKGESPVEPAEPCHYSCPREEEGSTIPIQEDYRKPEPACSP

CD40
                                (SEQ ID NO: 86)
KKVAKKPTNKAPHPKQEPQEINFPDDLPGSNTAAPVQETLHGCQPVTQED

GKESRISVQERQ

CD28
                                (SEQ ID NO: 65)
RSKRSRLLHSDYMNMTPRRPGPTRKHYQPYAPPRDFAAYRS

DAP10
                                (SEQ ID NO: 77)
LCARPRRSPAQEDGKVYINMPGRG

DAP12
                                (SEQ ID NO: 80)
YFLGRLVPRGRGAAEAATRKQRITETESPYQELQGQRSDVYSDLNTQRPY

YK

CD3z
                                (SEQ ID NO: 83)
LRVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATKD

TYDALHMQALPPR
```

Constructs were expressed in primary T cells at roughly equivalent surface levels, cultured for fourteen days after CD3/CD28 activation and transduction, and 20,000 CAR T cells were plated at 10:1 target-to-effector cell ratios with the CD19+ luciferase transduced NALM6_fluc cell line. Nalm-6 was obtained from the ATCC, and transduced in-house. 24 hours after co-culture, NALM6_fluc lysis was quantified using a luminimeter and the percent lysis was calculated by subtracting the observed luciferase activity for each CAR-T construct from that observed in untreated cells at each concentration of 20,000 CAR-T cells. UT=Untransduced.

Example 2: CD69 Expression of CAR-T Cells
Expressing Various CAR Constructs

Figure 2:
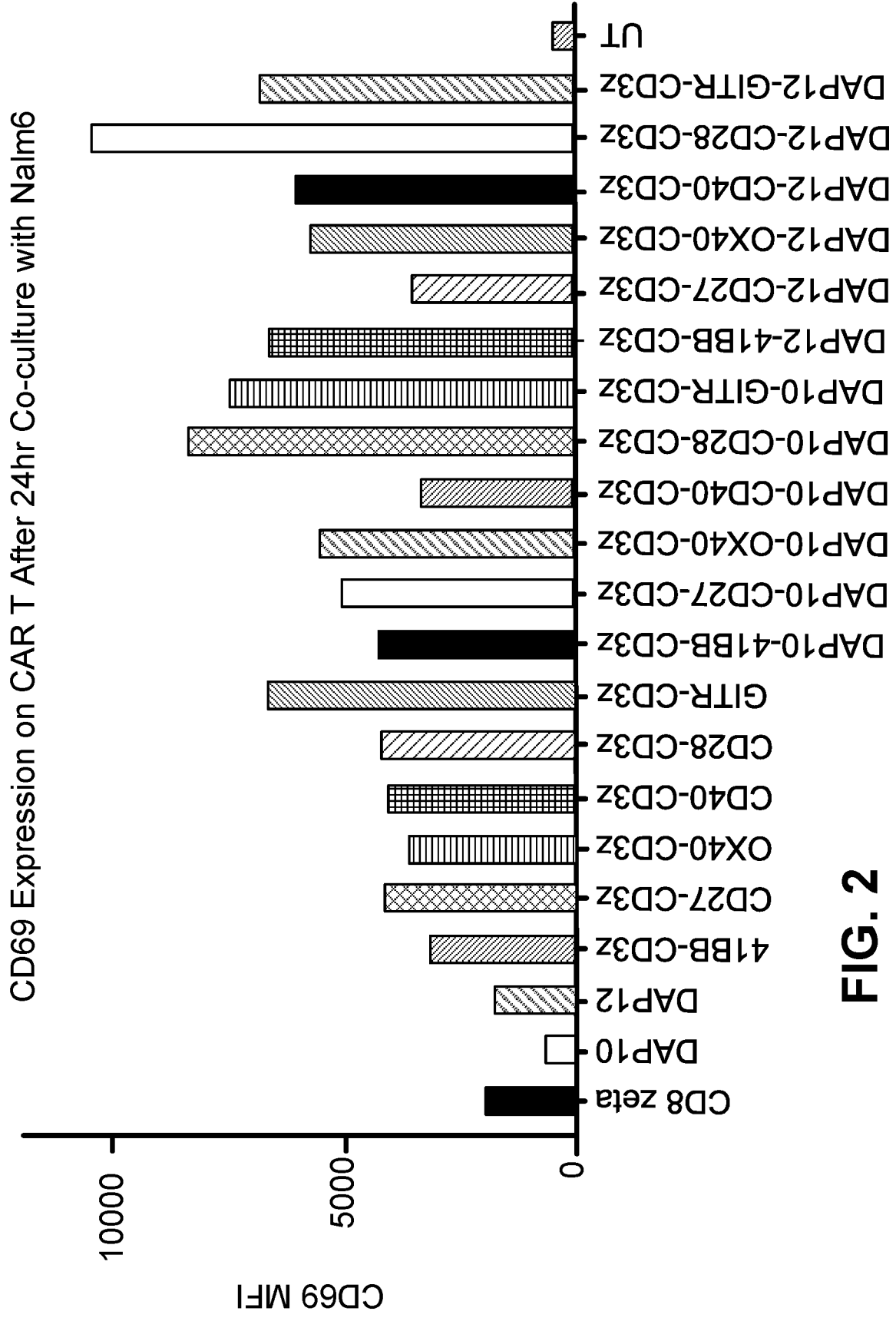
FIG. 2 shows CD69 expression of CAR-T cells expressing various tested CAR constructs. The X axis shows the intracellular signaling domain(s) and ITAM in each tested construct. The Y axis shows the expression of CD69. MFI=median fluorescence intensity. The sequences of the various intracellular sequences of the CAR constructs are described in Example 1. UT=Untransduced.

CAR-T cells were generated to express CARs that include the anti-CD19 FMC63 ScFv, the CD8 hinge region, the CD8 transmembrane region, and various co-stimulatory domains using standard molecular biology techniques. The X axis of FIG. 2 shows the intracellular signaling domain(s) and immunoreceptor tyrosine-based activation motifs in each tested construct. The sequences of the various intracellular signaling domain(s) and immunoreceptor tyrosine-based activation motifs are as described in Example 1. The Y axis of FIG. 2 shows the expression of CD69. MFI=median fluorescence intensity.

Constructs were expressed in primary T cells at roughly equivalent surface levels, cultured for fourteen days after CD3/CD28 activation and transduction, and plated at 1:1 ratios with the CD19+ cell line NALM6. 24 hours after co-culture, expression of activation marker CD69 was evaluated in the CAR-T cells by flow cytometry. UT=Untransduced Example 3: Cytokine Production of CAR-T Cells
Expressing Various CAR Constructs CAR-T cells were generated to express CARs that include the anti-CD19 FMC63 ScFv, the CD8 hinge region, the CD8 transmembrane region, and various co-stimulatory domains using standard molecular biology techniques. The X axes of FIGS. 3 A-C show the intracellular signaling domain(s) and immunoreceptor tyrosine-based activation motifs in each tested construct. The sequences of the various intracellular signaling domain(s) and immunoreceptor tyrosine-based activation motifs are as described in Example 1. The Y axes of FIGS. 3 A-C show the expression of TNF-alpha, interferon gamma, and interleukin 2 cytokines, respectively.

Figure 3A:
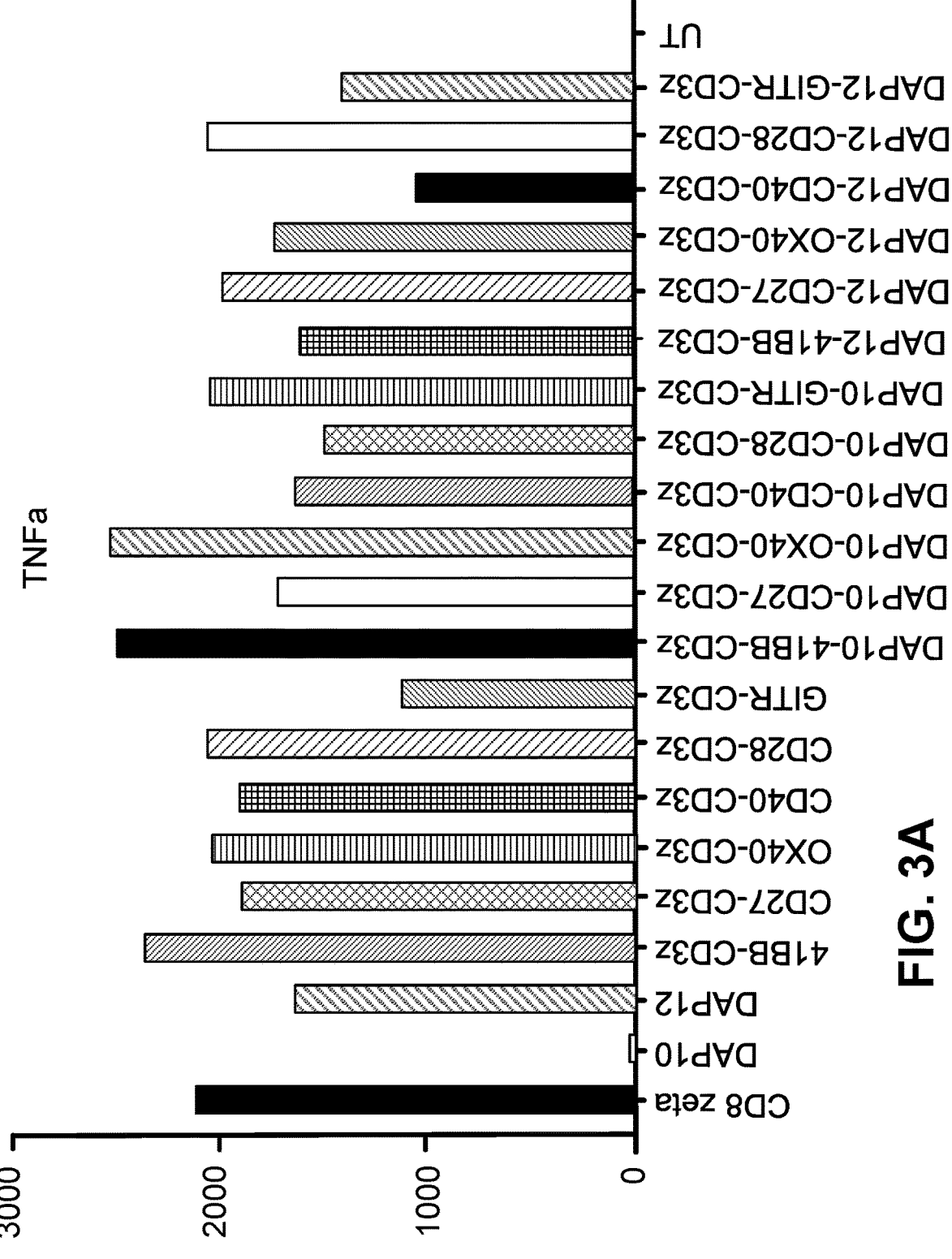
FIGS. 3A-C show cytokine production of CAR-T cells expressing various CAR constructs.
Figure 3B:
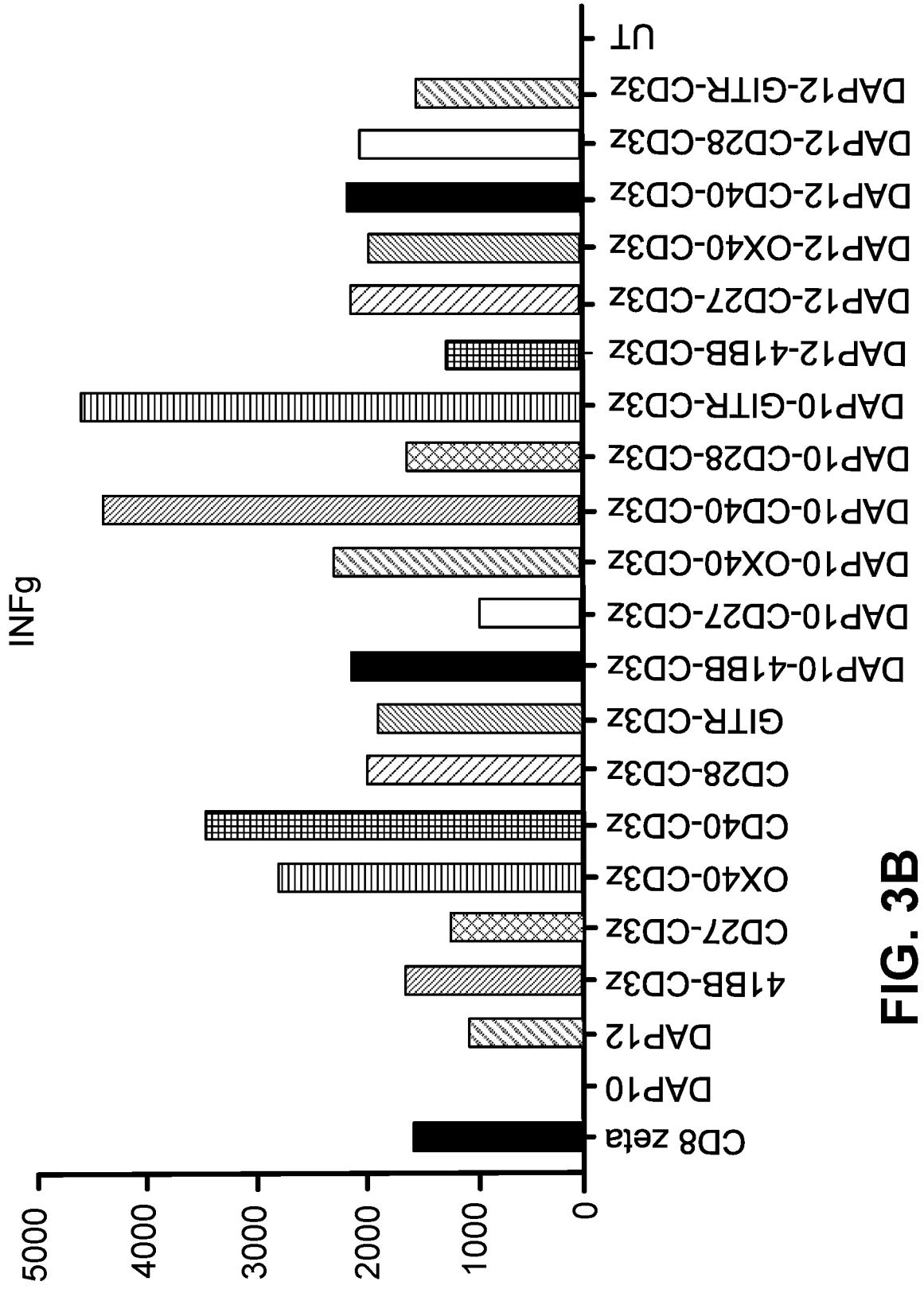
Figure 3C:
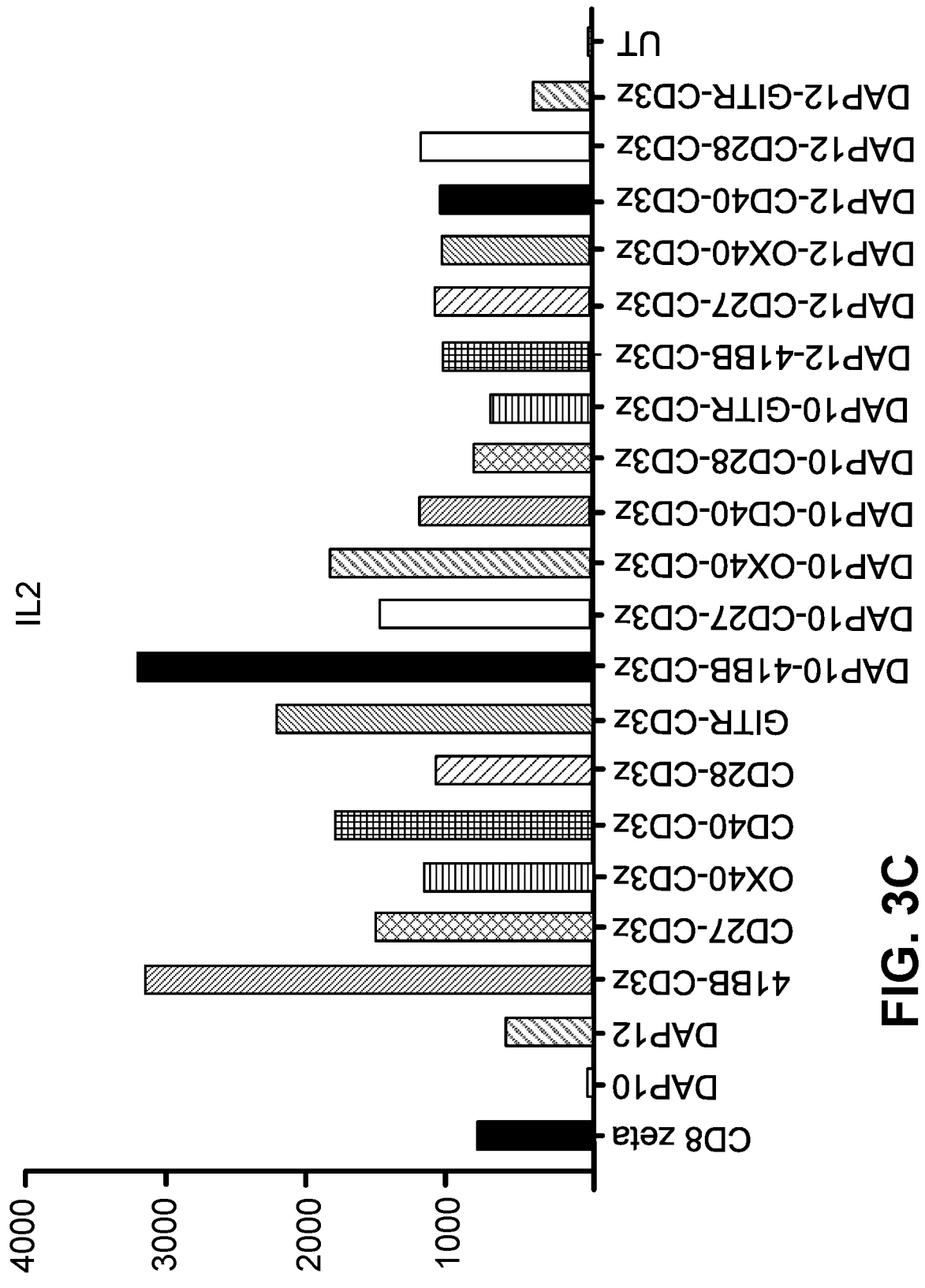

Constructs were expressed in primary T cells at roughly equivalent surface levels, cultured for fourteen days after CD3/CD28 activation and transduction, and plated at 1:1 ratios with the CD19+ cell line NALM6. 24 hours after co-culture, supernatant was collected from each sample and Luminex Assays Millipore/Sigma (Cat. Number HSTCMAG28SPMX21) were performed to quantitate the levels of TNF-alpha, interferon gamma, and interleukin 2 cytokines. The cytokine concentrations shown in FIGS. 3A-C are displayed in pg/mL. UT=Untransduced.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A single-chain chimeric antigen receptor, wherein the single-chain chimeric antigen receptor comprises a single-chain polypeptide, the single-chain polypeptide comprising from N-terminal to C-terminal or from C-terminal to N-terminal:

an extracellular antigen-binding domain that specifically binds to human CD19;

a first intracellular signaling domain from human DAP-12;

a second intracellular signaling domain from human CD28; and a CD3ζ immunoreceptor tyrosine-based activation motif (ITAM);

wherein when the single-chain chimeric antigen receptor is expressed in a human T cell; and wherein CD69 and TNFα expression is increased relative to a corresponding human T cell expressing a single-chain chimeric antigen receptor wherein the second intracellular signaling domain from human CD28 is absent or substituted with an intracellular signaling domain from human 4-1BB, CD27, OX40, CD40, or GITR.

2. A multi-chain chimeric antigen receptor, wherein the multi-chain chimeric antigen receptor comprises at least two or more of the single-chain polypeptides of claim 1.

3. The multi-chain chimeric antigen receptor of claim 2, wherein the extracellular antigen-binding domain binds to a second tumor antigen selected from the group consisting of: MAGE, MUC16, WT-1, CD22, LI-CAM, ROR-1, CEA, 4-1BB, ETA, 5T4, adenocarcinoma antigen, alpha-fetoprotein (AFP), BAFF, B-lymphoma cell, C242 antigen, CA-125, carbonic anhydrase 9 (CA-IX), C-MET, CCR4, CD152, CD20, CD125 CD200, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgGl, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R a, PDL192, phosphatidylserine, prostatic carcinoma cells, RANKL, RON, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, and vimentin.

4. The multi-chain chimeric antigen receptor of claim 2, further comprising a transmembrane domain, wherein the transmembrane domain comprises a human CD8α transmembrane domain.

5. A nucleic acid that encodes the multi-chain chimeric receptor of claim 2.

6. A set of nucleic acids that together encode the multi-chain chimeric receptor of claim 2.

7. A human T cell comprising the set of nucleic acids of claim 6.

8. The single-chain chimeric antigen receptor of claim 1, wherein the extracellular antigen-binding domain is selected from the group consisting of: a scFv, a sc(Fv)₂, a V_H H domain, and a V_NAR domain.

9. The single-chain chimeric antigen receptor of claim 1, further comprising a transmembrane domain, wherein the transmembrane domain comprises a human CD8α transmembrane domain.

10. A nucleic acid comprising a nucleotide sequence encoding the single-chain chimeric antigen receptor of claim 1.

11. A human T cell comprising the nucleic acid of claim 10.

12. The human T cell of claim 11, wherein the human T cell is selected from the group consisting of: a CD8⁺ T cell, a CD4⁺ T cell, a memory T cell, and a Treg cell.

13. A method of generating a chimeric antigen receptor-expressing cell, the method comprising introducing into a human T cell the nucleic acid of claim 10.

14. The single-chain chimeric antigen receptor of claim 1, wherein the single-chain polypeptide comprises from N-terminal to C-terminal:

the extracellular antigen-binding domain that specifically binds to human CD19;

the first intracellular signaling domain from human DAP-12;

the second intracellular signaling domain from human CD28; and the CD3ζ immunoreceptor tyrosine-based activation motif (ITAM).

15. The single-chain chimeric antigen receptor of claim 14, wherein the extracellular antigen-binding domain is a scFv.

16. The single-chain chimeric antigen receptor of claim 15, further comprising a hinge domain, wherein the hinge domain comprises a human CD8α hinge domain.

17. The single-chain chimeric antigen receptor of claim 15, further comprising a transmembrane domain, wherein the transmembrane domain comprises a human CD8α transmembrane domain.

18. The single-chain chimeric antigen receptor of claim 15, further comprising a hinge domain and a transmembrane domain, wherein the hinge domain comprises a human CD8α hinge domain and the transmembrane domain comprises a human CD8α transmembrane domain.

19. The single-chain chimeric antigen receptor of claim 18, wherein the single-chain polypeptide comprises from N-terminal to C-terminal:

the scFv that specifically binds to human CD19;

the human CD8α hinge domain that comprises the sequence set forth in SEQ ID NO:1;

the human CD8α transmembrane domain that comprises the sequence set forth in SEQ ID NO: 6;

the first intracellular signaling domain from human DAP-12 that comprises the sequence set forth in SEQ ID NO:80;

the second intracellular signaling domain from human CD28 that comprises the sequence set forth in SEQ ID NO:65; and the CD3ζ immunoreceptor tyrosine-based activation motif (ITAM) that comprises the sequence set forth in SEQ ID NO:83.

20. A nucleic acid comprising a nucleotide sequence encoding the single-chain chimeric antigen receptor of claim 19.

21. A human T cell comprising the nucleic acid of claim 20.

22. A method of generating a chimeric antigen receptor-expressing cell, the method comprising introducing into a human T cell the nucleic acid of claim 20.

23. A nucleic acid comprising a nucleotide sequence encoding the single-chain chimeric antigen receptor of claim 18.

24. A human T cell comprising the nucleic acid of claim 23.

25. A method of generating a chimeric antigen receptor-expressing cell, the method comprising introducing into a human T cell the nucleic acid of claim 23.

26. The single-chain chimeric antigen receptor of claim 15, wherein the single-chain polypeptide comprises from N-terminal to C-terminal:

the scFv that specifically binds to human CD19;

the first intracellular signaling domain from human DAP-12 that comprises the sequence set forth in SEQ ID NO:80 the second intracellular signaling domain from human CD28 that comprises the sequence set forth in SEQ ID NO:65; and the CD3ζ immunoreceptor tyrosine-based activation motif (ITAM) that comprises the sequence set forth in SEQ ID NO:83.

27. A nucleic acid comprising a nucleotide sequence encoding the single-chain chimeric antigen receptor of claim 26.

28. A human T cell comprising the nucleic acid of claim 27.

29. A method of generating a chimeric antigen receptor-expressing cell, the method comprising introducing into a human T cell the nucleic acid of claim 27.

30. A nucleic acid comprising a nucleotide sequence encoding the single-chain chimeric antigen receptor of claim 14.

31. A human T cell comprising the nucleic acid of claim 30.

32. A method of generating a chimeric antigen receptor-expressing cell, the method comprising introducing into a human T cell the nucleic acid of claim 30.

33. A pharmaceutical composition comprising the human T cell of claim 12 and a pharmaceutically acceptable carrier.

* * * * *